United States Patent
Takahashi et al.

(10) Patent No.: US 8,962,674 B2
(45) Date of Patent: Feb. 24, 2015

(54) CURCUMIN DERIVATIVE

(75) Inventors: Takashi Takahashi, Tokyo (JP); Ichiro Hijikuro, Tokyo (JP); Hachiro Sugimoto, Kyoto (JP); Takeshi Kihara, Kyoto (JP); Yoshiari Shimmyo, Kyoto (JP); Tetsuhiro Niidome, Kyoto (JP)

(73) Assignees: Tokyo Institute of Technology, Tokyo (JP); Kyoto University, Kyoto-Shi (JP)

( * ) Notice: Subject to any disclaimer, the term of this patent is extended or adjusted under 35 U.S.C. 154(b) by 48 days.

(21) Appl. No.: 12/516,948

(22) PCT Filed: Nov. 30, 2007

(86) PCT No.: PCT/JP2007/073155
§ 371 (c)(1),
(2), (4) Date: Jul. 21, 2009

(87) PCT Pub. No.: WO2008/066151
PCT Pub. Date: Jun. 5, 2008

(65) Prior Publication Data
US 2010/0048901 A1 Feb. 25, 2010

(30) Foreign Application Priority Data
Nov. 30, 2006 (JP) .................. 2006-323707

(51) Int. Cl.
*A61K 31/404* (2006.01)
*C07D 209/12* (2006.01)
*C07D 209/08* (2006.01)

(52) U.S. Cl.
CPC ............ *C07D 209/08* (2013.01); *A61K 31/404* (2013.01); *C07D 209/12* (2013.01)
USPC ......................................... 514/419; 548/494

(58) Field of Classification Search
CPC ............................. A61K 31/404; C07D 209/12
USPC ............................................ 514/419; 548/494
See application file for complete search history.

(56) References Cited

FOREIGN PATENT DOCUMENTS

WO     WO 2007/051314 A1     5/2007

OTHER PUBLICATIONS

Findeis et al. Pharmacology & Therapeutics 2007, 116, 266-286.*
WebMD entry for Alzheimer's Disease prevention (http://www.webmd.com/alzheimers/tc/alzheimers-disease-prevention, accessed Sep. 13, 2010, last updated Nov. 10, 2008.*
Shao et al. Tetrahedron Letters 2006, 47, 4085-4089.*
CAPlus entry for Gerhard et al. Zeitschrift fuer Chemie 1987, 27, 172-173.*
Lin et al. J. Med. Chem. 2006, 49, 3963-3972.*
Sharma et al. European Journal of Cancer 2005, 41, 1955-1968.*
Arrieta et al., "Synthesis and proton NMR Spectroscopic Investigations of New Curcumin Analogs", Journal fur praktische Chemie/Chemiker-Zeitung, 1992, vol. 334, p. 696-700, compound 3h, p. 697, Table 1.
Anto et al., "Anti-tumour and free radical scavenging activity of synthetic curcuminoids", International Journal of Pharmaceutics, 1996, vol. 131, No. 1, p. 1-7, compound (5), p. 2, Fig. 1.
Yang et al., "Curcumin Inhibits Formation of Amyloid Beta Oligomers and Fibrils, Binds Plaques, and Reduces Amyloid in Vivo", The Journal of Biological Chemistry, 2005, vol. 280, No. 7, p. 5892-5901.
Shao et al., "Facile preparation of new unsymmetrical curcumin derivatives by solid-phase synthesis strategy", Tetrahedron Letters, Jun. 2006, vol. 47, No. 24, p. 4085-4089, compound 1b, p. 4087, Table 2.
Lin et al., "Antitumor Agents. 250 Design and Synthesis of New Curcumin Analogues as Potential Anti-Prostate Cancer Agents", Journal of Medicinal Chemistry, 2006, vol. 49, No. 13, p. 3963-3972, compound 16, p. 3966, Table 1C.
Chinese Office Action issued in Chinese Patent Application No. 200780043730.8 on Dec. 3, 2010.
Begum et al., "The Phenolic Antioxidant Compound Curcumin (CURC), and One of Its Metabolite Tetrahydrocurcumin (THC) Prevent Aβ Oligomer Formation, De-Aggregate Previously Formed Oligomers . . . ", Neurobiology of Aging, vol. 25, Supp. 2, 2004, pp. S592-S593, P4-417.
Cole et al., "NSAID and Antioxidant Prevention of Alzheimer's Disease Lessons from in Vitro and Animal Models," Annals of the New York Academy of Sciences, vol. 1035, 2004, pp. 68-84.
Office Action for Japanese Application No. 2008-547050, dated Dec. 18, 2012, including a partial English translation.

* cited by examiner

*Primary Examiner* — Joseph Kosack
*Assistant Examiner* — Matthew Coughlin
(74) *Attorney, Agent, or Firm* — Birch, Stewart, Kolasch & Birch, LLP

(57) ABSTRACT

The present invention provides a novel compound that is structurally similar to curcumin and has a suppressive effect on Aβ aggregation, a degradative effect on Aβ aggregates, an inhibitory effect on β-secretase, and a protective effect on neurons. The novel compound is a compound represented by the following general formula (Ia) or a salt thereof:

[Formula 1]

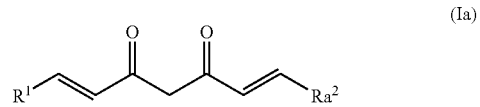

(Ia)

wherein $R^1$ represents a 4-hydroxy-3-methoxyphenyl group or the like, and $R^2$ represents a 1H-indol-6-yl group or the like.

4 Claims, 2 Drawing Sheets

Fig. 1

| Compound No. | Inhibition % |
|---|---|
| CU001 | 52.7 |
| CU003 | 35.9 |
| CU004 | 35.1 |
| CU005 | 29.5 |
| CU006 | 32.5 |
| CU007 | 26.0 |
| CU008 | 31.9 |
| CU009 | 31.4 |
| CU010 | 26.0 |
| CU011 | 28.9 |
| CU012 | 29.4 |
| CU014 | 20.2 |
| CU015 | 12.0 |
| CU016 | 22.8 |
| CU017 | 49.1 |
| CU018 | 30.0 |
| CU019 | 23.2 |
| CU020 | 16.7 |
| CU021 | 6.7 |
| CU022 | 22.7 |
| CU023 | 18.5 |
| CU024 | 12.0 |
| CU027 | 29.8 |
| CU028 | 21.5 |
| CU029 | 38.7 |
| CU030 | 61.1 |
| CU031 | 51.0 |
| CU032 | 16.2 |
| CU033 | 7.8 |
| CU035 | 15.3 |
| CU036 | 10.0 |
| CU039 | 6.0 |
| CU040 | 8.3 |
| CU042 | N.D |
| CU043 | N.D |
| CU044 | N.D |
| CU045 | N.D |
| CU046 | 26.9 |
| CU048 | 13.8 |
| CU049 | 15.7 |
| CU051 | 6.5 |
| CU052 | N.D |
| CU056 | N.D |
| CU057 | 33.4 |
| CU058 | 10.1 |
| CU059 | 15.4 |
| CU065 | 19.8 |
| CU066 | 20.2 |
| CU067 | 7.6 |
| CU068 | 12.3 |
| CU069 | 11.6 |
| CU070 | 10.8 |
| CU071 | 21.6 |
| CU072 | 19.3 |
| CU073 | 9.4 |
| CU074 | 2.7 |
| CU075 | N.D |
| CU076 | N.D |
| CU077 | N.D |
| CU078 | 3.8 |
| CU079 | 7.1 |
| CU080 | 24.6 |
| CU081 | 0.6 |
| CU082 | N.D |
| CU083 | N.D |
| CU084 | N.D |
| CU085 | N.D |
| CU086 | N.D |
| CU088 | 1.8 |
| CU089 | 17.9 |
| CU090 | 7.6 |
| CU091 | N.D |
| CU092 | N.D |
| CU093 | N.D |
| CU094 | 42.7 |
| CU098 | 30.5 |
| CU099 | 36.7 |
| CU100 | 14.7 |
| CU101 | 18.7 |
| CU102 | 29.1 |
| CU103 | 30.5 |
| CU104 | 40.8 |
| CU105 | 23.6 |
| CU106 | 31.5 |
| CU107 | 32.8 |
| CU108 | 28.9 |
| CU110 | 57.5 |
| CU111 | 9.5 |
| CU112 | 52.7 |
| CU113 | 27.2 |
| CU114 | 28.3 |
| CU115 | 24.9 |
| CU116 | 54.2 |
| CU118 | 18.4 |
| CU119 | 20.0 |
| CU120 | 25.3 |
| CU121 | 42.5 |
| CU122 | 41.0 |
| CU123 | 18.5 |
| CU124 | 23.5 |
| CU125 | 16.7 |
| CU126 | 16.3 |
| CU127 | 13.8 |
| CU128 | N.D |
| CU129 | N.D |
| CU130 | N.D |
| CU131 | N.D |
| CU132 | 8.9 |
| CU133 | 15.2 |
| CU134 | N.D |
| CU136 | N.D |
| CU137 | N.D |
| CU138 | N.D |
| CU139 | 5.6 |
| CU140 | 9.7 |
| CU141 | N.D |
| CU143 | 9.9 |
| CU144 | 0.4 |
| CU147 | 15.9 |
| CU148 | 58.1 |
| CU149 | N.D |
| CU150 | N.D |
| CU151 | 2.5 |
| CU152 | 21.1 |
| CU153 | 0.6 |
| CU154 | N.D |
| CU155 | 0.7 |
| CU157 | N.D |
| CU158 | 9.5 |
| CU160 | 25.1 |
| CU163 | N.D |
| CU165 | N.D |
| CU166 | 4.5 |
| CU168 | N.D |
| CU171 | 24.6 |
| CU174 | N.D |
| CU176 | 49.7 |
| CU177 | 30.1 |
| CU178 | N.D |
| CU179 | 11.3 |
| CU180 | 21.4 |
| CU181 | 18.8 |
| CU182 | 1.5 |
| CU184 | N.D |
| CU185 | N.D |
| CU186 | N.D |
| CU187 | 68.4 |
| CU189 | 81.2 |
| CU190 | 54.1 |
| CU191 | 14.7 |
| CU192 | 3.3 |
| CU193 | 60.7 |
| CU194 | 45.5 |
| CU195 | 31.8 |
| CU196 | 7.0 |
| CU197 | N.D |
| CU198 | 40.7 |
| CU199 | N.D |
| CU200 | 5.0 |
| CU201 | N.D |
| CU202 | N.D |
| CU203 | N.D |
| CU204 | N.D |
| CU205 | 6.4 |
| CU207 | 5.5 |
| CU208 | N.D |
| CU209 | N.D |
| CU210 | N.D |
| CU211 | N.D |
| CU212 | N.D |
| CU213 | 20.1 |
| CU214 | N.D |
| CU215 | N.D |
| CU216 | N.D |
| CU217 | N.D |
| CU218 | 31.5 |
| CU219 | N.D |
| CU220 | 2.7 |
| CU229 | N.D |
| CU231 | N.D |
| CU232 | N.D |
| CU233 | 21.7 |
| CU235 | 7.6 |
| CU236 | 7.1 |
| CU237 | N.D |
| CU241 | N.D |
| CU247 | N.D |
| CU248 | N.D |
| CU249 | N.D |
| CU250 | N.D |
| CU251 | 5.0 |
| CU253 | 34.0 |
| CU256 | 5.7 |
| CU257 | N.D |
| CU258 | 11.4 |
| CU259 | N.D |
| CU261 | N.D |
| CU262 | N.D |
| CU263 | 3.6 |
| CU264 | N.D |
| CU265 | 4.4 |
| CU273 | N.D |
| CU275 | N.D |
| CU276 | N.D |
| CU277 | N.D |
| CU278 | N.D |
| CU279 | N.D |
| CU280 | N.D |
| CU281 | N.D |
| CU282 | N.D |

Fig. 2

| CU | IC$_{50}$ [$\mu$M] |
|---|---|
| CU029 | 0.72 |
| CU042 | 0.73 |
| CU072 | 0.97 |
| CU085 | 1.2 |
| CU086 | 2.1 |
| CU090 | 2.2 |
| CU091 | 1.4 |
| CU100 | 3.4 |
| CU110 | 1.7 |
| CU115 | 1.6 |
| CU118 | 1.2 |
| CU127 | 1.0 |
| CU129 | 0.81 |
| CU130 | 1.5 |
| CU131 | 0.91 |
| CU132 | 0.79 |
| CU133 | 0.63 |
| CU137 | 1.6 |
| CU138 | 2.2 |
| CU148 | 1.3 |
| CU150 | 2.0 |
| CU153 | 1.1 |
| CU168 | 1.8 |
| CU176 | 2.9 |
| CU188 | 1.9 |
| CU189 | 0.80 |
| CU192 | 1.5 |
| CU193 | 2.3 |
| CU194 | 1.2 |
| CU195 | 1.2 |
| CU196 | 2.0 |
| CU197 | 1.2 |
| CU202 | 1.8 |
| CU204 | 4.0 |
| CU205 | 3.0 |
| CU220 | 2.6 |
| CU247 | 2.4 |
| CU249 | 0.75 |
| CU253 | 0.96 |
| CU256 | 1.2 |
| CU259 | 0.98 |
| CU261 | 2.0 |
| CU279 | 1.4 |
| CU280 | 1.4 |
| CU281 | 9.9 |
| CU302 | 1.6 |
| CU313 | 1.2 |
| CU315 | 1.2 |

| CU | IC$_{50}$ [$\mu$M] |
|---|---|
| CU319 | 1.7 |
| CU323 | 2.0 |
| CU331 | 2.3 |
| CU358 | 0.48 |
| CU362 | 0.72 |
| CU380 | 1.6 |
| CU381 | 0.79 |
| CU392 | 0.94 |
| CU400 | 0.92 |
| CU402 | 3.3 |
| CU418 | 1.2 |
| CU420 | 3.4 |
| CU422 | 2.1 |
| CU423 | 2.2 |
| CU426 | 1.0 |
| CU429 | 1.1 |
| CU455 | 1.7 |
| CU456 | 2.2 |
| CU461 | 0.83 |
| CU463 | 1.4 |
| CU464 | 3.1 |
| CU465 | 1.5 |
| CU467 | 0.85 |
| CU468 | 2.3 |
| CU472 | 0.88 |
| CU473 | 5.1 |
| CU474 | 3.3 |
| CU475 | 0.74 |
| CU477 | 1.9 |
| CU478 | 1.2 |
| CU481 | 3.4 |
| CU484 | 0.95 |
| CU516 | 0.48 |
| CU519 | 2.4 |
| CU520 | 0.61 |
| CU522 | 1.1 |
| CU523 | 2.1 |
| CU524 | 2.4 |
| CU526 | 1.0 |
| CU527 | 0.48 |
| CU528 | 0.49 |
| CU529 | 2.7 |
| CU530 | 0.60 |
| CU531 | 0.37 |
| CU532 | 0.33 |
| CU539 | 1.4 |
| CU544 | 0.87 |

CURCUMIN DERIVATIVE

TECHNICAL FIELD

The present invention relates to a novel curcumin derivative. The curcumin derivative of the present invention has an inhibitory effect on β-secretase, a suppressive effect on amyloid β protein (Aβ) aggregation, a degradative effect on Aβ aggregates, a protective effect on neurons, etc., and is therefore useful in the prevention or treatment of Alzheimer's disease. Moreover, the curcumin derivative of the present invention probably has even an anti-inflammatory effect, an antioxidant effect, an anticancer effect, an inhibitory effect on HIV integrase, an antirheumatic effect, and an antiallergic effect and therefore, can also be utilized as a drug for diseases other than Alzheimer's disease. Furthermore, the curcumin derivative of the present invention is also expected to be applied to electronic materials such as liquid crystals and photoresists.

BACKGROUND ART

Senile dementia has become a serious problem both medically and socially with the arrival of a rapidly aging society in recent years. Thus, effective anti-dementia drugs have been strongly demanded. Although a great deal of research has been conducted on Alzheimer's disease (AD), the cause of the disease still remains to be elucidated. Aricept, the only therapeutic drug approved in Japan to treat Alzheimer's disease, is a drug having an inhibitory effect on acetylcholine esterase based on the cholinergic hypothesis. This drug is very useful as symptomatic treatment and however, does not serve as a drug for disease-modifying therapy.

Curcumin, a substance contained in turmeric, etc., has recently been reported to have a suppressive effect on Aβ aggregation and a degradative effect on Aβ aggregates (Non-Patent Document 1) and has therefore been expected as a novel therapeutic drug for Alzheimer's disease. Non-Patent Document 1: Yang. F, et al. J. Biol. Chem. 2005 Feb. 18; 280 (7) 5892-901

DISCLOSURE OF THE INVENTION

Problems to be Solved by the Invention

As described above, curcumin has already been known to have a suppressive effect on Aβ aggregation and a degradative effect on Aβ aggregates. However, whether curcumin derivatives have similar effects has been unknown.

The present invention has been made against this technical background, and an object of the present invention is to provide a novel and useful compound that is structurally similar to curcumin.

Means for Solving the Problems

The present inventor has conducted diligent studies for attaining the object. As a result, the present inventor has successfully synthesized a novel compound having a suppressive effect on Aβ aggregation and a degradative effect on Aβ aggregates that are more excellent than those of curcumin. Moreover, the present inventor has newly found that this compound also has an inhibitory effect on the Aβ-producing enzyme β-secretase (BACE-1) and a protective effect on neurons against Aβ-induced neurotoxicity, etc. Based on these findings, the present invention has been completed.

Specifically, the present invention provides the following (1) to (4):

(1) A compound represented by the following general formula (Ia) or a salt thereof:

[Formula 1]

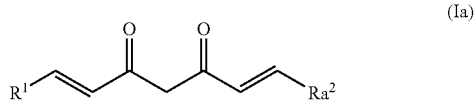

(Ia)

wherein $R^1$ represents an aryl or heteroaryl group which may be substituted by one or two or more substituent(s) selected from a substituent group A shown below, and $Ra^2$ represents a 1H-indol-2-yl, 1H-indol-3-yl, 1H-indol-4-yl, 1H-indol-5-yl, 1H-indol-6-yl, or 1H-indol-7-yl group which may be substituted by one or two or more substituent(s) selected from the substituent group A shown below; and the substituent group A is a group consisting of halogen atoms, alkyl groups having 1 to 6 carbon atom(s), alkoxy groups having 1 to 6 carbon atom(s), dialkylamino groups (wherein the alkyl group has 1 to 6 carbon atom(s)), alkylamino groups (wherein the alkyl group has 1 to 6 carbon atom(s)), amino groups, alkoxyalkoxy groups having 2 to 6 carbon atoms, hydroxy groups, acetylamino groups, phenoxy groups, methanesulfonyl groups, methylthio groups, nitro groups, 3-dimethylaminopropoxy groups, 2-dimethylaminoethoxy groups, dimethylaminomethoxy groups, acetoxy groups, methoxycarbonyl groups, pyridin-2-yl groups, 1H-imidazol-1-yl groups, 4-benzylpiperazin-1-yl groups, 4-methylphenoxy groups, morpholino groups, 4-methylphenyl groups, phenyl groups, benzimidazol-1-yl groups, 4-methylpiperazin-1-yl groups, 2-(t-butoxycarbonylamino)acetylamino groups, 2-t-butoxycarbonylamino-3-phenylpropionylamino groups, benzyl groups, acetyl groups, tosyl groups, methylsulfonyloxy groups, t-butoxycarbonylamino groups, N-(t-butoxycarbonyl)-N-methylamino groups, t-butyldimethylsilyloxy groups, t-butyldimethylsilyloxymethyl groups, 2-amino-3-phenylpropionylamino groups, hydroxymethyl groups, benzoyloxy groups, prenyloxy groups, benzyloxy groups, i-propyloxy groups, 2-hydroxyethoxy groups, 2-(amino)acetylamino groups, 4-methoxybenzyloxy groups, pyridin-3-ylmethoxy groups, 2-chloro-6-fluorobenzyloxy groups, 2,4-dichlorobenzyloxy groups, 4-t-butylbenzyloxy groups, trifluoromethyl groups, hydroxycarbonyl groups, dimethylaminocarbonyl groups, dimethylaminosulfonyl groups, methylsulfinyl groups, pyrrolidin-1-yl groups, piperidin-1-yl groups, t-butoxycarbonylpiperazin-1-yl groups, methylsulfonylpiperazin-1-yl groups, 2-hydroxyethylpiperazin-1-yl groups, pyridin-3-yl groups, pyridin-4-yl groups, piperazin-3-yl groups, naphthalen-1-yl groups, and naphthalen-2-yl groups.

(2) The compound or a salt thereof according to (1), characterized in that in the general formula (Ia), $R^1$ is a phenyl group which may be substituted by a hydroxy or methoxy group.

(3) The compound or a salt thereof according to (1), characterized in that in the general formula (Ia), $R^1$ is a 4-hydroxy-3-methoxyphenyl, 4-hydroxyphenyl, or 3-hydroxy-4-methoxy group.

(4) The compound or a salt thereof according to any of (1) to (3), characterized in that in the general formula (Ia), $Ra^2$ is a 1H-indol-2-yl, 1H-indol-3-yl, 1H-indol-4-yl, 1H-indol-5-yl, 1H-indol-6-yl, 1H-indol-7-yl, 1-methyl-1H-indol-3-yl, 1-methyl-1H-indol-2-yl, 1-benzyl-1H-indol-3-yl, 1-benzyl-1H-indol-6-yl, 1-acetyl-1H-indol-3-yl, 1-acetyl-1H-indol-6- yl, 1-methylsulfonyl-1H-indol-3-yl, 1-methylsulfonyl-1H-indol-6-yl, 1-tosyl-1H-indol-3-yl, 1-tosyl-1H-indol-6-yl, or 4-nitro-1H-indol-3-yl group.

Advantages of the Invention

A compound of the present invention has an inhibitory effect on β-secretase, a suppressive effect on Aβ aggregation, a degradative effect on Aβ aggregates, a protective effect on neurons, etc., and is therefore useful in the prevention or treatment of Alzheimer's disease. Moreover, the compound of the present invention is structurally similar to curcumin contained in food and therefore, can probably exhibit preventive and therapeutic effects without having adverse effects on the human body.

BRIEF DESCRIPTION OF THE DRAWINGS

FIG. 1 is a diagram showing an inhibitory effect [%] on β-secretase exhibited by 1.0 μM each of compounds synthesized in Examples. In the diagram, N.D means that the activity was not detected; and FIG. 2 is a diagram showing $IC_{50}$ values, for β-secretase, of compounds synthesized in Examples.

BEST MODE FOR CARRYING OUT THE INVENTION

Hereinafter, the present invention will be described in detail.

The present invention includes a compound represented by the following general formula (I):

[Formula 2]

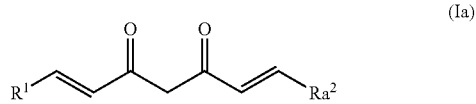

(I)

wherein $R^1$ and $R^2$ are the same or different and each represents an aryl or heteroaryl group which may be substituted by one or two or more substituent(s) selected from a substituent group A shown below; and the substituent group A is a group consisting of halogen atoms, alkyl groups having 1 to 6 carbon atom(s), alkoxy groups having 1 to 6 carbon atom(s), dialkylamino groups (wherein the alkyl group has 1 to 6 carbon atom(s)), alkylamino groups (wherein the alkyl group has 1 to 6 carbon atom(s)), amino groups, alkoxyalkoxy groups having 2 to 6 carbon atoms, hydroxy groups, acetylamino groups, phenoxy groups, methanesulfonyl groups, methylthio groups, nitro groups, 3-dimethylaminopropoxy groups, 2-dimethylaminoethoxy groups, dimethylaminomethoxy groups, acetoxy groups, methoxycarbonyl groups, pyridin-2-yl groups, 1H-imidazol-1-yl groups, 4-benzylpiperazin-1-yl groups, 4-methylphenoxy groups, morpholino groups, 4-methylphenyl groups, phenyl groups, benzimidazol-1-yl groups, 4-methylpiperazin-1-yl groups, 2-(t-butoxycarbonylamino)acetylamino groups, 2-t-butoxycarbonylamino-3-phenylpropionylamino groups, benzyl groups, acetyl groups, tosyl groups, methylsulfonyloxy groups, t-butoxycarbonylamino groups, N-(t-butoxycarbonyl)-N-methylamino groups, t-butyldimethylsilyloxy groups, t-butyldimethylsilyloxymethyl groups, 2-amino-3-phenylpropionylamino groups, hydroxymethyl groups, benzoyloxy groups, prenyloxy groups, benzyloxy groups, i-propyloxy groups, 2-hydroxyethoxy groups, 2-(amino)acetylamino groups, 4-methoxybenzyloxy groups, pyridin-3-ylmethoxy groups, 2-chloro-6-fluorobenzyloxy groups, 2,4-dichlorobenzyloxy groups, 4-t-butylbenzyloxy groups, trifluoromethyl groups, hydroxycarbonyl groups, dimethylaminocarbonyl groups, dimethylaminosulfonyl groups, methylsulfinyl groups, pyrrolidin-1-yl groups, piperidin-1-yl groups, t-butoxycarbonylpiperazin-1-yl groups, methylsulfonylpiperazin-1-yl groups, 2-hydroxyethylpiperazin-1-yl groups, pyridin-3-yl groups, pyridin-4-yl groups, piperazin-3-yl groups, naphthalen-1-yl groups, and naphthalen-2-yl groups.

Among these compounds represented by the general formula (I), a preferable compound can be exemplified by a compound represented by the following general formula (Ia):

[Formula 3]

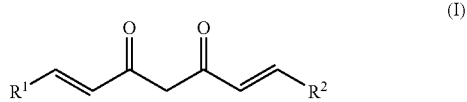

(Ia)

wherein $R^1$ represents an aryl or heteroaryl group which may be substituted by one or two or more substituent(s) selected from a substituent group A shown below, and $Ra^2$ represents a 1H-indol-2-yl, 1H-indol-3-yl, 1H-indol-4-yl, 1H-indol-5-yl, 1H-indol-6-yl, or 1H-indol-7-yl group which may be substituted by one or two or more substituent(s) selected from the substituent group A shown below; and the substituent group A is a group consisting of halogen atoms, alkyl groups having 1 to 6 carbon atom(s), alkoxy groups having 1 to 6 carbon atom(s), dialkylamino groups (wherein the alkyl group has 1 to 6 carbon atom(s)), alkylamino groups (wherein the alkyl group has 1 to 6 carbon atom(s)), amino groups, alkoxyalkoxy groups having 2 to 6 carbon atoms, hydroxy groups, acetylamino groups, phenoxy groups, methanesulfonyl groups, methylthio groups, nitro groups, 3-dimethylaminopropoxy groups, 2-dimethylaminoethoxy groups, dimethylaminomethoxy groups, acetoxy groups, methoxycarbonyl groups, pyridin-2-yl groups, 1H-imidazol-1-yl groups, 4-benzylpiperazin-1-yl groups, 4-methylphenoxy groups, morpholino groups, 4-methylphenyl groups, phenyl groups, benzimidazol-1-yl groups, 4-methylpiperazin-1-yl groups, 2-(t-butoxycarbonylamino)acetylamino groups, 2-t-butoxycarbonylamino-3-phenylpropionylamino groups, benzyl groups, acetyl groups, tosyl groups, methylsulfonyloxy groups, t-butoxycarbonylamino groups, N-(t-butoxycarbonyl)-N-methylamino groups, t-butyldimethylsilyloxy groups, t-butyldimethylsilyloxymethyl groups, 2-amino-3-phenylpropionylamino groups, hydroxymethyl groups, benzoyloxy groups, prenyloxy groups, benzyloxy groups, i-propyloxy groups, 2-hydroxyethoxy groups, 2-(amino)acetylamino groups, 4-methoxybenzyloxy groups, pyridin-3-ylmethoxy groups, 2-chloro-6-fluorobenzyloxy groups, 2,4-dichlorobenzyloxy groups, 4-t-butylbenzyloxy groups, trifluoromethyl groups, hydroxycarbonyl groups, dimethylaminocarbonyl groups, dimethylaminosulfonyl groups, methylsulfinyl groups, pyrrolidin-1-yl groups, piperidin-1-yl groups, t-butoxycarbonylpiperazin-1-yl groups, methylsulfonylpiperazin-1-yl groups, 2-hydroxyethylpiperazin-1-yl groups, pyridin-3-yl groups, pyridin-4-yl groups, piperazin-3-yl groups, naphthalen-1-yl groups, and naphthalen-2-yl groups.

Moreover, the present invention also includes a compound represented by the general formula (II) (tetrahydro form):

[Formula 4]

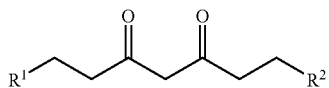

(II)

wherein R¹ and R² are as defined above, and
a compound represented by the general formula (III) (dihydro form):

[Formula 5]

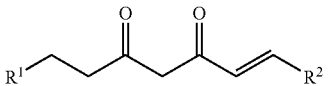

(III)

which are reduced forms of the compound represented by the general formula (I).

In the present invention, examples of the "halogen atoms" include fluorine, chlorine, bromine, and iodine atoms. The halogen atoms are preferably fluorine, chlorine, and bromine atoms.

In the present invention, examples of the "alkyl groups having 1 to 6 carbon atom(s)" include methyl, ethyl, propyl, isopropyl, butyl, isobutyl, s-butyl, t-butyl, pentyl, isopentyl, and hexyl groups. The alkyl groups having 1 to 6 carbon atom(s) are preferably methyl, ethyl, propyl, and isopropyl groups, more preferably a methyl group.

In the present invention, examples of the "alkoxy groups having 1 to 6 carbon atom(s)" include methoxy, ethoxy, propoxy, isopropoxy, butoxy, isobutoxy, s-butoxy, t-butoxy, pentyloxy, isopentyloxy, and hexyloxy groups. The alkoxy groups having 1 to 6 carbon atom(s) are preferably methoxy, ethoxy, propoxy, and isopropoxy groups, more preferably a methoxy group.

In the present invention, examples of the "dialkylamino groups (wherein the alkyl group has 1 to 6 carbon atom(s))" include dimethylamino, diethylamino, dipropylamino, diisopropylamino, dibutylamino, dipentylamino, and dihexylamino groups. The dialkylamino groups are preferably dimethylamino, diethylamino, dipropylamino, and diisopropylamino groups, more preferably a dimethylamino group.

In the present invention, examples of the "alkylamino groups (wherein the alkyl group has 1 to 6 carbon atom(s))" include methylamino, ethylamino, propylamino, isopropylamino, butylamino, pentylamino, and hexylamino groups. The alkylamino groups are preferably methylamino, ethylamino, propylamino, and isopropylamino groups, more preferably a methylamino group.

In the present invention, examples of the "alkoxyalkoxy groups having 2 to 6 carbon atoms" include methoxymethoxy, methoxyethoxy, ethoxymethoxy, methoxypropoxy, propoxymethoxy, ethoxypropoxy, propoxyethoxy, and propoxypropoxy groups. The alkoxyalkoxy groups having 2 to 6 carbon atoms are preferably methoxymethoxy, methoxyethoxy, and ethoxymethoxy groups, more preferably a methoxymethoxy group.

In the present invention, examples of the "aryl group" include phenyl, naphthalen-1-yl, and naphthalen-2-yl groups. The aryl group is preferably a phenyl group.

In the present invention, examples of the "aryl group which may be substituted by one or two or more substituent(s) selected from the substituent group A" include 4-chlorophenyl, 2-methoxyphenyl, 3-methoxyphenyl, 4-methoxyphenyl, 4-dimethylaminophenyl, 2-hydroxyphenyl, 3-hydroxyphenyl, 4-hydroxyphenyl, 4-acetylaminophenyl, 3-phenoxyphenyl, 4-phenoxyphenyl, 4-methanesulfonylphenyl, 4-methylthiophenyl, 3,4-difluorophenyl, 2,4-dichlorophenyl, 2,5-dichlorophenyl, 3,4-dichlorophenyl, 3,5-dichlorophenyl, 3,4-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-dihydroxyphenyl, 2,4-dihydroxyphenyl, 2,5-dihydroxyphenyl, 3,4-dihydroxyphenyl, 3,5-dihydroxyphenyl, 4-fluoro-3-methoxyphenyl, 3-fluoro-4-hydroxyphenyl, 2-chloro-4-hydroxyphenyl, 3-chloro-4-hydroxyphenyl, 2-chloro-4-dimethylaminophenyl, 4-hydroxy-3-methylphenyl, 2-hydroxy-3-methoxyphenyl, 2-hydroxy-4-methoxyphenyl, 2-hydroxy-5-methoxyphenyl, 2-hydroxy-6-methoxyphenyl, 3-hydroxy-2-methoxyphenyl, 3-hydroxy-4-methoxyphenyl, 3-hydroxy-5-methoxyphenyl, 4-hydroxy-2-methoxyphenyl, 4-hydroxy-3-methoxyphenyl, 5-hydroxy-2-methoxyphenyl, 3-methoxy-4-nitrophenyl, 4-dimethylamino-2-methoxyphenyl, 4-dimethylamino-3-methoxyphenyl, 4-dimethylamino-2-nitrophenyl, 4-diethylamino-2-hydroxyphenyl, 4-diethylamino-2-methoxymethoxyphenyl, 3-hydroxy-2-methoxymethoxyphenyl, 2-hydroxy-6-methoxymethoxyphenyl, 4-hydroxy-3-nitrophenyl, 5-hydroxy-2-nitrophenyl, 4-(3-dimethylaminopropoxy)phenyl, 4-acetoxy-3-methoxyphenyl, 3,4,5-trimethoxyphenyl, 3,5-dichloro-2-hydroxyphenyl, 4-hydroxy-3,5-dimethoxyphenyl, 2-methoxynaphthalen-1-yl, 4-methoxynaphthalen-1-yl, 6-methoxynaphthalen-2-yl, and 4-dimethylaminonaphthalen-1-yl groups.

In the present invention, examples of the "heteroaryl group" include furan-2-yl, furan-3-yl, thiophen-2-yl, thiophen-3-yl, 1H-pyrrol-1-yl, 1H-pyrrol-2-yl, 1H-pyrrol-3-yl, pyridin-2-yl, pyridin-3-yl, pyridin-4-yl, pyrimidin-5-yl, pyrazin-2-yl, 1H-indol-1-yl, 1H-indol-2-yl, 1H-indol-3-yl, 1H-indol-4-yl, 1H-indol-5-yl, 1H-indol-6-yl, 1H-indol-7-yl, quinoxalin-6-yl, benzimidazol-5-yl, benzoxazol-5-yl, benzothiazol-4-yl, 1H-indazol-5-yl, quinolin-2-yl, quinolin-5-yl, quinolin-8-yl, 1H-imidazol-1-yl, 1H-imidazol-2-yl, 1H-imidazol-4-yl, 1H-imidazol-5-yl, 1H-pyrazol-1-yl, 1H-pyrazol-3-yl, 1H-pyrazol-4-yl, 1H-pyrazol-5-yl, 9H-carbazol-3-yl, benzofuran-2-yl, benzothiophen-2-yl, benzo[1,3]dioxol-5-yl, 2,3-dihydrobenzo[1,4]dioxin-6-yl, thiazol-4-yl, 1H-benzotriazol-5-yl, benzimidazol-5-yl, quinolin-6-yl, 1H-indazol-5-yl, quinolin-5-yl, chromon-3-yl, coumarin-6-yl, and indolin-6-yl groups. The heteroaryl group is preferably furan-2-yl, thiophen-2-yl, 1H-pyrrol-2-yl, pyridin-2-yl, pyridin-3-yl, 1H-indol-2-yl, 1H-indol-3-yl, 1H-indol-5-yl, 1H-indol-6-yl, 1H-imidazol-2-yl, 1H-imidazol-4-yl, 1H-pyrazol-4-yl, 9H-carbazol-3-yl, benzo[1,3]dioxol-5-yl, and 2,3-dihydrobenzo[1,4]dioxin-6-yl groups.

In the present invention, examples of the "heteroaryl group which may be substituted by one or two or more substituent(s) selected from the substituent group A" include 9-ethyl-9H-carbazol-3-yl, 1-methyl-1H-pyrrol-3-yl, 1-methyl-1H-pyrazol-4-yl, 1-methyl-1H-indol-2-yl, 1-methyl-1H-indol-3-yl, 1-benzyl-1H-indol-3-yl, 6-(4-benzylpiperazino)pyridin-3-yl, 6-(4-methylphenoxy)pyridin-3-yl, 6-morpholinopyridin-3-yl, 2-(4-benzylpiperazino)pyridin-3-yl, 2-(4-methylphenoxy)pyridin-3-yl, 2-morpholinopyridin-3-yl, 4-(imidazol-1-yl)phenyl, 4-(1H-1,3-benzimidazol-1-yl)phenyl, 4-(4-methylpiperazino)phenyl, 4-(2-pyridinyl)phenyl, 2-phenyl-1,3-thiazol-4-yl, 1-(4-methylphenyl)-1H-pyrrol-2-yl, and 5-pyridin-2-yl-thiophen-2-yl groups.

In the general formulas (I), (II), and (III), $R^1$ is preferably a phenyl group which may be substituted by a hydroxy or methoxy group, more preferably a 4-hydroxy-3-methoxyphenyl, 4-hydroxyphenyl, or 3-hydroxy-4-methoxy group.

In the general formulas (I), (II), and (III), $R^2$ is preferably a 1H-indol-2-yl, 1H-indol-3-yl, 1H-indol-4-yl, 1H-indol-5-yl, 1H-indol-6-yl, or 1H-indol-7-yl group which may be substituted by one or two or more substituent(s) selected from the substituent group A, more preferably a 1H-indol-2-yl, 1H-indol-3-yl, 1H-indol-4-yl, 1H-indol-5-yl, 1H-indol-6-yl, 1H-indol-7-yl, 1-methyl-1H-indol-3-yl, 1-methyl-1H-indol-2-yl, 1-benzyl-1H-indol-3-yl, 1-benzyl-1H-indol-6-yl, 1-acetyl-1H-indol-3-yl, 1-acetyl-1H-indol-6-yl, 1-methylsulfonyl-1H-indol-3-yl, 1-methylsulfonyl-1H-indol-6-yl, 1-tosyl-1H-indol-3-yl, 1-tosyl-1H-indol-6-yl, or 4-nitro-1H-indol-3-yl group. Alternatively, when the compound represented by the general formula (I) is used for the purpose of inhibiting β-secretase, $R^2$ may also be a 2,6-dimethoxyphenyl, 3-fluoro-4-hydroxyphenyl, 1-methyl-1H-pyrrol-2-yl, 9-ethyl-9H-carbazol-3-yl, 1H-indol-3-yl, 1H-indol-5-yl, or 1H-indol-6-yl group. When the compound represented by the general formula (I) is used for the purpose of suppressing Aβ aggregation, $R^2$ may also be a 3,4-dimethylphenyl, 3-hydroxyphenyl, 4-dimethylamino-2-methoxyphenyl, or 5-hydroxy-2-methoxyphenyl group. When the compound represented by the general formula (I) is used for the purpose of degrading Aβ aggregates, $R^2$ may also be a 4-methanesulfonylphenyl, 4-dimethylaminonaphthalen-1-yl, or 1H-pyrrol-2-yl group. When the compound represented by the general formula (I) is used for the purpose of protecting neurons, $R^2$ may also be a 3-hydroxyphenyl or 3,5-dihydroxyphenyl group.

Typical examples of the compound represented by the general formula (I) can include compounds CU001 to CU504 (including unassigned numbers), CU513 to CU515, CU526 to CU529, CU531 to CU539, CU543, and CU544 described in Examples. Typical examples of the compound represented by the general formula (II) can include compounds CU505 to CU512 described in Examples. Typical examples of the compound represented by the general formula (III) can include compounds CU517 to CU520, CU522 to CU525, CU530, CU540 to CU542, and CU545 to CU549 described in Examples.

When the compounds represented by the general formulas (I) to (III) are used for the purpose of inhibiting β-secretase, a preferable compound among the compounds described above can be exemplified by CU010, CU029, CU039, CU042, CU072, CU078, CU083, CU085, CU086, CU090, CU091, CU100, CU108, CU110, CU115, CU118, CU119, CU127, CU129, CU130, CU131, CU132, CU133, CU137, CU138, CU148, CU150, CU153, CU168, CU176, CU188, CU189, CU192, CU193, CU194, CU195, CU196, CU197, CU202, CU204, CU205, CU220, CU246, CU247, CU249, CU253, CU256, CU259, CU261, CU279, CU280, CU281, CU313, CU315, CU319, CU323, CU331, CU358, CU362, CU380, CU381, CU387, CU392, CU400, CU402, CU418, CU420, CU422, CU423, CU426, CU429, CU456, CU461, CU463, CU464, CU465, CU467, CU468, CU472, CU473, CU474, CU475, CU477, CU478, CU481, CU484, CU519, CU520, CU522, CU523, CU524, CU526, CU527, CU528, CU529, CU530, CU531, CU532, CU533, CU536, CU537, CU538, CU539, CU541, CU542, and CU544. When the compound represented by the general formula (I) is used for the purpose of suppressing Aβ aggregation, a preferable compound among the compounds described above can be exemplified by CU056, CU078, CU153, and CU177. When the compound represented by the general formula (I) is used for the purpose of degrading Aβ aggregates, a preferable compound among the compounds described above can be exemplified by CU005, CU019, and CU022. When the compound represented by the general formula (I) is used for the purpose of protecting neurons, a preferable compound among the compounds described above can be exemplified by CU078 and CU092.

Instead of the compound of the present invention, a salt of the compound of the present invention can also be used. Such a salt is preferably a pharmacologically/pharmaceutically acceptable salt and can be exemplified by alkali metal salts (sodium salts and potassium salts), alkaline-earth metal salts (calcium salts and magnesium salts), sulfate, hydrochloride, nitrate, mesilate, and maleate.

The compound represented by the general formula (I) can be produced according to a method known in the art (e.g., the method described in National Publication of International Patent Application No. 1999-502232). Specifically, the compound represented by the general formula (I) can be produced by the following steps 1 and 2:

[Formula 6]

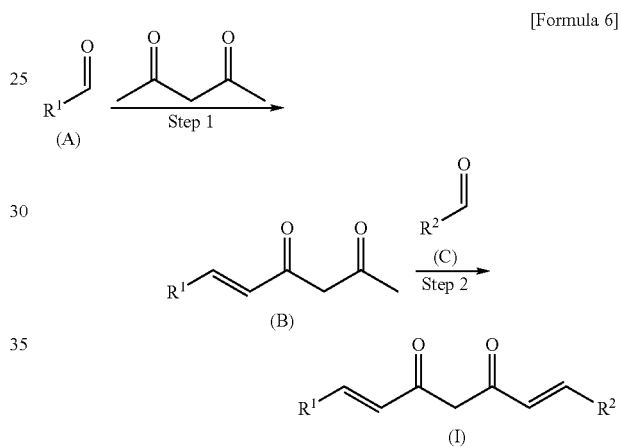

wherein $R^1$ and $R^2$ are as defined above.

The step 1 is a step of reacting an aldehyde represented by the general formula (A) with 2,4-pentanedione in the presence of a solvent and a catalyst to obtain a compound represented by the general formula (B).

The solvent used is not particularly limited as long as it does not inhibit the reaction. Examples thereof include ethyl acetate, N,N-dimethylacetamide, N,N-dimethylformamide, N-methylpyrrolidinone, dimethyl sulfoxide, tetrahydrofuran, and acetonitrile. These solvents may be used alone or, if necessary, as a mixture of two or more of them at an appropriate ratio.

The catalyst used is not particularly limited. Examples thereof include bases such as primary amine and secondary amine and more specifically include n-butylamine, ethanolamine, piperidine, and morpholine.

Moreover, a water scavenger for scavenging water formed through the reaction may be added thereto. Examples of the water scavenger include alkyl borate, alkyl phosphate, and ortho ester and more specifically include trimethyl orthoformate and tri-n-butyl borate.

The quantitative ratio between the aldehyde represented by the general formula (A) and 2,4-pentanedione is not particularly limited and is preferably 0.5 to 10 mol of the latter, more preferably 1 to 5 mol of the latter, with respect to 1 mol of the former.

The reaction temperature is not particularly limited and is preferably 0 to 200° C., more preferably 50 to 100° C.

The reaction time is not particularly limited and is preferably 0.5 to 48 hours, more preferably 1 to 24 hours.

The aldehyde represented by the general formula (A), which is used in the step 1, is a commercially available product, a product synthesized from a commercially available product by a known method, or a product synthesized by a novel method described in Examples. Moreover, the 2,4-pentanedione is a commercially available product.

The step 2 is a step of reacting the compound represented by the general formula (B) with an aldehyde represented by the general formula (C) in the presence of a solvent and a catalyst to obtain the compound represented by the general formula (I).

The solvent used is not particularly limited as long as it does not inhibit the reaction. Examples thereof include ethyl acetate, N,N-dimethylacetamide, N,N-dimethylformamide, N-methylpyrrolidinone, dimethyl sulfoxide, tetrahydrofuran, and acetonitrile. These solvents may be used alone or, if necessary, as a mixture of two or more of them at an appropriate ratio.

The catalyst used is not particularly limited. Examples thereof include bases such as primary amine and secondary amine and more specifically include n-butylamine, ethanolamine, piperidine, and morpholine.

Moreover, a water scavenger for scavenging water formed through the reaction may be added thereto. Examples of the water scavenger include alkyl borate, alkyl phosphate, and ortho ester and more specifically include trimethyl orthoformate and tri-n-butyl borate.

The quantitative ratio between the compound represented by the general formula (B) and the aldehyde represented by the general formula (C) is not particularly limited and is preferably 0.1 to 10 mol of the latter, more preferably 0.5 to 5 mol of the latter, with respect to 1 mol of the former.

The reaction temperature is not particularly limited and is preferably 0 to 200° C., more preferably 50 to 100° C.

The reaction time is not particularly limited and is preferably 0.5 to 48 hours, more preferably 1 to 24 hours.

The aldehyde represented by the general formula (A), which is used in the step 2, is a commercially available product, a product synthesized from a commercially available product by a known method, or a product synthesized by a novel method described in Examples.

When the aldehyde used in the step 2 is low reactive due to its free hydroxy group, an aldehyde having a protected hydroxy group may be used instead thereof for improving reactivity. In this case, the protecting group is not particularly limited and is preferably a protecting group which can be eliminated with an acid when the deprotection is also performed by a hydrochloric acid treatment in the present step. Examples thereof include methoxymethyl and t-butyldimethylsilyl groups.

Of the compounds represented by the general formula (I), a compound wherein $R^1$ and $R^2$ are the same groups is formed by the step 1 and may therefore be produced only by the step 1. In this case, the quantitative ratio between the aldehyde and 2,4-pentanedione is not particularly limited and is preferably 0.01 to 10 mol of the latter, more preferably 0.1 to 0.5 mol of the latter, with respect to 1 mol of the former.

The compound represented by the general formula (II) can be produced by the following step 3:

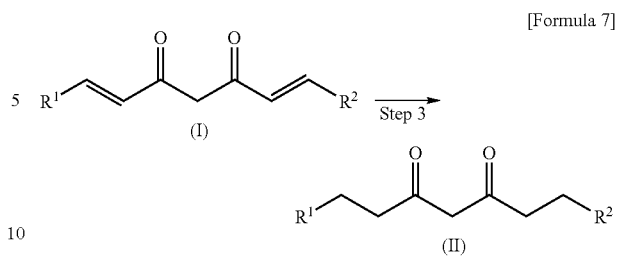

[Formula 7]

wherein $R^1$ and $R^2$ are as defined above.

The step 3 is a step of reducing the compound represented by the general formula (I) in the presence of a solvent and a catalyst to obtain the compound represented by the general formula (II).

The solvent used is not particularly limited as long as it does not inhibit the reaction. Examples thereof include: ester-based solvents such as ethyl acetate; alcohol-based solvents such as methanol, ethanol, and isopropanol; and ether-based solvents such as tetrahydrofuran, diethyl ether, and dimethoxyethane. These solvents may be used alone or, if necessary, as a mixture of two or more of them at an appropriate ratio.

The catalyst used is not particularly limited. Examples thereof include: palladium-based catalysts such as palladium carbon; and nickel-based catalysts such as Raney nickel and nickel-diatomaceous earth.

The reaction temperature is not particularly limited and is preferably −40 to 200° C., more preferably 0 to 100° C.

The reaction time is not particularly limited and is preferably 0.1 to 48 hours, more preferably 0.5 to 24 hours.

The compound represented by the general formula (III) can be produced by the following steps 4 and 5:

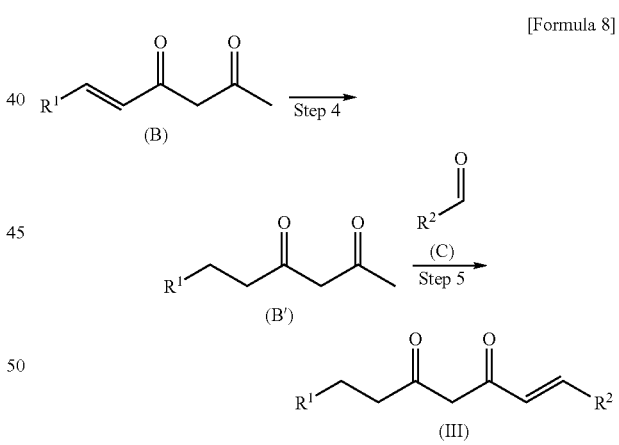

[Formula 8]

wherein $R^1$ and $R^2$ are as defined above.

The step 4 is a step of reducing the compound represented by the general formula (B) in the presence of a solvent and a catalyst to obtain a compound represented by the general formula (B').

The solvent used is not particularly limited as long as it does not inhibit the reaction. Examples thereof include: ester-based solvents such as ethyl acetate; alcohol-based solvents such as methanol, ethanol, and isopropanol; and ether-based solvents such as tetrahydrofuran, diethyl ether, and dimethoxyethane. These solvents may be used alone or, if necessary, as a mixture of two or more of them at an appropriate ratio.

The catalyst used is not particularly limited. Examples thereof include: palladium-based catalysts such as palladium carbon; and nickel-based catalysts such as Raney nickel and nickel-diatomaceous earth.

The reaction temperature is not particularly limited and is preferably −40 to 200° C., more preferably 0 to 100° C.

The reaction time is not particularly limited and is preferably 0.1 to 48 hours, more preferably 0.5 to 24 hours.

The step 5 is a step of reacting the compound represented by the general formula (B') with the aldehyde represented by the general formula (C) in the presence of a solvent and a catalyst to obtain the compound represented by the general formula (III). The step 5 can be performed in the same way as the step 2.

The compound of the present invention has an inhibitory activity on β-secretase, a suppressive effect on Aβ aggregation, a degradative effect on Aβ aggregates, and a protective effect on neurons and is therefore useful in the prevention and treatment of Alzheimer's disease (familial Alzheimer's disease and sporadic Alzheimer's disease) or the like.

When the compound of the present invention is used as a preventive or therapeutic agent for Alzheimer's disease, this compound can be made into a preparation by mixing the compound with a pharmaceutically acceptable carrier or diluent according to a method known in the art. The dosage form thereof is not particularly limited and can be a tablet, powder, granule, capsule, solution, injection, suppository, sustained-release agent, adhesive skin patch, or the like. The administration method thereof is not particularly limited and can be oral or parenteral (e.g., local, rectal, or intravenous) administration. The dose thereof differs depending on an individual that receives administration, an administration method, a disease type, etc. For example, when the compound of the present invention is orally administered as a therapeutic drug for Alzheimer's disease to an adult, the therapeutic drug can be administered at one to several dose(s) a day such that the content of the compound of the present invention is 0.1 to 500 mg per dose.

EXAMPLES

Hereinafter, the present invention will be described in more detail with reference to Examples, etc. In this context, compounds synthesized in Examples are designated as compounds having a structure represented by the general formula (I), (II), or (III) shown below. In 1H NMR (deuterated acetone solvent, room temperature), they are respectively detected as compounds having a structure represented by the general formula (I'), (II'), (II''), or (III') shown below. Thus, the compounds synthesized in Examples also include those detected in 1H NMR as compounds having the structure represented by the general formula (I'), (II'), (II''), or (III'), not the structure represented by the general formula (I), (II), or (III). Moreover, melting points may be indicated in numeric values different from those shown in Synthetic Examples, depending on a crystal system or a degree of contamination with impurities.

[Formula 9]

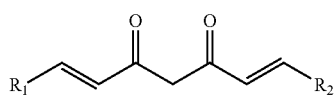
(I)

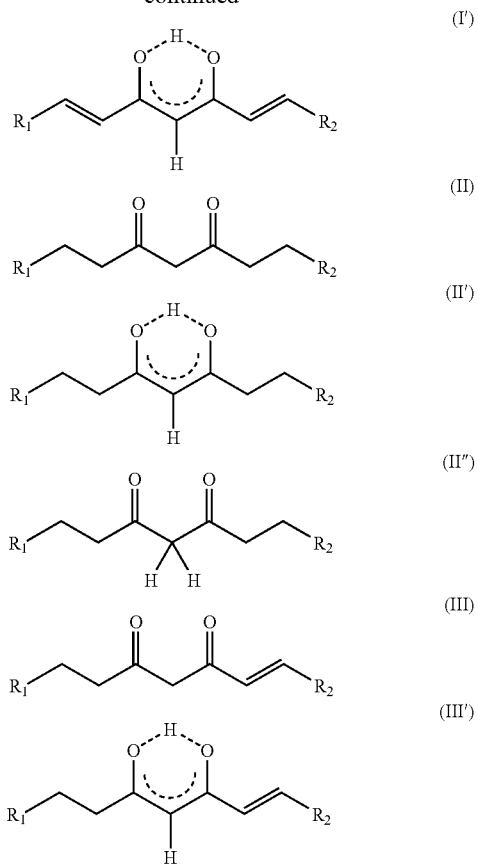

Example 1

Synthesis of (1E,6E)-1-(3-hydroxy-2-methoxyphenyl)-7-(4-hydroxy-3-methoxyphenyl)hepta-1,6-diene-3,5-dione (CU001)

6-(4-Hydroxy-3-methoxyphenyl)hex-5-ene-2,4-dione (20 mg, 85 µmol) and boron trioxide (11 mg, 0.16 mmol) was placed in a 20 mL reaction vessel, and dissolved in 0.4 mL of ethyl acetate. To the stirring mixture at 80° C. was added a solution of 3-hydroxy-2-methoxybenzaldehyde (16 mg, 0.11 mmol) and tri-n-butyl borate (25 µL, 93 µmol) in 0.7 mL of ethyl acetate. After the reaction mixture was stirred for 2 h at the same temperature, n-butylamine (10 µL, 0.10 mmol) was added with additional stirring for 1 h. The reaction mixture was treated with a 1:1 solution of 1N HCl and brine, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound (10.2 mg, 32%) as a solid.

$^1$H NMR (δ, acetone-d$_6$): 3.83 (s, 3H), 3.92 (s, 3H), 6.04 (s, 1H), 6.75 (d, J=16 Hz, 1H), 6.84 (d, J=16 Hz, 1H), 6.88 (d, J=8.2 Hz, 1H), 6.96 (dd, J=~2, 8 Hz, 1H), 7.01 (dd, J=7.7, 8.2 Hz, 1H), 7.19 (dd, J=~2, 8.2 Hz, 1H), 7.22 (dd, J=~2, 8 Hz, 1H), 7.35 (d, J=~2 Hz, 1H), 7.64 (d, J=16 Hz, 1H), 7.90 (d, J=16 Hz, 1H), 8.2 (br s, OH), 8.3 (br s, OH).

Melting Point 152-155° C., MS (ESI+) m/z 369 (M+1), 391 (M+Na).

Example 2

Synthesis of (1E,6E)-N-{4-[7-(4-hydroxy-3-methoxyphenyl)-3,5-dioxohepta-1,6-dienyl]phenyl}acetamide (CU003)

The title compound was synthesized using the same procedure employed for Example 1, but with 4-acetamidobenzaldehyde (18 mg, 0.11 mmol) instead of 3-hydroxy-2-methoxybenzaldehyde (16 mg, 0.11 mmol). The product was obtained as a solid (6.6 mg, 20%) having the following characteristics.

$^1$H NMR (δ, acetone-$d_6$): 2.05 (s, 3H), 3.88 (s, 3H), 5.96 (s, 1H), 6.68 (d, J=16 Hz, 1H), 6.70 (d, J=16 Hz, 1H), 6.84 (d, J=8.2 Hz, 1H), 7.14 (dd, J=1.9, 8.2 Hz, 1H), 7.30 (d, J=1.9 Hz, 1H), 7.56 (d, J=16 Hz, 1H), 7.56 (d, J=16 Hz, 1H), 7.58 (d, J=8.7 Hz, 2H), 7.68 (d, J=8.7 Hz, 2H), 8.1 (brs, 1H, OH), 9.3 (brs, 1H).

Melting Point 193-195° C., MS (ESI+) m/z 380 (M+1), 402 (M+Na).

Example 3

Synthesis of (1E,6E)-1-(4-hydroxy-3-methoxyphenyl)-7-(4-phenoxyphenyl)hepta-1,6-diene-3,5-dione (CU004)

The title compound was synthesized using the same procedure employed for Example 1, but with 4-phenoxybenzaldehyde (22 mg, 0.11 mmol) instead of 3-hydroxy-2-methoxybenzaldehyde (16 mg, 0.11 mmol). The product was obtained as a solid (10.8 mg, 31%) having the following characteristics.

$^1$H NMR (δ, acetone-$d_6$): 3.92 (s, 3H), 6.05 (s, 1H), 6.74 (d, J=16 Hz, 1H), 6.85 (d, J=16 Hz, 1H), 6.89 (d, J=8.2 Hz, 1H), 7.01~7.08 (m, 3H), 7.14~7.2 (m, 1H), 7.19 (dd, J=1.9, 8.2 Hz, 1H), 7.35 (d, J=1.9 Hz, 1H), 7.35 (m, 1H), 7.4~7.47 (m, 4H), 7.62 (d, J=16 Hz, 1H), 7.64 (d, J=16 Hz, 1H), 8.2 (brs, 1H, OH).

Melting Point 45-46° C., MS (ESI+) m/z 415 (M+1), 437 (M+Na).

Example 4

Synthesis of (1E,6E)-1-(4-hydroxy-3-methoxyphenyl)-7-(4-methanesulfonylphenyl)hepta-1,6-diene-3,5-dione (CU005)

The title compound was synthesized using the same procedure employed for Example 1, but with 4-methanesulfonylbenzaldehyde (20 mg, 0.11 mmol) instead of 3-hydroxy-2-methoxybenzaldehyde (16 mg, 0.11 mmol). The product was obtained as a solid (4.0 mg, 12%) having the following characteristics.

$^1$H NMR (δ, acetone-$d_6$): 3.15 (s, 3H), 3.92 (s, 3H), 6.12 (s, 1H), 6.78 (d, J=16 Hz, 1H), 6.89 (d, J=8.2 Hz, 1H), 7.04 (d, J=16 Hz, 1H), 7.22 (dd, J=1.9, 8.2 Hz, 1H), 7.37 (d, J=1.9 Hz, 1H), 7.67 (d, J=16 Hz, 1H), 7.70 (d, J=16 Hz, 1H), 7.95 (d, J=8.2 Hz, 2H), 7.99 (d, J=8.2 Hz, 2H), 8.2 (brs, 1H, OH).

Melting Point 117-120° C., MS (ESI+) m/z 401 (M+1).

Example 5

Synthesis of (1E,6E)-1-(4-hydroxy-3-methoxyphenyl)-7-(3,4,5-trimethoxyphenyl)hepta-1,6-diene-3,5-dione (CU006)

The title compound was synthesized using the same procedure employed for Example 1, but with 3,4,5-trimethoxybenzaldehyde (22 mg, 0.11 mmol) instead of 3-hydroxy-2-methoxybenzaldehyde (16 mg, 0.11 mmol). The product was obtained as a solid (4.8 mg, 15%) having the following characteristics.

$^1$H NMR (δ, acetone-$d_6$): 3.77 (s, 3H), 3.89 (s, 6H), 3.92 (s, 3H), 6.01 (s, 1H), 6.72 (d, J=16 Hz, 1H), 6.81 (d, J=16 Hz, 1H), 6.89 (d, J=8.2 Hz, 1H), 7.03 (s, 2H), 7.19 (dd, J=1.9, 8.2 Hz, 1H), 7.34 (d, J=1.9 Hz, 1H), 7.59 (d, J=16 Hz, 1H), 7.62 (d, J=16 Hz, 1H), 8.2 (brs, 1H, OH).

Melting Point 80-83° C., MS (ESI+) m/z 413 (M+1), 435 (M+Na).

Example 6

Synthesis of (1E,6E)-1-(3-chloro-4-hydroxyphenyl)-7-(4-hydroxy-3-methoxyphenyl)hepta-1,6-diene-3,5-dione (CU007)

The title compound was synthesized using the same procedure employed for Example 1, but with 3-chloro-4-hydroxybenzaldehyde (17 mg, 0.11 mmol) instead of 3-hydroxy-2-methoxybenzaldehyde (16 mg, 0.11 mmol). The product was obtained as a solid (15.0 mg, 46%) having the following characteristics.

$^1$H NMR (δ, acetone-$d_6$): 3.92 (s, 3H), 6.00 (s, 1H), 6.73 (d, J=16 Hz, 1H), 6.75 (d, J=16 Hz, 1H), 6.88 (d, J=8.2 Hz, 1H), 7.07 (d, J=8.2 Hz, 1H), 7.19 (dd, J=1.9, 8.2 Hz, 1H), 7.35 (d, J=1.9 Hz, 1H), 7.52 (dd, J=1.9, 8.2 Hz, 1H), 7.56 (d, J=16 Hz, 1H), 7.62 (d, J=16 Hz, 1H), 7.73 (d, J=1.9 Hz, 1H).

Melting Point 90-95° C., MS (ESI+) m/z 373 (M+1), 395 (M+Na).

Example 7

Synthesis of (1E,6E)-1-(4-hydroxy-3-methyoxyphenyl)-7-(6-methoxynaphthalen-2-yl)hepta-1,6-diene-3,5-dione (CU008)

The title compound was synthesized using the same procedure employed for Example 1, but with 6-methoxy-2-naphthaldehyde (20 mg, 0.11 mmol) instead of 3-hydroxy-2-methoxybenzaldehyde (16 mg, 0.11 mmol). The product was obtained as a solid (7.6 mg, 22%) having the following characteristics.

$^1$H NMR (δ, acetone-$d_6$): 3.93 (s, 3H), 3.94 (s, 3H), 6.06 (s, 1H), 6.75 (d, J=16 Hz, 1H), 6.89 (d, J=8.2 Hz, 1H), 6.92 (d, J=16 Hz, 1H), 7.18~7.22 (m, 2H), 7.34 (dd, J=1.9 Hz, 1H), 7.36 (dd, J=2.4 Hz, 1H), 7.64 (d, J=16 Hz, 1H), 7.80 (d, J=16 Hz, 1H), 7.82~7.9 (m, 3H), 8.08 (s, 1H), 8.2 (brs, 1H, OH).

Melting Point 182-185° C., MS (ESI+) m/z 403 (M+1), 425 (M+Na).

Example 8

Synthesis of (1E,6E)-1-(benzo[1,3]dioxol-5-yl)-7-(4-hydroxy-3-methoxyphenyl)hepta-1,6-diene-3,5-dione (CU009)

The title compound was synthesized using the same procedure employed for Example 1, but with piperonal (16 mg, 0.11 mmol) instead of 3-hydroxy-2-methoxybenzaldehyde (16 mg, 0.11 mmol). The product was obtained as a solid (10.8 mg, 35%) having the following characteristics.

$^1$H NMR (δ, acetone-$d_6$): 3.92 (s, 3H), 5.98 (s, 1H), 6.08 (s, 2H), 6.71 (d, J=16 Hz, 1H), 6.72 (d, J=16 Hz, 1H), 6.88 (d, J=8.2 Hz, 1H), 6.91 (d, J=8.2 Hz, 1H), 7.18 (d, J=8.2 Hz, 1H), 7.18 (d, J=8.2 Hz, 1H), 7.26 (s, 1H), 7.34 (s, 1H), 7.58 (d, J=16 Hz, 1H), 7.61 (d, J=16 Hz, 1H).

Melting Point 149-152° C., MS (ESI+) m/z 367 (M+1), 389 (M+Na).

Example 9

Synthesis of (1E,6E)-1-(4-dimethylaminophenyl)-7-(4-hydroxy-3-methoxyphenyl)hepta-1,6-diene-3,5-dione (CU010)

The title compound was synthesized using the same procedure employed for Example 1, but with 4-dimethylaminobenzaldehyde (16 mg, 0.11 mmol) instead of 3-hydroxy-2-methoxybenzaldehyde (16 mg, 0.11 mmol). The product was obtained as a solid (4.2 mg, 14%) having the following characteristics.

$^1$H NMR (δ, acetone-$d_6$): 3.04 (s, 6H), 3.92 (s, 3H), 5.92 (s, 1H), 6.57 (d, J=16 Hz, 1H), 6.69 (d, J=16 Hz, 1H), 6.76 (d, J=8.2 Hz, 2H), 6.87 (d, J=7.7 Hz, 1H), 7.17 (d, J=~2, 7.7 Hz, 1H), 7.33 (d, J=~2 Hz, 1H), 7.53 (d, J=8.2 Hz, 2H), 7.56 (d, J=16 Hz, 1H), 7.60 (d, J=16 Hz, 1H), 8.1 (brs, 1H, OH).

Melting Point 83-87° C., MS (ESI+) m/z 366 (M+1), 388 (M+Na).

Example 10

Synthesis of (1E,6E)-1-(4-hydroxy-3-methoxyphenyl)-7-(3-phenoxyphenyl)hepta-1,6-diene-3,5-dione (CU011)

The title compound was synthesized using the same procedure employed for Example 1, but with 3-phenoxybenzaldehyde (22 mg, 0.11 mmol) instead of 3-hydroxy-2-methoxybenzaldehyde (16 mg, 0.11 mmol). The product was obtained as a solid (7.8 mg, 22%) having the following characteristics.

$^1$H NMR (δ, acetone-$d_6$): 3.92 (s, 3H), 6.02 (s, 1H), 6.73 (d, J=16 Hz, 1H), 6.78 (d, J=16 Hz, 1H), 6.89 (d, J=8.2 Hz, 1H), 7.0~7.1 (m, 3H), 7.1~7.25 (m, 1H), 7.19 (dd, J=1.9, 8.2 Hz, 1H), 7.35 (m, 2H), 7.4~7.47 (m, 3H), 7.62 (d, J=16 Hz, 1H), 7.6~7.68 (m, 1H), 7.71 (d, J=8.7 Hz, 1H), 8.2 (brs, 1H, OH).

MS (ESI+) m/z 415 (M+1), 437 (M+Na).

Example 11

Synthesis of (1E,6E)-1-(4-hydroxy-3-methoxyphenyl)-7-(4-methylthiophenyl)hepta-1,6-diene-3,5-dione (CU012)

The title compound was synthesized using the same procedure employed for Example 1, but with 4-methylthiobenzaldehyde (16 mg, 0.11 mmol) instead of 3-hydroxy-2-methoxybenzaldehyde (16 mg, 0.11 mmol). The product was obtained as a solid (5.6 mg, 18%) having the following characteristics.

$^1$H NMR (δ, acetone-$d_6$): 2.54 (s, 3H), 3.92 (s, 3H), 6.02 (s, 1H), 6.74 (d, J=16 Hz, 1H), 6.81 (d, J=16 Hz, 1H), 6.89 (d, J=8.2 Hz, 1H), 7.19 (dd, J=1.9, 8.2 Hz, 1H), 7.31 (d, J=8.2 Hz, 2H), 7.35 (d, J=1.9 Hz, 1H), 7.62 (d, J=16 Hz, 1H), 7.63 (d, J=16 Hz, 1H), 7.63 (d, J=8.2 Hz, 2H), 8.2 (brs, 1H, OH).

Melting Point 147-149° C., MS (ESI+) m/z 369 (M+1), 391 (M+Na).

Example 12

Synthesis of (5E)-6-(4-hydroxy-3-methoxyphenyl)-3-(pyridin-4-ylmethylene)hex-5-ene-2,4-dione (CU014)

The title compound was synthesized using the same procedure employed for Example 1, but with pyridine-4-carboxaldehyde (12 mg, 0.11 mmol) instead of 3-hydroxy-2-methoxybenzaldehyde (16 mg, 0.11 mmol). The product was obtained as a solid (16.2 mg, 59%) having the following characteristics.

$^1$H NMR (δ, acetone-$d_6$): 2.46 (s, 3H), 3.87 (s, 3H), 6.78 (d, J=16 Hz, 1H), 6.83 (d, J=8.2 Hz, 1H), 7.08 (dd, J=1.9, 8.2 Hz, 1H), 7.29 (d, J=1.9 Hz, 1H), 7.40 (dd, J=1.5, 4.4 Hz, 2H), 7.46 (d, J=16 Hz, 1H), 7.76 (s, 1H), 8.3 (s, 1H, OH), 8.57 (dd, J=1.5, 4.4 Hz, 2H).

Melting Point 92-95° C., MS (ESI+) m/z 324 (M+1).

Example 13

Synthesis of (1E,6E)-1-(furan-2-yl)-7-(4-hydroxy-3-methoxyphenyl)hepta-1,6-diene-3,5-dione (CU015)

The title compound was synthesized using the same procedure employed for Example 1, but with furfural (11 mg, 0.11 mmol) instead of 3-hydroxy-2-methoxybenzaldehyde (16 mg, 0.11 mmol). The product was obtained as a solid (17.0 mg, 64%) having the following characteristics.

$^1$H NMR (δ, acetone-$d_6$): 3.92 (s, 3H), 6.02 (s, 1H), 6.57 (d, J=16 Hz, 1H), 6.60 (dd, J=1.9, 3.4 Hz, 1H), 6.73 (d, J=16 Hz, 1H), 6.84 (d, J=3.4 Hz, 1H), 6.89 (d, J=8.2 Hz, 1H), 7.19 (dd, J=1.9, 8.2 Hz, 1H), 7.35 (d, J=1.9 Hz, 1H), 7.44 (d, J=16 Hz, 1H), 7.63 (d, J=16 Hz, 1H), 7.72 (d, J=1.4 Hz, 1H).

Melting Point 48-50° C., MS (ESI+) m/z 313 (M+1), 335 (M+Na).

Example 14

Synthesis of (1E,6E)-1-(4-hydroxy-3-methoxyphenyl)-7-(thiophen-2-yl)hepta-1,6-diene-3,5-dione (CU016)

The title compound was synthesized using the same procedure employed for Example 1, but with 2-thiophenecarboxaldehyde (12 mg, 0.11 mmol) instead of 3-hydroxy-2-methoxybenzaldehyde (16 mg, 0.11 mmol). The product was obtained as a solid (9.2 mg, 33%) having the following characteristics.

$^1$H NMR (δ, acetone-$d_6$): 3.92 (s, 3H), 6.02 (s, 1H), 6.56 (d, J=16 Hz, 1H), 6.72 (d, J=16 Hz, 1H), 6.89 (d, J=8.2 Hz, 1H), 7.15 (dd, J=3.4, 5.4 Hz, 1H), 7.19 (dd, J=1.9, 8.2 Hz, 1H), 7.35 (d, J=1.9 Hz, 1H), 7.46 (d, J=3.4 Hz, 1H), 7.62 (d, J=5.4 Hz, 1H), 7.63 (d, J=16 Hz, 1H), 7.80 (d, J=16 Hz, 1H).

Melting Point 52-54° C., MS (ESI+) m/z 329 (M+1), 351 (M+Na).

Example 15

Synthesis of (1E,6E)-1-(9-ethyl-9H-carbazol-3-yl)-7-(4-hydroxy-3-methoxyphenyl)hepta-1,6-diene-3,5-dione (CU017)

The title compound was synthesized using the same procedure employed for Example 1, but with 9-ethyl-9H-carbazole-3-carboxaldehyde (24 mg, 0.11 mmol) instead of 3-hydroxy-2-methoxybenzaldehyde (16 mg, 0.11 mmol). The product was obtained as a solid (2.8 mg, 8%) having the following characteristics.

$^1$H NMR (δ, acetone-$d_6$): 1.42 (t, J=7 Hz, 3H), 3.93 (s, 3H), 4.52 (q, J=7 Hz, 2H), 6.04 (s, 1H), 6.74 (d, J=16 Hz, 1H), 6.89 (d, J=16 Hz, 1H), 6.89 (d, J=8.2 Hz, 1H), 7.20 (dd, J=1.9, 8.2 Hz, 1H), 7.27 (dd, J=7.3, 7.8 Hz, 1H), 7.35 (d, J=1.9 Hz, 1H), 7.50 (ddd, J=1, 7.3, 8.3 Hz, 1H), 7.61 (d, J=8.3 Hz, 1H), 7.62 (d, J=16 Hz, 1H), 7.64 (d, J=8.7 Hz, 1H), 7.84 (dd, J=1, 8.7 Hz, 1H), 7.89 (d, J=16 Hz, 1H), 8.22 (d, J=7.8 Hz, 1H), 8.51 (s, 1H).

Melting Point 165-169° C., MS (ESI+) m/z 440 (M+1), 462 (M+Na).

Example 16

Synthesis of (1E,6E)-1-(4-dimethylaminonaphthalen-1-yl)-7-(4-hydroxy-3-methoxyphenyl)hepta-1,6-diene-3,5-dione (CU019)

The title compound was synthesized using the same procedure employed for Example 1, but with 4-dimethylamino-1-naphthaldehyde (22 mg, 0.11 mmol) instead of 3-hydroxy-2-methoxybenzaldehyde (16 mg, 0.11 mmol). The product was obtained as a solid (24.6 mg, 70%) having the following characteristics.

$^1$H NMR (δ, acetone-$d_6$): 2.93 (s, 6H), 3.92 (s, 3H), 6.09 (s, 1H), 6.75 (d, J=16 Hz, 1H), 6.83 (d, J=16 Hz, 1H), 6.89 (d, J=8.2 Hz, 1H), 7.16 (d, J=8.2 Hz, 1H), 7.20 (dd, J=1.9, 8.2 Hz, 1H), 7.36 (d, J=1.9 Hz, 1H), 7.5~7.66 (m, 2H), 7.64 (d, J=16 Hz, 1H), 7.92 (d, J=8.2 Hz, 1H), 8.1 (br s, 1H, OH), 8.26~7.3 (m, 2H), 8.47 (d, J=16 Hz, 1H).

MS (ESI+) m/z 416 (M+1), 438 (M+Na).

Example 17

Synthesis of (1E,6E)-1-(4-chlorophenyl)-7-(4-hydroxy-3-methoxyphenyl)hepta-1,6-diene-3,5-dione (CU020)

The title compound was synthesized using the same procedure employed for Example 1, but with 4-chlorobenzaldehyde (15 mg, 0.11 mmol) instead of 3-hydroxy-2-methoxybenzaldehyde (16 mg, 0.11 mmol). The product was obtained as a solid (8.4 mg, 28%) having the following characteristics.

$^1$H NMR (δ, acetone-$d_6$): 3.91 (s, 3H), 6.04 (s, 1H), 6.74 (d, J=16 Hz, 1H), 6.86 (d, J=16 Hz, 1H), 6.88 (d, J=8.2 Hz, 1H), 7.19 (dd, J=2, 8.2 Hz, 1H), 7.35 (d, J=2 Hz, 1H), 7.46 (d, J=8.2 Hz, 2H), 7.61 (d, J=16 Hz, 1H), 7.63 (d, J=16 Hz, 1H), 7.70 (d, J=8.2 Hz, 2H), 8.2 (br s, 1H, OH).

Melting Point 59-61° C., MS (ESI+) m/z 357 (M+1), 379 (M+Na).

Example 18

Synthesis of (1E,6E)-1-(3,5-dichloro-2-hydroxyphenyl)-7-(4-hydroxy-3-methoxyphenyl)hepta-1,6-diene-3,5-dione (CU021) and (5E)-(3,5-dichloro-2-hydroxybenzylidene)-6-(4-hydroxy-3-methoxylphenyl)hex-5-ene-2,4-dione The title compounds were synthesized using the same procedure employed for Example 1, but with 3,5-dichlorosalicylaldehyde (20 mg, 0.11 mmol) instead of 3-hydroxy-2-methoxybenzaldehyde (16 mg, 0.11 mmol). (1E,6E)-1-(3,5-dichloro-2-hydroxyphenyl)-7-(4-hydroxy-3-methoxyphenyl)hepta-1,6-diene-3,5-dione (5.6 mg, 16%) and (5E)-(3,5-dichloro-2-hydroxybenzylidene)-6-(4-hydroxy-3-methoxyl phenyl)hex-5-ene-2,4-dione (4.6 mg, 13%) were obtained, respectively, as solids having the following characteristics.

(1E,6E)-1-(3,5-dichloro-2-hydroxyphenyl)-7-(4-hydroxy-3-methoxyphenyl)hepta-1,6-diene-3,5-dione (CU021)

$^1$H NMR (δ, acetone-$d_6$): 3.92 (s, 3H), 6.05 (s, 1H), 6.76 (d, J=16 Hz, 1H), 6.89 (d, J=8.2 Hz, 1H), 6.99 (d, J=16 Hz, 1H), 7.20 (dd, J=~2, 8.2 Hz, 1H), 7.36 (d, J=~2 Hz, 1H), 7.47 (d, J=2.4 Hz, 1H), 7.65 (d, J=16 Hz, 1H), 7.67 (d, J=2.4 Hz, 1H), 7.91 (d, J=16 Hz, 1H), 8.2 (br s, OH).

Melting Point 185-188° C., MS (ESI+) m/z 407 (M+1), 429 (M+Na).

(5E)-(3,5-dichloro-2-hydroxybenzylidene)-6-(4-hydroxy-3-methoxyl phenyl)hex-5-ene-2,4-dione $^1$H NMR (δ, acetone-$d_6$): 1.97 (s, 3H), 3.91 (s, 3H), 6.40 (br s, 1H), 6.90 (d, J=8.2 Hz, 1H), 7.25 (dd, J=1.9, 8.2 Hz, 1H), 7.36 (d, J=16 Hz, 1H), 7.40 (d, J=1.9 Hz, 1H), 7.42 (d, J=2.4 Hz, 1H), 7.47 (d, J=2.4 Hz, 1H), 7.57 (s, 1H), 7.65 (d, J=16 Hz, 1H), 8.2 (br s, OH).

MS (ESI+) m/z 407 (M+1).

Example 19

Synthesis of (1E,6E)-1-(4-hydroxy-3-methoxyphenyl)-7-(1H-pyrrol-2-yl)hepta-1,6-diene-3,5-dione (CU022)

The title compound was synthesized using the same procedure employed for Example 1, but with pyrrole-2-carboxaldehyde (10 mg, 0.11 mmol) instead of 3-hydroxy-2-methoxybenzaldehyde (16 mg, 0.11 mmol). The product was obtained as a solid (9.8 mg, 37%) having the following characteristics.

$^1$H NMR (δ, acetone-$d_6$): 3.91 (s, 3H), 5.84 (s, 1H), 6.24 (m, 1H), 6.45 (d, J=16 Hz, 1H), 6.62 (m, 1H), 6.67 (d, J=16 Hz, 1H), 6.87 (d, J=8.2 Hz, 1H), 7.05 (m, 1H), 7.16 (dd, J=2, 8.2 Hz, 1H), 7.31 (d, J=~2 Hz, 1H), 7.55 (d, J=16 Hz, 1H), 7.57 (d, J=16 Hz, 1H), 8.1 (br s, OH).

Melting Point 83-87° C., MS (ESI+) m/z 312 (M+1), 334 (M+Na).

Example 20

Synthesis of (1E,6E)-1-(4-hydroxy-3-methoxyphenyl)-7-(pyridin-2-yl)hepta-1,6-diene-3,5-dione (CU023) and (5E)-6-(4-hydroxy-3-methoxyl phenyl)-3-(pyridin-2-ylmethylene)hex-5-ene-2,4-dione (CU061)

The title compounds were synthesized using the same procedure employed for Example 1, but with pyridine-2-carboxaldehyde (12 mg, 0.11 mmol) instead of 3-hydroxy-2-methoxybenzaldehyde (16 mg, 0.11 mmol). (1E,6E)-1-(4-hydroxy-3-methoxyphenyl)-7-(pyridin-2-yl)hepta-1,6-diene-3,5-dione (4.0 mg, 15%) and (5E)-6-(4-hydroxy-3-methoxyl phenyl)-3-(pyridin-2-ylmethylene)hex-5-ene-2,4-dione (2.4 mg, 9%) were obtained, respectively, as solids having the following characteristics.

(1E,6E)-1-(4-hydroxy-3-methoxyphenyl)-7-(pyridin-2-yl)hepta-1,6-diene-3,5-dione (CU023)

$^1$H NMR (δ, acetone-$d_6$): 3.92 (s, 3H), 6.14 (s, 1H), 6.78 (d, J=16 Hz, 1H), 6.89 (d, J=8.2 Hz, 1H), 7.20 (dd, J=~2, 8.2 Hz, 1H), 7.25 (d, J=16 Hz, 1H), 7.34~7.4 (m, 1H), 7.37 (d, J=2

Hz, 1H), 7.63 (d, J=16 Hz, 1H), 7.64 (d, J=7.6 Hz, 1H), 7.68 (d, J=16 Hz, 1H), 7.85 (ddd, J=2, 7.6, 7.6 Hz, 1H), 8.2 (br s, OH), 8.65 (d, J=3.8 Hz, 1H).

Melting Point 70-75° C., MS (ESI+) m/z 324 (M+1).

(5E)-6-(4-hydroxy-3-methoxyl phenyl)-3-(pyridin-2-ylmethylene)hex-5-ene-2,4-dione (CU061)

$^1$H NMR (δ, acetone-d$_6$): 2.41 (s, 3H), 3.92 (s, 3H), 6.91 (d, J=8.2 Hz, 1H), 7.29 (dd, J=1.9, 8.2 Hz, 1H), 7.36~7.42 (m, 1H), 7.42 (d, J=1.9 Hz, 1H), 7.46 (d, J=16 Hz, 1H), 7.66 (d, J=16 Hz, 1H), 7.65-7.72 (m, 1H), 7.68 (s, 1H), 7.89 (ddd, J=2, 8, 8 Hz, 1H), 8.3 (br s, OH), 8.62 (d, J=3.8 Hz, 1H).

MS (ESI+) m/z 324 (M+1).

Example 21

Synthesis of (1E,6E)-1-(4-hydroxy-3-methoxyphenyl)-7-(pyridin-3-yl)hepta-1,6-diene-3,5-dione (CU024)

The title compound was synthesized using the same procedure employed for Example 1, but with pyridine-3-carboxaldehyde (12 mg, 0.11 mmol) instead of 3-hydroxy-2-methoxybenzaldehyde (16 mg, 0.11 mmol). The product was obtained as a solid (1.6 mg, 6%) having the following characteristics.

$^1$H NMR (δ, acetone-d$_6$): 3.91 (s, 3H), 6.07 (s, 1H), 6.75 (d, J=16 Hz, 1H), 6.88 (d, J=8.2 Hz, 1H), 6.96 (d, J=16 Hz, 1H), 7.20 (dd, J=1.9, 8.2 Hz, 1H), 7.35 (d, J=16 Hz, 1H), 7.41 (dd, J=4.8, 7.7 Hz, 1H), 7.65 (d, J=16 Hz, 1H), 7.66 (d, J=16 Hz, 1H), 8.08 (ddd, J=~2, ~2, 7.7 Hz, 1H), 8.2 (br s, OH), 8.56 (dd, J=~2, 4.8 Hz, 1H), 8.84 (d, J=~2 Hz, 1H).

Melting Point 176-179° C., MS (ESI+) m/z 324 (M+1).

Example 22

Synthesis of (1E,6E)-1-(3-hydroxy-4-methoxyphenyl)-7-(4-hydroxyphenyl)hepta-1,6-diene-3,5-dione (CU027)

6-(4-Hydroxyphenyl)hex-5-ene-2,4-dione (17.5 mg, 85 μmol) and boron trioxide (11 mg, 0.16 mmol) was placed in a 20 mL reaction vessel, and dissolved in 0.4 mL of ethyl acetate. To the stirring mixture at 80° C. was added a solution of 3-hydroxy-4-methoxybenzaldehyde (16 mg, 0.11 mmol) and tri-n-butyl borate (25 μL, 93 μmol) in 0.7 mL of ethyl acetate. After the reaction mixture was stirred for 2 h at the same temperature, n-butylamine (10 μL, 0.10 mmol) was added with additional stirring for 1 h. The reaction mixture was treated with a 1:1 solution of 1N HCl and brine, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound (24.8 mg, 86%) as a solid.

$^1$H NMR (δ, acetone-d$_6$): 3.89 (s, 3H), 5.99 (s, 1H), 6.67 (d, J=16 Hz, 1H), 6.67 (d, J=16 Hz, 1H), 6.90 (d, J=8.7 Hz, 2H), 6.99 (d, J=8.2 Hz, 1H), 7.14 (dd, J=2.4, 8.2 Hz, 1H), 7.20 (d, J=2.4 Hz, 1H), 7.56 (d, J=16 Hz, 1H), 7.57 (d, J=8.7 Hz, 2H), 7.61 (d, J=16 Hz, 1H), 8.3 (br s, OH).

Melting Point 207-210° C., MS (ESI+) m/z 339 (M+1).

Example 23

Synthesis of (1E,6E)-1-(3,4-dimethoxyphenyl)-7-(4-hydroxyphenyl)hepta-1,6-diene-3,5-dione (CU028)

The title compound was synthesized using the same procedure employed for Example 22, but with 3,4-dimethoxybenzaldehyde (18 mg, 0.11 mmol) instead of 3-hydroxy-4-methoxybenzaldehyde (16 mg, 0.11 mmol). The product was obtained as a solid (6.6 mg, 22%) having the following characteristics.

$^1$H NMR (δ, acetone-d$_6$): 3.85 (s, 3H), 3.87 (s, 3H), 5.98 (s, 1H), 6.66 (d, J=16 Hz, 1H), 6.74 (d, J=16 Hz, 1H), 6.89 (d, J=8.7 Hz, 2H), 6.99 (d, J=8.2 Hz, 1H), 7.23 (dd, J=1.9, 8.2 Hz, 1H), 7.32 (d, J=1.9 Hz, 1H), 7.56 (d, J=8.7 Hz, 2H), 7.60 (d, J=16 Hz, 1H), 7.61 (d, J=16 Hz, 1H), 8.9 (br s, OH).

Melting Point 94-96° C., MS (ESI+) m/z 353 (M+1).

Example 24

Synthesis of (1E,6E)-1-(4-hydroxy-3-methylphenyl)-7-(4-hydroxyphenyl)hepta-1,6-diene-3,5-dione (CU029)

The title compound was synthesized using the same procedure employed for Example 22, but with 4-hydroxy-3-methylbenzaldehyde (15 mg, 0.11 mmol) instead of 3-hydroxy-4-methoxybenzaldehyde (16 mg, 0.11 mmol). The product was obtained as a solid (11.4 mg, 42%) having the following characteristics.

$^1$H NMR (δ, acetone-d$_6$): 2.22 (s, 3H), 5.96 (s, 1H), 6.65 (d, J=16 Hz, 1H), 6.66 (d, J=16 Hz, 1H), 6.87 (d, J=8.2 Hz, 1H), 6.89 (d, J=8.7 Hz, 2H), 7.36 (dd, J=2, 8.2 Hz, 1H), 7.47 (br s, 1H), 7.55 (d, J=8.7 Hz, 2H), 7.56 (d, J=16 Hz, 1H), 7.58 (d, J=16 Hz, 1H), 8.8 (br s, OH).

Melting Point 197-199° C., MS (ESI+) m/z 323 (M+1).

Example 25

Synthesis of (1E,6E)-1-(3-fluoro-4-hydroxyphenyl)-7-(4-hydroxyphenyl)hepta-1,6-diene-3,5-dione (CU030)

The title compound was synthesized using the same procedure employed for Example 22, but with 3-fluoro-4-hydroxybenzaldehyde (15 mg, 0.11 mmol) instead of 3-hydroxy-4-methoxybenzaldehyde (16 mg, 0.11 mmol). The product was obtained as a solid (12.6 mg, 45%) having the following characteristics.

$^1$H NMR (δ, acetone-d$_6$): 5.99 (s, 1H), 6.68 (d, J=16 Hz, 1H), 6.73 (d, J=16 Hz, 1H), 6.90 (d, J=8.7 Hz, 2H), 7.04 (dd, J=8.7, 8.7 Hz, 1H), 7.51 (dd, J=~2, 12.6 Hz, 1H), 7.5~7.55 (m, 1H), 7.56 (d, J=16 Hz, 1H), 7.57 (d, J=8.7 Hz, 2H), 7.62 (d, J=16 Hz, 1H), 9.0 (br s, OH).

Melting Point 190-192° C., MS (ESI+) m/z 327 (M+1).

Example 26

Synthesis of (1E,6E)-1-(4-hydroxy-3-methoxyphenyl)-7-(4-hydroxy-3-methylphenyl)hepta-1,6-diene-3,5-dione (CU031)

The title compound was synthesized using the same procedure employed for Example 1, but with 4-hydroxy-3-methylbenzaldehyde (15 mg, 0.11 mmol) instead of 3-hydroxy-2-methoxybenzaldehyde (16 mg, 0.11 mmol). The product was obtained as a solid (19.0 mg, 63%) having the following characteristics.

$^1$H NMR (δ, acetone-d$_6$): 2.23 (s, 3H), 3.91 (s, 3H), 5.96 (s, 1H), 6.64 (d, J=16 Hz, 1H), 6.70 (d, J=16 Hz, 1H), 6.88 (d, J=8.2 Hz, 1H), 6.88 (d, J=8.2 Hz, 1H), 7.17 (dd, J=1.9, 8.2 Hz, 1H), 7.33 (d, J=1.9 Hz, 1H), 7.37 (dd, J=~2, 8.2 Hz, 1H), 7.47 (d, J=~2 Hz, 1H), 7.57 (d, J=16 Hz, 1H), 7.59 (d, J=16 Hz, 1H), 8.1 (br s, OH), 8.8 (br s, OH).

Melting Point 173-175° C., MS (ESI+) m/z 353 (M+1).

Example 27

Synthesis of (1E,6E)-1-(3-fluoro-4-hydroxyphenyl)-7-(4-hydroxy-3-methoxyphenyl)hepta-1,6-diene-3,5-dione (CU032)

The title compound was synthesized using the same procedure employed for Example 1, but with 3-fluoro-4-hydroxybenzaldehyde (15 mg, 0.11 mmol) instead of 3-hydroxy-2-methoxybenzaldehyde (16 mg, 0.11 mmol). The product was obtained as a solid (14.6 mg, 48%) having the following characteristics.

$^1$H NMR (δ, acetone-$d_6$): 3.91 (s, 3H), 5.98 (s, 1H), 6.72 (d, J=16 Hz, 1H), 6.72 (d, J=16 Hz, 1H), 6.88 (d, J=8.2 Hz, 1H), 7.04 (dd, J=8.7, 8.7 Hz, 1H), 7.18 (dd, J=1.9, 8.2 Hz, 1H), 7.34 (d, J=1.9 Hz, 1H), 7.35 (m, 1H), 7.50 (dd, J=1.9, 12.1 Hz, 1H), 7.56 (d, J=16 Hz, 1H), 7.61 (d, J=16 Hz, 1H).

Melting Point 186-189° C., MS (ESI+) m/z 357 (M+1).

Example 28

Synthesis of (1E,6E)-1-(4-dimethylamino-3-methoxyphenyl)-7-(4-hydroxy-3-methoxyphenyl)hepta-1,6-diene-3,5-dione (CU033)

(1) Synthesis of 4-dimethylamino-3-methoxybenzaldehyde

4-Fluoro-3-methoxybenzaldehyde (500 mg, 3.24 mmol) was dissolved in 6.9 mL of DMSO and 2.8 mL of water, and then potassium carbonate (0.45 g, 3.3 mmol) and dimethylamine solution in ethanol (0.88 mL, 5.5 M, 4.8 mmol) were added to the solution at room temperature, successively. After being stirred at 100° C. for 5 h, the reaction mixture was cooled to room temperature. The reaction mixture was diluted with ethyl acetate, and the solution was washed with water, brine, and dried over MgSO$_4$. After filtration, the filtrate was concentrated in vacuo, and the residue was purified by silica gel column chromatography (eluting with hexane/ethyl acetate=4/1 to 2/1) to obtain the title compound as a pale yellow oil (569 mg, 98%).

(2) (1E,6E)-1-(4-dimethylamino-3-methoxyphenyl)-7-(4-hydroxy-3-methoxyphenyl)hepta-1,6-diene-3,5-dione (CU033)

The title compound was synthesized using the same procedure employed for Example 1, but with 4-dimethylamino-3-methoxybenzaldehyde (20 mg, 0.11 mmol) instead of 3-hydroxy-2-methoxybenzaldehyde (16 mg, 0.11 mmol). The product was obtained as a solid (13.2 mg, 39%) having the following characteristics.

$^1$H NMR (δ, acetone-$d_6$): 2.84 (s, 6H), 3.90 (s, 3H), 3.91 (s, 3H), 5.97 (s, 1H), 6.70 (d, J=16 Hz, 1H), 6.70 (d, J=16 Hz, 1H), 6.86 (d, J=8.2 Hz, 1H), 6.88 (d, J=8.2 Hz, 1H), 7.17 (dd, J=1.9, 8.2 Hz, 1H), 7.18 (dd, J=1.9, 8.2 Hz, 1H), 7.26 (d, J=1.9 Hz, 1H), 7.33 (d, J=1.9 Hz, 1H), 7.59 (d, J=16 Hz, 1H), 7.60 (d, J=16 Hz, 1H), 8.2 (br s, OH).

Melting Point 68-75° C., MS (ESI+) m/z 396 (M+1).

Example 29

Synthesis of (1E,6E)-1-(3-fluoro-4-hydroxyphenyl)-7-(3-hydroxy-4-methoxyphenyl)hepta-1,6-diene-3,5-dione (CU035)

6-(3-Hydroxy-4-methoxyphenyl)hex-5-ene-2,4-dione (20 mg, 85 μmol) and boron trioxide (11 mg, 0.16 mmol) was placed in a 20 mL reaction vessel, and dissolved in 0.4 mL of ethyl acetate. To the stirring solution at 80° C. was added a solution of 3-fluoro-4-hydroxybenzaldehyde (15 mg, 0.11 mmol) and tri-n-butyl borate (25 μL, 93 μmol) in 0.7 mL of ethyl acetate. After being stirred for 2 h at the same temperature, n-butylamine (10 μL, 0.10 mmol) was added with additional stirring for 1 h. The reaction mixture was treated with a 1:1 solution (1 mL) of 1N HCl and brine, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound as a solid (14.4 mg, 47%).

$^1$H NMR (δ, acetone-$d_6$): 3.89 (s, 3H), 6.01 (s, 1H), 6.68 (d, J=16 Hz, 1H), 6.74 (d, J=16 Hz, 1H), 6.99 (d, J=8.2 Hz, 1H), 7.04 (dd, J=8.7, 8.7 Hz, 1H), 7.14 (dd, J=1.9, 8.2 Hz, 1H), 7.20 (d, J=1.9 Hz, 1H), 7.37 (m, 1H), 7.51 (dd, J=1.9, 12.5 Hz, 1H), 7.57 (d, J=16 Hz, 1H), 7.57 (d, J=16 Hz, 1H).

Melting Point 173-176° C., MS (ESI+) m/z 357 (M+1).

Example 30

Synthesis of (1E,6E)-1-(4-dimethylamino-3-methoxyphenyl)-7-(3-hydroxy-4-methoxyphenyl)hepta-1,6-diene-3,5-dione (CU036)

The title compound was synthesized using the same procedure employed for Example 29, but with 4-dimethylamino-3-methoxybenzaldehyde (20 mg, 0.11 mmol) instead of 3,4-dimethoxybenzaldehyde (18 mg, 0.11 mmol). The product was obtained as a solid (14.6 mg, 43%) having the following characteristics.

$^1$H NMR (δ, acetone-$d_6$): 2.84 (s, 6H), 3.89 (s, 3H), 3.91 (s, 3H), 5.98 (s, 1H), 6.66 (d, J=16 Hz, 1H), 6.71 (d, J=16 Hz, 1H), 6.86 (d, J=8.2 Hz, 1H), 7.00 (d, J=8.2 Hz, 1H), 7.13 (dd, J=1.9, 8.2 Hz, 1H), 7.18-7.25 (m, 2H), 7.27 (d, J=1.9 Hz, 1H), 7.55 (d, J=16 Hz, 1H), 7.60 (d, J=16 Hz, 1H), 7.8 (br s, OH).

Melting Point 65-70° C., MS (ESI+) m/z 396 (M+1).

Example 31

Synthesis of (1E,6E)-1-(4-hydroxy-3-nitrophenyl)-7-(4-hydroxyphenyl)hepta-1,6-diene-3,5-dione (CU039)

The title compound was synthesized using the same procedure employed for Example 22, but with 4-hydroxy-3-nitrobenzaldehyde (18 mg, 0.11 mmol) instead of 3-hydroxy-4-methoxybenzaldehyde (16 mg, 0.11 mmol). The product was obtained as a solid (4.2 mg, 14%) having the following characteristics.

$^1$H NMR (δ, acetone-$d_6$): 6.06 (s, 1H), 6.69 (d, J=16 Hz, 1H), 6.90 (d, J=16 Hz, 1H), 6.91 (d, J=8.7 Hz, 2H), 7.26 (d, J=8.3 Hz, 1H), 7.58 (d, J=8.7 Hz, 2H), 7.65 (d, J=16 Hz, 1H), 7.66 (d, J=16 Hz, 1H), 8.04 (dd, J=~2, 8.3 Hz, 1H), 8.39 (d, J=~2 Hz, 1H).

Melting Point 240-245° C., MS (ESI+) m/z 354 (M+1).

Example 32

Synthesis of (1E,6E)-1-(4-hydroxy-3-methoxyphenyl)-7-(4-hydroxy-3-nitrophenyl)hepta-1,6-diene-3,5-dione (CU040)

The title compound was synthesized using the same procedure employed for Example 1, but with 4-hydroxy-3-nitrobenzaldehyde (18 mg, 0.11 mmol) instead of 3-hydroxy-2-methoxybenzaldehyde (16 mg, 0.11 mmol). The product was obtained as a solid (4.0 mg, 12%) having the following characteristics.

$^1$H NMR (δ, acetone-$d_6$): 3.92 (s, 3H), 6.06 (s, 1H), 6.74 (d, J=16 Hz, 1H), 6.88 (d, J=8.2 Hz, 1H), 6.90 (d, J=16 Hz, 1H), 7.20 (dd, J=1.9, 8.2 Hz, 1H), 7.26 (d, J=8.7 Hz, 1H), 7.35 (d, J=1.9 Hz, 1H), 7.64 (d, J=16 Hz, 1H), 7.66 (d, J=16 Hz, 1H), 8.04 (d, J=2.4, 8.7 Hz, 1H), 8.40 (d, J=2.4 Hz, 1H).

Melting Point 209-213° C., MS (ESI+) m/z 384 (M+1).

Example 33

Synthesis of (1E,6E)-1-(3-hydroxy-4-methoxyphenyl)-7-(4-hydroxy-3-nitrophenyl)hepta-1,6-diene-3,5-dione (CU041)

The title compound was synthesized using the same procedure employed for Example 29, but with 4-hydroxy-3-nitrobenzaldehyde (18 mg, 0.11 mmol) instead of 3,4-dimethoxybenzaldehyde (18 mg, 0.11 mmol). The product was obtained as a solid (4.4 mg, 14%) having the following characteristics.

$^1$H NMR (δ, acetone-$d_6$): 3.90 (s, 3H), 6.08 (s, 1H), 6.72 (d, J=16 Hz, 1H), 6.89 (d, J=16 Hz, 1H), 7.01 (d, J=8.7 Hz, 1H), 7.15 (dd, J=2.4, 8.2 Hz, 1H), 7.21 (d, J=2.4 Hz, 1H), 7.24 (d, J=8.2 Hz, 1H), 7.60 (d, J=16 Hz, 1H), 7.66 (d, J=16 Hz, 1H), 8.04 (dd, J=1.9, 8.7 Hz, 1H), 8.39 (d, J=1.9 Hz, 1H).

Melting Point 220-224° C., MS (ESI+) m/z 384 (M+1).

Example 34

Synthesis of (1E,6E)-1-(3-chloro-4-hydroxyphenyl)-7-(4-hydroxyphenyl)hepta-1,6-diene-3,5-dione (CU042)

The title compound was synthesized using the same procedure employed for Example 22, but with 3-chloro-4-hydroxybenzaldehyde (17 mg, 0.11 mmol) instead of 3-hydroxy-4-methoxybenzaldehyde (16 mg, 0.11 mmol). The product was obtained as a solid (8.4 mg, 29%) having the following characteristics.

$^1$H NMR (δ, acetone-$d_6$): 6.00 (s, 1H), 6.68 (d, J=16 Hz, 1H), 6.75 (d, J=16 Hz, 1H), 6.91 (d, J=8.7 Hz, 2H), 7.07 (d, J=8.2 Hz, 1H), 7.52 (dd, J=1.9, 8.2 Hz, 1H), 7.53~7.6 (m, 3H), 7.62 (d, J=16 Hz, 1H), 7.73 (d, J=1.9 Hz, 1H).

Melting Point 184-190° C., MS (ESI+) m/z 343 (M+1).

Example 35

Synthesis of (1E,6E)-1-(3-chloro-4-hydroxyphenyl)-7-(3-hydroxy-4-methoxyphenyl)hepta-1,6-diene-3,5-dione (CU044)

The title compound was synthesized using the same procedure employed for Example 29, but with 3-chloro-4-hydroxybenzaldehyde (17 mg, 0.11 mmol) instead of 3,4-dimethoxybenzaldehyde (18 mg, 0.11 mmol). The product was obtained as a solid (8.6 mg, 27%) having the following characteristics.

$^1$H NMR (δ, acetone-$d_6$): 3.89 (s, 3H), 6.02 (s, 1H), 6.68 (d, J=16 Hz, 1H), 6.76 (d, J=16 Hz, 1H), 7.00 (d, J=8.2 Hz, 1H), 7.07 (d, J=8.2 Hz, 1H), 7.14 (dd, J=~2, 8.2 Hz, 1H), 7.20 (d, J=~2 Hz, 1H), 7.53 (dd, J=~2, 8.2 Hz, 1H), 7.56 (d, J=16 Hz, 1H), 7.57 (d, J=16 Hz, 1H), 7.74 (d, J=~2 Hz, 1H).

Melting Point 195-197° C., MS (ESI+) m/z 373 (M+1).

Example 36

Synthesis of (1E,6E)-1-(3,4-dichlorophenyl)-7-(4-hydroxyphenyl)hepta-1,6-diene-3,5-dione (CU045)

The title compound was synthesized using the same procedure employed for Example 22, but with 3,4-dichlorobenzaldehyde (19 mg, 0.11 mmol) instead of 3-hydroxy-4-methoxybenzaldehyde (16 mg, 0.11 mmol). The product was obtained as a solid (1.2 mg, 4%) having the following characteristics.

$^1$H NMR (δ, acetone-$d_6$): 6.07 (s, 1H), 6.71 (d, J=16 Hz, 1H), 6.91 (d, J=8.7 Hz, 2H), 6.96 (d, J=16 Hz, 1H), 7.53 (dd, J=2, 8.3 Hz, 1H), 7.53~7.7 (m, 5H), 7.93 (d, J=~2 Hz, 1H).

Melting Point 83-85° C., MS (ESI+) m/z 361 (M+1).

Example 37

Synthesis of (1E,6E)-1-(3,4-dichlorophenyl)-7-(4-hydroxy-3-methoxyphenyl)hepta-1,6-diene-3,5-dione (CU046)

The title compound was synthesized using the same procedure employed for Example 1, but with 3,4-dichlorobenzaldehyde (19 mg, 0.11 mmol) instead of 3-hydroxy-2-methoxybenzaldehyde (16 mg, 0.11 mmol). The product was obtained as a solid (2.0 mg, 6%) having the following characteristics.

$^1$H NMR (δ, acetone-$d_6$): 3.92 (s, 3H), 6.06 (s, 1H), 6.75 (d, J=16 Hz, 1H), 6.89 (d, J=8.2 Hz, 1H), 6.95 (d, J=16 Hz, 1H), 7.20 (dd, J=~2, 8.2 Hz, 1H), 7.36 (d, J=~2 Hz, 1H), 7.59 (d, J=16 Hz, 1H), 7.6~7.7 (m, 3H), 7.92 (d, J=1.5 Hz, 1H), 8.2 (br s, OH).

Melting Point 70-76° C., MS (ESI+) m/z 391 (M+1), 413 (M+Na).

Example 38

Synthesis of (1E,6E)-1-(4-dimethylamino-3-methoxyphenyl)-7-(4-hydroxyphenyl)hepta-1,6-diene-3,5-dione (CU048)

The title compound was synthesized using the same procedure employed for Example 22, but with 4-dimethylamino-3-methoxybenzaldehyde (20 mg, 0.11 mmol) instead of 3-hydroxy-4-methoxybenzaldehyde (16 mg, 0.11 mmol). The product was obtained as a solid (12.8 mg, 41%) having the following characteristics.

$^1$H NMR (δ, acetone-$d_6$): 2.84 (s, $d_6$), 3.91 (s, 3H), 5.97 (s, 1H), 6.65 (d, J=16 Hz, 1H), 6.70 (d, J=16 Hz, 1H), 6.86 (d, J=8.2 Hz, 1H), 6.90 (d, J=8.7 Hz, 2H), 7.19 (dd, J=~2, 8.2 Hz, 1H), 7.26 (d, J=2 Hz, 1H), 7.56 (d, J=8.7 Hz, 2H), 7.59 (d, J=16 Hz, 1H), 7.59 (d, J=16 Hz, 1H), 8.9 (br s, OH).

Melting Point 84-86° C., MS (ESI+) m/z 366 (M+1).

Example 39

Synthesis of (1E,6E)-1-(3-hydroxy-4-methoxyphenyl)-7-(3-methoxy-4-nitrophenyl)hepta-1,6-diene-3,5-dione (CU049)

(1) Synthesis of 3-methoxy-4-nitrobenzaldehyde

3-Hydroxy-4-nitrobenzaldehyde (500 mg, 2.99 mmol) and potassium carbonate (0.42 g, 3.0 mmol) were dissolved in 6.0 mL of N,N-dimethylormamide. After addition of iodemethane (0.38 mL, 6.0 mmol) at room temperature, the mixture was stirred for 5 h at the same temperature. The reaction mixture was diluted with ethyl acetate and water, and separated. The organic layer was washed with brine twice, and dried over MgSO$_4$. After filtration, the filtrate was concentrated in vacuo, and the residue was purified by silica gel column chromatography (hexane/ethyl acetate=4/1 to 1/1) to obtain the title compound as a pale yellow powder (518 mg, 96%).

(2) Synthesis of (1E,6E)-1-(3-hydroxy-4-methoxyphenyl)-7-(3-methoxy-4-nitrophenyl)hepta-1,6-diene-3,5-dione (CU049)

The title compound was synthesized using the same procedure employed for Example 29, but with 3-methoxy-4-nitrobenzaldehyde (20 mg, 0.11 mmol) instead of 3,4-dimethoxybenzaldehyde (18 mg, 0.11 mmol). The product was obtained as a solid (2.5 mg, 7%) having the following characteristics.

$^1$H NMR (δ, acetone-d$_6$): 3.90 (s, 3H), 4.06 (s, 3H), 6.11 (s, 1H), 6.72 (d, J=16 Hz, 1H), 7.01 (d, J=8.2 Hz, 1H), 7.06 (d, J=16 Hz, 1H), 7.17 (dd, J=~2, 8.2 Hz, 1H), 7.21 (d, J=2 Hz, 1H), 7.45 (dd, J=~2, 8.2 Hz, 1H), 7.63 (d, J=16 Hz, 1H), 7.65 (d, J=16 Hz, 1H), 7.66 (d, J=2 Hz, 1H), 7.89 (d, J=8.2 Hz, 1H).

Melting Point 196-199° C., MS (ESI+) m/z 398 (M+1).

Example 40

Synthesis of (1E,6E)-1-(4-hydroxyphenyl)-7-(3-methoxy-4-nitrophenyl)hepta-1,6-diene-3,5-dione (CU050)

The title compound was synthesized using the same procedure employed for Example 22, but with 3-methoxy-4-nitrobenzaldehyde (20 mg, 0.11 mmol) instead of 3-hydroxy-4-methoxybenzaldehyde (16 mg, 0.11 mmol). The product was obtained as a solid (4.2 mg, 13%) having the following characteristics.

$^1$H NMR (δ, acetone-d$_6$): 4.05 (s, 3H), 6.10 (s, 1H), 6.72 (d, J=16 Hz, 1H), 6.91 (d, J=8.7 Hz, 2H), 7.05 (d, J=16 Hz, 1H), 7.45 (dd, J=~2, 8.2 Hz, 1H), 7.60 (d, J=8.7 Hz, 2H), 7.66 (d, J=16 Hz, 1H), 7.66 (d, J=~2 Hz, 1H), 7.68 (d, J=16 Hz, 1H), 7.89 (d, J=8.2 Hz, 1H), 8.9 (br s, OH).

Melting Point 190-192° C., MS (ESI+) m/z 368 (M+1).

Example 41

Synthesis of (1E,6E)-1-(3-hydroxy-4-methoxyphenyl)-7-(4-hydroxy-3-methylphenyl)hepta-1,6-diene-3,5-dione (CU052)

The title compound was synthesized using the same procedure employed for Example 29, but with 4-hydroxy-3-methylbenzaldehyde (15 mg, 0.11 mmol) instead of 3,4-dimethoxybenzaldehyde (18 mg, 0.11 mmol). The product was obtained as a solid (9.4 mg, 31%) having the following characteristics.

$^1$H NMR (δ, acetone-d$_6$): 2.23 (s, 3H), 3.89 (s, 3H), 5.99 (s, 1H), 6.66 (d, J=16 Hz, 1H), 6.66 (d, J=16 Hz, 1H), 6.88 (d, J=8.2 Hz, 1H), 7.00 (d, J=8.2 Hz, 1H), 7.13 (dd, J=2.4, 8.2 Hz, 1H), 7.20 (d, J=2.4 Hz, 1H), 7.38 (dd, J=~2, 8.7 Hz, 1H), 7.49 (d, J=~2 Hz, 1H), 7.55 (d, J=16 Hz, 1H), 7.58 (d, J=16 Hz, 1H), 7.8 (br s, OH), 8.8 (br s, OH).

Melting Point 215-218° C., MS (ESI+) m/z 353 (M+1), 375 (M+Na).

Example 42

Synthesis of (1E,6E)-1-(3,4-dimethylphenyl)-7-(4-hydroxyphenyl)hepta-1,6-diene-3,5-dione (CU056)

The title compound was synthesized using the same procedure employed for Example 22, but with 3,4-dimethylbenzaldehyde (15 mg, 0.11 mmol) instead of 3-hydroxy-4-methoxybenzaldehyde (16 mg, 0.11 mmol). The product was obtained as a solid (6.8 mg, 25%) having the following characteristics.

$^1$H NMR (δ, acetone-d$_6$): 2.28 (br s, 6H), 6.02 (s, 1H), 6.68 (d, J=16 Hz, 1H), 6.79 (d, J=16 Hz, 1H), 6.90 (d, J=8.7 Hz, 2H), 7.19 (br d, J=7.7 Hz, 1H), 7.40 (br d, J=7.7 Hz, 1H), 7.46 (br s, 1H), 7.58 (d, J=8.7 Hz, 2H), 7.60 (d, J=16 Hz, 1H), 7.63 (d, J=16 Hz, 1H), 8.9 (br s, OH).

Melting Point 150-152° C., MS (ESI+) m/z 321 (M+1), 343 (M+Na).

Example 43

Synthesis of (1E,6E)-1-(3,4-dimethylphenyl)-7-(4-hydroxy-3-methoxyphenyl)hepta-1,6-diene-3,5-dione (CU057)

The title compound was synthesized using the same procedure employed for Example 1, but with 3,4-dimethylbenzaldehyde (15 mg, 0.11 mmol) instead of 3-hydroxy-2-methoxybenzaldehyde (16 mg, 0.11 mmol). The product was obtained as a solid (4.8 mg, 16%) having the following characteristics.

$^1$H NMR (δ, acetone-d$_6$): 2.28 (br s, 6H), 3.92 (s, 3H), 6.02 (s, 1H), 6.72 (d, J=16 Hz, 1H), 6.78 (d, J=16 Hz, 1H), 6.88 (d, J=8.2 Hz, 1H), 7.15~7.25 (m, 2H), 7.35 (d, J=1.9 Hz, 1H), 7.40 (br d, J=7.7 Hz, 1H), 7.46 (br s, 1H), 7.60 (d, J=16 Hz, 1H), 7.62 (d, J=16 Hz, 1H), 8.1 (br s, OH).

Melting Point 132-133° C., MS (ESI+) m/z 351 (M+1), 373 (M+Na).

Example 44

Synthesis of (1E,6E)-1-(3,4-dimethylphenyl)-7-(3-hydroxy-4-methoxyphenyl)hepta-1,6-diene-3,5-dione (CU058)

The title compound was synthesized using the same procedure employed for Example 29, but with 3,4-dimethylbenzaldehyde (15 mg, 0.11 mmol) instead of 3,4-dimethoxybenzaldehyde (18 mg, 0.11 mmol). The product was obtained as a solid (7.2 mg, 24%) having the following characteristics.

$^1$H NMR (δ, acetone-d$_6$): 2.282 (s, 3H), 2.288 (s, 3H), 3.90 (s, 3H), 6.04 (s, 1H), 6.68 (d, J=16 Hz, 1H), 6.80 (d, J=16 Hz, 1H), 7.00 (d, J=8.2 Hz, 1H), 7.13 (dd, J=2.4, 8.2 Hz, 1H), 7.15~7.25 (m, 2H), 7.41 (br d, J=7.7 Hz, 1H), 7.47 (br s, 1H), 7.58 (d, J=16 Hz, 1H), 7.60 (d, J=16 Hz, 1H), 7.8 (br s, OH).

Melting Point 150-154° C., MS (ESI+) m/z 351 (M+1), 373 (M+Na).

Example 45

Synthesis of (1E,6E)-1-(3-hydroxy-4-methoxyphenyl)-7-(3-methoxyphenyl)hepta-1,6-diene-3,5-dione (CU059)

The title compound was synthesized using the same procedure employed for Example 29, but with 3-methoxybenzaldehyde (15 mg, 0.11 mmol) instead of 3,4-dimethoxybenzaldehyde (18 mg, 0.11 mmol). The product was obtained as a solid (6.2 mg, 21%) having the following characteristics.

$^1$H NMR (δ, acetone-d$_6$): 3.85 (s, 3H), 3.90 (s, 3H), 6.06 (s, 1H), 6.70 (d, J=16 Hz, 1H), 6.87 (d, J=16 Hz, 1H), 6.95~7.0 (m, 1H), 7.01 (d, J=8.2 Hz, 1H), 7.16 (dd, J=2.4, 8.2 Hz, 1H), 7.21 (d, J=2.4 Hz, 1H), 7.25~7.3 (m, 2H), 7.34 (dd, J=8.2, 8.2 Hz, 1H), 7.60 (d, J=16 Hz, 1H), 7.62 (d, J=16 Hz, 1H), 7.8 (br s, OH).

MS (ESI+) m/z 353 (M+1), 375 (M+Na).

Example 46

Synthesis of (1E,6E)-1-(3-hydroxy-4-methoxyphenyl)-7-(4-methoxyphenyl)hepta-1,6-diene-3,5-dione (CU065)

The title compound was synthesized using the same procedure employed for Example 29, but with 4-methoxybenzaldehyde (15 mg, 0.11 mmol) instead of 3,4-dimethoxybenzaldehyde (18 mg, 0.11 mmol). The product was obtained as a solid (8.6 mg, 29%) having the following characteristics.

$^1$H NMR (δ, acetone-d$_6$): 3.85 (s, 3H), 3.89 (s, 3H), 6.01 (s, 1H), 6.67 (d, J=16 Hz, 1H), 6.72 (d, J=16 Hz, 1H), 6.95~7.05 (m, 3H), 7.14 (dd, J=1.9, 8.2 Hz, 1H), 7.20 (d, J=1.9 Hz, 1H), 7.57 (d, J=16 Hz, 1H), 7.63 (d, J=16 Hz, 1H), 7.65 (d, J=8.7 Hz, 2H), 7.8 (br s, OH).

Melting Point 137-140° C., MS (ESI+) m/z 353 (M+1).

Example 47

Synthesis of (1E,6E)-1-(4-hydroxyphenyl)-7-(2-methoxyphenyl)hepta-1,6-diene-3,5-dione (CU066)

The title compound was synthesized using the same procedure employed for Example 22, but with 2-methoxybenzaldehyde (15 mg, 0.11 mmol) instead of 3-hydroxy-4-methoxybenzaldehyde (16 mg, 0.11 mmol). The product was obtained as a solid (10.8 mg, 39%) having the following characteristics.

$^1$H NMR (δ, acetone-d$_6$): 3.93 (s, 3H), 6.02 (s, 1H), 6.70 (d, J=16 Hz, 1H), 6.87 (d, J=16 Hz, 1H), 6.90 (d, J=8.7 Hz, 2H), 6.99 (dd, J=7.7, 7.7 Hz, 1H), 7.08 (d, J=8.2 Hz, 1H), 7.35~7.45 (m, 1H), 7.58 (d, J=8.7 Hz, 2H), 7.63 (d, J=16 Hz, 1H), 7.68 (dd, J=~2, 7.7 Hz, 1H), 7.98 (d, J=16 Hz, 1H), 8.9 (br s, OH).

Melting Point 171-178° C., MS (ESI+) m/z 323 (M+1).

Example 48

Synthesis of (1E,6E)-1-(4-hydroxy-3-methoxyphenyl)-7-(2-methoxyphenyl)hepta-1,6-diene-3,5-dione (CU067)

The title compound was synthesized using the same procedure employed for Example 1, but with 2-methoxybenzaldehyde (15 mg, 0.11 mmol) instead of 3-hydroxy-2-methoxybenzaldehyde (16 mg, 0.11 mmol). The product was obtained as a solid (9.4 mg, 31%) having the following characteristics.

$^1$H NMR (δ, acetone-d$_6$): 3.92 (s, 3H), 3.93 (s, 3H), 6.01 (s, 1H), 6.74 (d, J=16 Hz, 1H), 6.86 (d, J=16 Hz, 1H), 6.88 (d, J=8.2 Hz, 1H), 7.00 (dd, J=7.3, 7.7 Hz, 1H), 7.09 (d, J=8.2 Hz, 1H), 7.19 (dd, J=2, 8.2 Hz, 1H), 7.36 (d, J=~2 Hz, 1H), 7.35~7.45 (m, 1H), 7.62 (d, J=16 Hz, 1H), 7.68 (dd, J=~2, 7.7 Hz, 1H), 7.97 (d, J=16 Hz, 1H), 8.2 (br s, OH).

Melting Point 61-66° C., MS (ESI+) m/z 353 (M+1), 375 (M+Na).

Example 49

Synthesis of (1E,6E)-1-(3-hydroxy-4-methoxyphenyl)-7-(2-methoxyphenyl)hepta-1,6-diene-3,5-dione (CU068)

The title compound was synthesized using the same procedure employed for Example 29, but with 2-methoxybenzaldehyde (15 mg, 0.11 mmol) instead of 3,4-dimethoxybenzaldehyde (18 mg, 0.11 mmol). The product was obtained as a solid (11.0 mg, 37%) having the following characteristics.

$^1$H NMR (δ, acetone-d$_6$): 3.89 (s, 3H), 3.93 (s, 3H), 6.03 (s, 1H), 6.70 (d, J=16 Hz, 1H), 6.88 (d, J=16 Hz, 1H), 6.98~7.06 (m, 2H), 7.08 (d, J=8.7 Hz, 1H), 7.15 (dd, J=2, 8.2 Hz, 1H), 7.22 (d, J=~2 Hz, 1H), 7.35~7.45 (m, 1H), 7.59 (d, J=16 Hz, 1H), 7.69 (br d, J=7.7 Hz, 1H), 7.8 (br s, OH), 7.98 (d, J=16 Hz, 1H).

Melting Point 102-108° C., MS (ESI+) m/z 353 (M+1).

Example 50

Synthesis of (1E,6E)-1-(2,3-dimethoxyphenyl)-7-(4-hydroxyphenyl)hepta-1,6-diene-3,5-dione (CU069)

The title compound was synthesized using the same procedure employed for Example 22, but with 2,3-dimethoxybenzaldehyde (18 mg, 0.11 mmol) instead of 3-hydroxy-4-methoxybenzaldehyde (16 mg, 0.11 mmol). The product was obtained as a solid (7.8 mg, 26%) having the following characteristics.

$^1$H NMR (δ, acetone-d$_6$): 3.85 (s, 3H), 3.88 (s, 3H), 6.05 (s, 1H), 6.70 (d, J=16 Hz, 1H), 6.85 (d, J=16 Hz, 1H), 6.91 (d, J=8.7 Hz, 2H), 7.0~7.1 (m, 2H), 7.32 (dd, J=2.9, 6.3 Hz, 1H), 7.58 (d, J=8.7 Hz, 2H), 7.64 (d, J=16 Hz, 1H), 7.95 (d, J=16 Hz, 1H), 8.9 (br s, OH).

Melting Point 70-72° C., MS (ESI+) m/z 353 (M+1), 375 (M+Na).

Example 51

Synthesis of (1E,6E)-1-(2,3-dimethoxyphenyl)-7-(4-hydroxy-3-methoxyphenyl)hepta-1,6-diene-3,5-dione (CU070)

The title compound was synthesized using the same procedure employed for Example 1, but with 2,3-dimethoxybenzaldehyde (18 mg, 0.11 mmol) instead of 3-hydroxy-2-methoxybenzaldehyde (16 mg, 0.11 mmol). The product was obtained as a solid (8.8 mg, 27%) having the following characteristics.

$^1$H NMR (δ, acetone-d$_6$): 3.85 (s, 3H), 3.88 (s, 3H), 3.92 (s, 3H), 6.04 (s, 1H), 6.75 (d, J=16 Hz, 1H), 6.84 (d, J=16 Hz, 1H), 6.88 (d, J=8.2 Hz, 1H), 7.08~7.15 (m, 2H), 7.19 (dd, J=1.9, 8.2 Hz, 1H), 7.31 (dd, J=2.9, 6.3 Hz, 1H), 7.36 (d, J=1.9 Hz, 1H), 7.63 (d, J=16 Hz, 1H), 7.94 (d, J=16 Hz, 1H), 8.2 (br s, OH).

Melting Point 57-65° C., MS (ESI+) m/z 383 (M+1), 405 (M+Na).

Example 52

Synthesis of (1E,6E)-1-(2,3-dimethoxyphenyl)-7-(3-hydroxy-4-methoxyphenyl)hepta-1,6-diene-3,5-dione (CU071)

The title compound was synthesized using the same procedure employed for Example 29, but with 2,3-dimethoxybenzaldehyde (18 mg, 0.11 mmol) instead of 3,4-dimethoxybenzaldehyde (18 mg, 0.11 mmol). The product was obtained as a solid (4.4 mg, 14%) having the following characteristics.

$^1$H NMR (δ, acetone-$d_6$): 3.85 (s, 3H), 3.88 (s, 3H), 3.90 (s, 3H), 6.06 (s, 1H), 6.71 (d, J=16 Hz, 1H), 6.85 (d, J=16 Hz, 1H), 7.01 (d, J=8.2 Hz, 1H), 7.08~7.15 (m, 2H), 7.16 (dd, J=1.9, 8.2 Hz, 1H), 7.21 (d, J=1.9 Hz, 1H), 7.32 (dd, J=2.9, 6.3 Hz, 1H), 7.60 (d, J=16 Hz, 1H), 7.8 (br s, OH), 7.95 (d, J=16 Hz, 1H).

Melting Point 144-148° C., MS (ESI+) m/z 383 (M+1), 405 (M+Na).

Example 53

Synthesis of (1E,6E)-1-(2,4-dimethoxyphenyl)-7-(4-hydroxyphenyl)hepta-1,6-diene-3,5-dione (CU072)

The title compound was synthesized using the same procedure employed for Example 22, but with 2,4-dimethoxybenzaldehyde (18 mg, 0.11 mmol) instead of 3-hydroxy-4-methoxybenzaldehyde (16 mg, 0.11 mmol). The product was obtained as a solid (13.8 mg, 46%) having the following characteristics.

$^1$H NMR (δ, acetone-$d_6$): 3.86 (s, 3H), 3.93 (s, 3H), 5.95 (s, 1H), 6.59 (dd, J=~2, 8.2 Hz, 1H), 6.62 (d, J=~2 Hz, 1H), 6.67 (d, J=16 Hz, 1H), 6.75 (d, J=16 Hz, 1H), 6.90 (d, J=8.7 Hz, 2H), 7.57 (d, J=8.7 Hz, 2H), 7.60 (d, J=16 Hz, 1H), 7.63 (d, J=8.2 Hz, 1H), 7.92 (d, J=16 Hz, 1H), 8.9 (br s, OH).

Melting Point 161-167° C., MS (ESI+) m/z 353 (M+1), 375 (M+Na).

Example 54

Synthesis of (1E,6E)-1-(2,4-dimethoxyphenyl)-7-(4-hydroxy-3-methoxyphenyl)hepta-1,6-diene-3,5-dione (CU073)

The title compound was synthesized using the same procedure employed for Example 1, but with 2,4-dimethoxybenzaldehyde (18 mg, 0.11 mmol) instead of 3-hydroxy-2-methoxybenzaldehyde (16 mg, 0.11 mmol). The product was obtained as a solid (14.4 mg, 44%) having the following characteristics.

$^1$H NMR (δ, acetone-$d_6$): 3.86 (s, 3H), 3.92 (s, 3H), 3.93 (s, 3H), 5.94 (s, 1H), 6.59 (dd, J=1.9, 8.7 Hz, 1H), 6.62 (d, J=1.9 Hz, 1H), 6.71 (d, J=16 Hz, 1H), 6.74 (d, J=16 Hz, 1H), 6.88 (d, J=8.2 Hz, 1H), 7.18 (dd, J=1.9, 8.2 Hz, 1H), 7.34 (d, J=1.9 Hz, 1H), 7.59 (d, J=16 Hz, 1H), 7.62 (d, J=8.7 Hz, 1H), 7.91 (d, J=16 Hz, 1H), 8.2 (br s, OH).

Melting Point 108-113° C., MS (ESI+) m/z 383 (M+1), 405 (M+Na).

Example 55

Synthesis of (1E,6E)-1-(2,4-dimethoxyphenyl)-7-(3-hydroxy-4-methoxyphenyl)hepta-1,6-diene-3,5-dione (CU074)

The Title Compound was Synthesized Using the Same Procedure Employed for Example 29, but with 2,4-dimethoxybenzaldehyde (18 mg, 0.11 mmol) instead of 3,4-dimethoxybenzaldehyde (18 mg, 0.11 mmol). The product was obtained as a solid (9.0 mg, 28%) having the following characteristics.

$^1$H NMR (δ, acetone-$d_6$): 3.86 (s, 3H), 3.89 (s, 3H), 3.93 (s, 3H), 5.97 (s, 1H), 6.59 (dd, J=1.9, 8.7 Hz, 1H), 6.62 (d, J=1.9 Hz, 1H), 6.67 (d, J=16 Hz, 1H), 6.76 (d, J=16 Hz, 1H), 7.00 (d, J=8.2 Hz, 1H), 7.13 (dd, J=2.4, 8.2 Hz, 1H), 7.20 (d, J=2.4 Hz, 1H), 7.55 (d, J=16 Hz, 1H), 7.63 (d, J=8.7 Hz, 1H), 7.8 (br s, OH), 7.92 (d, J=16 Hz, 1H).

Melting Point 64-70° C., MS (ESI+) m/z 383 (M+1), 405 (M+Na).

Example 56

Synthesis of (1E,6E)-1-(2,5-dimethoxyphenyl)-7-(4-hydroxyphenyl)hepta-1,6-diene-3,5-dione (CU075)

The title compound was synthesized using the same procedure employed for Example 22, but with 2,5-dimethoxybenzaldehyde (18 mg, 0.11 mmol) instead of 3-hydroxy-4-methoxybenzaldehyde (16 mg, 0.11 mmol). The product was obtained as a solid (8.0 mg, 27%) having the following characteristics.

$^1$H NMR (δ, acetone-$d_6$): 3.80 (s, 3H), 3.88 (s, 3H), 6.01 (s, 1H), 6.69 (d, J=16 Hz, 1H), 6.88 (d, J=16 Hz, 1H), 6.90 (d, J=8.7 Hz, 2H), 6.97 (dd, J=2.9, 9.2 Hz, 1H), 7.02 (d, J=9.2 Hz, 1H), 7.26 (d, J=2.9 Hz, 1H), 7.58 (d, J=8.7 Hz, 2H), 7.63 (d, J=16 Hz, 1H), 7.95 (d, J=16 Hz, 1H), 8.9 (br s, OH).

Melting Point 70-74° C., MS (ESI+) m/z 353 (M+1), 375 (M+Na).

Example 57

Synthesis of (1E,6E)-1-(2,5-dimethoxyphenyl)-7-(4-hydroxy-3-methoxyphenyl)hepta-1,6-diene-3,5-dione (CU076)

The title compound was synthesized using the same procedure employed for Example 1, but with 2,5-dimethoxybenzaldehyde (18 mg, 0.11 mmol) instead of 3-hydroxy-2-methoxybenzaldehyde (16 mg, 0.11 mmol). The product was obtained as a solid (5.8 mg, 18%) having the following characteristics.

$^1$H NMR (δ, acetone-$d_6$): 3.80 (s, 3H), 3.88 (s, 3H), 3.92 (s, 3H), 6.01 (s, 1H), 6.74 (d, J=16 Hz, 1H), 6.88 (d, J=16 Hz, 1H), 6.88 (d, J=8.2 Hz, 1H), 6.98 (dd, J=2.9, 9.2 Hz, 1H), 7.02 (d, J=9.2 Hz, 1H), 7.19 (dd, J=1.9, 8.2 Hz, 1H), 7.25 (d, J=2.9 Hz, 1H), 7.35 (d, J=1.9 Hz, 1H), 7.62 (d, J=16 Hz, 1H), 7.95 (d, J=16 Hz, 1H), 8.2 (br s, OH).

Melting Point 127-129° C., MS (ESI+) m/z 383 (M+1), 405 (M+Na).

Example 58

Synthesis of (1E,6E)-1-(2,5-dimethoxyphenyl)-7-(3-hydroxy-4-methoxyphenyl)hepta-1,6-diene-3,5-dione (CU077)

The title compound was synthesized using the same procedure employed for Example 29, but with 2,5-dimethoxybenzaldehyde (18 mg, 0.11 mmol) instead of 3,4-dimethoxybenzaldehyde (18 mg, 0.11 mmol). The product was obtained as a solid (11.2 mg, 34%) having the following characteristics.

$^1$H NMR (δ, acetone-$d_6$): 3.80 (s, 3H), 3.88 (s, 3H), 3.90 (s, 3H), 6.03 (s, 1H), 6.70 (d, J=16 Hz, 1H), 6.89 (d, J=16 Hz, 1H), 6.98 (dd, J=2.9, 9.2 Hz, 1H), 6.99 (d, J=8.2 Hz, 1H), 7.02 (d, J=9.2 Hz, 1H), 7.15 (dd, J=1.9, 8.2 Hz, 1H), 7.21 (d, J=1.9 Hz, 1H), 7.26 (d, J=2.9 Hz, 1H), 7.59 (d, J=16 Hz, 1H), 7.8 (br s, OH), 7.96 (d, J=16 Hz, 1H).

Melting Point 63-68° C., MS (ESI+) m/z 383 (M+1), 405 (M+Na).

Example 59

Synthesis of (1E,6E)-1-(3-hydroxyphenyl)-7-(4-hydroxyphenyl)hepta-1,6-diene-3,5-dione (CU078)

The title compound was synthesized using the same procedure employed for Example 22, but with 3-hydroxybenzaldehyde (13 mg, 0.11 mmol) instead of 3-hydroxy-4-methoxybenzaldehyde (16 mg, 0.11 mmol). The product was obtained as a solid (6.8 mg, 22%) having the following characteristics.

$^1$H NMR (δ, acetone-$d_6$): 6.04 (s, 1H), 6.68 (d, J=16 Hz, 1H), 6.78 (d, J=16 Hz, 1H), 6.88~6.98 (m, 3H), 7.13 (d, J=~2 Hz, 1H), 7.16 (br d, J=7.7 Hz, 1H), 7.26 (dd, J=7.7, 7.7 Hz, 1H), 7.57 (d, J=16 Hz, 1H), 7.58 (d, J=8.7 Hz, 2H), 7.64 (d, J=16 Hz, 1H), 8.5-9 (br s, OH).

Melting Point 217° C., MS (ESI+) m/z 309 (M+1), 331 (M+Na).

Example 60

Synthesis of (1E,6E)-1-(4-hydroxy-3-methoxyphenyl)-7-(3-hydroxyphenyl)hepta-1,6-diene-3,5-dione (CU079)

The title compound was synthesized using the same procedure employed for Example 1, but with 3-hydroxybenzaldehyde (13 mg, 0.11 mmol) instead of 3-hydroxy-2-methoxybenzaldehyde (16 mg, 0.11 mmol). The product was obtained as a solid (9.6 mg, 33%) having the following characteristics.

$^1$H NMR (δ, acetone-$d_6$): 3.92 (s, 3H), 6.04 (s, 1H), 6.74 (d, J=16 Hz, 1H), 6.77 (d, J=16 Hz, 1H), 6.87~6.94 (m, 1H), 6.88 (d, J=8.2 Hz, 1H), 7.12 (d, J=~2 Hz, 1H), 7.15 (br d, J=7.7 Hz, 1H), 7.19 (dd, J=~2, 8.2 Hz, 1H), 7.26 (dd, J=7.7, 7.7 Hz, 1H), 7.35 (d, J=~2 Hz, 1H), 7.57 (d, J=16 Hz, 1H), 7.63 (d, J=16 Hz, 1H), 8.1~8.8 (br s, OH).

Melting Point 74-80° C., MS (ESI+) m/z 339 (M+1), 361 (M+Na).

Example 61

Synthesis of (1E,6E)-1-(3-hydroxy-4-methoxyphenyl)-7-(3-hydroxyphenyl)hepta-1,6-diene-3,5-dione (CU081)

The title compound was synthesized using the same procedure employed for Example 29, but with 3-hydroxybenzaldehyde (13 mg, 0.11 mmol) instead of 3,4-dimethoxybenzaldehyde (18 mg, 0.11 mmol). The product was obtained as a solid (7.6 mg, 26%) having the following characteristics.

$^1$H NMR (δ, acetone-$d_6$): 3.90 (s, 3H), 6.06 (s, 1H), 6.69 (d, J=16 Hz, 1H), 6.79 (d, J=16 Hz, 1H), 6.88-6.94 (m, 1H), 7.00 (d, J=8.2 Hz, 1H), 7.12~7.2 (m, 3H), 7.21 (d, J=1.9 Hz, 1H), 7.26 (dd, J=7.7, 8.3 Hz, 1H), 7.58 (d, J=16 Hz, 1H), 7.59 (d, J=16 Hz, 1H), 7.8 (br s, OH), 8.5 (br s, OH).

Melting Point 200-206° C., MS (ESI+) m/z 339 (M+1).

Example 62

Synthesis of (1E,6E)-1-(4-hydroxy-3-methoxyphenyl)-7-(2-hydroxyphenyl)hepta-1,6-diene-3,5-dione (CU082)

The title compound was synthesized using the same procedure employed for Example 1, but with 2-hydroxybenzaldehyde (13 mg, 0.11 mmol) instead of 3-hydroxy-2-methoxybenzaldehyde (16 mg, 0.11 mmol). The product was obtained as a solid (3.0 mg, 10%) having the following characteristics.

$^1$H NMR (δ, acetone-$d_6$): 3.92 (s, 3H), 6.01 (s, 1H), 6.74 (d, J=16 Hz, 1H), 6.86~6.94 (m, 3H), 6.97 (d, J=8.2 Hz, 1H), 7.19 (dd, J=~2, 8.2 Hz, 1H), 7.2~7.26 (m, 1H), 7.35 (d, J=~2 Hz, 1H), 7.62 (d, J=16 Hz, 1H), 7.6~7.65 (m, 1H), 8.00 (d, J=16 Hz, 1H), 8.2 (br s, OH).

Melting Point 77-83° C., MS (ESI+) m/z 339 (M+1), 361 (M+Na).

Example 63

Synthesis of (1E,6E)-1-(4-hydroxyphenyl)-7-(4-hydroxy-2-methoxyphenyl)hepta-1,6-diene-3,5-dione (CU083)

The title compound was synthesized using the same procedure employed for Example 22, but with 4-hydroxy-2-methoxybenzaldehyde (16 mg, 0.11 mmol) instead of 3-hydroxy-4-methoxybenzaldehyde (16 mg, 0.11 mmol). The product was obtained as a solid (9.2 mg, 32%) having the following characteristics.

$^1$H NMR (δ, acetone-$d_6$): 3.89 (s, 3H), 5.93 (s, 1H), 6.51 (dd, J=1.9, 8.2 Hz, 1H), 6.54 (d, J=1.9 Hz, 1H), 6.66 (d, J=16 Hz, 1H), 6.71 (d, J=16 Hz, 1H), 6.90 (d, J=8.7 Hz, 2H), 7.54 (d, J=8.2 Hz, 1H), 7.56 (d, J=8.7 Hz, 2H), 7.59 (d, J=16 Hz, 1H), 7.91 (d, J=16 Hz, 1H), 8.9 (br s, OH).

Melting Point 105-110° C., MS (ESI+) m/z 339 (M+1), 361 (M+Na).

Example 64

Synthesis of (1E,6E)-1-(2-hydroxyphenyl)-7-(3-hydroxy-4-methoxyphenyl)hepta-1,6-diene-3,5-dione (CU084)

The title compound was synthesized using the same procedure employed for Example 29, but with 2-hydroxybenzaldehyde (13 mg, 0.11 mmol) instead of 3,4-dimethoxybenzaldehyde (18 mg, 0.11 mmol). The product was obtained as a solid (2.7 mg, 9%) having the following characteristics.

$^1$H NMR (δ, acetone-$d_6$): 3.90 (s, 3H), 6.03 (s, 1H), 6.70 (d, J=16 Hz, 1H), 6.85~7.05 (m, 4H), 7.15 (dd, J=~2, 8.2 Hz, 1H), 7.2~7.3 (m, 2H), 7.58 (d, J=16 Hz, 1H), 7.63 (dd, J=~2, 7.7 Hz, 1H), 7.8 (br s, OH), 8.00 (d, J=16 Hz, 1H).

Melting Point 90-96° C., MS (ESI+) m/z 339 (M+1), 361 (M+Na).

Example 65

Synthesis of (1E,6E)-1-(4-hydroxy-2-methoxyphenyl)-7-(4-hydroxy-3-methoxyphenyl)hepta-1,6-diene-3,5-dione (CU085)

The title compound was synthesized using the same procedure employed for Example 1, but with 4-hydroxy-2-methoxybenzaldehyde (16 mg, 0.11 mmol) instead of 3-hydroxy-2-methoxybenzaldehyde (16 mg, 0.11 mmol). The product was obtained as a solid (14.2 mg, 45%) having the following characteristics.

$^1$H NMR (δ, acetone-$d_6$): 3.89 (s, 3H), 3.92 (s, 3H), 5.92 (s, 1H), 6.51 (dd, J=2, 8.2 Hz, 1H), 6.54 (d, J=2 Hz, 1H), 6.70 (d, J=16 Hz, 1H), 6.70 (d, J=16 Hz, 1H), 6.87 (d, J=8.2 Hz, 1H), 7.17 (dd, J=~2, 8.2 Hz, 1H), 7.34 (d, J=~2 Hz, 1H), 7.54 (d, J=8.2 Hz, 1H), 7.58 (d, J=16 Hz, 1H), 7.91 (d, J=16 Hz, 1H), 8.5 (br s, OH).

Example 66

Synthesis of (1E,6E)-1-(4-hydroxy-2-methoxyphenyl)-7-(3-hydroxy-4-methoxyphenyl)hepta-1,6-diene-3,5-dione (CU086)

The title compound was synthesized using the same procedure employed for Example 29, but with 4-hydroxy-2-methoxybenzaldehyde (16 mg, 0.11 mmol) instead of 3,4-dimethoxybenzaldehyde (18 mg, 0.11 mmol). The product was obtained as a solid (12.6 mg, 40%) having the following characteristics.

$^1$H NMR (δ, acetone-$d_6$): 3.89 (s, 3H), 3.89 (s, 3H), 5.95 (s, 1H), 6.51 (dd, J=~2, 8.2 Hz, 1H), 6.54 (d, J=~2 Hz, 1H), 6.67 (d, J=16 Hz, 1H), 6.72 (d, J=16 Hz, 1H), 6.99 (d, J=8.2 Hz, 1H), 7.13 (dd, J=~2, 8.2 Hz, 1H), 7.20 (d, J=~2 Hz, 1H), 7.54 (d, J=16 Hz, 1H), 7.55 (dd, J=8.2 Hz, 1H), 7.92 (d, J=16 Hz, 1H).

Melting Point 90-95° C., MS (ESI+) m/z 369 (M+1), 391 (M+Na).

Example 67

Synthesis of (1E,6E)-1-(2-hydroxy-5-methoxyphenyl)-7-(4-hydroxy-3-methoxyphenyl)hepta-1,6-diene-3,5-dione (CU088)

The title compound was synthesized using the same procedure employed for Example 1, but with 2-hydroxy-5-methoxybenzaldehyde (16 mg, 0.11 mmol) instead of 3-hydroxy-2-methoxybenzaldehyde (16 mg, 0.11 mmol). The product was obtained as a solid (2.3 mg, 7%) having the following characteristics.

$^1$H NMR (δ, acetone-$d_6$): 3.78 (s, 3H), 3.92 (s, 3H), 6.00 (s, 1H), 6.74 (d, J=16 Hz, 1H), 6.85~6.95 (m, 4H), 7.16~7.24 (m, 2H), 7.35 (d, J=~2 Hz, 1H), 7.61 (d, J=16 Hz, 1H), 7.98 (d, J=16 Hz, 1H), 8.2 (br s, OH), 8.6 (br s, OH).

Melting Point 78-80° C., MS (ESI+) m/z 369 (M+1), 391 (M+Na).

Example 68

Synthesis of (1E,6E)-1-(2-hydroxy-5-methoxyphenyl)-7-(3-hydroxy-4-methoxyphenyl)hepta-1,6-diene-3,5-dione (CU089)

The title compound was synthesized using the same procedure employed for Example 29, but with 2-hydroxy-5-methoxybenzaldehyde (16 mg, 0.11 mmol) instead of 3,4-dimethoxybenzaldehyde (18 mg, 0.11 mmol). The product was obtained as a solid (2.2 mg, 7%) having the following characteristics.

$^1$H NMR (δ, acetone-$d_6$): 3.78 (s, 3H), 3.90 (s, 3H), 6.03 (s, 1H), 6.70 (d, J=16 Hz, 1H), 6.86 (dd, J=2.9, 8.7 Hz, 1H), 6.90 (d, J=8.7 Hz, 1H), 6.91 (d, J=16 Hz, 1H), 7.00 (d, J=8.2 Hz, 1H), 7.14 (dd, J=1.9, 8.2 Hz, 1H), 7.20 (d, J=2.9 Hz, 1H), 7.21 (d, J=1.9 Hz, 1H), 7.58 (d, J=16 Hz, 1H), 7.8 (br s, OH), 7.99 (d, J=16 Hz, 1H), 8.6 (br s, OH).

Melting Point 80-86° C., MS (ESI+) m/z 369 (M+1).

Example 69

Synthesis of (1E,6E)-1-(2,5-dihydroxyphenyl)-7-(4-hydroxyphenyl)hepta-1,6-diene-3,5-dione (CU090)

The title compound was synthesized using the same procedure employed for Example 22, but with 2,5-dihydroxybenzaldehyde (15 mg, 0.11 mmol) instead of 3-hydroxy-4-methoxybenzaldehyde (16 mg, 0.11 mmol). The product was obtained as a solid (2.6 mg, 9%) having the following characteristics.

$^1$H NMR (δ, acetone-$d_6$): 6.01 (s, 1H), 6.69 (d, J=16 Hz, 1H), 6.77 (dd, J=2.4, 8.7 Hz, 1H), 6.80 (d, J=16 Hz, 1H), 6.81 (d, J=8.7 Hz, 1H), 6.90 (d, J=8.7 Hz, 2H), 7.07 (d, J=2.4 Hz, 1H), 7.57 (d, J=8.7 Hz, 2H), 7.62 (d, J=16 Hz, 1H), 7.95 (d, J=16 Hz, 1H), 8.2~8.9 (br s, OH).

Melting Point 133-140° C., MS (ESI+) m/z 325 (M+1).

Example 70

Synthesis of (1E,6E)-1-(2,5-dihydroxyphenyl)-7-(3-hydroxy-4-methoxyphenyl)hepta-1,6-diene-3,5-dione (CU091)

The title compound was synthesized using the same procedure employed for Example 29, but with 2,5-dihydroxybenzaldehyde (15 mg, 0.11 mmol) instead of 3,4-dimethoxybenzaldehyde (18 mg, 0.11 mmol). The product was obtained as a solid (2.0 mg, 7%) having the following characteristics.

$^1$H NMR (δ, acetone-$d_6$): 3.90 (s, 3H), 6.03 (s, 1H), 6.70 (d, J=16 Hz, 1H), 6.77 (dd, J=2, 8.7 Hz, 1H), 6.81 (d, J=16 Hz, 1H), 6.81 (d, J=8.7 Hz, 1H), 7.00 (d, J=8.2 Hz, 1H), 7.07 (d, J=2 Hz, 1H), 7.13 (dd, J=~2, 8.2 Hz, 1H), 7.21 (d, J=~2 Hz, 1H), 7.57 (d, J=16 Hz, 1H), 7.8 (br s, OH), 7.9 (br s, OH), 7.96 (d, J=16 Hz, 1H), 8.5 (br s, OH).

Melting Point 115-121° C., MS (ESI+) m/z 355 (M+1), 377 (M+Na).

Example 71

Synthesis of (1E,6E)-1-(3,5-dihydroxyphenyl)-7-(4-hydroxyphenyl)hepta-1,6-diene-3,5-dione (CU092)

The title compound was synthesized using the same procedure employed for Example 22, but with 3,5-dihydroxybenzaldehyde (15 mg, 0.11 mmol) instead of 3-hydroxy-4-methoxybenzaldehyde (16 mg, 0.11 mmol). The product was obtained as a solid (6.4 mg, 23%) having the following characteristics.

$^1$H NMR (δ, acetone-$d_6$): 6.03 (s, 1H), 6.42 (t, J=1.9 Hz, 1H), 6.64 (d, J=1.9 Hz, 2H), 6.69 (d, J=16 Hz, 1H), 6.70 (d, J=16 Hz, 1H), 6.90 (d, J=8.7 Hz, 2H), 7.48 (d, J=16 Hz, 1H), 7.58 (d, J=8.7 Hz, 2H), 7.63 (d, J=16 Hz, 1H), 8.4 (br s, OH).

Melting Point 238-241° C., MS (ESI+) m/z 325 (M+1).

Example 72

Synthesis of (1E,6E)-1-(3,5-dihydroxyphenyl)-7-(4-hydroxy-3-methoxyphenyl)hepta-1,6-diene-3,5-dione (CU093)

The title compound was synthesized using the same procedure employed for Example 1, but with 3,5-dihydroxybenzaldehyde (15 mg, 0.11 mmol) instead of 3-hydroxy-2-methoxybenzaldehyde (16 mg, 0.11 mmol). The product was obtained as a solid (5.4 mg, 18%) having the following characteristics.

$^1$H NMR (δ, acetone-$d_6$): 3.92 (s, 3H), 6.02 (s, 1H), 6.42 (t, J=1.9 Hz, 1H), 6.64 (d, J=1.9 Hz, 2H), 6.68 (d, J=16 Hz, 1H), 6.73 (d, J=16 Hz, 1H), 6.88 (d, J=8.2 Hz, 1H), 7.19 (dd, J=1.9, 8.2 Hz, 1H), 7.35 (d, J=1.9 Hz, 1H), 7.48 (d, J=16 Hz, 1H), 7.62 (d, J=16 Hz, 1H), 8.2 (br s, OH), 8.4 (br s, OH).

Melting Point 85-90° C., MS (ESI+) m/z 355 (M+1).

Example 73

Synthesis of (1E,6E)-1-(3,5-dihydroxyphenyl)-7-(3-hydroxy-4-methoxyphenyl)hepta-1,6-diene-3,5-dione (CU094)

The title compound was synthesized using the same procedure employed for Example 29, but with 3,5-dihydroxybenzaldehyde (15 mg, 0.11 mmol) instead of 3,4-dimethoxybenzaldehyde (18 mg, 0.11 mmol). The product was obtained as a solid (9.0 mg, 30%) having the following characteristics.

$^1$H NMR (δ, acetone-$d_6$): 3.90 (s, 3H), 6.05 (s, 1H), 6.42 (t, J=1.9 Hz, 1H), 6.65 (d, J=1.9 Hz, 2H), 6.69 (d, J=16 Hz, 1H), 6.70 (d, J=16 Hz, 1H), 7.00 (d, J=8.2 Hz, 1H), 7.15 (dd, J=1.9, 8.2 Hz, 1H), 7.21 (d, J=1.9 Hz, 1H), 7.49 (d, J=16 Hz, 1H), 7.59 (d, J=16 Hz, 1H), 7.8 (br s, OH), 8.4 (br s, OH).

Melting Point 190-193° C., MS (ESI+) m/z 355 (M+1).

Example 74

Synthesis of (1E,6E)-1-(2,3-dihydroxyphenyl)-7-(4-hydroxy-3-methoxyphenyl)hepta-1,6-diene-3,5-dione (CU096)

The title compound was synthesized using the same procedure employed for Example 1, but with 2,3-dihydroxybenzaldehyde (15 mg, 0.11 mmol) instead of 3-hydroxy-2-methoxybenzaldehyde (16 mg, 0.11 mmol). The product was obtained as a solid (9.0 mg, 30%) having the following characteristics.

$^1$H NMR (δ, acetone-$d_6$): 3.92 (s, 3H), 6.01 (s, 1H), 6.73 (dd, J=7.7, 8.2 Hz, 1H), 6.74 (d, J=16 Hz, 1H), 6.85~6.93 (m, 3H), 7.14 (dd, J=~2, 8.2 Hz, 1H), 7.19 (dd, J=~2, 8.2 Hz, 1H), 7.36 (d, J=~2 Hz, 1H), 7.62 (d, J=16 Hz, 1H), 8.00 (d, J=16 Hz, 1H), 8.0 (br s, OH), 8.1 (br s, OH), 8.7 (br s, OH).

Melting Point 82-89° C., MS (ESI+) m/z 355 (M+1).

Example 75

Synthesis of (1E,6E)-1-(3,5-dimethoxyphenyl)-7-(4-hydroxyphenyl)hepta-1,6-diene-3,5-dione (CU099)

The title compound was synthesized using the same procedure employed for Example 22, but with 3,5-dimethoxybenzaldehyde (18 mg, 0.11 mmol) instead of 3-hydroxy-4-methoxybenzaldehyde (16 mg, 0.11 mmol). The product was obtained as a solid (4.4 mg, 15%) having the following characteristics.

$^1$H NMR (δ, acetone-$d_6$): 3.83 (s, 6H), 6.04 (s, 1H), 6.53 (t, J=2.4 Hz, 1H), 6.69 (d, J=16 Hz, 1H), 6.86 (d, J=2.4 Hz, 2H), 6.86 (d, J=16 Hz, 1H), 6.91 (d, J=8.7 Hz, 2H), 7.57 (d, J=16 Hz, 1H), 7.58 (d, J=8.7 Hz, 2H), 7.64 (d, J=16 Hz, 1H), 8.9 (br s, OH).

Melting Point 75-80° C., MS (ESI+) m/z 353 (M+1), 375 (M+Na).

Example 76

Synthesis of (1E,6E)-1-(3,5-dimethoxyphenyl)-7-(4-hydroxy-3-methoxyphenyl)hepta-1,6-diene-3,5-dione (CU100)

The title compound was synthesized using the same procedure employed for Example 1, but with 3,5-dimethoxybenzaldehyde (18 mg, 0.11 mmol) instead of 3-hydroxy-2-methoxybenzaldehyde (16 mg, 0.11 mmol). The product was obtained as a solid (3.2 mg, 10%) having the following characteristics.

$^1$H NMR (δ, acetone-$d_6$): 3.83 (s, 6H), 3.92 (s, 3H), 6.04 (s, 1H), 6.54 (t, J=2.4 Hz, 1H), 6.73 (d, J=16 Hz, 1H), 6.85 (d, J=16 Hz, 1H), 6.86 (d, J=2.4 Hz, 2H), 6.88 (d, J=8.2 Hz, 1H), 7.19 (dd, J=1.9, 8.2 Hz, 1H), 7.35 (d, J=1.9 Hz, 1H), 7.57 (d, J=16 Hz, 1H), 7.63 (d, J=16 Hz, 1H), 8.2 (br s, OH).

Melting Point 50-55° C., MS (ESI+) m/z 383 (M+1), 405 (M+Na).

Example 77

Synthesis of (1E,6E)-1-(3,5-dimethoxyphenyl)-7-(3-hydroxy-4-methoxyphenyl)hepta-1,6-diene-3,5-dione (CU101)

The title compound was synthesized using the same procedure employed for Example 29, but with 3,5-dimethoxybenzaldehyde (18 mg, 0.11 mmol) instead of 3,4-dimethoxybenzaldehyde (18 mg, 0.11 mmol). The product was obtained as a solid (4.8 mg, 15%) having the following characteristics.

$^1$H NMR (δ, acetone-$d_6$): 3.83 (s, 6H), 3.90 (s, 3H), 6.05 (s, 1H), 6.53 (t, J=1.9 Hz, 1H), 6.69 (d, J=16 Hz, 1H), 6.87 (d, J=2.4 Hz, 2H), 6.87 (d, J=16 Hz, 1H), 7.01 (d, J=8.2 Hz, 1H), 7.15 (dd, J=1.9, 8.2 Hz, 1H), 7.21 (d, J=1.9 Hz, 1H), 7.58 (d, J=16 Hz, 1H), 7.60 (d, J=16 Hz, 1H), 7.8 (br s, OH).

Melting Point 187-193° C., MS (ESI+) m/z 383 (M+1), 405 (M+Na).

Example 78

Synthesis of (1E,6E)-1-(2,6-dimethoxyphenyl)-7-(4-hydroxyphenyl)hepta-1,6-diene-3,5-dione (CU102)

The title compound was synthesized using the same procedure employed for Example 22, but with 2,6-dimethoxybenzaldehyde (18 mg, 0.11 mmol) instead of 3-hydroxy-4-methoxybenzaldehyde (16 mg, 0.11 mmol). The product was obtained as a solid (14.2 mg, 47%) having the following characteristics.

$^1$H NMR (δ, acetone-$d_6$): 3.93 (s, 6H), 5.95 (s, 1H), 6.68 (d, J=16 Hz, 1H), 6.71 (d, J=8.2 Hz, 2H), 6.90 (d, J=8.7 Hz, 2H), 7.18 (d, J=16 Hz, 1H), 7.33 (t, J=8.2 Hz, 1H), 7.57 (d, J=8.7 Hz, 2H), 7.61 (d, J=16 Hz, 1H), 8.12 (d, J=16 Hz, 1H), 8.9 (br s, OH).

Melting Point 165-170° C., MS (ESI+) m/z 353 (M+1), 375 (M+Na).

Example 79

Synthesis of (1E,6E)-1-(2,6-dimethoxyphenyl)-7-(4-hydroxy-3-methoxyphenyl)hepta-1,6-diene-3,5-dione (CU103)

The title compound was synthesized using the same procedure employed for Example 1, but with 2,6-dimethoxybenzaldehyde (18 mg, 0.11 mmol) instead of 3-hydroxy-2-methoxybenzaldehyde (16 mg, 0.11 mmol). The product was obtained as a solid (7.8 mg, 24%) having the following characteristics.

$^1$H NMR (δ, acetone-$d_6$): 3.92 (s, 3H), 3.93 (s, 6H), 5.95 (s, 1H), 6.72 (d, J=8.2 Hz, 2H), 6.73 (d, J=16 Hz, 1H), 6.88 (d, J=8.2 Hz, 1H), 7.18 (d, J=16 Hz, 1H), 7.18 (dd, J=1.9, 8.2 Hz, 1H), 7.33 (t, J=8.2 Hz, 1H), 7.34 (d, J=1.9 Hz, 1H), 7.60 (d, J=16 Hz, 1H), 8.12 (d, J=16 Hz, 1H), 8.2 (br s, OH).

Melting Point 136-139° C., MS (ESI+) m/z 383 (M+1).

Example 80

Synthesis of (1E,6E)-1-(2,6-dimethoxyphenyl)-7-(3-hydroxy-4-methoxyphenyl)hepta-1,6-diene-3,5-dione (CU104)

The title compound was synthesized using the same procedure employed for Example 29, but with 2,6-dimethoxybenzaldehyde (18 mg, 0.11 mmol) instead of 3,4-dimethoxybenzaldehyde (18 mg, 0.11 mmol). The product was obtained as a solid (16.2 mg, 50%) having the following characteristics.

$^1$H NMR ($\delta$, acetone-$d_6$): 3.90 (s, 3H), 3.93 (s, 6H), 5.97 (s, 1H), 6.69 (d, J=16 Hz, 1H), 6.72 (d, J=8.2 Hz, 2H), 7.01 (d, J=8.2 Hz, 1H), 7.15 (dd, J=~2, 8.2 Hz, 1H), 7.19 (d, J=16 Hz, 1H), 7.20 (d, J=~2 Hz, 1H), 7.34 (t, J=8.2 Hz, 1H), 7.56 (d, J=16 Hz, 1H), 7.8 (br s, OH), 8.13 (d, J=16 Hz, 1H).

Melting Point 74-80° C., MS (ESI+) m/z 383 (M+1), 405 (M+Na).

Example 81

Synthesis of (1E,6E)-1-(3-hydroxy-4-methoxyphenyl)-7-(4-hydroxy-3-methoxyphenyl)hepta-1,6-diene-3,5-dione (CU105)

The title compound was synthesized using the same procedure employed for Example 1, but with 3-hydroxy-4-methoxybenzaldehyde (16 mg, 0.11 mmol) instead of 3-hydroxy-2-methoxybenzaldehyde (16 mg, 0.11 mmol). The product was obtained as a solid (11.0 mg, 48%) having the following characteristics.

$^1$H NMR ($\delta$, acetone-$d_6$): 3.89 (s, 3H), 3.92 (s, 3H), 5.99 (s, 1H), 6.66 (d, J=16 Hz, 1H), 6.72 (d, J=16 Hz, 1H), 6.88 (d, J=8.2 Hz, 1H), 6.99 (d, J=8.2 Hz, 1H), 7.13 (dd, J=2, 8.2 Hz, 1H), 7.18 (dd, J=2, 8.2 Hz, 1H), 7.19 (d, J=~2 Hz, 1H), 7.34 (d, J=~2 Hz, 1H), 7.56 (d, J=16 Hz, 1H), 7.60 (d, J=16 Hz, 1H), 7.9 (br s, OH).

Melting Point 78-85° C., MS (ESI+) m/z 369 (M+1), 391 (M+Na).

Example 82

Synthesis of (1E,6E)-1-(2,5-dihydroxyphenyl)-7-(4-hydroxy-3-methoxyphenyl)hepta-1,6-diene-3,5-dione (CU106)

The title compound was synthesized using the same procedure employed for Example 1, but with 2,5-dihydroxybenzaldehyde (15 mg, 0.11 mmol) instead of 3-hydroxy-2-methoxybenzaldehyde (16 mg, 0.11 mmol). The product was obtained as a solid (3.0 mg, 10%) having the following characteristics.

$^1$H NMR ($\delta$, acetone-$d_6$): 3.92 (s, 3H), 6.00 (s, 1H), 6.74 (d, J=16 Hz, 1H), 6.76~6.84 (m, 3H), 6.88 (d, J=8.2 Hz, 1H), 7.06 (d, J=2.9 Hz, 1H), 7.19 (dd, J=~2, 8.2 Hz, 1H), 7.35 (d, J=~2 Hz, 1H), 7.61 (d, J=16 Hz, 1H), 7.9 (br s, OH), 7.96 (d, J=16 Hz, 1H), 8.1 (br s, OH), 8.5 (br s, OH).

Melting Point 125-130° C., MS (ESI+) m/z 355 (M+1).

Example 83

Synthesis of (1E,6E)-1-(9-ethyl-9H-carbazol-3-yl)-7-(4-hydroxyphenyl)hepta-1,6-diene-3,5-dione (CU107)

The title compound was synthesized using the same procedure employed for Example 22, but with 9-ethyl-9H-carbazole-3-carboxaldehyde (24 mg, 0.11 mmol) instead of 3-hydroxy-4-methoxybenzaldehyde (16 mg, 0.11 mmol). The product was obtained as a solid (18.4 mg, 53%) having the following characteristics.

$^1$H NMR ($\delta$, acetone-$d_6$): 1.41 (t, J=7.2 Hz, 3H), 4.50 (q, J=7.2 Hz, 2H), 6.04 (s, 1H), 6.69 (d, J=16 Hz, 1H), 6.68~6.9 (m, 1H), 6.91 (d, J=8.7 Hz, 2H), 7.26 (dd, J=7.3, 7.7 Hz, 1H), 7.48~7.66 (m, 6H), 7.83 (dd, J=~2, 8.2 Hz, 1H), 7.89 (d, J=16 Hz, 1H), 8.21 (d, J=7.7 Hz, 1H), 8.51 (s, 1H), 8.9 (br s, OH).

MS (ESI+) m/z 410 (M+1), 432 (M+Na).

Example 84

Synthesis of (1E,6E)-1-(9-ethyl-9H-carbazol-3-yl)-7-(3-hydroxy-4-methoxyphenyl)hepta-1,6-diene-3,5-dione (CU108)

The title compound was synthesized using the same procedure employed for Example 29, but with 9-ethyl-9H-carbazole-3-carboxaldehyde (24 mg, 0.11 mmol) instead of 3,4-dimethoxybenzaldehyde (18 mg, 0.11 mmol). The product was obtained as a solid (14.6 mg, 39%) having the following characteristics.

$^1$H NMR ($\delta$, acetone-$d_6$): 1.42 (t, J=7.2 Hz, 3H), 3.90 (s, 3H), 4.51 (q, J=7.2 Hz, 2H), 6.06 (s, 1H), 6.70 (d, J=16 Hz, 1H), 6.89 (d, J=16 Hz, 1H), 7.00 (d, J=8.2 Hz, 1H), 7.14 (dd, J=~2, 8.2 Hz, 1H), 7.22 (d, J=~2 Hz, 1H), 7.26 (dd, J=7.3, 7.7 Hz, 1H), 7.50 (dd, J=7.3, 8.2 Hz, 1H), 7.55~7.65 (m, 3H), 7.8 (br s, OH), 7.84 (dd, J=~2, 8.2 Hz, 1H), 7.89 (d, J=16 Hz, 1H), 8.22 (d, J=7.7 Hz, 1H), 8.52 (s, 1H).

Melting Point 100-103° C., MS (ESI+) m/z 440 (M+1).

Example 85

Synthesis of (1E,6E)-1-(4-hydroxyphenyl)-7-(1H-indol-3-yl)hepta-1,6-diene-3,5-dione (CU110)

The title compound was synthesized using the same procedure employed for Example 22, but with 1H-indole-3-carboxaldehyde (16 mg, 0.11 mmol) instead of 3-hydroxy-4-methoxybenzaldehyde (16 mg, 0.11 mmol). The product was obtained as a solid (7.2 mg, 26%) having the following characteristics.

$^1$H NMR ($\delta$, acetone-$d_6$): 6.02 (s, 1H), 6.64 (d, J=16 Hz, 1H), 6.80 (d, J=16 Hz, 1H), 6.90 (d, J=8.7 Hz, 2H), 7.2~7.3 (m, 2H), 7.5~7.55 (m, 1H), 7.56 (d, J=8.7 Hz, 2H), 7.57 (d, J=16 Hz, 1H), 7.90 (d, J=2.9 Hz, 1H), 7.97 (d, J=16 Hz, 1H), 8.03 (dd, J=~2, 6.8 Hz, 1H), 8.9 (br s, OH).

Melting Point 215-220° C., MS (ESI+) m/z 332 (M+1), 354 (M+Na).

Example 86

Synthesis of (1E,6E)-1-(4-hydroxy-3-methoxyphenyl)-7-(naphthalen-2-yl)hepta-1,6-diene-3,5-dione (CU111)

The title compound was synthesized using the same procedure employed for Example 1, but with 2-naphthaldehyde (17 mg, 0.11 mmol) instead of 3-hydroxy-2-methoxybenzaldehyde (16 mg, 0.11 mmol).

The product was obtained as a solid (5.0 mg, 16%) having the following characteristics.

$^1$H NMR ($\delta$, acetone-$d_6$): 3.93 (s, 3H), 6.09 (s, 1H), 6.76 (d, J=16 Hz, 1H), 6.89 (d, J=8.2 Hz, 1H), 6.99 (d, J=16 Hz, 1H), 7.21 (dd, J=~2, 8.2 Hz, 1H), 7.37 (d, J=~2 Hz, 1H), 7.54~7.6

(m, 2H), 7.65 (d, J=16 Hz, 1H), 7.83 (d, J=16 Hz, 1H), 7.88 (dd, J=~2, 8.7 Hz, 1H), 7.9~8.0 (m, 3H), 8.15 (s, 1H), 8.2 (br s, OH).
MS (ESI+) m/z 373 (M+1), 395 (M+Na).

Example 87

Synthesis of (1E,6E)-1-(4-hydroxyphenyl)-7-(naphthalen-1-yl)hepta-1,6-diene-3,5-dione (CU112)

The title compound was synthesized using the same procedure employed for Example 22, but with 1-naphthaldehyde (17 mg, 0.11 mmol) instead of 3-hydroxy-4-methoxybenzaldehyde (16 mg, 0.11 mmol). The product was obtained as a solid (19.6 mg, 67%) having the following characteristics.
$^1$H NMR (δ, acetone-$d_6$): 6.15 (s, 1H), 6.73 (d, J=16 Hz, 1H), 6.92 (d, J=8.7 Hz, 2H), 6.94 (d, J=16 Hz, 1H), 7.5~7.7 (m, 5H), 7.68 (d, J=16 Hz, 1H), 7.95~8.02 (m, 3H), 8.31 (d, J=8.2 Hz, 1H), 8.50 (d, J=16 Hz, 1H).
MS (ESI+) m/z 343 (M+1).

Example 88

Synthesis of (1E,6E)-1-(3-hydroxy-4-methoxyphenyl)-7-(naphthalen-1-yl)hepta-1,6-diene-3,5-dione (CU113)

The title compound was synthesized using the same procedure employed for Example 29, but with 1-naphthaldehyde (17 mg, 0.11 mmol) instead of 3,4-dimethoxybenzaldehyde (18 mg, 0.11 mmol). The product was obtained as a solid (9.2 mg, 67%) having the following characteristics.
$^1$H NMR (δ, acetone-$d_6$): 3.90 (s, 3H), 6.18 (s, 1H), 6.74 (d, J=16 Hz, 1H), 6.95 (d, J=16 Hz, 1H), 7.01 (d, J=8.2 Hz, 1H), 7.16~7.2 (m, 1H), 7.23 (d, J=1.9 Hz, 1H), 7.5~7.7 (m, 4H), 7.8 (br s, OH), 7.96-8.04 (m, 3H), 8.32 (d, J=8.2 Hz, 1H), 8.51 (d, J=16 Hz, 1H).
MS (ESI+) m/z 373 (M+1), 395 (M+Na).

Example 89

Synthesis of (1E,6E)-1-(4-hydroxy-3-methoxyphenyl)-7-(2-methoxynaphthalen-1-yl)hepta-1,6-diene-3,5-dione (CU114)

The title compound was synthesized using the same procedure employed for Example 1, but with 2-methoxy-1-naphthaldehyde (20 mg, 0.11 mmol) instead of 3-hydroxy-2-methoxybenzaldehyde (16 mg, 0.11 mmol). The product was obtained as a solid (6.6 mg, 19%) having the following characteristics.
$^1$H NMR (δ, acetone-$d_6$): 3.93 (s, 3H), 4.08 (s, 3H), 6.08 (s, 1H), 6.76 (d, J=16 Hz, 1H), 6.89 (d, J=8.2 Hz, 1H), 7.08 (d, J=16 Hz, 1H), 7.20 (dd, J=1.9, 8.2 Hz, 1H), 7.37 (d, J=1.9 Hz, 1H), 7.4~7.46 (m, 1H), 7.52 (d, J=8.7 Hz, 1H), 7.59 (ddd, J=~2, 8.2, 8.2 Hz, 1H), 7.65 (d, J=16 Hz, 1H), 7.90 (d, J=8.2 Hz, 1H), 8.01 (d, J=9.2 Hz, 1H), 8.2 (br s, OH), 8.25 (d, J=8.7 Hz, 1H), 8.33 (d, J=16 Hz, 1H).
MS (ESI+) m/z 403 (M+1), 425 (M+Na).

Example 90

Synthesis of (1E,6E)-1-(4-hydroxyphenyl)-7-(2-methoxynaphthalen-1-yl)hepta-1,6-diene-3,5-dione (CU115)

The title compound was synthesized using the same procedure employed for Example 22, but with 2-methoxy-1-naphthaldehyde (20 mg, 0.11 mmol) instead of 3-hydroxy-4-methoxybenzaldehyde (16 mg, 0.11 mmol). The product was obtained as a solid (16.6 mg, 52%) having the following characteristics.
$^1$H NMR (δ, acetone-$d_6$): 4.08 (s, 3H), 6.09 (s, 1H), 6.72 (d, J=16 Hz, 1H), 6.91 (d, J=8.7 Hz, 2H), 7.08 (d, J=16 Hz, 1H), 7.4~7.46 (m, 1H), 7.51 (d, J=8.7 Hz, 1H), 7.59 (d, J=8.7 Hz, 2H), 7.6 (m, 1H), 7.66 (d, J=16 Hz, 1H), 7.89 (d, J=8.2 Hz, 1H), 8.00 (d, J=9.2 Hz, 1H), 8.25 (d, J=8.7 Hz, 1H), 8.34 (d, J=16 Hz, 1H), 8.9 (br s, OH).
MS (ESI+) m/z 373 (M+1), 395 (M+Na).

Example 91

Synthesis of (1E,6E)-1-(4-hydroxyphenyl)-7-(4-methoxynaphthalen-1-yl)hepta-1,6-diene-3,5-dione (CU116)

The title compound was synthesized using the same procedure employed for Example 22, but with 4-methoxy-1-naphthaldehyde (20 mg, 0.11 mmol) instead of 3-hydroxy-4-methoxybenzaldehyde (16 mg, 0.11 mmol). The product was obtained as a solid (10.8 mg, 34%) having the following characteristics.
$^1$H NMR (δ, acetone-$d_6$): 4.08 (s, 3H), 6.10 (s, 1H), 6.71 (d, J=16 Hz, 1H), 6.84 (d, J=16 Hz, 1H), 6.91 (d, J=8.7 Hz, 2H), 7.06 (d, J=8.2 Hz, 1H), 7.55~7.65 (m, 2H), 7.59 (d, J=8.7 Hz, 2H), 7.65~7.7 (m, 1H), 7.97 (d, J=8.2 Hz, 1H), 8.27~8.34 (m, 2H), 8.45 (d, J=16 Hz, 1H), 8.9 (br s, OH).
Melting Point 193-198° C., MS (ESI+) m/z 373 (M+1), 395 (M+Na).

Example 92

Synthesis of (1E,6E)-1-(3-hydroxy-4-methoxyphenyl)-7-(2-methoxynaphthalen-1-yl)hepta-1,6-diene-3,5-dione (CU117)

The title compound was synthesized using the same procedure employed for Example 29, but with 2-methoxy-1-naphthaldehyde (20 mg, 0.11 mmol) instead of 3,4-dimethoxybenzaldehyde (18 mg, 0.11 mmol). The product was obtained as a solid (13.0 mg, 38%) having the following characteristics.
$^1$H NMR (δ, acetone-$d_6$): 3.90 (s, 3H), 4.08 (s, 3H), 6.11 (s, 1H), 6.72 (d, J=16 Hz, 1H), 7.01 (d, J=8.2 Hz, 1H), 7.09 (d, J=16 Hz, 1H), 7.16 (dd, J=2.4, 8.2 Hz, 1H), 7.23 (d, J=2.4 Hz, 1H), 7.4~7.46 (m, 1H), 7.52 (d, J=9.2 Hz, 1H), 7.6 (m, 1H), 7.61 (d, J=16 Hz, 1H), 7.90 (d, J=8.7 Hz, 1H), 8.00 (d, J=9.2 Hz, 1H), 8.25 (d, J=8.7 Hz, 1H), 8.35 (d, J=16 Hz, 1H).
Melting Point 150-155° C., MS (ESI+) m/z 403 (M+1), 425 (M+Na).

Example 93

Synthesis of (1E,6E)-1-(4-hydroxy-3-methoxyphenyl)-7-(4-methoxynaphthalen-1-yl)hepta-1,6-diene-3,5-dione (CU118)

The title compound was synthesized using the same procedure employed for Example 1, but with 4-methoxy-1-naphthaldehyde (20 mg, 0.11 mmol) instead of 3-hydroxy-2-methoxybenzaldehyde (16 mg, 0.11 mmol). The product was obtained as a solid (11.2 mg, 33%) having the following characteristics.
$^1$H NMR (δ, acetone-$d_6$): 3.93 (s, 3H), 4.09 (s, 3H), 6.09 (s, 1H), 6.75 (d, J=16 Hz, 1H), 6.84 (d, J=16 Hz, 1H), 6.89 (d, J=8.2 Hz, 1H), 7.06 (d, J=8.2 Hz, 1H), 7.19 (dd, J=2, 8.2 Hz, 1H), 7.35 (d, J=2 Hz, 1H), 7.55~7.7 (m, 3H), 7.97 (d, J=7.7 Hz, 1H), 8.25~8.34 (m, 2H), 8.45 (d, J=16 Hz, 1H).

Melting Point 193-196° C., MS (ESI+) m/z 403 (M+1), 425 (M+Na).

Example 94

Synthesis of (1E,6E)-1-(4-dimethylaminonaphthalen-1-yl)-7-(4-hydroxyphenyl)hepta-1,6-diene-3,5-dione (CU119)

The title compound was synthesized using the same procedure employed for Example 22, but with 4-dimethylamino-1-naphthaldehyde (22 mg, 0.11 mmol) instead of 3-hydroxy-4-methoxybenzaldehyde (16 mg, 0.11 mmol). The product was obtained as a solid (4.6 mg, 14%) having the following characteristics.

$^1$H NMR ($\delta$, acetone-$d_6$): 2.94 (s, 6H), 6.10 (s, 1H), 6.71 (d, J=16 Hz, 1H), 6.84 (d, J=16 Hz, 1H), 6.91 (d, J=8.7 Hz, 2H), 7.16 (d, J=7.7 Hz, 1H), 7.5~7.7 (m, 3H), 7.59 (d, J=8.7 Hz, 2H), 7.93 (d, J=8.2 Hz, 1H), 8.28 (dd, J=7.7, 8.2 Hz, 1H), 8.47 (d, J=16 Hz, 1H), 8.9 (br s, OH).

Melting Point 82-86° C., MS (ESI+) m/z 386 (M+1), 408 (M+Na).

Example 95

Synthesis of (1E,6E)-1-(4-hydroxyphenyl)-7-(1-methyl-1H-pyrrol-2-yl)hepta-1,6-diene-3,5-dione (CU120)

The title compound was synthesized using the same procedure employed for Example 22, but with 1-methyl-1H-pyrrole-2-carboxaldehyde (12 mg, 0.11 mmol) instead of 3-hydroxy-4-methoxybenzaldehyde (16 mg, 0.11 mmol). The product was obtained as a solid (11.0 mg, 44%) having the following characteristics.

$^1$H NMR ($\delta$, acetone-$d_6$): 3.79 (s, 3H), 5.90 (s, 1H), 6.14 (dd, J=2.4, 3.9 Hz, 1H), 6.49 (d, J=16 Hz, 1H), 6.63 (d, J=16 Hz, 1H), 6.76 (m, 1H), 6.89 (d, J=8.7 Hz, 2H), 6.95 (m, 1H), 7.55 (d, J=8.7 Hz, 2H), 7.57 (d, J=16 Hz, 1H), 7.61 (d, J=16 Hz, 1H), 8.9 (br s, OH).

Melting Point 169-173° C., MS (ESI+) m/z 296 (M+1), 318 (M+Na).

Example 96

Synthesis of (1E,6E)-1-(4-hydroxy-3-methoxyphenyl)-7-(1-methyl-1H-pyrrol-2-yl)hepta-1,6-diene-3,5-dione (CU121)

The title compound was synthesized using the same procedure employed for Example 1, but with 1-methyl-1H-pyrrole-2-carboxaldehyde (12 mg, 0.11 mmol) instead of 3-hydroxy-2-methoxybenzaldehyde (16 mg, 0.11 mmol). The product was obtained as a solid (3.0 mg, 11%) having the following characteristics.

$^1$H NMR ($\delta$, acetone-$d_6$): 3.80 (s, 3H), 3.91 (s, 3H), 5.90 (s, 1H), 6.14 (m, 1H), 6.48 (d, J=16 Hz, 1H), 6.67 (d, J=16 Hz, 1H), 6.75 (m, 1H), 6.87 (d, J=8.2 Hz, 1H), 6.95 (m, 1H), 7.16 (dd, J=~2, 8.2 Hz, 1H), 7.32 (d, J=~2 Hz, 1H), 7.56 (d, J=16 Hz, 1H), 7.61 (d, J=16 Hz, 1H), 8.1 (br s, OH).

Melting Point 131-132° C., MS (ESI+) m/z 326 (M+1).

Example 97

Synthesis of (1E,6E)-1-(3-hydroxy-4-methoxyphenyl)-7-(1-methyl-1H-pyrrol-2-yl)hepta-1,6-diene-3,5-dione (CU122)

The title compound was synthesized using the same procedure employed for Example 29, but with 1-methyl-1H-pyrrole-2-carboxaldehyde (12 mg, 0.11 mmol) instead of 3,4-dimethoxybenzaldehyde (18 mg, 0.11 mmol). The product was obtained as a solid (3.0 mg, 11%) having the following characteristics.

$^1$H NMR ($\delta$, acetone-$d_6$): 3.80 (s, 3H), 3.89 (s, 3H), 5.92 (s, 1H), 6.14 (m, 1H), 6.50 (d, J=16 Hz, 1H), 6.63 (d, J=16 Hz, 1H), 6.78 (m, 1H), 6.95 (m, 1H), 6.99 (d, J=8.2 Hz, 1H), 7.12 (dd, J=1.9, 8.2 Hz, 1H), 7.18 (d, J=1.9 Hz, 1H), 7.52 (d, J=16 Hz, 1H), 7.62 (d, J=16 Hz, 1H), 7.8 (br s, OH).

MS (ESI+) m/z 326 (M+1), 348 (M+Na).

Example 98

Synthesis of (1E,6E)-1-(4-hydroxyphenyl)-7-(1-methyl-1H-indol-3-yl)hepta-1,6-diene-3,5-dione (CU123)

The title compound was synthesized using the same procedure employed for Example 22, but with 1-methyl-1H-indole-3-carboxaldehyde (17 mg, 0.11 mmol) instead of 3-hydroxy-4-methoxybenzaldehyde (16 mg, 0.11 mmol). The product was obtained as a solid (7.0 mg, 24%) having the following characteristics.

$^1$H NMR ($\delta$, acetone-$d_6$): 3.91 (s, 3H), 6.00 (s, 1H), 6.63 (d, J=16 Hz, 1H), 6.76 (d, J=16 Hz, 1H), 6.90 (d, J=8.7 Hz, 2H), 7.25 (ddd, J=~2, 7.7, 8.2 Hz, 1H), 7.31 (ddd, J=~2, 8.2, 8.2 Hz, 1H), 7.50 (d, J=8.2 Hz, 1H), 7.55 (d, J=8.7 Hz, 2H), 7.57 (d, J=16 Hz, 1H), 7.79 (s, 1H), 7.92 (d, J=16 Hz, 1H), 8.02 (d, J=7.7 Hz, 1H), 8.8 (br s, OH).

Melting Point 185-190° C., MS (ESI+) m/z 346 (M+1), 368 (M+Na).

Example 99

Synthesis of (1E,6E)-1-(4-hydroxy-3-methoxyphenyl)-7-(1-methyl-1H-indol-3-yl)hepta-1,6-diene-3,5-dione (CU124)

The title compound was synthesized using the same procedure employed for Example 1, but with 1-methyl-1H-indole-3-carboxaldehyde (17 mg, 0.11 mmol) instead of 3-hydroxy-2-methoxybenzaldehyde (16 mg, 0.11 mmol). The product was obtained as a solid (5.4 mg, 17%) having the following characteristics.

$^1$H NMR ($\delta$, acetone-$d_6$): 3.91 (s, 3H), 3.92 (s, 3H), 5.99 (s, 1H), 6.68 (d, J=16 Hz, 1H), 6.76 (d, J=16 Hz, 1H), 6.88 (d, J=8.2 Hz, 1H), 7.16 (dd, J=1.9, 8.2 Hz, 1H), 7.23~7.34 (m, 2H), 7.32 (d, J=1.9 Hz, 1H), 7.51 (d, J=7.7 Hz, 1H), 7.56 (d, J=16 Hz, 1H), 7.79 (s, 1H), 7.92 (d, J=16 Hz, 1H), 8.01 (d, J=7.7 Hz, 1H), 8.1 (br s, OH).

Melting Point 173-175° C., MS (ESI+) m/z 376 (M+1), 398 (M+Na).

Example 100

Synthesis of (1E,6E)-1-(3-hydroxy-4-methoxyphenyl)-7-(1-methyl-1H-indol-3-yl)hepta-1,6-diene-3,5-dione (CU125)

The title compound was synthesized using the same procedure employed for Example 29, but with 1-methyl-1H-indole-3-carboxaldehyde (17 mg, 0.11 mmol) instead of 3,4-dimethoxybenzaldehyde (18 mg, 0.11 mmol). The product was obtained as a solid (7.8 mg, 24%) having the following characteristics.

$^1$H NMR ($\delta$, acetone-$d_6$): 3.90 (s, 3H), 3.92 (s, 3H), 6.02 (s, 1H), 6.64 (d, J=16 Hz, 1H), 6.78 (d, J=16 Hz, 1H), 7.00 (d, J=8.2 Hz, 1H), 7.13 (dd, J=1.9, 8.2 Hz, 1H), 7.20 (d, J=1.9 Hz, 1H), 7.24~7.28 (m, 1H), 7.29-7.34 (m, 1H), 7.51 (d, J=7.8 Hz, 1H), 7.53 (d, J=16 Hz, 1H), 7.8 (br s, OH), 7.81 (s, 1H), 7.94 (d, J=16 Hz, 1H), 8.02 (d, J=7.8 Hz, 1H).

Melting Point 162-166° C., MS (ESI+) m/z 376 (M+1), 398 (M+Na).

Example 101

Synthesis of (1E,6E)-1-(4-hydroxyphenyl)-7-(1-methyl-1H-indol-2-yl)hepta-1,6-diene-3,5-dione (CU126)

The title compound was synthesized using the same procedure employed for Example 22, but with 1-methyl-1H-indole-2-carboxaldehyde (17 mg, 0.11 mmol) instead of 3-hydroxy-4-methoxybenzaldehyde (16 mg, 0.11 mmol). The product was obtained as a solid (10.8 mg, 37%) having the following characteristics.

$^1$H NMR ($\delta$, acetone-$d_6$): 3.93 (s, 3H), 6.06 (s, 1H), 6.70 (d, J=16 Hz, 1H), 6.90 (d, J=16 Hz, 1H), 6.91 (d, J=8.7 Hz, 2H), 7.07 (dd, J=7.3, 7.8 Hz, 1H), 7.11 (s, 1H), 7.22~7.26 (m, 1H), 7.46 (d, J=8.8 Hz, 1H), 7.55~7.62 (m, 1H), 7.59 (d, J=8.7 Hz, 2H), 7.65 (d, J=16 Hz, 1H), 7.81 (d, J=16 Hz, 1H), 8.9 (br s, OH).

Melting Point 208-213° C., MS (ESI+) m/z 346 (M+1), 368 (M+Na).

Example 102

Synthesis of (1E,6E)-1-(2-chloro-4-hydroxyphenyl)-7-(4-hydroxyphenyl)hepta-1,6-diene-3,5-dione (CU127)

The title compound was synthesized using the same procedure employed for Example 22, but with 2-chloro-4-hydroxybenzaldehyde (17 mg, 0.11 mmol) instead of 3-hydroxy-4-methoxybenzaldehyde (16 mg, 0.11 mmol). The product was obtained as a solid (13.2 mg, 45%) having the following characteristics.

$^1$H NMR ($\delta$, acetone-$d_6$): 6.01 (s, 1H), 6.69 (d, J=16 Hz, 1H), 6.74 (d, J=16 Hz, 1H), 6.87~6.9 (m, 1H), 6.91 (d, J=8.7 Hz, 2H), 6.98 (d, J=2.4 Hz, 1H), 7.58 (d, J=8.7 Hz, 2H), 7.63 (d, J=16 Hz, 1H), 7.78 (d, J=8.7 Hz, 1H), 7.97 (d, J=16 Hz, 1H), 9.0 (br s, OH).

Melting Point 131-138° C., MS (ESI+) m/z 343 (M+1), 365 (M+Na).

Example 103

Synthesis of (1E,6E)-1-(3-hydroxy-4-methoxyphenyl)-7-(1-methyl-1H-indol-2-yl)hepta-1,6-diene-3,5-dione (CU128)

The title compound was synthesized using the same procedure employed for Example 29, but with 1-methyl-1H-indole-2-carboxaldehyde (17 mg, 0.11 mmol) instead of 3,4-dimethoxybenzaldehyde (18 mg, 0.11 mmol). The product was obtained as a solid (5.8 mg, 18%) having the following characteristics.

$^1$H NMR ($\delta$, acetone-$d_6$): 3.90 (s, 3H), 3.93 (s, 3H), 6.07 (s, 1H), 6.70 (d, J=16 Hz, 1H), 6.90 (d, J=16 Hz, 1H), 7.01 (d, J=8.2 Hz, 1H), 7.07 (dd, J=7.3, 7.8 Hz, 1H), 7.12 (s, 1H), 7.16 (dd, J=1.9, 8.2 Hz, 1H), 7.21 (d, J=1.9 Hz, 1H), 7.22~7.26 (m, 1H), 7.46 (d, J=8.3 Hz, 1H), 7.58 (d, J=7.8 Hz, 1H), 7.60 (d, J=16 Hz, 1H), 7.8 (br s, OH), 7.82 (d, J=16 Hz, 1H).

Melting Point 185-193° C., MS (ESI+) m/z 376 (M+1), 398 (M+Na).

Example 104

Synthesis of (1E,6E)-1-(2-chloro-4-hydroxyphenyl)-7-(4-hydroxy-3-methoxyphenyl)hepta-1,6-diene-3,5-dione (CU129)

The title compound was synthesized using the same procedure employed for Example 1, but with 2-chloro-4-hydroxybenzaldehyde (17 mg, 0.11 mmol) instead of 3-hydroxy-2-methoxybenzaldehyde (16 mg, 0.11 mmol). The product was obtained as a solid (8.0 mg, 25%) having the following characteristics.

$^1$H NMR ($\delta$, acetone-$d_6$): 3.92 (s, 3H), 6.01 (s, 1H), 6.74 (d, J=16 Hz, 1H), 6.74 (d, J=16 Hz, 1H), 6.89 (d, J=8.2 Hz, 1H), 6.90 (dd, J=2.4, 8.8 Hz, 1H), 6.98 (d, J=2.4 Hz, 1H), 7.19 (dd, J=1.9, 8.2 Hz, 1H), 7.36 (d, J=1.9 Hz, 1H), 7.63 (d, J=16 Hz, 1H), 7.79 (d, J=8.8 Hz, 1H), 7.97 (d, J=16 Hz, 1H).

Melting Point 185-192° C., MS (ESI+) m/z 373 (M+1).

Example 105

Synthesis of (1E,6E)-1-(2-chloro-4-hydroxyphenyl)-7-(3-hydroxy-4-methoxyphenyl)hepta-1,6-diene-3,5-dione (CU130)

The title compound was synthesized using the same procedure employed for Example 29, but with 2-chloro-4-hydroxybenzaldehyde (17 mg, 0.11 mmol) instead of 3,4-dimethoxybenzaldehyde (18 mg, 0.11 mmol). The product was obtained as a solid (7.4 mg, 23%) having the following characteristics.

$^1$H NMR ($\delta$, acetone-$d_6$): 3.90 (s, 3H), 6.03 (s, 1H), 6.70 (d, J=16 Hz, 1H), 6.76 (d, J=16 Hz, 1H), 6.89 (dd, J=2.4, 8.8 Hz, 1H), 6.98 (d, J=2.4 Hz, 1H), 7.01 (d, J=8.2 Hz, 1H), 7.15 (dd, J=1.9, 8.2 Hz, 1H), 7.21 (d, J=1.9 Hz, 1H), 7.59 (d, J=16 Hz, 1H), 7.80 (d, J=8.8 Hz, 1H), 7.98 (d, J=16 Hz, 1H).

Melting Point 120-130° C., MS (ESI+) m/z 373 (M+1).

Example 106

Synthesis of (1E,6E)-1-(4-hydroxyphenyl)-7-(5-hydroxy-2-nitrophenyl)hepta-1,6-diene-3,5-dione (CU131)

The title compound was synthesized using the same procedure employed for Example 22, but with 5-hydroxy-2-nitrobenzaldehyde (18 mg, 0.11 mmol) instead of 3-hydroxy-4-methoxybenzaldehyde (16 mg, 0.11 mmol). The product was obtained as a solid (7.8 mg, 26%) having the following characteristics.

$^1$H NMR ($\delta$, acetone-$d_6$): 6.12 (s, 1H), 6.73 (d, J=16 Hz, 1H), 6.73 (d, J=16 Hz, 1H), 6.91 (d, J=8.7 Hz, 2H), 7.06 (dd, J=2.4, 8.8 Hz, 1H), 7.22 (d, J=2.4 Hz, 1H), 7.60 (d, J=8.7 Hz, 2H), 7.68 (d, J=16 Hz, 1H), 8.08 (d, J=8.8 Hz, 1H), 8.11 (d, J=16 Hz, 1H).

Melting Point 187-194° C., MS (ESI+) m/z 354 (M+1), 376 (M+Na).

Example 107

Synthesis of (1E,6E)-1-(4-hydroxy-3-methoxyphenyl)-7-(5-hydroxy-2-nitrophenyl)hepta-1,6-diene-3,5-dione (CU132)

The title compound was synthesized using the same procedure employed for Example 1, but with 5-hydroxy-2-nitrobenzaldehyde (18 mg, 0.11 mmol) instead of 3-hydroxy-2-methoxybenzaldehyde (16 mg, 0.11 mmol). The product was obtained as a solid (5.8 mg, 18%) having the following characteristics.

$^1$H NMR (δ, acetone-$d_6$): 3.93 (s, 3H), 6.10 (s, 1H), 6.72 (d, J=16 Hz, 1H), 6.78 (d, J=16 Hz, 1H), 6.89 (d, J=8.2 Hz, 1H), 7.06 (dd, J=2.4, 8.8 Hz, 1H), 7.25~7.35 (m, 2H), 7.37 (d, J=1.9 Hz, 1H), 7.67 (d, J=16 Hz, 1H), 8.08 (d, J=8.8 Hz, 1H), 8.11 (d, J=16 Hz, 1H).

Melting Point 147-152° C., MS (ESI+) m/z 384 (M+1), 406 (M+Na).

Example 108

Synthesis of (1E,6E)-1-(3-hydroxy-4-methoxyphenyl)-7-(5-hydroxy-2-nitrophenyl)hepta-1,6-diene-3,5-dione (CU133)

The title compound was synthesized using the same procedure employed for Example 29, but with 5-hydroxy-2-nitrobenzaldehyde (18 mg, 0.11 mmol) instead of 3,4-dimethoxybenzaldehyde (18 mg, 0.11 mmol). The product was obtained as a solid (11.4 mg, 35%) having the following characteristics.

$^1$H NMR (δ, acetone-$d_6$): 3.90 (s, 3H), 6.12 (s, 1H), 6.72 (d, J=16 Hz, 1H), 6.73 (d, J=16 Hz, 1H), 7.01 (d, J=8.7 Hz, 1H), 7.05 (dd, J=2.4, 8.7 Hz, 1H), 7.17 (dd, J=1.9, 8.7 Hz, 1H), 7.21 (d, J=2.4 Hz, 1H), 7.22 (d, J=1.9 Hz, 1H), 7.63 (d, J=16 Hz, 1H), 8.07 (d, J=8.7 Hz, 1H), 8.11 (d, J=16 Hz, 1H).

Melting Point 107-111° C., MS (ESI+) m/z 384 (M+1), 406 (M+Na).

Example 109

Synthesis of (1E,6E)-1-(4-hydroxy-3,5-dimethoxyphenyl)-7-(4-hydroxyphenyl)hepta-1,6-diene-3,5-dione (CU134)

The title compound was synthesized using the same procedure employed for Example 22, but with 4-hydroxy-3,5-dimethoxybenzaldehyde (20 mg, 0.11 mmol) instead of 3-hydroxy-4-methoxybenzaldehyde (16 mg, 0.11 mmol). The product was obtained as a solid (13.2 mg, 42%) having the following characteristics.

$^1$H NMR (δ, acetone-$d_6$): 3.89 (s, 6H), 5.96 (s, 1H), 6.65 (d, J=16 Hz, 1H), 6.74 (d, J=16 Hz, 1H), 6.90 (d, J=8.7 Hz, 2H), 7.04 (s, 2H), 7.56 (d, J=8.7 Hz, 2H), 7.58 (d, J=16 Hz, 1H), 7.60 (d, J=16 Hz, 1H).

Melting Point 228-233° C., MS (ESI+) m/z 369 (M+1), 391 (M+Na).

Example 110

Synthesis of (1E,6E)-1-(4-hydroxy-3,5-dimethoxyphenyl)-7-(3-hydroxy-4-methoxyphenyl)hepta-1,6-diene-3,5-dione (CU136)

The title compound was synthesized using the same procedure employed for Example 29, but with 4-hydroxy-3,5-dimethoxybenzaldehyde (20 mg, 0.11 mmol) instead of 3,4-dimethoxybenzaldehyde (18 mg, 0.11 mmol). The product was obtained as a solid (15.2 mg, 45%) having the following characteristics.

$^1$H NMR (δ, acetone-$d_6$): 3.89 (s, 3H), 3.89 (s, 6H), 5.98 (s, 1H), 6.65 (d, J=16 Hz, 1H), 6.75 (d, J=16 Hz, 1H), 6.99 (d, J=8.2 Hz, 1H), 7.04 (s, 2H), 7.13 (dd, J=1.9, 8.2 Hz, 1H), 7.19 (d, J=1.9 Hz, 1H), 7.56 (d, J=16 Hz, 1H), 7.59 (d, J=16 Hz, 1H), 7.8 (br s, 2OH).

Melting Point 91-95° C., MS (ESI+) m/z 399 (M+1), 421 (M+Na).

Example 111

Synthesis of (1E,6E)-1-(4-fluoro-3-methoxyphenyl)-7-(4-hydroxyphenyl)hepta-1,6-diene-3,5-dione (CU137)

The title compound was synthesized using the same procedure employed for Example 22, but with 4-fluoro-3-methoxybenzaldehyde (17 mg, 0.11 mmol) instead of 3-hydroxy-4-methoxybenzaldehyde (16 mg, 0.11 mmol). The product was obtained as a solid (12.0 mg, 42%) having the following characteristics.

$^1$H NMR (δ, acetone-$d_6$): 3.96 (s, 3H), 6.02 (s, 1H), 6.68 (d, J=16 Hz, 1H), 6.84 (d, J=16 Hz, 1H), 6.90 (d, J=8.7 Hz, 2H), 7.18 (dd, J=8.2, 11.1 Hz, 1H), 7.25~7.3 (m, 1H), 7.51 (dd, J=~2, 8.2 Hz, 1H), 7.57 (d, J=8.7 Hz, 2H), 7.60 (d, J=16 Hz, 1H), 7.63 (d, J=16 Hz, 1H), 8.9 (br s, OH).

Melting Point 136-143° C., MS (ESI+) m/z 341 (M+1), 363 (M+Na).

Example 112

Synthesis of (1E,6E)-1-(4-fluoro-3-methoxyphenyl)-7-(4-hydroxy-3-methoxyphenyl)hepta-1,6-diene-3,5-dione (CU138)

The title compound was synthesized using the same procedure employed for Example 1, but with 4-fluoro-3-methoxybenzaldehyde (17 mg, 0.11 mmol) instead of 3-hydroxy-2-methoxybenzaldehyde (16 mg, 0.11 mmol). The product was obtained as a solid (7.6 mg, 24%) having the following characteristics.

$^1$H NMR (δ, acetone-$d_6$): 3.92 (s, 3H), 3.96 (s, 3H), 6.02 (s, 1H), 6.72 (d, J=16 Hz, 1H), 6.83 (d, J=16 Hz, 1H), 6.88 (d, J=8.2 Hz, 1H), 7.16~7.22 (m, 2H), 7.25~7.3 (m, 1H), 7.34 (d, J=~2 Hz, 1H), 7.49 (dd, J=~2, 8.2 Hz, 1H), 7.61 (d, J=16 Hz, 1H), 7.63 (d, J=16 Hz, 1H), 8.2 (br s, OH).

Melting Point 150-155° C., MS (ESI+) m/z 371 (M+1), 393 (M+Na).

Example 113

Synthesis of (1E,6E)-1-(4-fluoro-3-methoxyphenyl)-7-(3-hydroxy-4-methoxyphenyl)hepta-1,6-diene-3,5-dione (CU139)

The title compound was synthesized using the same procedure employed for Example 29, but with 4-fluoro-3-methoxybenzaldehyde (17 mg, 0.11 mmol) instead of 3,4-dimethoxybenzaldehyde (18 mg, 0.11 mmol). The product was obtained as a solid (9.0 mg, 29%) having the following characteristics.

$^1$H NMR ($\delta$, acetone-$d_6$): 3.90 (s, 3H), 3.96 (s, 3H), 6.03 (s, 1H), 6.68 (d, J=16 Hz, 1H), 6.84 (d, J=16 Hz, 1H), 7.00 (d, J=8.2 Hz, 1H), 7.16~7.22 (m, 2H), 7.20 (d, J=2.4 Hz, 1H), 7.25~7.3 (m, 1H), 7.51 (dd, J=~2, 8.7 Hz, 1H), 7.59 (d, J=16 Hz, 1H), 7.61 (d, J=16 Hz, 1H), 7.8 (br s, 20H).

Melting Point 145-147° C., MS (ESI+) m/z 371 (M+1), 393 (M+Na).

Example 114

Synthesis of (1E,6E)-1-(3,5-dichlorophenyl)-7-(4-hydroxy-3-methoxyphenyl)hepta-1,6-diene-3,5-dione (CU140)

The title compound was synthesized using the same procedure employed for Example 1, but with 3,5-dichlorobenzaldehyde (19 mg, 0.11 mmol) instead of 3-hydroxy-2-methoxybenzaldehyde (16 mg, 0.11 mmol). The product was obtained as a solid (5.6 mg, 17%) having the following characteristics.

$^1$H NMR ($\delta$, acetone-$d_6$): 3.92 (s, 3H), 6.08 (s, 1H), 6.76 (d, J=16 Hz, 1H), 6.89 (d, J=8.2 Hz, 1H), 7.01 (d, J=16 Hz, 1H), 7.21 (dd, J=~2, 8.2 Hz, 1H), 7.36 (d, J=~2 Hz, 1H), 7.49 (t, J=1.5 Hz, 1H), 7.57 (d, J=16 Hz, 1H), 7.66 (d, J=16 Hz, 1H), 7.71 (d, J=1.5 Hz, 2H), 8.2 (br s, OH).

Melting Point 170-173° C., MS (ESI+) m/z 391 (M+1).

Example 115

Synthesis of (1E,6E)-1-(3,5-dichlorophenyl)-7-(3-hydroxy-4-methoxyphenyl)hepta-1,6-diene-3,5-dione (CU141)

The title compound was synthesized using the same procedure employed for Example 29, but with 3,5-dichlorobenzaldehyde (19 mg, 0.11 mmol) instead of 3,4-dimethoxybenzaldehyde (18 mg, 0.11 mmol). The product was obtained as a solid (6.0 mg, 18%) having the following characteristics.

$^1$H NMR ($\delta$, acetone-$d_6$): 3.90 (s, 3H), 6.10 (s, 1H), 6.72 (d, J=16 Hz, 1H), 7.01 (d, J=8.2 Hz, 1H), 7.03 (d, J=16 Hz, 1H), 7.16 (dd, J=~2, 8.2 Hz, 1H), 7.22 (d, J=~2 Hz, 1H), 7.49 (t, J=~2 Hz, 1H), 7.57 (d, J=16 Hz, 1H), 7.62 (d, J=16 Hz, 1H), 7.72 (d, J=~2 Hz, 2H), 7.8 (br s, OH).

Melting Point 176-183° C., MS (ESI+) m/z 391 (M+1), 413 (M+Na).

Example 116

Synthesis of (1E,6E)-1-(2,4-dichlorophenyl)-7-(4-hydroxy-3-methoxyphenyl)hepta-1,6-diene-3,5-dione (CU144)

The title compound was synthesized using the same procedure employed for Example 1, but with 2,4-dichlorobenzaldehyde (19 mg, 0.11 mmol) instead of 3-hydroxy-2-methoxybenzaldehyde (16 mg, 0.11 mmol). The product was obtained as a solid (6.2 mg, 19%) having the following characteristics.

$^1$H NMR ($\delta$, acetone-$d_6$): 3.92 (s, 3H), 6.09 (s, 1H), 6.77 (d, J=16 Hz, 1H), 6.89 (d, J=8.2 Hz, 1H), 6.93 (d, J=16 Hz, 1H), 7.20 (dd, J=2, 8.2 Hz, 1H), 7.36 (d, J=~2 Hz, 1H), 7.45 (dd, J=2.4, 7.8 Hz, 1H), 7.61 (d, J=2.4 Hz, 1H), 7.67 (d, J=16 Hz, 1H), 7.91 (d, J=7.8 Hz, 1H), 7.92 (d, J=16 Hz, 1H), 8.2 (br s, OH).

Melting Point 124-130° C., MS (ESI+) m/z 391 (M+1), 413 (M+Na).

Example 117

Synthesis of (1E,6E)-1-(2,4-dichlorophenyl)-7-(3-hydroxy-4-methoxyphenyl)hepta-1,6-diene-3,5-dione (CU145)

The title compound was synthesized using the same procedure employed for Example 29, but with 2,4-dichlorobenzaldehyde (19 mg, 0.11 mmol) instead of 3,4-dimethoxybenzaldehyde (18 mg, 0.11 mmol). The product was obtained as a solid (8.7 mg, 26%) having the following characteristics.

$^1$H NMR ($\delta$, acetone-$d_6$): 3.90 (s, 3H), 6.10 (s, 1H), 6.72 (d, J=16 Hz, 1H), 6.93 (d, J=16 Hz, 1H), 6.98 (d, J=8.2 Hz, 1H), 7.10 (dd, J=~2, 8.2 Hz, 1H), 7.22 (d, J=~2 Hz, 1H), 7.45 (dd, J=2.4, 7.8 Hz, 1H), 7.60 (d, J=2.4 Hz, 1H), 7.63 (d, J=16 Hz, 1H), 7.8 (br s, OH), 7.92 (d, J=7.8 Hz, 1H), 7.93 (d, J=161 Hz, 1H).

MS (ESI+) m/z 391 (M+1), 413 (M+Na).

Example 118

Synthesis of (1E,6E)-1-(2,4-dichlorophenyl)-7-(4-hydroxyphenyl)hepta-1,6-diene-3,5-dione (CU146)

The title compound was synthesized using the same procedure employed for Example 22, but with 2,4-dichlorobenzaldehyde (19 mg, 0.11 mmol) instead of 3-hydroxy-4-methoxybenzaldehyde (16 mg, 0.11 mmol). The product was obtained as a solid (6.6 mg, 22%) having the following characteristics.

$^1$H NMR ($\delta$, acetone-$d_6$): 6.09 (s, 1H), 6.72 (d, J=16 Hz, 1H), 6.91 (d, J=8.7 Hz, 2H), 6.93 (d, J=16 Hz, 1H), 7.45 (dd, J=~2, 8.7 Hz, 1H), 7.57 (d, J=8.7 Hz, 2H), 7.60 (d, J=~2 Hz, 1H), 7.67 (d, J=16 Hz, 1H), 7.91 (d, J=8.7 Hz, 1H), 7.92 (d, J=16 Hz, 1H), 8.9 (br s, OH).

MS (ESI+) m/z 361 (M+1).

Example 119

Synthesis of (1E,6E)-1-(4-hydroxy-3-methoxyphenyl)-7-(1-methyl-1H-indol-2-yl)hepta-1,6-diene-3,5-dione (CU147)

The title compound was synthesized using the same procedure employed for Example 1, but with 1-methyl-1H-indole-2-carboxaldehyde (17 mg, 0.11 mmol) instead of 3-hydroxy-2-methoxybenzaldehyde (16 mg, 0.11 mmol). The product was obtained as a solid (1.7 mg, 5%) having the following characteristics.

$^1$H NMR ($\delta$, acetone-$d_6$): 3.92 (s, 3H), 3.93 (s, 3H), 6.04 (s, 1H), 6.74 (d, J=16 Hz, 1H), 6.89 (d, J=8.2 Hz, 1H), 6.89 (d, J=16 Hz, 1H), 7.06 (dd, J=7.7, 8.2 Hz, 1H), 7.10 (s, 1H), 7.20 (dd, J=~2, 8.2 Hz, 1H), 7.23 (dd, J=7.7, 7.7 Hz, 1H), 7.36 (d, J=~2 Hz, 1H), 7.46 (d, J=8.2 Hz, 1H), 7.58 (d, J=7.7 Hz, 1H), 7.63 (d, J=16 Hz, 1H), 7.81 (d, J=16 Hz, 1H), 8.2 (br s, OH).

Example 120

Synthesis of (1E,6E)-1-(4-hydroxyphenyl)-7-(naphthalen-2-yl)hepta-1,6-diene-3,5-dione (CU149)

The title compound was synthesized using the same procedure employed for Example 22, but with 2-naphthaldehyde (17 mg, 0.11 mmol) instead of 3-hydroxy-4-methoxybenzaldehyde (16 mg, 0.11 mmol). The product was obtained as a solid (7.8 mg, 27%) having the following characteristics.

$^1$H NMR ($\delta$, acetone-$d_6$): 6.10 (s, 1H), 6.71 (d, J=16 Hz, 1H), 6.91 (d, J=8.7 Hz, 2H), 6.99 (d, J=16 Hz, 1H), 7.55 (d, J=6.3 Hz, 1H), 7.56 (d, J=6.3 Hz, 1H), 7.59 (d, J=8.7 Hz, 2H), 7.66 (d, J=16 Hz, 1H), 7.82 (d, J=16 Hz, 1H), 7.88 (dd, J=~2, 8.7 Hz, 1H), 7.9~8.0 (m, 3H), 8.15 (s, 1H), 8.9 (br s, OH).

Melting Point 225-230° C., MS (ESI+) m/z 343 (M+1), 365 (M+Na).

Example 121

Synthesis of (1E,6E)-1-(4-hydroxy-3-methoxyphenyl)-7-(naphthalen-1-yl)hepta-1,6-diene-3,5-dione (CU150)

The title compound was synthesized using the same procedure employed for Example 1, but with 1-naphthaldehyde (17 mg, 0.11 mmol) instead of 3-hydroxy-2-methoxybenzaldehyde (16 mg, 0.11 mmol). The product was obtained as a solid (7.0 mg, 22%) having the following characteristics.

$^1$H NMR ($\delta$, acetone-$d_6$): 3.93 (s, 3H), 6.15 (s, 1H), 6.77 (d, J=16 Hz, 1H), 6.89 (d, J=8.2 Hz, 1H), 6.93 (d, J=16 Hz, 1H), 7.21 (dd, J=1.9, 8.2 Hz, 1H), 7.37 (d, J=1.9 Hz, 1H), 7.57~7.61 (m, 2H), 7.64~7.68 (m, 1H), 7.67 (d, J=16 Hz, 1H), 7.96 (d, J=8.2 Hz, 1H), 7.98 (br d, J=7.7 Hz, 1H), 8.00 (d, J=7.7 Hz, 1H), 8.2 (br s, OH), 8.31 (d, J=8.2 Hz, 1H), 8.50 (d, J=16 Hz, 1H).

MS (ESI+) m/z 373 (M+1), 395 (M+Na).

Example 122

Synthesis of (1E,6E)-1-(3-hydroxy-4-methoxyphenyl)-7-(1H-imidazol-2-yl)hepta-1,6-diene-3,5-dione (CU151)

The title compound was synthesized using the same procedure employed for Example 29, but with 1H-imidazole-2-carboxaldehyde (11 mg, 0.11 mmol) instead of 3,4-dimethoxybenzaldehyde (18 mg, 0.11 mmol). The product was obtained as a solid (9.0 mg, 34%) having the following characteristics.

$^1$H NMR ($\delta$, acetone-$d_6$): 3.89 (s, 3H), 5.99 (s, 1H), 6.68 (d, J=16 Hz, 1H), 6.80 (d, J=16 Hz, 1H), 7.00 (d, J=8.2 Hz, 1H), 7.14 (dd, J=~2, 8.2 Hz, 1H), 7.20 (d, J=~2 Hz, 1H), 7.53 (br s, 1H), 7.55 (d, J=16 Hz, 1H), 7.60 (d, J=16 Hz, 1H), 7.74 (br s, 1H), 7.8 (br s, OH).

Melting Point 219-221° C., MS (ESI+) m/z 313 (M+1).

Example 123

Synthesis of (1E,6E)-1-(4-hydroxy-3-methoxyphenyl)-7-(1H-imidazol-2-yl)hepta-1,6-diene-3,5-dione (CU152)

The title compound was synthesized using the same procedure employed for Example 1, but with 1H-imidazole-2-carboxaldehyde (11 mg, 0.11 mmol) instead of 3-hydroxy-2-methoxybenzaldehyde (16 mg, 0.11 mmol). The product was obtained as a solid (5.2 mg, 20%) having the following characteristics.

$^1$H NMR ($\delta$, acetone-$d_6$): 3.92 (s, 3H), 5.95 (s, 1H), 6.72 (d, J=16 Hz, 1H), 6.79 (d, J=16 Hz, 1H), 6.88 (d, J=8.2 Hz, 1H), 7.17 (dd, J=1.9, 8.2 Hz, 1H), 7.34 (d, J=1.9 Hz, 1H), 7.53 (br s, 1H), 7.59 (d, J=16 Hz, 1H), 7.74 (br s, 1H), 7.86 (d, J=16 Hz, 1H), 8.1 (br s, OH).

Melting Point 235-240° C., MS (ESI+) m/z 313 (M+1).

Example 124

Synthesis of (1E,6E)-1-(4-dimethylamino-2-methoxyphenyl)-7-(4-hydroxyphenyl)hepta-1,6-diene-3,5-dione (CU153)

The title compound was synthesized using the same procedure employed for Example 22, but with 4-dimethylamino-2-methoxybenzaldehyde (20 mg, 0.11 mmol) instead of 3-hydroxy-4-methoxybenzaldehyde (16 mg, 0.11 mmol). The product was obtained as a solid (6.2 mg, 20%) having the following characteristics.

$^1$H NMR ($\delta$, acetone-$d_6$): 3.06 (s, 6H), 3.92 (s, 3H), 5.87 (s, 1H), 6.31 (d, J=2.4 Hz, 1H), 6.38 (dd, J=2.4, 9.2 Hz, 1H), 6.61 (d, J=16 Hz, 1H), 6.64 (d, J=16 Hz, 1H), 6.89 (d, J=8.7 Hz, 2H), 7.51 (d, J=9.2 Hz, 1H), 7.55 (d, J=8.7 Hz, 2H), 7.55 (d, J=16 Hz, 1H), 7.94 (d, J=16 Hz, 1H), 8.8 (br s, OH).

Melting Point 100-105° C., MS (ESI+) m/z 366 (M+1).

Example 125

Synthesis of (1E,6E)-1-(4-dimethylamino-2-methoxyphenyl)-7-(4-hydroxy-3-methoxyphenyl)hepta-1,6-diene-3,5-dione (CU154)

The title compound was synthesized using the same procedure employed for Example 1, but with 4-dimethylamino-2-methoxybenzaldehyde (20 mg, 0.11 mmol) instead of 3-hydroxy-2-methoxybenzaldehyde (16 mg, 0.11 mmol). The product was obtained as a solid (5.0 mg, 15%) having the following characteristics.

$^1$H NMR ($\delta$, acetone-$d_6$): 3.06 (s, 6H), 3.92 (s, 3H), 3.93 (s, 3H), 5.87 (s, 1H), 6.31 (d, J=2.4 Hz, 1H), 6.38 (dd, J=2.4, 8.7 Hz, 1H), 6.61 (d, J=16 Hz, 1H), 6.68 (d, J=16 Hz, 1H), 6.87 (d, J=8.2 Hz, 1H), 7.15 (dd, J=~2, 8.2 Hz, 1H), 7.32 (d, J=2 Hz, 1H), 7.50 (d, J=8.7 Hz, 1H), 7.54 (d, J=16 Hz, 1H), 7.94 (d, J=16 Hz, 1H), 8.1 (br s, OH).

Melting Point 117-119° C., MS (ESI+) m/z 396 (M+1).

Example 126

Synthesis of (1E,6E)-1-(4-dimethylamino-2-methoxyphenyl)-7-(3-hydroxy-4-methoxyphenyl)hepta-1,6-diene-3,5-dione (CU155)

The title compound was synthesized using the same procedure employed for Example 29, but with 4-dimethylamino-2-methoxybenzaldehyde (20 mg, 0.11 mmol) instead of 3,4-dimethoxybenzaldehyde (18 mg, 0.11 mmol). The product was obtained as a solid (8.0 mg, 24%) having the following characteristics.

$^1$H NMR ($\delta$, acetone-$d_6$): 3.06 (s, 6H), 3.89 (s, 3H), 3.92 (s, 3H), 5.89 (s, 1H), 6.31 (d, J=~2 Hz, 1H), 6.38 (dd, J=~2, 8.7 Hz, 1H), 6.62 (d, J=16 Hz, 1H), 6.64 (d, J=16 Hz, 1H), 6.99

(d, J=8.2 Hz, 1H), 7.12 (dd, J=2, 8.2 Hz, 1H), 7.19 (d, J=2 Hz, 1H), 7.50 (d, J=16 Hz, 1H), 7.51 (d, J=8.7 Hz, 1H), 7.8 (br s, OH), 7.95 (d, J=16 Hz, 1H).

Melting Point 108-113° C., MS (ESI+) m/z 396 (M+1).

Example 127

Synthesis of (1E,6E)-1-(4-hydroxyphenyl)-7-(1H-imidazol-4-yl)hepta-1,6-diene-3,5-dione (CU157)

The title compound was synthesized using the same procedure employed for Example 22, but with 1H-imidazole-4-carboxaldehyde (11 mg, 0.11 mmol) instead of 3-hydroxy-4-methoxybenzaldehyde (16 mg, 0.11 mmol). The product was obtained as a solid (2.1 mg, 9%) having the following characteristics.

$^1$H NMR (δ, acetone-$d_6$): 6.02 (s, 1H), 6.70 (d, J=16 Hz, 1H), 6.89 (d, J=16 Hz, 1H), 6.91 (d, J=8.7 Hz, 2H), 7.18 (br s, 1H), 7.32 (br s, 1H), 7.48 (d, J=16 Hz, 1H), 7.58 (d, J=8.7 Hz, 2H), 7.64 (d, J=16 Hz, 1H).

Melting Point 168-172° C., MS (ESI+) m/z 283 (M+1).

Example 128

Synthesis of (1E,6E)-1-(3,4-difluorophenyl)-7-(4-hydroxy-3-methoxyphenyl)hepta-1,6-diene-3,5-dione (CU160)

The title compound was synthesized using the same procedure employed for Example 1, but with 3,4-difluorobenzaldehyde (16 mg, 0.11 mmol) instead of 3-hydroxy-2-methoxybenzaldehyde (16 mg, 0.11 mmol). The product was obtained as a solid (11.1 mg, 36%) having the following characteristics.

$^1$H NMR (δ, acetone-$d_6$): 3.92 (s, 3H), 6.03 (s, 1H), 6.74 (d, J=16 Hz, 1H), 6.85 (d, J=16 Hz, 1H), 6.88 (d, J=8.2 Hz, 1H), 7.19 (dd, J=~2, 8.2 Hz, 1H), 7.35 (d, J=~2 Hz, 1H), 7.35~7.45 (m, 1H), 7.5~7.6 (m, 1H), 7.59 (d, J=16 Hz, 1H), 7.64 (d, J=16 Hz, 1H), 7.7~7.76 (m, 1H), 8~8.5 (br s, OH).

MS (ESI+) m/z 359 (M+1), 381 (M+Na).

Example 129

Synthesis of (1E,6E)-1-(3,4-difluorophenyl)-7-(3-hydroxy-4-methoxyphenyl)hepta-1,6-diene-3,5-dione (CU161)

The title compound was synthesized using the same procedure employed for Example 29, but with 3,4-difluorobenzaldehyde (16 mg, 0.11 mmol) instead of 3,4-dimethoxybenzaldehyde (18 mg, 0.11 mmol). The product was obtained as a solid (4.9 mg, 16%) having the following characteristics.

$^1$H NMR (δ, acetone-$d_6$): 3.90 (s, 3H), 6.06 (s, 1H), 6.70 (d, J=16 Hz, 1H), 6.88 (d, J=16 Hz, 1H), 7.01 (d, J=8.2 Hz, 1H), 7.10 (dd, J=1.9, 8.2 Hz, 1H), 7.21 (d, J=1.9 Hz, 1H), 7.39 (dt, J=8.2, 10.6 Hz, 1H), 7.5~7.6 (m, 1H), 7.60 (d, J=16 Hz, 1H), 7.61 (d, J=16 Hz, 1H), 7.73 (dt, J=1.9, 8.7 Hz, 1H), 7.8 (br s, OH).

MS (ESI+) m/z 359 (M+1), 381 (M+Na).

Example 130

Synthesis of (1E,6E)-1-(3,4-difluorophenyl)-7-(4-hydroxyphenyl)hepta-1,6-diene-3,5-dione (CU162)

The title compound was synthesized using the same procedure employed for Example 22, but with 3,4-difluorobenzaldehyde (16 mg, 0.11 mmol) instead of 3-hydroxy-4-methoxybenzaldehyde (16 mg, 0.11 mmol). The product was obtained as a solid (2.1 mg, 8%) having the following characteristics.

$^1$H NMR (δ, acetone-$d_6$): 6.04 (s, 1H), 6.70 (d, J=16 Hz, 1H), 6.87 (d, J=16 Hz, 1H), 6.90 (d, J=8.7 Hz, 2H), 7.35~7.45 (m, 1H), 7.5~7.6 (m, 1H), 7.58 (d, J=8.7 Hz, 2H), 7.59 (d, J=16 Hz, 1H), 7.65 (d, J=16 Hz, 1H), 7.7~7.76 (m, 1H).

MS (ESI+) m/z 329 (M+1), 351 (M+Na).

Example 131

Synthesis of (1E,6E)-1-(3-hydroxy-4-methoxyphenyl)-7-(4-methoxynaphthalen-1-yl)hepta-1,6-diene-3,5-dione (CU163)

The title compound was synthesized using the same procedure employed for Example 29, but with 4-methyoxy-1-naphthaldehyde (20 mg, 0.11 mmol) instead of 3,4-dimethoxybenzaldehyde (18 mg, 0.11 mmol). The product was obtained as a solid (15.8 mg, 46%) having the following characteristics.

$^1$H NMR (δ, acetone-$d_6$): 3.90 (s, 3H), 4.09 (s, 3H), 6.12 (s, 1H), 6.71 (d, J=16 Hz, 1H), 6.85 (d, J=16 Hz, 1H), 7.01 (d, J=8.2 Hz, 1H), 7.06 (d, J=8.2 Hz, 1H), 7.16 (dd, J=~2, 8.2 Hz, 1H), 7.22 (d, J=~2 Hz, 1H), 7.55~7.65 (m, 2H), 7.67 (dd, J=7.2, 7.7 Hz, 1H), 7.8 (br s, OH), 7.98 (d, J=8.2 Hz, 1H), 8.28-8.36 (m, 2H), 8.46 (d, J=16 Hz, 1H).

Melting Point 170-175° C., MS (ESI+) m/z 403 (M+1), 425 (M+Na).

Example 132

Synthesis of (1E,6E)-1-(3-hydroxy-4-methoxyphenyl)-7-(naphthalen-2-yl)hepta-1,6-diene-3,5-dione (CU165)

The title compound was synthesized using the same procedure employed for Example 29, but with 2-naphthaldehyde (17 mg, 0.11 mmol) instead of 3,4-dimethoxybenzaldehyde (18 mg, 0.11 mmol). The product was obtained as a solid (7.6 mg, 24%) having the following characteristics.

$^1$H NMR (δ, acetone-$d_6$): 3.90 (s, 3H), 6.12 (s, 1H), 6.72 (d, J=16 Hz, 1H), 7.00 (d, J=16 Hz, 1H), 7.01 (d, J=8.2 Hz, 1H), 7.16 (br d, J=8.2 Hz, 1H), 7.22 (br s, 1H), 7.54~7.6 (m, 2H), 7.61 (d, J=16 Hz, 1H), 7.8~8.0 (m, 5H+ OH), 8.16 (s, 1H).

Melting Point 193-194° C., MS (ESI+) m/z 373 (M+1), 395 (M+Na).

Example 133

Synthesis of (1E,6E)-1-(4-hydroxyphenyl)-7-(6-methoxynaphthalen-2-yl)hepta-1,6-diene-3,5-dione (CU166)

The title compound was synthesized using the same procedure employed for Example 22, but with 6-methoxy-2-naphthaldehyde (20 mg, 0.11 mmol) instead of 3-hydroxy-4-methoxybenzaldehyde (16 mg, 0.11 mmol). The product was obtained as a solid (7.4 mg, 23%) having the following characteristics.

$^1$H NMR (δ, acetone-$d_6$): 3.94 (s, 3H), 6.07 (s, 1H), 6.70 (d, J=16 Hz, 1H), 6.91 (d, J=8.7 Hz, 2H), 6.92 (d, J=16 Hz, 1H), 7.19 (dd, J=2.4, 8.7 Hz, 1H), 7.33 (d, J=2.4 Hz, 1H), 7.59 (d, J=8.7 Hz, 2H), 7.64 (d, J=16 Hz, 1H), 7.79 (d, J=16 Hz, 1H), 7.82~7.88 (m, 2H), 7.87 (d, J=9.2 Hz, 1H), 8.07 (s, 1H), 8.9 (br s, OH).

Melting Point 217-220° C., MS (ESI+) m/z 373 (M+1).

Example 134

Synthesis of (1E,6E)-1-(4-dimethylaminonaphthalen-1-yl)-7-(3-hydroxy-4-methoxyphenyl)hepta-1,6-diene-3,5-dione (CU168)

The title compound was synthesized using the same procedure employed for Example 29, but with 4-dimethylamino-1-naphthaldehyde (22 mg, 0.11 mmol) instead of 3,4-dimethoxybenzaldehyde (18 mg, 0.11 mmol). The product was obtained as a solid (13.0 mg, 37%) having the following characteristics.

$^1$H NMR (δ, acetone-$d_6$): 2.93 (s, 6H), 3.90 (s, 3H), 6.12 (s, 1H), 6.71 (d, J=16 Hz, 1H), 6.85 (d, J=16 Hz, 1H), 7.01 (d, J=8.2 Hz, 1H), 7.12~7.0 (m, 2H), 7.22 (d, J=2.4 Hz, 1H), 7.54~7.66 (m, 2H), 7.60 (d, J=16 Hz, 1H), 7.8 (br s, OH), 7.93 (d, J=7.7 Hz, 1H), 8.27 (d, J=7.7 Hz, 1H), 8.29 (d, J=8.2 Hz, 1H), 8.48 (d, J=16 Hz, 1H).

Melting Point 146-150° C., MS (ESI+) m/z 416 (M+1).

Example 135

Synthesis of (1E,6E)-1-(3-hydroxy-4-methoxyphenyl)-7-(6-methoxynaphthalen-2-yl)hepta-1,6-diene-3,5-dione (CU171)

The title compound was synthesized using the same procedure employed for Example 29, but with 6-methoxy-2-naphthaldehyde (20 mg, 0.11 mmol) instead of 3,4-dimethoxybenzaldehyde (18 mg, 0.11 mmol). The product was obtained as a solid (9.0 mg, 26%) having the following characteristics.

$^1$H NMR (δ, acetone-$d_6$): 3.90 (s, 3H), 3.94 (s, 3H), 6.08 (s, 1H), 6.71 (d, J=16 Hz, 1H), 6.93 (d, J=16 Hz, 1H), 7.01 (d, J=8.2 Hz, 1H), 7.16 (dd, J=1.9, 8.2 Hz, 1H), 7.19 (dd, J=2.4, 9.2 Hz, 1H), 7.22 (d, J=1.9 Hz, 1H), 7.34 (d, J=2.4 Hz, 1H), 7.60 (d, J=16 Hz, 1H), 7.80 (d, J=16 Hz, 1H), 7.8 (br s, OH), 7.8-7.88 (m, 2H), 7.87 (d, J=9.2 Hz, 1H), 8.08 (s, 1H).

Melting Point 175-181° C., MS (ESI+) m/z 403 (M+1), 425 (M+Na).

Example 136

Synthesis of (1E,6E)-1-(4-hydroxyphenyl)-7-(3-hydroxy-2-methoxyphenyl)hepta-1,6-diene-3,5-dione (CU174)

The title compound was synthesized using the same procedure employed for Example 22, but with 3-hydroxy-2-methoxyaldehyde (16 mg, 0.11 mmol) instead of 3-hydroxy-4-methoxybenzaldehyde (16 mg, 0.11 mmol). The product was obtained as a solid (16.2 mg, 56%) having the following characteristics.

$^1$H NMR (δ, acetone-$d_6$): 3.83 (s, 3H), 6.05 (s, 1H), 6.70 (d, J=16 Hz, 1H), 6.85 (d, J=16 Hz, 1H), 6.91 (d, J=8.7 Hz, 2H), 6.96 (dd, J=2, 7.7 Hz, 1H), 7.01 (dd, J=7.7, 8 Hz, 1H), 7.23 (dd, J=2, 7.7 Hz, 1H), 7.58 (d, J=8.7 Hz, 2H), 7.64 (d, J=16 Hz, 1H), 7.90 (d, J=16 Hz, 1H), 8.6 (br s, OH).

Melting Point 165-169° C., MS (ESI+) m/z 339 (M+1), 361 (M+Na).

Example 137

Synthesis of (1E,6E)-1-(3-hydroxy-2-methoxyphenyl)-7-(3-hydroxy-4-methoxyphenyl)hepta-1,6-diene-3,5-dione (CU176)

The title compound was synthesized using the same procedure employed for Example 29, but with 3-hydroxy-2-methoxybenzaldehyde (16 mg, 0.11 mmol) instead of 3,4-dimethoxybenzaldehyde (18 mg, 0.11 mmol). The product was obtained as a solid (8.8 mg, 28%) having the following characteristics.

$^1$H NMR (δ, acetone-$d_6$): 3.84 (s, 3H), 3.90 (s, 3H), 6.07 (s, 1H), 6.71 (d, J=16 Hz, 1H), 6.86 (d, J=16 Hz, 1H), 6.96 (d, J=~2, 8 Hz, 1H), 6.98~7.04 (m, 2H), 7.16 (dd, J=~2, 8.2 Hz, 1H), 7.22 (d, J=~2 Hz, 1H), 7.23 (dd, J=~2, 8 Hz, 1H), 7.60 (d, J=16 Hz, 1H), 7.91 (d, J=16 Hz, 1H), 8.3 (br s, OH).

Melting Point 190-192° C., MS (ESI+) m/z 369 (M+1), 391 (M+Na).

Example 138

Synthesis of (1E,6E)-1-(4-hydroxyphenyl)-7-(5-hydroxy-2-methoxyphenyl)hepta-1,6-diene-3,5-dione (CU177)

The title compound was synthesized using the same procedure employed for Example 22, but with 5-hydroxy-2-methoxyaldehyde (16 mg, 0.11 mmol) instead of 3-hydroxy-4-methoxybenzaldehyde (16 mg, 0.11 mmol). The product was obtained as a solid (3.8 mg, 13%) having the following characteristics.

$^1$H NMR (δ, acetone-$d_6$): 3.85 (s, 3H), 6.01 (s, 1H), 6.69 (d, J=16 Hz, 1H), 6.78 (d, J=16 Hz, 1H), 6.93 (d, J=8.7 Hz, 2H), 6.86~6.96 (m, 2H), 7.14 (d, J=2.9 Hz, 1H), 7.58 (d, J=8.7 Hz, 2H), 7.62 (d, J=16 Hz, 1H), 7.93 (d, J=16 Hz, 1H), 8.6 (br s, OH).

Melting Point 183-186° C., MS (ESI+) m/z 339 (M+1).

Example 139

Synthesis of (1E,6E)-1-(4-hydroxy-3-methoxyphenyl)-7-(5-hydroxy-2-methoxyphenyl)hepta-1,6-diene-3,5-dione (CU178)

The title compound was synthesized using the same procedure employed for Example 1, but with 5-hydroxy-2-methoxybenzaldehyde (16 mg, 0.11 mmol) instead of 3-hydroxy-2-methoxybenzaldehyde (16 mg, 0.11 mmol). The product was obtained as a solid (14.2 mg, 45%) having the following characteristics.

$^1$H NMR (δ, acetone-$d_6$): 3.85 (s, 3H), 3.92 (s, 3H), 6.00 (s, 1H), 6.74 (d, J=16 Hz, 1H), 6.77 (d, J=16 Hz, 1H), 6.88 (d, J=8.2 Hz, 1H), 6.89 (dd, J=2.9, 8.7 Hz, 1H), 6.93 (d, J=8.7 Hz, 1H), 7.13 (d, J=2.9 Hz, 1H), 7.19 (dd, J=1.9, 8.2 Hz, 1H), 7.35 (d, J=1.9 Hz, 1H), 7.62 (d, J=16 Hz, 1H), 7.93 (d, J=16 Hz, 1H), 8.1 (br s, OH).

Melting Point 75-80° C., MS (ESI+) m/z 369 (M+1), 391 (M+Na).

Example 140

Synthesis of (1E,6E)-1-(3-hydroxy-4-methoxyphenyl)-7-(5-hydroxy-2-methoxyphenyl)hepta-1,6-diene-3,5-dione (CU179)

The title compound was synthesized using the same procedure employed for Example 29, but with 5-hydroxy-2- methoxybenzaldehyde (16 mg, 0.11 mmol) instead of 3,4-dimethoxybenzaldehyde (18 mg, 0.11 mmol). The product was obtained as a solid (5.2 mg, 17%) having the following characteristics.

$^1$H NMR (δ, acetone-$d_6$): 3.85 (s, 3H), 3.90 (s, 3H), 6.03 (s, 1H), 6.70 (d, J=16 Hz, 1H), 6.79 (d, J=16 Hz, 1H), 6.89 (dd, J=2.9, 8.7 Hz, 1H), 6.93 (d, J=8.7 Hz, 1H), 7.00 (d, J=8.2 Hz, 1H), 7.13~7.18 (m, 1H), 7.14 (d, J=2.9 Hz, 1H), 7.21 (d, J=1.9 Hz, 1H), 7.58 (d, J=16 Hz, 1H), 7.8 (br s, OH), 7.93 (d, J=16 Hz, 1H), 8.1 (br s, OH).

Melting Point 116-120° C., MS (ESI+) m/z 369 (M+1), 391 (M+Na).

Example 141

Synthesis of (1E,6E)-1-(4-hydroxyphenyl)-7-(3-hydroxy-5-methoxyphenyl)hepta-1,6-diene-3,5-dione (CU180)

The title compound was synthesized using the same procedure employed for Example 22, but with 3-hydroxy-5-methoxyaldehyde (16 mg, 0.11 mmol) instead of 3-hydroxy-4-methoxybenzaldehyde (16 mg, 0.11 mmol). The product was obtained as a solid (6.6 mg, 23%) having the following characteristics.

$^1$H NMR (δ, acetone-$d_6$): 3.80 (s, 3H), 6.04 (s, 1H), 6.46 (dd, J=~2, ~2 Hz, 1H), 6.69 (d, J=16 Hz, 1H), 6.73 (dd, J=~2, ~2 Hz, 1H), 6.77 (dd, J=~2, ~2 Hz, 1H), 6.78 (d, J=16 Hz, 1H), 6.90 (d, J=8.7 Hz, 2H), 7.52 (d, J=16 Hz, 1H), 7.58 (d, J=8.7 Hz, 2H), 7.64 (d, J=16 Hz, 1H), 8.7 (br s, OH).

Melting Point 161-165° C., MS (ESI+) m/z 339 (M+1).

Example 142

Synthesis of (1E,6E)-1-(3-hydroxy-5-methoxyphenyl)-7-(4-hydroxy-3-methoxyphenyl)hepta-1,6-diene-3,5-dione (CU181)

The title compound was synthesized using the same procedure employed for Example 1, but with 3-hydroxy-5-methoxybenzaldehyde (16 mg, 0.11 mmol) instead of 3-hydroxy-2-methoxybenzaldehyde (16 mg, 0.11 mmol). The product was obtained as a solid (9.2 mg, 29%) having the following characteristics.

$^1$H NMR (δ, acetone-$d_6$): 3.80 (s, 3H), 3.92 (s, 3H), 6.03 (s, 1H), 6.46 (m, 1H), 6.73 (d, J=16 Hz, 1H), 6.73 (m, 1H), 6.77 (d, J=16 Hz, 1H), 6.77 (m, 1H), 6.88 (d, J=8.2 Hz, 1H), 7.19 (dd, J=1.9, 8.2 Hz, 1H), 7.35 (d, J=1.9 Hz, 1H), 7.52 (d, J=16 Hz, 1H), 7.63 (d, J=16 Hz, 1H), 8.2 (br s, OH), 8.6 (br s, OH).

Melting Point 69-75° C., MS (ESI+) m/z 369 (M+1).

Example 143

Synthesis of (1E,6E)-1-(3-hydroxy-4-methoxyphenyl)-7-(3-hydroxy-5-methoxyphenyl)hepta-1,6-diene-3,5-dione (CU182)

The title compound was synthesized using the same procedure employed for Example 29, but with 3-hydroxy-5-methoxybenzaldehyde (16 mg, 0.11 mmol) instead of 3,4-dimethoxybenzaldehyde (18 mg, 0.11 mmol). The product was obtained as a solid (4.2 mg, 13%) having the following characteristics.

$^1$H NMR (δ, acetone-$d_6$): 3.80 (s, 3H), 3.90 (s, 3H), 6.05 (s, 1H), 6.46 (dd, J=1.9, 2.4 Hz, 1H), 6.69 (d, J=16 Hz, 1H), 6.74 (dd, J=~2, ~2 Hz, 1H), 6.78 (dd, J=~2, ~2 Hz, 1H), 6.79 (d, J=16 Hz, 1H), 7.00 (d, J=8.2 Hz, 1H), 7.15 (dd, J=1.9, 8.2 Hz, 1H), 7.21 (d, J=1.9 Hz, 1H), 7.53 (d, J=16 Hz, 1H), 7.59 (d, J=16 Hz, 1H), 7.8 (br s, OH), 8.6 (br s, OH).

Melting Point 196-200° C., MS (ESI+) m/z 369 (M+1).

Example 144

Synthesis of (1E,6E)-1-(2,5-dichlorophenyl)-7-(4-hydroxy-3-methoxyphenyl)hepta-1,6-diene-3,5-dione (CU184)

The title compound was synthesized using the same procedure employed for Example 1, but with 2,5-dichlorobenzaldehyde (19 mg, 0.11 mmol) instead of 3-hydroxy-2-methoxybenzaldehyde (16 mg, 0.11 mmol). The product was obtained as a solid (7.4 mg, 22%) having the following characteristics.

$^1$H NMR (δ, acetone-$d_6$): 3.92 (s, 3H), 6.11 (s, 1H), 6.79 (d, J=16 Hz, 1H), 6.89 (d, J=8.2 Hz, 1H), 7.01 (d, J=16 Hz, 1H), 7.22 (dd, J=~2, 8.2 Hz, 1H), 7.38 (d, J=~2 Hz, 1H), 7.45 (dd, J=2.4, 8.7 Hz, 1H), 7.54 (d, J=8.7 Hz, 1H), 7.68 (d, J=16 Hz, 1H), 7.90 (d, J=16 Hz, 1H), 7.92 (d, J=2.4 Hz, 1H).

Melting Point 142-147° C., MS (ESI+) m/z 391 (M+1), 413 (M+Na).

Example 145

Synthesis of (1E,6E)-1-(2,5-dichlorophenyl)-7-(3-hydroxy-4-methoxyphenyl)hepta-1,6-diene-3,5-dione (CU185)

The title compound was synthesized using the same procedure employed for Example 29, but with 2,5-dichlorobenzaldehyde (19 mg, 0.11 mmol) instead of 3,4-dimethoxybenzaldehyde (18 mg, 0.11 mmol). The product was obtained as a solid (6.8 mg, 20%) having the following characteristics.

$^1$H NMR (δ, acetone-$d_6$): 3.90 (s, 3H), 6.13 (s, 1H), 6.74 (d, J=16 Hz, 1H), 7.01 (d, J=8.2 Hz, 1H), 7.03 (d, J=16 Hz, 1H), 7.18 (dd, J=1.9, 8.2 Hz, 1H), 7.23 (d, J=1.9 Hz, 1H), 7.45 (dd, J=2.4, 8.7 Hz, 1H), 7.54 (d, J=8.7 Hz, 1H), 7.64 (d, J=16 Hz, 1H), 7.90 (d, J=16 Hz, 1H), 7.94 (d, J=2.4 Hz, 1H).

Melting Point 140-146° C., MS (ESI+) m/z 391 (M+1), 413 (M+Na).

Example 146

Synthesis of (1E,6E)-1-(3,4-dichlorophenyl)-7-(3-hydroxy-4-methoxyphenyl)hepta-1,6-diene-3,5-dione (CU186)

The title compound was synthesized using the same procedure employed for Example 29, but with 3,4-dichlorobenzaldehyde (19 mg, 0.11 mmol) instead of 3,4-dimethoxybenzaldehyde (18 mg, 0.11 mmol). The product was obtained as a solid (9.4 mg, 28%) having the following characteristics.

$^1$H NMR (δ, acetone-$d_6$): 3.90 (s, 3H), 6.09 (s, 1H), 6.72 (d, J=16 Hz, 1H), 6.97 (d, J=16 Hz, 1H), 7.01 (d, J=8.2 Hz, 1H), 7.16 (dd, J=~2, 8.2 Hz, 1H), 7.22 (d, J=~2 Hz, 1H), 7.59 (d, J=16 Hz, 1H), 7.61 (d, J=16 Hz, 1H), 7.63 (d, J=8.2 Hz, 1H), 7.68 (dd, J=~2, 8.2 Hz, 1H), 7.8 (br s, OH), 7.93 (d, J=~2 Hz, 1H).

Melting Point (decomposed before melting), MS (ESI+) m/z 391 (M+1), 413 (M+Na).

Example 147

Synthesis of (1E,6E)-1-(4-hydroxyphenyl)-7-(1H-indol-5-yl)hepta-1,6-diene-3,5-dione (CU187)

The title compound was synthesized using the same procedure employed for Example 22, but with 1H-indole-5-carboxaldehyde (16 mg, 0.11 mmol) instead of 3-hydroxy-4-methoxybenzaldehyde (16 mg, 0.11 mmol). The product was obtained as a solid (3.4 mg, 12%) having the following characteristics.

$^1$H NMR (δ, acetone-$d_6$): 6.01 (s, 1H), 6.55 (m, 1H), 6.68 (d, J=16 Hz, 1H), 6.77 (d, J=16 Hz, 1H), 6.90 (d, J=8.7 Hz, 2H), 7.39 (m, 1H), 7.48 (d, J=8.2 Hz, 1H), 7.52 (dd, J=~2, 8.2 Hz, 1H), 7.57 (d, J=8.7 Hz, 2H), 7.60 (d, J=16 Hz, 1H), 7.80 (d, J=16 Hz, 1H), 7.90 (s, 1H), 8.8 (br s, OH).

Melting Point 222-226° C., MS (ESI+) m/z 332 (M+1), 354 (M+Na).

Example 148

Synthesis of (1E,6E)-1-(4-hydroxy-3-methoxyphenyl)-7-(1H-indol-5-yl)hepta-1,6-diene-3,5-dione (CU188)

The title compound was synthesized using the same procedure employed for Example 1, but with 1H-indole-5-carboxaldehyde (16 mg, 0.11 mmol) instead of 3-hydroxy-2-methoxybenzaldehyde (16 mg, 0.11 mmol). The product was obtained as a solid (4.2 mg, 14%) having the following characteristics.

$^1$H NMR (δ, acetone-$d_6$): 3.92 (s, 3H), 6.00 (s, 1H), 6.55 (m, 1H), 6.72 (d, J=16 Hz, 1H), 6.77 (d, J=16 Hz, 1H), 6.88 (d, J=8.2 Hz, 1H), 7.18 (dd, J=~2, 8.2 Hz, 1H), 7.35 (d, J=~2 Hz, 1H), 7.39 (m, 1H), 7.48 (d, J=8.7 Hz, 1H), 7.51 (dd, J=~2, 8.7 Hz, 1H), 7.59 (d, J=16 Hz, 1H), 7.80 (d, J=16 Hz, 1H), 7.90 (s, 1H), 8.1 (br s, OH).

Melting Point 135-138° C., MS (ESI+) m/z 362 (M+1), 384 (M+Na).

Example 149

Synthesis of (1E,6E)-1-(4-hydroxyphenyl)-7-(1H-indol-6-yl)hepta-1,6-diene-3,5-dione (CU189)

The title compound was synthesized using the same procedure employed for Example 22, but with 1H-indole-6-carboxaldehyde (16 mg, 0.11 mmol) instead of 3-hydroxy-4-methoxybenzaldehyde (16 mg, 0.11 mmol). The product was obtained as a solid (5.2 mg, 14%) having the following characteristics.

$^1$H NMR (δ, acetone-$d_6$): 6.02 (s, 1H), 6.52 (m, 1H), 6.68 (d, J=16 Hz, 1H), 6.80 (d, J=16 Hz, 1H), 6.90 (d, J=8.7 Hz, 2H), 7.43 (dd, J=~2, 8.2 Hz, 1H), 7.46 (m, 1H), 7.57 (d, J=8.7 Hz, 2H), 7.61 (d, J=16 Hz, 1H), 7.61 (d, J=8.7 Hz, 1H), 7.73 (s, 1H), 7.78 (d, J=16 Hz, 1H), 8.8 (br s, OH), 10.5 (br s, NH).

Melting Point 238-243° C., MS (ESI+) m/z 332 (M+1), 354 (M+Na).

Example 150

Synthesis of (1E,6E)-1-(4-hydroxy-3-methoxyphenyl)-7-(1H-indol-6-yl)hepta-1,6-diene-3,5-dione (CU190)

The title compound was synthesized using the same procedure employed for Example 1, but with 1H-indole-6-carboxaldehyde (16 mg, 0.11 mmol) instead of 3-hydroxy-2-methoxybenzaldehyde (16 mg, 0.11 mmol). The product was obtained as a solid (8.6 mg, 28%) having the following characteristics.

$^1$H NMR (δ, acetone-$d_6$): 3.92 (s, 3H), 6.01 (s, 1H), 6.52 (m, 1H), 6.72 (d, J=16 Hz, 1H), 6.79 (d, J=16 Hz, 1H), 6.88 (d, J=8.2 Hz, 1H), 7.18 (dd, J=1.9, 8.2 Hz, 1H), 7.35 (d, J=1.9 Hz, 1H), 7.43 (dd, J=~2, 8.2 Hz, 1H), 7.46 (m, 1H), 7.60 (d, J=16 Hz, 1H), 7.61 (d, J=8.2 Hz, 1H), 7.73 (s, 1H), 7.78 (d, J=16 Hz, 1H), 8.1 (br s, OH), 10.5 (br s, NH).

Melting Point 201-206° C., MS (ESI+) m/z 362 (M+1), 384 (M+Na).

Example 151

Synthesis of (1E,6E)-1-(3-hydroxy-4-methoxyphenyl)-7-(1H-indol-6-yl)hepta-1,6-diene-3,5-dione (CU191)

The title compound was synthesized using the same procedure employed for Example 29, but with 1H-indole-6-carboxaldehyde (16 mg, 0.11 mmol) instead of 3,4-dimethoxybenzaldehyde (18 mg, 0.11 mmol). The product was obtained as a solid (8.0 mg, 26%) having the following characteristics.

$^1$H NMR (δ, acetone-$d_6$): 3.89 (s, 3H), 6.04 (s, 1H), 6.52 (m, 1H), 6.68 (d, J=16 Hz, 1H), 6.80 (d, J=16 Hz, 1H), 7.00 (d, J=8.2 Hz, 1H), 7.14 (dd, J=~2, 8.2 Hz, 1H), 7.20 (d, J=~2 Hz, 1H), 7.43 (dd, J=~2, 8.2 Hz, 1H), 7.46 (m, 1H), 7.57 (d, J=16 Hz, 1H), 7.62 (d, J=8.2 Hz, 1H), 7.73 (s, 1H), 7.79 (d, J=16 Hz, 1H), 7.8 (br s, OH), 10.5 (br s, NH).

Melting Point 197-202° C., MS (ESI+) m/z 362 (M+1), 384 (M+Na).

Example 152

Synthesis of (1E,6E)-1-(4-dimethylamino-2-nitrophenyl)-7-(4-hydroxy-3-methoxyphenyl)hepta-1,6-diene-3,5-dione (CU192)

The title compound was synthesized using the same procedure employed for Example 1, but with 4-dimethylamino-2-nitrobenzaldehyde (21 mg, 0.11 mmol) instead of 3-hydroxy-2-methoxybenzaldehyde (16 mg, 0.11 mmol). The product was obtained as a solid (6.4 mg, 18%) having the following characteristics.

$^1$H NMR (δ, acetone-$d_6$): 3.13 (s, 6H), 3.92 (s, 3H), 5.99 (s, 1H), 6.70 (d, J=16 Hz, 1H), 6.73 (d, J=16 Hz, 1H), 6.88 (d, J=8.2 Hz, 1H), 7.05 (dd, J=2.9, 9.2 Hz, 1H), 7.16 (d, J=2.9 Hz, 1H), 7.18 (dd, J=~2, 8.2 Hz, 1H), 7.34 (d, J=~2 Hz, 1H), 7.61 (d, J=16 Hz, 1H), 7.81 (d, J=16 Hz, 1H), 7.82 (d, J=9.2 Hz, 1H), 8.1 (br s, OH).

Melting Point 203-210° C., MS (ESI+) m/z 411 (M+1).

Example 153

Synthesis of (1E,6E)-1-(3-hydroxy-4-methoxyphenyl)-7-(1H-indol-5-yl)hepta-1,6-diene-3,5-dione (CU193)

The title compound was synthesized using the same procedure employed for Example 29, but with 1H-indole-5-carboxaldehyde (16 mg, 0.11 mmol) instead of 3,4-dimethoxybenzaldehyde (18 mg, 0.11 mmol). The product was obtained as a solid (5.8 mg, 19%) having the following characteristics.

$^1$H NMR (δ, acetone-$d_6$): 3.90 (s, 3H), 6.03 (s, 1H), 6.55 (m, 1H), 6.68 (d, J=16 Hz, 1H), 6.78 (d, J=16 Hz, 1H), 7.00 (d, J=8.2 Hz, 1H), 7.14 (dd, J=2.4, 8.2 Hz, 1H), 7.20 (d, J=2.4 Hz, 1H), 7.39 (m, 1H), 7.48 (d, J=8.7 Hz, 1H), 7.52 (dd, J=~2, 8.7 Hz, 1H), 7.56 (d, J=16 Hz, 1H), 7.81 (d, J=16 Hz, 1H), 7.8 (br s, OH), 7.91 (s, 1H).

Melting Point 182-185° C., MS (ESI+) m/z 362 (M+1), 384 (M+Na).

Example 154

Synthesis of (1E,6E)-1-(4-dimethylamino-2-nitrophenyl)-7-(4-hydroxyphenyl)hepta-1,6-diene-3,5-dione (CU194)

The title compound was synthesized using the same procedure employed for Example 22, but with 4-dimethylamino-2-nitrobenzaldehyde (21 mg, 0.11 mmol) instead of 3-hydroxy-4-methoxybenzaldehyde (16 mg, 0.11 mmol). The product was obtained as a solid (8.4 mg, 26%) having the following characteristics.

$^1$H NMR (δ, acetone-$d_6$): 3.12 (s, 6H), 5.99 (s, 1H), 6.68 (d, J=16 Hz, 1H), 6.71 (d, J=16 Hz, 1H), 6.90 (d, J=8.7 Hz, 2H), 7.04 (dd, J=2.4, 8.7 Hz, 1H), 7.15 (d, J=2.4 Hz, 1H), 7.57 (d, J=8.7 Hz, 2H), 7.62 (d, J=16 Hz, 1H), 7.81 (d, J=16 Hz, 1H), 7.82 (d, J=8.7 Hz, 1H), 8.9 (br s, OH).

Melting Point 217-222° C., MS (ESI+) m/z 381 (M+1).

Example 155

Synthesis of (1E,6E)-1-(2-chloro-4-dimethylaminophenyl)-7-(4-hydroxyphenyl)hepta-1,6-diene-3,5-dione (CU195)

The title compound was synthesized using the same procedure employed for Example 22, but with 2-chloro-4-dimethylaminobenzaldehyde (20 mg, 0.11 mmol) instead of 3-hydroxy-4-methoxybenzaldehyde (16 mg, 0.11 mmol). The product was obtained as a solid (3.8 mg, 12%) having the following characteristics.

$^1$H NMR (δ, acetone-$d_6$): 3.06 (s, 6H), 5.96 (s, 1H), 6.65 (d, J=16 Hz, 1H), 6.67 (d, J=16 Hz, 1H), 6.73~6.78 (m, 2H), 6.90 (d, J=8.7 Hz, 2H), 7.57 (d, J=8.7 Hz, 2H), 7.60 (d, J=16 Hz, 1H), 7.75 (d, J=9.7 Hz, 1H), 8.00 (d, J=16 Hz, 1H), 8.9 (br s, OH).

Melting Point decomposed at 112° C., MS (ESI+) m/z 370 (M+1), 392 (M+Na).

Example 156

Synthesis of (1E,6E)-1-(2-chloro-4-dimethylaminophenyl)-7-(4-hydroxy-3-methoxyphenyl)hepta-1,6-diene-3,5-dione (CU196)

The title compound was synthesized using the same procedure employed for Example 1, but with 2-chloro-4-dimethylaminobenzaldehyde (20 mg, 0.11 mmol) instead of 3-hydroxy-2-methoxybenzaldehyde (16 mg, 0.11 mmol). The product was obtained as a solid (4.4 mg, 13%) having the following characteristics.

$^1$H NMR (δ, acetone-$d_6$): 3.06 (s, 6H), 3.92 (s, 3H), 5.95 (s, 1H), 6.64 (d, J=16 Hz, 1H), 6.71 (d, J=16 Hz, 1H), 6.73~6.78 (m, 2H), 6.88 (d, J=8.2 Hz, 1H), 7.18 (dd, J=1.9, 8.2 Hz, 1H), 7.34 (d, J=1.9 Hz, 1H), 7.59 (d, J=16 Hz, 1H), 7.74 (d, J=9.7 Hz, 1H), 7.99 (d, J=16 Hz, 1H), 8.1 (br s, OH).

Melting Point 113-120° C., MS (ESI+) m/z 400 (M+1).

Example 157

Synthesis of (1E,6E)-1-(4-dimethylamino-2-nitrophenyl)-7-(3-hydroxy-4-methoxyphenyl)hepta-1,6-diene-3,5-dione (CU197)

The title compound was synthesized using the same procedure employed for Example 29, but with 4-dimethylamino-2-nitrobenzaldehyde (21 mg, 0.11 mmol) instead of 3,4-dimethoxybenzaldehyde (18 mg, 0.11 mmol). The product was obtained as a solid (7.0 mg, 20%) having the following characteristics.

$^1$H NMR (δ, acetone-$d_6$): 3.13 (s, 6H), 3.89 (s, 3H), 6.01 (s, 1H), 6.69 (d, J=16 Hz, 1H), 6.72 (d, J=16 Hz, 1H), 7.00 (d, J=8.7 Hz, 1H), 7.05 (dd, J=~2, 8.7 Hz, 1H), 7.14 (dd, J=~2, 8.7 Hz, 1H), 7.15 (d, J=~2 Hz, 1H), 7.21 (d, J=~2 Hz, 1H), 7.57 (d, J=16 Hz, 1H), 7.8 (br s, OH), 7.81 (d, J=16 Hz, 1H), 7.83 (d, J=8.7 Hz, 1H).

Melting Point 183-186° C., MS (ESI+) m/z 411 (M+1), 433 (M+Na).

Example 158

Synthesis of (1E,6E)-1-(4-hydroxy-3-methoxyphenyl)-7-(1-methyl-1H-pyrrazol-4-yl)hepta-1,6-diene-3,5-dione (CU199)

The title compound was synthesized using the same procedure employed for Example 1, but with 1-methyl-1H-pyrrazole-4-carboxaldehyde (12 mg, 0.11 mmol) instead of 3-hydroxy-2-methoxybenzaldehyde (16 mg, 0.11 mmol). The product was obtained as a solid (5.8 mg, 21%) having the following characteristics.

$^1$H NMR (δ, acetone-$d_6$): 3.90 (s, 3H), 3.91 (s, 3H), 5.89 (s, 1H), 6.53 (d, J=16 Hz, 1H), 6.69 (d, J=16 Hz, 1H), 6.87 (d, J=8.2 Hz, 1H), 7.17 (dd, J=1.9, 8.2 Hz, 1H), 7.32 (d, J=1.9 Hz, 1H), 7.56 (d, J=16 Hz, 1H), 7.57 (d, J=16 Hz, 1H), 7.78 (s, 1H), 7.96 (s, 1H), 8.1 (br s, OH).

Melting Point 80-83° C., MS (ESI+) m/z 327 (M+1), 349 (M+Na).

Example 159

Synthesis of (1E,6E)-1-(3-hydroxy-4-methoxyphenyl)-7-(1-methyl-1H-pyrrazol-4-yl)hepta-1,6-diene-3,5-dione (CU200)

The title compound was synthesized using the same procedure employed for Example 29, but with 1-methyl-1H-pyrrazole-4-carboxaldehyde (12 mg, 0.11 mmol) instead of 3,4-dimethoxybenzaldehyde (18 mg, 0.11 mmol). The product was obtained as a solid (25.0 mg, 90%) having the following characteristics.

$^1$H NMR (δ, acetone-$d_6$): 3.89 (s, 3H), 3.90 (s, 3H), 5.91 (s, 1H), 6.54 (d, J=16 Hz, 1H), 6.65 (d, J=16 Hz, 1H), 6.99 (d, J=8.2 Hz, 1H), 7.13 (dd, J=1.9, 8.2 Hz, 1H), 7.19 (d, J=1.9 Hz, 1H), 7.54 (d, J=16 Hz, 1H), 7.56 (d, J=16 Hz, 1H), 7.79 (s, 1H), 7.97 (s, 1H).

Melting Point decomposed at 188° C., MS (ESI+) m/z 327 (M+1).

Example 160

Synthesis of (1E,6E)-1-(3,5-dichlorophenyl)-7-(4-hydroxyphenyl)hepta-1,6-diene-3,5-dione (CU201)

The title compound was synthesized using the same procedure employed for Example 22, but with 3,5-dichlorobenzaldehyde (19 mg, 0.11 mmol) instead of 3-hydroxy-4-methoxybenzaldehyde (16 mg, 0.11 mmol). The product was obtained as a solid (3.0 mg, 10%) having the following characteristics.

$^1$H NMR (δ, acetone-$d_6$): 6.08 (s, 1H), 6.72 (d, J=16 Hz, 1H), 6.91 (d, J=8.7 Hz, 2H), 7.02 (d, J=16 Hz, 1H), 7.49 (t, J=1.9 Hz, 1H), 7.56 (d, J=16 Hz, 1H), 7.59 (d, J=8.7 Hz, 2H), 7.67 (d, J=16 Hz, 1H), 7.72 (t, J=1.9 Hz, 2H), 8.9 (br s, OH).

Melting Point 165-172° C., MS (ESI+) m/z 361 (M+1).

Example 161

Synthesis of (1E,6E)-1-(2-chloro-4-dimethylaminophenyl)-7-(3-hydroxy-4-methoxyphenyl)hepta-1,6-diene-3,5-dione (CU202)

The title compound was synthesized using the same procedure employed for Example 29, but with 2-chloro-4-dimethylaminobenzaldehyde (20 mg, 0.11 mmol) instead of 3,4-dimethoxybenzaldehyde (18 mg, 0.11 mmol). The product was obtained as a solid (12.6 mg, 37%) having the following characteristics.

$^1$H NMR (δ, acetone-$d_6$): 3.06 (s, 6H), 3.89 (s, 3H), 5.97 (s, 1H), 6.65 (d, J=16 Hz, 1H), 6.67 (d, J=16 Hz, 1H), 6.73~6.78 (m, 2H), 6.99 (d, J=8.2 Hz, 1H), 7.14 (dd, J=2.4, 8.2 Hz, 1H), 7.20 (d, J=2.4 Hz, 1H), 7.55 (d, J=16 Hz, 1H), 7.74 (d, J=9.7 Hz, 1H), 7.8 (br s, 1H), 8.00 (d, J=16 Hz, 1H).

Melting Point 160-164° C., MS (ESI+) m/z 400 (M+1), 422 (M+Na).

Example 162

Synthesis of (1E,6E)-1-(4-hydroxyphenyl)-7-(4-methanesulfonylphenyl)hepta-1,6-diene-3,5-dione (CU203)

The title compound was synthesized using the same procedure employed for Example 22, but with 4-methanesulfonylbenzaldehyde (20 mg, 0.11 mmol) instead of 3-hydroxy-4-methoxybenzaldehyde (16 mg, 0.11 mmol). The product was obtained as a solid (1.5 mg, 5%) having the following characteristics.

$^1$H NMR (δ, acetone-$d_6$): 3.15 (s, 3H), 6.12 (s, 1H), 6.73 (d, J=16 Hz, 1H), 6.91 (d, J=8.7 Hz, 2H), 7.04 (d, J=16 Hz, 1H), 7.60 (d, J=8.7 Hz, 2H), 7.68 (d, J=16 Hz, 1H), 7.70 (d, J=16 Hz, 1H), 7.95 (d, J=8.7 Hz, 2H), 7.99 (d, J=8.7 Hz, 2H), 8.9 (br s, OH).

Melting Point 221-224° C., MS (ESI+) m/z 371 (M+1).

Example 163

Synthesis of (1E,6E)-1-(4-hydroxyphenyl)-7-(3,4,5-trimethoxyphenyl)hepta-1,6-diene-3,5-dione (CU204)

The title compound was synthesized using the same procedure employed for Example 22, but with 3,4,5-trimethoxybenzaldehyde (22 mg, 0.11 mmol) instead of 3-hydroxy-4-methoxybenzaldehyde (16 mg, 0.11 mmol). The product was obtained as a solid (8.8 mg, 27%) having the following characteristics.

$^1$H NMR (δ, acetone-$d_6$): 3.77 (s, 3H), 3.89 (s, 6H), 6.00 (s, 1H), 6.67 (d, J=16 Hz, 1H), 6.82 (d, J=16 Hz, 1H), 6.90 (d, J=8.7 Hz, 2H), 7.03 (s, 2H), 7.57 (d, J=8.7 Hz, 2H), 7.58 (d, J=16 Hz, 1H), 7.63 (d, J=16 Hz, 1H), 8.9 (br s, OH).

Melting Point 101-105° C., MS (ESI+) m/z 383 (M+1), 405 (M+Na).

Example 164

Synthesis of (1E,6E)-1-(3-hydroxy-4-methoxyphenyl)-7-(3,4,5-trimethoxyphenyl)hepta-1,6-diene-3,5-dione (CU205)

The title compound was synthesized using the same procedure employed for Example 29, but with 3,4,5-trimethoxybenzaldehyde (22 mg, 0.11 mmol) instead of 3,4-dimethoxybenzaldehyde (18 mg, 0.11 mmol). The product was obtained as a solid (5.8 mg, 17%) having the following characteristics.

$^1$H NMR (δ, acetone-$d_6$): 3.89 (s, 6H), 3.90 (s, 3H), 6.02 (s, 1H), 6.67 (d, J=16 Hz, 1H), 6.82 (d, J=16 Hz, 1H), 7.00 (d, J=8.2 Hz, 1H), 7.04 (s, 2H), 7.14 (dd, J=2.4, 8.2 Hz, 1H), 7.20 (d, J=2.4 Hz, 1H), 7.58 (d, J=16 Hz, 1H), 7.59 (d, J=16 Hz, 1H), 7.8 (br s, 1H).

Melting Point 195-200° C., MS (ESI+) m/z 413 (M+1), 435 (M+Na).

Example 165

Synthesis of (1E,6E)-1-(4-dimethylaminophenyl)-7-(4-hydroxyphenyl)hepta-1,6-diene-3,5-dione (CU207)

The title compound was synthesized using the same procedure employed for Example 22, but with 4-dimethylaminobenzaldehyde (16 mg, 0.11 mmol) instead of 3-hydroxy-4-methoxybenzaldehyde (16 mg, 0.11 mmol). The product was obtained as a solid (4.8 mg, 17%) having the following characteristics.

$^1$H NMR (δ, acetone-$d_6$): 3.03 (s, 6H), 5.93 (s, 1H), 6.57 (d, J=16 Hz, 1H), 6.64 (d, J=16 Hz, 1H), 6.76 (d, J=9.2 Hz, 2H), 6.90 (d, J=8.7 Hz, 2H), 7.53 (d, J=9.2 Hz, 2H), 7.55 (d, J=8.7 Hz, 2H), 7.57 (d, J=16 Hz, 1H), 7.59 (d, J=16 Hz, 1H), 8.9 (br s, OH).

Melting Point 205-209° C., MS (ESI+) m/z 336 (M+1).

Example 166

Synthesis of (1E,6E)-1-(4-dimethylaminophenyl)-7-(3-hydroxy-4-methoxyphenyl)hepta-1,6-diene-3,5-dione (CU208)

The title compound was synthesized using the same procedure employed for Example 29, but with 4-dimethylaminobenzaldehyde (16 mg, 0.11 mmol) instead of 3,4-dimethoxybenzaldehyde (18 mg, 0.11 mmol). The product was obtained as a solid (3.2 mg, 10%) having the following characteristics.

$^1$H NMR (δ, acetone-$d_6$): 3.04 (s, 6H), 3.89 (s, 3H), 5.95 (s, 1H), 6.58 (d, J=16 Hz, 1H), 6.65 (d, J=16 Hz, 1H), 6.76 (d, J=8.7 Hz, 2H), 6.99 (d, J=8.2 Hz, 1H), 7.12 (dd, J=1.9, 8.2 Hz, 1H), 7.19 (d, J=1.9 Hz, 1H), 7.52 (d, J=16 Hz, 1H), 7.53 (d, J=8.7 Hz, 2H), 7.60 (d, J=16 Hz, 1H), 7.8 (br s, 1H).

Melting Point 181-185° C., MS (ESI+) m/z 336 (M+1).

Example 167

Synthesis of (1E,6E)-1-(2,3-dihydrobenzo[1,4]dioxin-6-yl)-7-(4-hydroxy-3-methoxyphenyl)hepta-1,6-diene-3,5-dione (CU209)

The title compound was synthesized using the same procedure employed for Example 1, but with 2,3-dihydrobenzo[1,4]dioxine-6-carboxaldehyde (18 mg, 0.11 mmol) instead of 3-hydroxy-2-methoxybenzaldehyde (16 mg, 0.11 mmol). The product was obtained as a solid (12.6 mg, 39%) having the following characteristics.

$^1$H NMR (δ, acetone-$d_6$): 3.92 (s, 3H), 4.27~4.37 (m, 4H), 5.98 (s, 1H), 6.68 (d, J=16 Hz, 1H), 6.71 (d, J=16 Hz, 1H), 6.87 (d, J=8.2 Hz, 1H), 6.88 (d, J=8.2 Hz, 1H), 7.15~7.23 (m, 3H), 7.34 (d, J=1.9 Hz, 1H), 7.54 (d, J=16 Hz, 1H), 7.60 (d, J=16 Hz, 1H), 8.1 (br s, OH).

Example 168

Synthesis of (1E,6E)-1-(2,3-dihydrobenzo[1,4]dioxin-6-yl)-7-(3-hydroxy-4-methoxyphenyl)hepta-1,6-diene-3,5-dione (CU210)

The title compound was synthesized using the same procedure employed for Example 29, but with 2,3-dihydrobenzo[1,4]dioxine-6-carboxaldehyde (18 mg, 0.11 mmol) instead of 3,4-dimethoxybenzaldehyde (18 mg, 0.11 mmol). The product was obtained as a solid (8.0 mg, 25%) having the following characteristics.

$^1$H NMR (δ, acetone-$d_6$): 3.89 (s, 3H), 4.27~4.37 (m, 4H), 6.01 (s, 1H), 6.67 (d, J=16 Hz, 1H), 6.70 (d, J=16 Hz, 1H), 6.87 (d, J=8.2 Hz, 1H), 7.00 (d, J=8.2 Hz, 1H), 7.14 (dd, J=1.9, 8.2 Hz, 1H), 7.16~7.2 (m, 2H), 7.20 (d, J=1.9 Hz, 1H), 7.55 (d, J=16 Hz, 1H), 7.57 (d, J=16 Hz, 1H), 7.8 (br s, 1H).

Melting Point 163-165° C., MS (ESI+) m/z 381 (M+1), 403 (M+Na).

Example 169

Synthesis of (1E,6E)-1-(furan-2-yl)-7-(3-hydroxy-4-methoxyphenyl)hepta-1,6-diene-3,5-dione (CU211)

The title compound was synthesized using the same procedure employed for Example 29, but with furfural (11 mg, 0.11 mmol) instead of 3,4-dimethoxybenzaldehyde (18 mg, 0.11 mmol). The product was obtained as a solid (4.0 mg, 15%) having the following characteristics.

$^1$H NMR (δ, acetone-$d_6$): 3.90 (s, 3H), 6.05 (s, 1H), 6.57 (d, J=16 Hz, 1H), 6.6~6.62 (m, 1H), 6.68 (d, J=16 Hz, 1H), 6.85 (d, J=2.4 Hz, 1H), 7.00 (d, J=8.2 Hz, 1H), 7.15 (dd, J=2.4, 8.2 Hz, 1H), 7.20 (d, J=2.4 Hz, 1H), 7.44 (d, J=16 Hz, 1H), 7.59 (d, J=16 Hz, 1H), 7.72 (d, J=~2 Hz, 1H), 7.8 (br s, 1H).

Melting Point 120-123° C., MS (ESI+) m/z 313 (M+1), 335 (M+Na).

Example 170

Synthesis of (1E,6E)-1-(3-hydroxy-4-methoxyphenyl)-7-(thiophen-2-yl)hepta-1,6-diene-3,5-dione (CU212)

The title compound was synthesized using the same procedure employed for Example 29, but with 2-thiophenecarboxaldehyde (12 mg, 0.11 mmol) instead of 3,4-dimethoxybenzaldehyde (18 mg, 0.11 mmol). The product was obtained as a solid (3.4 mg, 12%) having the following characteristics.

$^1$H NMR (δ, acetone-$d_6$): 3.90 (s, 3H), 6.04 (s, 1H), 6.57 (d, J=16 Hz, 1H), 6.67 (d, J=16 Hz, 1H), 7.00 (d, J=8.2 Hz, 1H), 7.13~7.18 (m, 2H), 7.20 (d, J=1.9 Hz, 1H), 7.46 (d, J=3.4 Hz, 1H), 7.58 (d, J=16 Hz, 1H), 7.62 (d, J=4.8 Hz, 1H), 7.80 (d, J=16 Hz, 1H), 7.8 (br s, OH).

Melting Point 128-133° C., MS (ESI+) m/z 329 (M+1), 351 (M+Na).

Example 171

Synthesis of (1E,6E)-1-(4-hydroxyphenyl)-7-(4-phenoxyphenyl)hepta-1,6-diene-3,5-dione (CU213)

The title compound was synthesized using the same procedure employed for Example 22, but with 4-phenoxybenzaldehyde (22 mg, 0.11 mmol) instead of 3-hydroxy-4-methoxybenzaldehyde (16 mg, 0.11 mmol). The product was obtained as a solid (14.4 mg, 44%) having the following characteristics.

$^1$H NMR (δ, acetone-$d_6$): 6.02 (s, 1H), 6.68 (d, J=16 Hz, 1H), 6.78 (d, J=16 Hz, 1H), 6.90 (d, J=8.2 Hz, 2H), 7.02 (d, J=8.2 Hz, 2H), 7.08 (d, J=7.7 Hz, 2H), 7.20 (t, J=7.3 Hz, 1H), 7.43 (dd, J=7.3, 7.7 Hz, 2H), 7.57 (d, J=8.2 Hz, 2H), 7.63 (d, J=16 Hz, 1H), 7.64 (d, J=16 Hz, 1H), 7.71 (d, J=8.2 Hz, 2H), 8.9 (br s, OH).

Melting Point 175-178° C., MS (ESI+) m/z 385 (M+1), 407 (M+Na).

Example 172

Synthesis of (1E,6E)-1-(4-hydroxyphenyl)-7-(3-phenoxyphenyl)hepta-1,6-diene-3,5-dione (CU214)

The title compound was synthesized using the same procedure employed for Example 22, but with 3-phenoxybenzaldehyde (22 mg, 0.11 mmol) instead of 3-hydroxy-4-methoxybenzaldehyde (16 mg, 0.11 mmol). The product was obtained as a solid (21.2 mg, 65%) having the following characteristics.

$^1$H NMR (δ, acetone-$d_6$): 6.04 (s, 1H), 6.68 (d, J=16 Hz, 1H), 6.84 (d, J=16 Hz, 1H), 6.90 (d, J=8.7 Hz, 2H), 7.02~7.05 (m, 1H), 7.05 (d, J=8.7 Hz, 2H), 7.16 (t, J=7.3 Hz, 1H), 7.34 (d, J=~2 Hz, 1H), 7.40 (dd, J=7.3, 8.7 Hz, 2H), 7.4~7.47 (m, 2H), 7.57 (d, J=8.7 Hz, 2H), 7.61 (d, J=16 Hz, 1H), 7.64 (d, J=16 Hz, 1H), 8.9 (br s, OH).

Melting Point 194-198° C., MS (ESI+) m/z 385 (M+1).

Example 173

Synthesis of (1E,6E)-1-(benzo[1,3]dioxol-5-yl)-7-(4-hydroxyphenyl)hepta-1,6-diene-3,5-dione (CU215)

The title compound was synthesized using the same procedure employed for Example 22, but with piperonal (16 mg, 0.11 mmol) instead of 3-hydroxy-4-methoxybenzaldehyde (16 mg, 0.11 mmol). The product was obtained as a solid (6.0 mg, 21%) having the following characteristics.

$^1$H NMR (δ, acetone-$d_6$): 5.99 (s, 1H), 6.07 (s, 2H), 6.67 (d, J=16 Hz, 1H), 6.72 (d, J=16 Hz, 1H), 6.90 (d, J=8.7 Hz, 2H), 6.90 (d, J=8.2 Hz, 1H), 7.18 (dd, J=~2, 8.2 Hz, 1H), 7.27 (d, J=~2 Hz, 1H), 7.57 (d, J=8.7 Hz, 2H), 7.58 (d, J=16 Hz, 1H), 7.61 (d, J=16 Hz, 1H), 8.9 (br s, OH).

Melting Point 197-200° C., MS (ESI+) m/z 337 (M+1), 359 (M+Na).

Example 174

Synthesis of (1E,6E)-1-(3-hydroxy-4-methoxyphenyl)-7-(4-methylthiophenyl)hepta-1,6-diene-3,5-dione (CU216)

The title compound was synthesized using the same procedure employed for Example 29, but with 4-methylthiobenzaldehyde (17 mg, 0.11 mmol) instead of 3,4-dimethoxybenzaldehyde (18 mg, 0.11 mmol). The product was obtained as a solid (10.2 mg, 33%) having the following characteristics.

$^1$H NMR (δ, acetone-$d_6$): 2.53 (s, 3H), 3.90 (s, 3H), 6.04 (s, 1H), 6.68 (d, J=16 Hz, 1H), 6.81 (d, J=16 Hz, 1H), 7.00 (d, J=8.2 Hz, 1H), 7.14 (d, J=1.9, 8.2 Hz, 1H), 7.21 (d, J=1.9 Hz, 1H), 7.31 (d, J=8.7 Hz, 2H), 7.58 (d, J=16 Hz, 1H), 7.62 (d, J=16 Hz, 1H), 7.63 (d, J=8.7 Hz, 2H), 7.8 (br s, OH).

Melting Point 158-162° C., MS (ESI+) m/z 369 (M+1), 391 (M+Na).

Example 175

Synthesis of (1E,6E)-1-(3-hydroxy-4-methoxyphenyl)-7-(pyridin-3-yl)hepta-1,6-diene-3,5-dione (CU217)

The title compound was synthesized using the same procedure employed for Example 29, but with pyridine-3-carboxaldehyde (12 mg, 0.11 mmol) instead of 3,4-dimethoxybenzaldehyde (18 mg, 0.11 mmol). The product was obtained as a solid (4.4 mg, 16%) having the following characteristics.
$^1$H NMR ($\delta$, acetone-$d_6$): 3.90 (s, 3H), 6.09 (s, 1H), 6.71 (d, J=16 Hz, 1H), 6.98 (d, J=16 Hz, 1H), 7.01 (d, J=8.2 Hz, 1H), 7.16 (d, J=1.9, 8.2 Hz, 1H), 7.22 (d, J=1.9 Hz, 1H), 7.43 (d, J=4.8, 7.7 Hz, 1H), 7.62 (d, J=16 Hz, 1H), 7.66 (d, J=16 Hz, 1H), 7.8 (br s, OH), 8.10 (m, 1H), 8.57 (dd, J=1.5, 4.8 Hz, 1H), 8.86 (d, J=~2 Hz, 1H).
Melting Point 174-175° C., MS (ESI+) m/z 324 (M+1).

Example 176

Synthesis of (1E,6E)-1-(3-hydroxy-4-methoxyphenyl)-7-(pyridin-2-yl)hepta-1,6-diene-3,5-dione (CU218)

The title compound was synthesized using the same procedure employed for Example 29, but with pyridine-2-carboxaldehyde (12 mg, 0.11 mmol) instead of 3,4-dimethoxybenzaldehyde (18 mg, 0.11 mmol). The product was obtained as a solid (4.4 mg, 16%) having the following characteristics.
$^1$H NMR ($\delta$, acetone-$d_6$): 3.90 (s, 3H), 6.17 (s, 1H), 6.74 (d, J=16 Hz, 1H), 7.01 (d, J=8.2 Hz, 1H), 7.17 (d, J=1.9, 8.2 Hz, 1H), 7.23 (d, J=1.9 Hz, 1H), 7.24 (d, J=16 Hz, 1H), 7.33~7.38 (m, 1H), 7.63 (d, J=16 Hz, 1H), 7.64 (d, J=16 Hz, 1H), 7.62~7.66 (m, 1H), 7.82~7.88 (m, 1H), 7.8 (br s, OH), 8.62~8.66 (m, 1H).
Melting Point 182-187° C., MS (ESI+) m/z 324 (M+1).

Example 177

Synthesis of (1E,6E)-1-(3-hydroxy-4-methoxyphenyl)-7-(4-phenoxyphenyl)hepta-1,6-diene-3,5-dione (CU219)

The title compound was synthesized using the same procedure employed for Example 29, but with 4-phenoxybenzaldehyde (22 mg, 0.11 mmol) instead of 3,4-dimethoxybenzaldehyde (18 mg, 0.11 mmol). The product was obtained as a solid (3.2 mg, 9%) having the following characteristics.
$^1$H NMR ($\delta$, acetone-$d_6$): 3.90 (s, 3H), 6.04 (s, 1H), 6.69 (d, J=16 Hz, 1H), 6.79 (d, J=16 Hz, 1H), 7.01 (d, J=8.2 Hz, 1H), 7.03 (d, J=8.7 Hz, 2H), 7.09 (dd, J=1, 8.7 Hz, 2H), 7.14 (d, J=1.9, 8.2 Hz, 1H), 7.20 (t, J=7.3 Hz, 1H), 7.20 (d, J=1.9 Hz, 1H), 7.43 (dd, J=7.3, 8.7 Hz, 2H), 7.58 (d, J=16 Hz, 1H), 7.65 (d, J=16 Hz, 1H), 7.72 (d, J=8.7 Hz, 2H), 7.8 (br s, OH).
Melting Point 185-187° C., MS (ESI+) m/z 415 (M+1), 437 (M+Na).

Example 178

Synthesis of (1E,6E)-1-(3-hydroxy-4-methoxyphenyl)-7-(3-phenoxyphenyl)hepta-1,6-diene-3,5-dione (CU220)

The title compound was synthesized using the same procedure employed for Example 29, but with 3-phenoxybenzaldehyde (22 mg, 0.11 mmol) instead of 3,4-dimethoxybenzaldehyde (18 mg, 0.11 mmol). The product was obtained as a solid (10.6 mg, 30%) having the following characteristics.
$^1$H NMR ($\delta$, acetone-$d_6$): 3.90 (s, 3H), 6.06 (s, 1H), 6.69 (d, J=16 Hz, 1H), 6.85 (d, J=16 Hz, 1H), 7.00 (d, J=8.2 Hz, 1H), 7.01~7.06 (m, 1H), 7.05 (dd, J=1.0, 8.7 Hz, 2H), 7.13~7.19 (m, 2H), 7.20 (d, J=1.9 Hz, 1H), 7.35 (d, J=~2 Hz, 1H), 7.41 (dd, J=7.3, 8.7 Hz, 2H), 7.4~7.48 (m, 2H), 7.59 (d, J=16 Hz, 1H), 7.62 (d, J=16 Hz, 1H), 7.8 (br s, OH).
Melting Point 148-150° C., MS (ESI+) m/z 415 (M+1), 437 (M+Na).

Example 179

Synthesis of (1E,6E)-1-(2,5-dichlorophenyl)-7-(4-hydroxyphenyl)hepta-1,6-diene-3,5-dione (CU229)

The title compound was synthesized using the same procedure employed for Example 22, but with 2,5-dichlorobenzaldehyde (19 mg, 0.11 mmol) instead of 3-hydroxy-4-methoxybenzaldehyde (16 mg, 0.11 mmol). The product was obtained as a solid (11.8 mg, 38%) having the following characteristics.
$^1$H NMR ($\delta$, acetone-$d_6$): 6.11 (s, 1H), 6.73 (d, J=16 Hz, 1H), 6.91 (d, J=8.7 Hz, 2H), 7.01 (d, J=16 Hz, 1H), 7.44 (dd, J=~2, 8 Hz, 1H), 7.55 (d, J=8 Hz, 1H), 7.60 (d, J=8.7 Hz, 2H), 7.68 (d, J=16 Hz, 1H), 7.90 (d, J=16 Hz, 1H), 7.92 (d, J=2 Hz, 1H).
MS (ESI+) m/z 361 (M+1).

Example 180

Synthesis of (1E,6E)-1-(furan-2-yl)-7-(4-hydroxyphenyl)hepta-1,6-diene-3,5-dione (CU231)

The title compound was synthesized using the same procedure employed for Example 22, but with furfural (11 mg, 0.11 mmol) instead of 3-hydroxy-4-methoxybenzaldehyde (16 mg, 0.11 mmol). The product was obtained as a solid (17.0 mg, 71%) having the following characteristics.
$^1$H NMR ($\delta$, acetone-$d_6$): 6.03 (s, 1H), 6.57 (d, J=16 Hz, 1H), 6.60 (d, J=1.9, 3.4 Hz, 1H), 6.68 (d, J=16 Hz, 1H), 6.84 (d, J=3.4 Hz, 1H), 6.90 (d, J=8.7 Hz, 2H), 7.44 (d, J=16 Hz, 1H), 7.58 (d, J=8.7 Hz, 2H), 7.63 (d, J=16 Hz, 1H), 7.71 (d, J=~2 Hz, 1H), 8.9 (br s, OH).
MS (ESI+) m/z 283 (M+1), 305 (M+Na).

Example 181

Synthesis of (1E,6E)-1-(2,3-dihydrobenzo[1,4]dioxin-6-yl)-7-(4-hydroxyphenyl)hepta-1,6-diene-3,5-dione (CU232)

The title compound was synthesized using the same procedure employed for Example 22, but with 2,3-dihydrobenzo[1,4]dioxine-6-carboxaldehyde (18 mg, 0.11 mmol) instead of 3-hydroxy-4-methoxybenzaldehyde (16 mg, 0.11 mmol). The product was obtained as a solid (17.0 mg, 47%) having the following characteristics.
$^1$H NMR ($\delta$, acetone-$d_6$): 4.27-4.37 (m, 4H), 5.99 (s, 1H), 6.67 (d, J=16 Hz, 1H), 6.69 (d, J=16 Hz, 1H), 6.87 (d, J=8.2 Hz, 1H), 6.90 (d, J=8.7 Hz, 2H), 7.17 (dd, J=~2, 8.2 Hz, 1H), 7.18 (br s, 1H), 7.54 (d, J=16 Hz, 1H), 7.57 (d, J=8.7 Hz, 2H), 7.61 (d, J=16 Hz, 1H), 8.9 (br s, OH).
Melting Point 169-173° C., MS (ESI+) m/z 351 (M+1), 373 (M+Na).

Example 182

Synthesis of (1E,6E)-1-(4-hydroxyphenyl)-7-(pyridin-2-yl)hepta-1,6-diene-3,5-dione (CU233)

The title compound was synthesized using the same procedure employed for Example 22, but with pyridine-2-carboxaldehyde (12 mg, 0.11 mmol) instead of 3-hydroxy-4-methoxybenzaldehyde (16 mg, 0.11 mmol). The product was obtained as a solid (4.4 mg, 18%) having the following characteristics.

$^1$H NMR (δ, acetone-$d_6$): 6.15 (s, 1H), 6.74 (d, J=16 Hz, 1H), 6.91 (d, J=8.7 Hz, 2H), 7.24 (d, J=16 Hz, 1H), 7.33~7.38 (m, 1H), 7.60 (d, J=8.7 Hz, 2H), 7.62 (d, J=16 Hz, 1H), 7.69 (d, J=16 Hz, 1H), 7.69 (ddd, J=1.9, 7.7, 7.7 Hz, 1H), 8.63~8.66 (m, 1H), 8.9 (br s, OH).

Melting Point 180-182° C., MS (ESI+) m/z 294 (M+1).

Example 183

Synthesis of (1E,6E)-1-(4-hydroxyphenyl)-7-(4-methylthiophenyl)hepta-1,6-diene-3,5-dione (CU235)

The title compound was synthesized using the same procedure employed for Example 22, but with 4-methylthiobenzaldehyde (16 mg, 0.11 mmol) instead of 3-hydroxy-4-methoxybenzaldehyde (16 mg, 0.11 mmol). The product was obtained as a solid (10.0 mg, 35%) having the following characteristics.

$^1$H NMR (δ, acetone-$d_6$): 2.53 (s, 3H), 6.02 (s, 1H), 6.68 (d, J=16 Hz, 1H), 6.81 (d, J=16 Hz, 1H), 6.90 (d, J=8.7 Hz, 2H), 7.31 (d, J=8.7 Hz, 2H), 7.58 (d, J=8.7 Hz, 2H), 7.62 (d, J=8.7 Hz, 2H), 7.63 (d, J=16 Hz, 1H), 7.55-7.6 (d, 1H), 8.9 (br s, OH).

Melting Point 169-171° C., MS (ESI+) m/z 339 (M+1), 361 (M+Na).

Example 184

Synthesis of (1E,6E)-1-[4-(3-dimethylaminopropoxy)phenyl]-7-(4-hydroxyphenyl)hepta-1,6-diene-3,5-dione (CU236)

The title compound was synthesized using the same procedure employed for Example 22, but with 4-(3-dimethylaminopropoxy)benzaldehyde (23 mg, 0.11 mmol) instead of 3-hydroxy-4-methoxybenzaldehyde (16 mg, 0.11 mmol). The product was obtained as a solid (2.1 mg, 6%) having the following characteristics.

$^1$H NMR (δ, acetone-$d_6$): 1.8-2.0 (m, 2H), 2.18 (s, 6H), 2.42 (t, J=6.8 Hz, 2H), 4.11 (t, J=6.3 Hz, 2H), 5.99 (s, 1H), 6.67 (d, J=16 Hz, 1H), 6.71 (d, J=16 Hz, 1H), 6.90 (d, J=8.7 Hz, 2H), 6.99 (d, J=8.7 Hz, 2H), 7.57 (d, J=8.7 Hz, 2H), 7.61 (d, J=16 Hz, 1H), 7.62 (d, J=16 Hz, 1H), 7.63 (d, J=8.7 Hz, 2H).

Melting Point 140-143° C., MS (ESI+) m/z 394 (M+1).

Example 185

Synthesis of (1E,6E)-1-(4-hydroxyphenyl)-7-(thiophen-2-yl)hepta-1,6-diene-3,5-dione (CU237)

The title compound was synthesized using the same procedure employed for Example 22, but with 2-thiophenecarboxaldehyde (12 mg, 0.11 mmol) instead of 3-hydroxy-4-methoxybenzaldehyde (16 mg, 0.11 mmol). The product was obtained as a solid (10.6 mg, 41%) having the following characteristics.

$^1$H NMR (δ, acetone-$d_6$): 6.03 (s, 1H), 6.56 (d, J=16 Hz, 1H), 6.67 (d, J=16 Hz, 1H), 6.90 (d, J=8.7 Hz, 2H), 7.14 (dd, J=3.9, 4.8 Hz, 1H), 7.45 (d, J=3.9 Hz, 1H), 7.57 (d, J=8.7 Hz, 2H), 7.61 (d, J=4.8 Hz, 1H), 7.63 (d, J=16 Hz, 1H), 7.79 (d, J=16 Hz, 1H), 8.9 (br s, OH).

MS (ESI+) m/z 299 (M+1), 321 (M+Na).

Example 186

Synthesis of (1E,6E)-1-[4-(3-dimethylaminopropoxy)phenyl]-7-(3-hydroxy-4-methoxyphenyl)hepta-1,6-diene-3,5-dione (CU241)

The title compound was synthesized using the same procedure employed for Example 29, but with 4-(3-dimethylaminopropoxy)benzaldehyde (23 mg, 0.11 mmol) instead of 3-hydroxy-2-methoxybenzaldehyde (16 mg, 0.11 mmol). The product was obtained as a solid (1.8 mg, 5%) having the following characteristics.

$^1$H NMR (δ, acetone-$d_6$): 1.8-2.0 (m, 2H), 2.18 (s, 6H), 2.4~2.45 (m, 2H), 3.90 (s, 3H), 4.11 (t, J=6.3 Hz, 2H), 6.01 (s, 1H), 6.67 (d, J=16 Hz, 1H), 6.71 (d, J=16 Hz, 1H), 6.99 (d, J=8.7 Hz, 2H), 7.00 (d, J=8.2 Hz, 1H), 7.14 (dd, J=1.9, 8.2 Hz, 1H), 7.20 (d, J=1.9 Hz, 1H), 7.56 (d, J=16 Hz, 1H), 7.62 (d, J=16 Hz, 1H), 7.64 (d, J=8.7 Hz, 2H).

Melting Point 183-186° C., MS (ESI+) m/z 424 (M+1).

Example 187

Synthesis of (1E,6E)-1-[3-hydroxy-2-(methoxymethoxy)phenyl]-7-(4-hydroxyphenyl)hepta-1,6-diene-3,5-dione (CU247)

(1) Synthesis of 2,3-bis(methoxymethoxy)benzaldehyde 2,3-Dihydroxybenzaldehyde (300 mg, 2.17 mmol) was placed in a 20 mL reaction vessel, and dissolved in 6.5 mL of dry dichloromethane. To the solution were added N,N-diisopropylethylamine (1.1 mL, 6.3 mmol), 4-dimethylaminopyridine (13 mg, 0.11 mmol), and chloromethyl methyl ether (412 μL, 5.43 mmol). After being stirred at room temperature overnight, the reaction mixture was diluted with 100 mL of ethyl acetate and 20 mL of 1N HCl, and extracted. The extract was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate) to obtain the title compound as a colorless oil (400 mg, 81%).

(2) Synthesis of (1E,6E)-1-[3-hydroxy-2-(methoxymethoxy)phenyl]-7-(4-hydroxyphenyl)hepta-1,6-diene-3,5-dione (CU247)

The title compound was synthesized using the same procedure employed for Example 22, but with 2,3-bis(methoxymethoxy)benzaldehyde (26 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. The product was obtained as a solid (4.4 mg, 14%) having the following characteristics.

$^1$H NMR (δ, acetone-$d_6$): 3.46 (s, 3H), 5.23 (s, 2H), 6.02 (s, 1H), 6.70 (d, J=16 Hz, 1H), 6.83 (dd, J=8.2, 8.2 Hz, 1H), 6.90 (d, J=16 Hz, 1H), 6.90 (d, J=8.7 Hz, 2H), 7.14 (dd, J=0.9, 8.2

Hz, 1H), 7.30 (dd, J=0.9, 8.2 Hz, 1H), 7.58 (d, J=8.7 Hz, 2H), 7.63 (d, J=16 Hz, 1H), 8.00 (d, J=16 Hz, 1H), 8.3 (br s, OH), 8.9 (br s, OH).

Melting Point 158-161° C., MS (ESI+) m/z 369 (M+1), 391 (M+Na).

Example 188

Synthesis of (1E,6E)-1-[3-hydroxy-2-(methoxymethoxy)phenyl]-7-(3-hydroxy-4-methoxyphenyl)hepta-1,6-diene-3,5-dione (CU248)

The title compound was synthesized using the same procedure employed for Example 29, but with 2,3-bis(methoxymethoxy)benzaldehyde (26 mg, 0.11 mmol) instead of 3,4-dimethoxybenzaldehyde (18 mg, 0.11 mmol), and the stirring time after addition of a 1:1 solution of 1N HCl and brine was extended to 5 h. The product was obtained as a solid (4.0 mg, 12%) having the following characteristics.

$^1$H NMR (δ, acetone-$d_6$): 3.47 (s, 3H), 3.90 (s, 3H), 5.23 (s, 2H), 6.04 (s, 1H), 6.70 (d, J=16 Hz, 1H), 6.83 (d, J=7.7, 8.2 Hz, 1H), 6.91 (d, J=16 Hz, 1H), 7.00 (d, J=8.2 Hz, 1H), 7.14 (dd, J=~1, 7.7 Hz, 1H), 7.15 (dd, J=1.9, 8.2 Hz, 1H), 7.21 (d, J=1.9 Hz, 1H), 7.30 (dd, J=1, 8.2 Hz, 1H), 7.58 (d, J=16 Hz, 1H), 7.8 (br s, 1H), 8.00 (d, J=16 Hz, 1H), 8.3 (br s, OH).

Melting Point 79-83° C., MS (ESI+) m/z 399 (M+1).

Example 189

Synthesis of (1E,6E)-1-(2-hydroxy-3-methoxyphenyl)-7-(4-hydroxyphenyl)hepta-1,6-diene-3,5-dione (CU249)

(1) Synthesis of 3-methoxy-2-(methoxymethoxy)benzaldehyde

2-Hydroxy-3-methoxybenzaldehyde (90 mg, 0.59 mmol) was placed in a 20 mL reaction vessel, and dissolved in 1.8 mL of dry dichloromethane. To the solution were added N,N-diisopropylethylamine (0.30 mL, 1.7 mmol), 4-dimethylaminopyridine (9 mg, 0.07 mmol), and chloromethyl methyl ether (112 µL, 1.48 mmol). After being stirred at room temperature overnight, the reaction mixture was diluted with 30 mL of ethyl acetate and 7 mL of 1N HCl, and extracted. The extract was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate) to obtain the title compound as a pale yellow oil (93.4 mg, 80%).

(2) Synthesis of (1E,6E)-1-(2-hydroxy-3-methoxyphenyl)-7-(4-hydroxyphenyl)hepta-1,6-diene-3,5-dione (CU249)

The title compound was synthesized using the same procedure employed for Example 22, but with 3-methoxy-2-(methoxymethoxy)benzaldehyde (22 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. The product was obtained as a solid (11.4 mg, 40%) having the following characteristics.

$^1$H NMR (δ, acetone-$d_6$): 3.88 (s, 3H), 6.02 (s, 1H), 6.70 (d, J=16 Hz, 1H), 6.84 (dd, J=8.2, 8.2 Hz, 1H), 6.89 (d, J=16 Hz, 1H), 6.90 (d, J=8.7 Hz, 2H), 7.00 (dd, J=~2, 8.2 Hz, 1H), 7.22 (dd, J=~2, 8.2 Hz, 1H), 7.58 (d, J=8.7 Hz, 2H), 7.63 (d, J=16 Hz, 1H), 8.01 (d, J=16 Hz, 1H), 8.2 (br s, OH), 8.9 (br s, OH).

Melting Point 169-175° C., MS (ESI+) m/z 339 (M+1).

Example 190

Synthesis of (1E,6E)-1-(2-hydroxy-3-methoxyphenyl)-7-(4-hydroxy-3-methoxyphenyl)hepta-1,6-diene-3,5-dione (CU250)

The title compound was synthesized using the same procedure employed for Example 1, but with 3-methoxy-2-(methoxymethoxy)benzaldehyde (22 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (7.4 mg, 24%) having the following characteristics.

$^1$H NMR (δ, acetone-$d_6$): 3.88 (s, 3H), 3.92 (s, 3H), 6.01 (s, 1H), 6.74 (d, J=16 Hz, 1H), 6.85 (dd, J=7.7, 8.2 Hz, 1H), 6.88 (d, J=8.2 Hz, 1H), 6.88 (d, J=16 Hz, 1H), 7.00 (dd, J=~2, 8.2 Hz, 1H), 7.19 (dd, J=1.9, 8.2 Hz, 1H), 7.22 (dd, J=~2, 7.7 Hz, 1H), 7.35 (d, J=1.9 Hz, 1H), 7.62 (d, J=16 Hz, 1H), 8.01 (d, J=16 Hz, 1H), 8.1 (br s, OH), 8.2 (br s, OH).

Melting Point 156-158° C., MS (ESI+) m/z 369 (M+1).

Example 191

Synthesis of (1E,6E)-1-(2-hydroxy-4-methoxyphenyl)-7-(4-hydroxyphenyl)hepta-1,6-diene-3,5-dione (CU251)

The title compound was synthesized using the same procedure employed for Example 22, but with 4-methoxy-2-(methoxymethoxy)benzaldehyde (22 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. The product was obtained as a solid (5.0 mg, 17%) having the following characteristics.

$^1$H NMR (δ, acetone-$d_6$): 3.78 (s, 3H), 5.94 (s, 1H), 6.5~6.54 (m, 2H), 6.66 (d, J=16 Hz, 1H), 6.77 (d, J=16 Hz, 1H), 6.89 (d, J=8.7 Hz, 2H), 7.56 (d, J=8.7 Hz, 2H), 7.57 (m, 1H), 7.58 (d, J=16 Hz, 1H), 7.94 (d, J=16 Hz, 1H), 9.0 (br s, OH).

Melting Point 137-139° C., MS (ESI+) m/z 339 (M+1).

Example 192

Synthesis of (1E,6E)-1-(2-hydroxy-5-methoxyphenyl)-7-(4-hydroxyphenyl)hepta-1,6-diene-3,5-dione (CU253)

The title compound was synthesized using the same procedure employed for Example 22, but with 5-methoxy-2-(methoxymethoxy)benzaldehyde (22 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. The product was obtained as a solid (9.0 mg, 31%) having the following characteristics.

$^1$H NMR (δ, acetone-$d_6$): 3.78 (s, 3H), 6.01 (s, 1H), 6.69 (d, J=16 Hz, 1H), 6.85 (dd, J=2.9, 8.7 Hz, 1H), 6.90 (d, J=8.7 Hz, 2H), 6.90 (d, J=8.7 Hz, 1H), 6.91 (d, J=16 Hz, 1H), 7.19 (d, J=2.9 Hz, 1H), 7.57 (d, J=8.7 Hz, 2H), 7.62 (d, J=16 Hz, 1H), 7.99 (d, J=16 Hz, 1H), 8.8 (br s, OH).

Melting Point 167-170° C., MS (ESI+) m/z 339 (M+1).

Example 193

Synthesis of (1E,6E)-1-(2-hydroxy-4-methoxyphenyl)-7-(4-hydroxy-3-methoxyphenyl)hepta-1,6-diene-3,5-dione (CU256)

The title compound was synthesized using the same procedure employed for Example 1, but with 4-methoxy-2-(methoxymethoxy)benzaldehyde (22 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (4.6 mg, 15%) having the following characteristics.

$^1$H NMR ($\delta$, acetone-$d_6$): 3.78 (s, 3H), 3.91 (s, 3H), 5.93 (s, 1H), 6.5~6.54 (m, 2H), 6.70 (d, J=16 Hz, 1H), 6.76 (d, J=16 Hz, 1H), 6.86 (d, J=8.2 Hz, 1H), 7.17 (dd, J=~2, 8.2 Hz, 1H), 7.33 (d, J=~2 Hz, 1H), 7.56 (d, J=9.7 Hz, 1H), 7.57 (d, J=16 Hz, 1H), 7.94 (d, J=16 Hz, 1H), 8.1 (br s, OH), 9.1 (br s, OH).

Melting Point 108-113° C., MS (ESI+) m/z 369 (M+1).

Example 194

Synthesis of (1E,6E)-1-(2,4-dihydroxyphenyl)-7-(4-hydroxy-3-methoxyphenyl)hepta-1,6-diene-3,5-dione (CU257)

The title compound was synthesized using the same procedure employed for Example 1, but with 2,4-bis(methoxymethoxy)benzaldehyde (26 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (2.8 mg, 9%) having the following characteristics.

$^1$H NMR ($\delta$, acetone-$d_6$): 3.91 (s, 3H), 5.91 (s, 1H), 6.43 (dd, J=1.9, 8.7 Hz, 1H), 6.47 (d, J=1.9 Hz, 1H), 6.70 (d, J=16 Hz, 1H), 6.72 (d, J=16 Hz, 1H), 6.86 (d, J=8.2 Hz, 1H), 7.16 (dd, J=1.9, 8.2 Hz, 1H), 7.32 (d, J=1.9 Hz, 1H), 7.48 (d, J=8.7 Hz, 1H), 7.52 (d, J=16 Hz, 1H), 7.94 (d, J=16 Hz, 1H), 8.1 (br s, OH), 8.8 (br s, OH).

Melting Point 99-108° C., MS (ESI+) m/z 355 (M+1).

Example 195

Synthesis of (1E,6E)-1-(2,4-dihydroxyphenyl)-7-(3-hydroxy-4-methoxyphenyl)hepta-1,6-diene-3,5-dione (CU258)

The title compound was synthesized using the same procedure employed for Example 29, but with 2,4-bis(methoxymethoxy)benzaldehyde (26 mg, 0.11 mmol) instead of 3,4-dimethoxybenzaldehyde (18 mg, 0.11 mmol), and the stirring time after addition of a 1:1 solution of 1N HCl and brine was extended to 5 h. The product was obtained as a solid (2.8 mg, 9%) having the following characteristics.

$^1$H NMR ($\delta$, acetone-$d_6$): 3.88 (s, 3H), 5.94 (s, 1H), 6.43 (dd, J=2.4, 8.7 Hz, 1H), 6.47 (d, J=2.4 Hz, 1H), 6.66 (d, J=16 Hz, 1H), 6.73 (d, J=16 Hz, 1H), 6.98 (d, J=8.2 Hz, 1H), 7.12 (dd, J=~2, 8.2 Hz, 1H), 7.18 (d, J=2 Hz, 1H), 7.49 (d, J=8.7 Hz, 1H), 7.52 (d, J=16 Hz, 1H), 7.8 (br s, OH), 7.94 (d, J=16 Hz, 1H), 8.8 (br s, OH).

Melting Point 104-109° C., MS (ESI+) m/z 355 (M+1).

Example 196

Synthesis of (1E,6E)-1-[2-hydroxy-6-(methoxymethoxy)phenyl]-7-(4-hydroxy-3-methoxyphenyl)hepta-1,6-diene-3,5-dione (CU259)

(1) Synthesis of 2,6-bis(methoxymethoxy)benzaldehyde 2,6-Dihydroxybenzaldehyde (75 mg, 0.54 mmol) was placed in a 20 mL reaction vessel, and dissolved in 1.6 mL of dry dichloromethane. To the solution were added N,N-diisopropylethylamine (0.30 mL, 1.7 mmol), 4-dimethylaminopyridine (4 mg, 0.03 mmol), and chloromethyl methyl ether (103 µL, 0.68 mmol). After being stirred at room temperature overnight, the reaction mixture was diluted with 25 mL of ethyl acetate and 5 mL of 1N HCl, and extracted. The extract was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate) to obtain the title compound as a pale yellow oil (96.9 mg, 79%).

(2) Synthesis of (1E,6E)-1-[2-hydroxy-6-(methoxymethoxy)phenyl]-7-(4-hydroxy-3-methoxyphenyl)hepta-1,6-diene-3,5-dione (CU259)

The title compound was synthesized using the same procedure employed for Example 1, but with 2,6-bis(methoxymethoxy)benzaldehyde (26 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (4.4 mg, 12%) having the following characteristics.

$^1$H NMR ($\delta$, acetone-$d_6$): 3.49 (s, 3H), 3.92 (s, 3H), 5.31 (s, 2H), 5.94 (s, 1H), 6.64 (d, J=8.2 Hz, 1H), 6.70 (d, J=7.7 Hz, 1H), 6.73 (d, J=16 Hz, 1H), 6.88 (d, J=8.2 Hz, 1H), 7.15 (dd, J=7.7, 8.2 Hz, 1H), 7.18 (dd, J=1.9, 8.2 Hz, 1H), 7.27 (d, J=16 Hz, 1H), 7.34 (d, J=1.9 Hz, 1H), 7.60 (d, J=16 Hz, 1H), 8.1 (br s, OH), 8.16 (d, J=16 Hz, 1H).

Melting Point 76-81° C., MS (ESI+) m/z 399 (M+1), 421 (M+Na).

Example 197

Synthesis of (1E,6E)-1-[4-diethylamino-2-(methoxymethoxy)phenyl]-7-(4-hydroxyphenyl)hepta-1,6-diene-3,5-dione (CU261) and (1E,6E)-1-(4-diethylamino-2-hydroxyphenyl)-7-(4-hydroxyphenyl)hepta-1,6-diene-3,5-dione (CU262)

(1) Synthesis of 4-diethylamino-2-(methoxymethoxy)benzaldehyde

4-Diethylamino-2-hydroxybenzaldehyde (300 mg, 1.55 mmol) was placed in a 20 mL reaction vessel, and dissolved in 4.7 mL of dry dichloromethane. To the solution were added N,N-diisopropylethylamine (0.40 mL, 2.3 mmol), 4-dimethylaminopyridine (13 mg, 0.11 mmol), and chloromethyl methyl ether (147 µL, 1.94 mmol). After the reaction mixture was stirred at room temperature overnight, N,N-diisopropylethylamine (0.40 mL, 2.3 mmol), 4-dimethylaminopyridine (13 mg, 0.11 mmol), and chloromethyl methyl ether (147 µL, 1.94 mmol) were added again with additional stirring for 3 h. The resulting mixture was diluted with 100 mL of ethyl acetate and 20 mL of 1N HCl, and extracted. The extract was washed with 1N HCl, saturated NaHCO$_3$ aqueous solution, brine, and dried over MgSO₄. After filtration, the filtrate was concentrated in vacuo, and the residue was purified by silica gel column chromatography (hexane/ethyl acetate) to obtain the title compound as a pale yellow oil (324.7 mg, 88%).

(2) Synthesis of (1E,6E)-1-[4-diethylamino-2-(methoxymethoxy)phenyl]-7-(4-hydroxyphenyl)hepta-1,6-diene-3,5-dione (CU261) and (1E,6E)-1-(4-diethylamino-2-hydroxyphenyl)-7-(4-hydroxyphenyl)hepta-1,6-diene-3,5-dione (CU262)

The title compound was synthesized using the same procedure employed for Example 22, but with 4-diethylamino-2-(methoxymethoxy)benzaldehyde (26 mg, 0.11 mmol) instead of 3-hydroxy-4-methoxybenzaldehyde (16 mg, 0.11 mmol), and the stirring time after addition of a 1:1 solution of 1N HCl and brine was extended to 5 h.

(1E,6E)-1-[4-diethylamino-2-(methoxymethoxy)phenyl]-7-(4-hydroxyphenyl)hepta-1,6-diene-3,5-dione (5.2 mg, 14%) and (1E,6E)-1-(4-diethylamino-2-hydroxyphenyl)-7-(4-hydroxyphenyl)hepta-1,6-diene-3,5-dione (3.4 mg, 10%) were obtained, respectively, as solids having the following characteristics.

(1E,6E)-1-[4-diethylamino-2-(methoxymethoxy)phenyl]-7-(4-hydroxyphenyl)hepta-1,6-diene-3,5-dione (CU261)
$^1$H NMR (δ, acetone-$d_6$): 1.18 (t, J=7 Hz, 6H), 3.45 (q, J=7 Hz, 4H), 3.49 (s, 3H), 5.32 (s, 2H), 5.87 (s, 1H), 6.43 (dd, J=2.4, 8.7 Hz, 1H), 6.48 (d, J=2.4 Hz, 1H), 6.60 (d, J=16 Hz, 1H), 6.64 (d, J=16 Hz, 1H), 6.89 (d, J=8.7 Hz, 2H), 7.52 (d, J=8.7 Hz, 1H), 7.55 (d, J=8.7 Hz, 2H), 7.55 (d, J=16 Hz, 1H), 7.97 (d, J=16 Hz, 1H), 8.8 (br s, OH).
Melting Point 72-76° C., MS (ESI+) m/z 424 (M+1).
(1E,6E)-1-(4-diethylamino-2-hydroxyphenyl)-7-(4-hydroxyphenyl)hepta-1,6-diene-3,5-dione (CU262)
$^1$H NMR (δ, acetone-$d_6$): 1.16 (t, J=7 Hz, 6H), 3.39 (q, J=7 Hz, 4H), 5.86 (s, 1H), 6.25 (d, J=2.9 Hz, 1H), 6.32 (dd, J=2.9, 8.7 Hz, 1H), 6.61 (d, J=16 Hz, 1H), 6.64 (d, J=16 Hz, 1H), 6.89 (d, J=8.7 Hz, 2H), 7.43 (d, J=8.7 Hz, 1H), 7.53 (d, J=16 Hz, 1H), 7.54 (d, J=8.7 Hz, 2H), 7.96 (d, J=16 Hz, 1H), 8.7 (br s, OH), 8.8 (br s, OH).
Melting Point 120-123° C., MS (ESI+) m/z 380 (M+1).

Example 198

Synthesis of (1E,6E)-1,7-bis(9-ethyl-9H-carbazol-3-yl)hepta-1,6-diene-3,5-dione (CU263)

Acetylacetone (20 µL, 195 µmol) and boron trioxide (16 mg, 0.23 mmol) was placed in a 20 mL reaction vessel, and dissolved in 2 mL of ethyl acetate. To the stirring mixture at 80° C. were added 9-ethyl-9H-carbazole-3-carboxaldehyde (110 mg, 0.49 mmol) and tri-n-butyl borate (57 µL, 0.21 mmol), successively. After the reaction mixture was stirred for 2 h at the same temperature, piperidine (52 µL, 0.53 mmol) was added with additional stirring for 1 h at 100° C. The reaction mixture was treated with a 1:1 solution (1 mL) of 1N HCl and brine, and was stirred at 50° C. for 1 h. The organic layer was purified directly by silica gel column chromatography (eluting with hexane/ethyl acetate or chloroform/methanol) to obtain the title compound (12.2 mg, 12%) as a solid.
$^1$H NMR (δ, acetone-$d_6$): 1.43 (t, J=7 Hz, 6H), 4.52 (q, J=7 Hz, 4H), 6.10 (s, 1H), 6.92 (d, J=16 Hz, 2H), 7.27 (d, J=7.2, 7.7 Hz, 2H), 7.50 (d, J=7.2, 8.7 Hz, 2H), 7.61 (d, J=8.7 Hz, 2H), 7.64 (d, J=8.7 Hz, 2H), 7.85 (d, J=8.7 Hz, 2H), 7.90 (d, J=16 Hz, 2H), 8.22 (d, J=7.7 Hz, 2H), 8.53 (s, 2H).
Melting Point 264-267° C., MS (ESI+) m/z 511 (M+1).

Example 199

Synthesis of (1E,6E)-1-(2,3-dihydroxyphenyl)-7-(4-hydroxyphenyl)hepta-1,6-diene-3,5-dione (CU264)

The title compound was synthesized using the same procedure employed for Example 188 (2), but the stirring time after addition of a 1:1 solution of 1N HCl and brine was extended to 9 h. The product was obtained as a solid (6.0 mg, 22%) having the following characteristics.
$^1$H NMR (δ, acetone-$d_6$): 6.02 (s, 1H), 6.70 (d, J=16 Hz, 1H), 6.73 (dd, J=7.7, 8.2 Hz, 1H), 6.88 (d, J=16 Hz, 1H), 6.90 (dd, J=2, 7.7 Hz, 1H), 6.90 (d, J=8.7 Hz, 2H), 7.14 (dd, J=~2, 8.2 Hz, 1H), 7.58 (d, J=8.7 Hz, 2H), 7.63 (d, J=16 Hz, 1H), 7.9 (br s, OH), 8.00 (d, J=16 Hz, 1H), 8.7 (br s, OH), 8.8 (br s, OH).
Melting Point 173-176° C., MS (ESI+) m/z 325 (M+1).

Example 200

Synthesis of (1E,6E)-1-(2,3-dihydroxyphenyl)-7-(3-hydroxy-4-methoxyphenyl)hepta-1,6-diene-3,5-dione (CU265)

The title compound was synthesized using the same procedure employed for Example 188, but the stirring time after addition of a 1:1 solution of 1N HCl and brine was extended to 9 h. The product was obtained as a solid (5.8 mg, 19%) having the following characteristics.
$^1$H NMR (δ, acetone-$d_6$): 3.90 (s, 3H), 6.04 (s, 1H), 6.70 (d, J=16 Hz, 1H), 6.73 (dd, J=7.7, 8.2 Hz, 1H), 6.89 (d, J=16 Hz, 1H), 6.90 (dd, J=2.4, 7.7 Hz, 1H), 7.00 (d, J=8.2 Hz, 1H), 7.14 (d, J=8.2 Hz, 1H), 7.14 (dd, J=2.4, 8.2 Hz, 1H), 7.21 (d, J=2.4 Hz, 1H), 7.58 (d, J=16 Hz, 1H), 7.8 (br s, OH), 8.0 (br s, OH), 8.00 (d, J=16 Hz, 1H), 8.7 (br s, OH).
Melting Point 170-172° C., MS (ESI+) m/z 355 (M+1).

Example 201

Synthesis of (1E,6E)-1-(2-hydroxy-3-methoxyphenyl)-7-(3-hydroxy-4-methoxyphenyl)hepta-1,6-diene-3,5-dione (CU273)

The title compound was synthesized using the same procedure employed for Example 29, but with 3-methoxy-2-(methoxymethoxy)benzaldehyde (22 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (4.2 mg, 14%) having the following characteristics.
$^1$H NMR (δ, acetone-$d_6$): 3.88 (s, 3H), 3.90 (s, 3H), 6.04 (s, 1H), 6.70 (d, J=16 Hz, 1H), 6.85 (dd, J=7.7, 8.2 Hz, 1H), 6.90 (d, J=16 Hz, 1H), 7.00 (dd, J=2, 8 Hz, 1H), 7.00 (d, J=8.2 Hz, 1H), 7.14 (dd, J=2.4, 8.2 Hz, 1H), 7.21 (d, J=2.4 Hz, 1H), 7.23 (dd, J=2, 8.2 Hz, 1H), 7.58 (d, J=16 Hz, 1H), 7.8 (br s, OH), 8.01 (d, J=16 Hz, 1H), 8.1 (br s, OH).
Melting Point 155-157° C., MS (ESI+) m/z 369 (M+1), 391 (M+Na).

Example 202

Synthesis of (1E,6E)-1-(2-hydroxy-6-methoxyphenyl)-7-(4-hydroxyphenyl)hepta-1,6-diene-3,5-dione (CU275)

(1) Synthesis of 6-methoxy-2-(methoxymethoxy)benzaldehyde

2-Hydroxy-6-methoxybenzaldehyde (200 mg, 1.31 mmol) was placed in a 20 mL reaction vessel, and dissolved in 3.9 mL of dry dichloromethane. To the solution were added N,N-diisopropylethylamine (0.70 mL, 4.0 mmol), 4-dimethylaminopyridine (20 mg, 0.16 mmol), and chloromethyl methyl ether (250 µL, 3.28 mmol). After being stirred at room temperature overnight, the reaction mixture was diluted with 70 mL of ethyl acetate and 15 mL of 1N HCl, and extracted. The extract was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate) to obtain the title compound as a pale yellow oil (224.4 mg, 87%).

(2) Synthesis of (1E,6E)-1-(2-hydroxy-6-methoxyphenyl)-7-(4-hydroxyphenyl)hepta-1,6-diene-3,5-dione (CU275)

The title compound was synthesized using the same procedure employed for Example 22, but with 6-methoxy-2-(methoxymethoxy)benzaldehyde (22 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. The product was obtained as a solid (12.2 mg, 42%) having the following characteristics.

$^1$H NMR (δ, acetone-d$_6$): 3.91 (s, 3H), 5.94 (s, 1H), 6.57 (d, J=8.2 Hz, 1H), 6.59 (d, J=8.2 Hz, 1H), 6.68 (d, J=16 Hz, 1H), 6.90 (d, J=8.7 Hz, 2H), 7.17 (dd, J=8.2, 8.2 Hz, 1H), 7.23 (d, J=16 Hz, 1H), 7.57 (d, J=8.7 Hz, 2H), 7.61 (d, J=16 Hz, 1H), 8.16 (d, J=16 Hz, 1H), 8.9 (br s, OH).

Melting Point 94-99° C., MS (ESI+) m/z 339 (M+1).

Example 203

Synthesis of (1E,6E)-1-(3,5-dichloro-2-hydroxyphenyl)-7-(3-hydroxy-4-methoxyphenyl)hepta-1,6-diene-3,5-dione (CU276)

(1) Synthesis of 3,5-dichloro-2-(methoxymethoxy)benzaldehyde 3,5-Dichloro-2-hydroxy-benzaldehyde (200 mg, 1.57 mmol) was placed in a 20 mL reaction vessel, and dissolved in 4.7 mL of dry dichloromethane. To the solution were added N,N-diisopropylethylamine (0.40 mL, 2.3 mmol), 4-dimethylaminopyridine (13 mg, 0.11 mmol), and chloromethyl methyl ether (149 µL, 1.96 mmol). After being stirred at room temperature overnight, the reaction mixture was diluted with 100 mL of ethyl acetate and 20 mL of 1N HCl, and extracted. The organic layer was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate) to obtain the title compound as a white solid (314.4 mg, 85%).

(2) Synthesis of (1E,6E)-1-(3,5-dichloro-2-hydroxyphenyl)-7-(3-hydroxy-4-methoxyphenyl)hepta-1,6-diene-3,5-dione (CU276)

The title compound was synthesized using the same procedure employed for Example 29, but with 3,5-dichloro-2-(methoxymethoxy)benzaldehyde (27 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (3.2 mg, 9%) having the following characteristics.

$^1$H NMR (δ, acetone-d$_6$): 3.90 (s, 3H), 6.08 (s, 1H), 6.72 (d, J=16 Hz, 1H), 7.00 (d, J=16 Hz, 1H), 7.01 (d, J=8.2 Hz, 1H), 7.16 (dd, J=1.9, 8.2 Hz, 1H), 7.22 (d, J=1.9 Hz, 1H), 7.47 (d, J=2.4 Hz, 1H), 7.61 (d, J=16 Hz, 1H), 7.69 (d, J=2.4 Hz, 1H), 7.91 (d, J=16 Hz, 1H).

Melting Point 212-214° C., MS (ESI+) m/z 407 (M+1).

Example 204

Synthesis of (1E,6E)-1-(4-diethylamino-2-hydroxyphenyl)-7-(4-hydroxy-3-methoxyphenyl)hepta-1,6-diene-3,5-dione (CU277)

6-(4-Hydroxy-3-methoxyphenyl)hex-5-ene-2,4-dione (20 mg, 0.085 mmol) and boron trioxide (11 mg, 0.16 mmol) were placed in a 20 mL reaction vessel, and dissolved in 0.4 mL of ethyl acetate. To the stirring solution at 80° C. was added a solution of 4-diethylamino-2-(methoxymethoxy)benzaldehyde (26 mg, 0.11 mmol) and tri-n-butyl borate (25 µL, 93 µmol) in 0.7 mL of ethyl acetate. After the reaction mixture was stirred for 2 h at the same temperature, n-butylamine (10 µL, 0.10 mmol) was added with additional stirring for 1 h. The resulting mixture was diluted with 25 mL of brine, and the solution was extracted with 50 mL of ethyl acetate. The extract was dried over MgSO$_4$, filtered, and concentrated in vacuo to give a crude solid of (1E,6E)-1-[4-diethylamino-2-(methoxymethoxy)phenyl]-7-(4-hydroxy-3-methoxyphenyl)hepta-1,6-diene-3,5-dione (61.5 mg).

To the above crude solid were added molecular sieves 4A (0.37 g) and 3.7 mL of dichloromethane under nitrogen. After cooled to −40° C., the mixture was treated with tert-butyldimethylsilyl bromide (181 µL, 1.36 mmol) with additional stirring for 30 min at −30° C. After quench with 20 mL of saturated NaHCO$_3$ aqueous solution, the solution was extracted with 40 mL of ethyl acetate twice. The extracts were washed with brine, and dried over MgSO$_4$. After filtration, the filtrate was concentrated in vacuo, and the residue was purified by silica gel column chromatography (hexane/ethyl acetate) to obtain the title compound as a solid (16.2 mg, 47%) having the following characteristics.

$^1$H NMR (δ, acetone-d$_6$): 1.15 (t, J=7 Hz, 6H), 3.40 (q, J=7 Hz, 4H), 3.91 (s, 3H), 5.86 (s, 1H), 6.25 (d, J=2.4 Hz, 1H), 6.32 (dd, J=2.4, 8.7 Hz, 1H), 6.61 (d, J=16 Hz, 1H), 6.68 (d, J=16 Hz, 1H), 6.87 (d, J=8.2 Hz, 1H), 7.15 (dd, J=1.9, 8.2 Hz, 1H), 7.32 (d, J=1.9 Hz, 1H), 7.43 (d, J=8.7 Hz, 1H), 7.53 (d, J=16 Hz, 1H), 7.96 (d, J=16 Hz, 1H), 8.0 (br s, OH), 8.7 (br s, OH).

Melting Point 89-92° C., MS (ESI+) m/z 410 (M+1).

Example 205

Synthesis of (1E,6E)-1-(4-diethylamino-2-hydroxyphenyl)-7-(3-hydroxy-4-methoxyphenyl)hepta-1,6-diene-3,5-dione (CU278)

6-(3-Hydroxy-4-methoxyphenyl)hex-5-ene-2,4-dione (20 mg, 0.085 mmol) and boron trioxide (11 mg, 0.16 mmol)

were placed in a 20 mL reaction vessel, and dissolved in 0.4 mL of ethyl acetate. To the stirring solution at 80° C. was added a solution of 4-diethylamino-2-(methoxymethoxy)benzaldehyde (26 mg, 0.11 mmol) and tri-n-butyl borate (25 μL, 93 μmol) in 0.7 mL of ethyl acetate. After the reaction mixture was stirred for 2 h at the same temperature, n-butylamine (10 μL, 0.10 mmol) was added with additional stirring for 1 h. The resulting mixture was diluted with 25 mL of brine, and the solution was extracted with 50 mL of ethyl acetate. The organic layer was dried over $MgSO_4$, filtered, and concentrated in vacuo to give a crude solid of (1E,6E)-1-[4-diethylamino-2-(methoxymethoxy)phenyl]-7-(4-hydroxy-3-methoxyphenyl)hepta-1,6-diene-3,5-dione (57.8 mg).

To the above crude solid were added molecular sieves 4A (0.35 g) and 3.5 mL of dry dichloromethane under nitrogen, After cooled to −40° C., the mixture was treated with tert-butyldimethylsilyl bromide (170 μL, 1.28 mmol) with additional stirring for 30 min at −30° C. After quench with 20 mL of saturated $NaHCO_3$ aqueous solution, the solution was extracted with 40 mL of ethyl acetate twice. The extracts were washed with brine, and dried over $MgSO_4$. After filtration, the filtrate was concentrated in vacuo, and the residue was purified by silica gel column chromatography (hexane/ethyl acetate) to obtain the title compound as a solid (10.8 mg, 31%) having the following characteristics.

$^1H$ NMR (δ, acetone-$d_6$): 1.16 (t, J=7 Hz, 6H), 3.40 (q, J=7 Hz, 4H), 3.89 (s, 3H), 5.89 (s, 1H), 6.25 (d, J=2.4 Hz, 1H), 6.32 (dd, J=2.4, 8.7 Hz, 1H), 6.62 (d, J=16 Hz, 1H), 6.64 (d, J=16 Hz, 1H), 6.98 (d, J=8.7 Hz, 1H), 7.11 (dd, J=1.9, 8.7 Hz, 1H), 7.18 (d, J=1.9 Hz, 1H), 7.44 (d, J=8.7 Hz, 1H), 7.49 (d, J=16 Hz, 1H), 7.7 (br s, OH), 7.97 (d, J=16 Hz, 1H), 8.7 (br s, OH).

Melting Point 101-108° C., MS (ESI+) m/z 410 (M+1).

Example 206

Synthesis of (1E,6E)-1-(2-hydroxy-6-methoxyphenyl)-7-(4-hydroxy-3-methoxyphenyl)hepta-1,6-diene-3,5-dione (CU279)

The title compound was synthesized using the same procedure employed for Example 1, but with 6-methoxy-2-(methoxymethoxy)benzaldehyde (22 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (10.0 mg, 32%) having the following characteristics.

$^1H$ NMR (δ, acetone-$d_6$): 3.91 (s, 3H), 3.92 (s, 3H), 5.94 (s, 1H), 6.57 (d, J=8.2 Hz, 1H), 6.59 (d, J=8.2 Hz, 1H), 6.72 (d, J=16 Hz, 1H), 6.88 (d, J=8.2 Hz, 1H), 7.17 (dd, J=8.2, 8.2 Hz, 1H), 7.18 (dd, J=1.9, 8.2 Hz, 1H), 7.23 (d, J=16 Hz, 1H), 7.34 (d, J=1.9 Hz, 1H), 7.59 (d, J=16 Hz, 1H), 8.16 (d, J=16 Hz, 1H).

Melting Point 161-164° C., MS (ESI+) m/z 369 (M+1).

Example 207

Synthesis of (1E,6E)-1-(2-hydroxy-6-methoxyphenyl)-7-(3-hydroxy-4-methoxyphenyl)hepta-1,6-diene-3,5-dione (CU280)

The title compound was synthesized using the same procedure employed for Example 29, but with 6-methoxy-2-(methoxymethoxy)benzaldehyde (22 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (10.4 mg, 33%) having the following characteristics.

$^1H$ NMR (δ, acetone-$d_6$): 3.89 (s, 3H), 3.91 (s, 3H), 5.96 (s, 1H), 6.57 (d, J=8.2 Hz, 1H), 6.60 (d, J=8.7 Hz, 1H), 6.69 (d, J=16 Hz, 1H), 7.00 (d, J=8.2 Hz, 1H), 7.14 (dd, J=1.9, 8.2 Hz, 1H), 7.17 (dd, J=8.2, 8.7 Hz, 1H), 7.20 (d, J=1.9 Hz, 1H), 7.24 (d, J=16 Hz, 1H), 7.56 (d, J=16 Hz, 1H), 8.17 (d, J=16 Hz, 1H).

Melting Point 181-185° C., MS (ESI+) m/z 369 (M+1).

Example 208

Synthesis of (1E,6E)-1-(3,5-dichloro-2-hydroxyphenyl)-7-(4-hydroxyphenyl)hepta-1,6-diene-3,5-dione (CU281)

The title compound was synthesized using the same procedure employed for Example 22, but with 3,5-dichloro-2-(methoxymethoxy)benzaldehyde (27 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. The product was obtained as a solid (2.8 mg, 9%) having the following characteristics.

$^1H$ NMR (δ, acetone-$d_6$): 6.06 (s, 1H), 6.72 (d, J=16 Hz, 1H), 6.91 (d, J=8.7 Hz, 2H), 6.99 (d, J=16 Hz, 1H), 7.47 (d, J=2.4 Hz, 1H), 7.59 (d, J=8.7 Hz, 2H), 7.66 (d, J=16 Hz, 1H), 7.68 (d, J=2.4 Hz, 1H), 7.91 (d, J=16 Hz, 1H), 8.9 (br s, OH).

Melting Point 199-201° C., MS (ESI+) m/z 377 (M+1).

Example 209

Synthesis of (1E,6E)-1-(2-hydroxy-4-methoxyphenyl)-7-(3-hydroxy-4-methoxyphenyl)hepta-1,6-diene-3,5-dione (CU282)

The title compound was synthesized using the same procedure employed for Example 29, but with 4-methoxy-2-(methoxymethoxy)benzaldehyde (22 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (10.0 mg, 32%) having the following characteristics.

$^1H$ NMR (δ, acetone-$d_6$): 3.79 (s, 3H), 3.89 (s, 3H), 5.97 (s, 1H), 6.5~6.55 (m, 2H), 6.67 (d, J=16 Hz, 1H), 6.78 (d, J=16 Hz, 1H), 6.99 (d, J=8.2 Hz, 1H), 7.13 (dd, J=1.9, 8.2 Hz, 1H), 7.20 (d, J=1.9 Hz, 1H), 7.54 (d, J=16 Hz, 1H), 7.57 (d, J=9.2 Hz, 1H), 7.96 (d, J=16 Hz, 1H).

Melting Point 147-152° C., MS (ESI+) m/z 369 (M+1).

Example 210

Synthesis of (1E,6E)-1-[4-(3-dimethylaminopropoxy)phenyl]-7-(4-hydroxy-3-methoxyphenyl)hepta-1,6-diene-3,5-dione (CU018)

The title compound was synthesized using the same procedure employed for Example 1, but with 4-(3-dimethylaminopropoxy)benzaldehyde (23 mg, 0.11 mmol) instead of 3-hydroxy-2-methoxybenzaldehyde (16 mg, 0.11 mmol). The product was obtained as a solid (4.1 mg, 11%) having the following characteristics.

$^1H$ NMR (δ, acetone-$d_6$): 1.8~2.0 (m, 2H), 2.18 (s, 6H), 2.41 (t, J=7 Hz, 2H), 3.92 (s, 3H), 4.11 (t, J=7 Hz, 2H), 5.99 (s, 1H), 6.70 (d, J=16 Hz, 1H), 6.71 (d, J=16 Hz, 1H), 6.88 (d, J=8.2 Hz, 1H), 6.99 (d, J=8.7 Hz, 2H), 7.17 (dd, J=~2, 8.2 Hz, 1H), 7.34 (d, J=~2 Hz, 1H), 7.60 (d, J=16 Hz, 1H), 7.62 (d, J=16 Hz, 1H), 7.63 (d, J=8.7 Hz, 2H).

Melting Point 155-159° C., MS (ESI+) m/z 424 (M+1).

Example 211

Synthesis of (1E,6E)-1-(3-chloro-4-hydroxyphenyl)-7-(4-hydroxy-3-methoxyphenyl)hepta-1,6-diene-3,5-dione (CU043)

The title compound was synthesized using the same procedure employed for Example 1, but with 3-chloro-4-hydroxybenzaldehyde (17 mg, 0.11 mmol) instead of 3-hydroxy-2-methoxybenzaldehyde (16 mg, 0.11 mmol). The product was obtained as a solid (6.1 mg, 18%) having the following characteristics.

$^1$H NMR (δ, acetone-$d_6$): 3.92 (s, 3H), 5.99 (s, 1H), 6.72 (d, J=16 Hz, 1H), 6.74 (d, J=16 Hz, 1H), 6.88 (d, J=8.2 Hz, 1H), 7.06 (d, J=8.2 Hz, 1H), 7.18 (dd, J=1.9, 8.2 Hz, 1H), 7.34 (d, J=1.9 Hz, 1H), 7.51 (dd, J=1.9, 8.2 Hz, 1H), 7.55 (d, J=16 Hz, 1H), 7.61 (d, J=16 Hz, 1H), 7.72 (d, J=1.9 Hz, 1H).

MS (ESI+) m/z 373 (M+1).

Example 212

Synthesis of (1E,6E)-1-(4-hydroxy-3-methoxyphenyl)-7-(3-methoxy-4-nitrophenyl)hepta-1,6-diene-3,5-dione (CU051)

The title compound was synthesized using the same procedure employed for Example 1, but with 3-methoxy-4-nitrobenzaldehyde (20 mg, 0.11 mmol) instead of 3-hydroxy-2-methoxybenzaldehyde (16 mg, 0.11 mmol). The product was obtained as a solid (6.8 mg, 20%) having the following characteristics.

$^1$H NMR (δ, acetone-$d_6$): 3.92 (s, 3H), 4.05 (s, 3H), 6.09 (s, 1H), 6.76 (d, J=16 Hz, 1H), 6.89 (d, J=8.2 Hz, 1H), 7.03 (d, J=16 Hz, 1H), 7.21 (dd, J=1.9, 8.2 Hz, 1H), 7.35 (d, J=1.9 Hz, 1H), 7.44 (dd, J=1.5, 8.2 Hz, 1H), 7.64 (d, J=1.5 Hz, 1H), 7.65 (d, J=16 Hz, 1H), 7.67 (d, J=16 Hz, 1H), 7.88 (d, J=8.2 Hz, 1H), 8.2 (br s, OH).

Melting Point 157-163° C., MS (ESI+) m/z 398 (M+1).

Example 213

Synthesis of (1E,6E)-1-(2-hydroxyphenyl)-7-(4-hydroxyphenyl)hepta-1,6-diene-3,5-dione (CU080)

The title compound was synthesized using the same procedure employed for Example 22, but with 2-hydroxybenzaldehyde (13 mg, 0.11 mmol) instead of 3-hydroxy-4-methoxybenzaldehyde (16 mg, 0.11 mmol). The product was obtained as a solid (2.1 mg, 8%) having the following characteristics.

$^1$H NMR (δ, acetone-$d_6$): 6.01 (s, 1H), 6.70 (d, J=16 Hz, 1H), 6.90 (d, J=16 Hz, 1H), 6.90 (d, J=8.7 Hz, 2H), 6.9~6.93 (m, 1H), 6.97 (dd, J=2, 8.2 Hz, 1H), 7.2~7.26 (m, 1H), 7.58 (d, J=8.7 Hz, 2H), 7.62 (d, J=16 Hz, 1H), 7.63 (dd, J=1.9, 8 Hz, 1H), 8.00 (d, J=16 Hz, 1H).

MS (ESI+) m/z 309 (M+1), 331 (M+Na).

Example 214

Synthesis of (1E,6E)-1-(4-hydroxyphenyl)-7-(1H-imidazol-2-yl)hepta-1,6-diene-3,5-dione (CU143)

The title compound was synthesized using the same procedure employed for Example 22, but with 1H-imidazole-2-carboxaldehyde (11 mg, 0.11 mmol) instead of 3-hydroxy-4-methoxybenzaldehyde (16 mg, 0.11 mmol). The product was obtained as a solid (2.3 mg, 10%) having the following characteristics.

$^1$H NMR (δ, acetone-$d_6$): 5.96 (s, 1H), 6.67 (d, J=16 Hz, 1H), 6.81 (d, J=16 Hz, 1H), 6.90 (d, J=8.7 Hz, 2H), 7.53 (br s, 1H), 7.57 (d, J=8.7 Hz, 2H), 7.60 (d, J=16 Hz, 1H), 7.5~7.6 (m, 1H), 7.75 (br s, 1H), 9.0 (br s, OH).

Melting Point 175-181° C., MS (ESI+) m/z 283 (M+1).

Example 215

Synthesis of (1E,6E)-1-(4-hydroxy-3-methoxyphenyl)-7-(1H-indol-3-yl)hepta-1,6-diene-3,5-dione (CU148)

The title compound was synthesized using the same procedure employed for Example 1, but with 1H-indole-3-carboxaldehyde (16 mg, 0.11 mmol) instead of 3-hydroxy-2-methoxybenzaldehyde (16 mg, 0.11 mmol). The product was obtained as a solid (2.3 mg, 8%) having the following characteristics.

$^1$H NMR (δ, acetone-$d_6$); 3.92 (s, 3H), 6.02 (s, 1H), 6.68 (d, J=16 Hz, 1H), 6.80 (d, J=16 Hz, 1H), 6.88 (d, J=8.2 Hz, 1H), 7.18 (dd, J=~2, 8.2 Hz, 1H), 7.2~7.3 (m, 2H), 7.33 (d, J=~2 Hz, 1H), 7.5~7.55 (m, 1H), 7.57 (d, J=16 Hz, 1H), 7.89 (d, J=2 Hz, 1H), 7.97 (d, J=16 Hz, 1H), 8.02 (dd, J=~2, 6.8 Hz, 1H), 8.1 (br s, OH).

Melting Point 99-103° C., MS (ESI+) m/z 332 (M+1), 354 (M+Na).

Example 216

Synthesis of (1E,6E)-1-(4-hydroxyphenyl)-7-(3-methoxyphenyl)hepta-1,6-diene-3,5-dione (CU158)

The title compound was synthesized using the same procedure employed for Example 22, but with 3-methoxybenzaldehyde (15 mg, 0.11 mmol) instead of 3-hydroxy-4-methoxybenzaldehyde (16 mg, 0.11 mmol). The product was obtained as a solid (17.9 mg, 65%) having the following characteristics.

$^1$H NMR (δ, acetone-$d_6$): 6.04 (s, 1H), 6.68 (d, J=16 Hz, 1H), 6.86 (d, J=16 Hz, 1H), 6.90 (d, J=8.7 Hz, 2H), 6.98 (dd, J=2.4, 8.2 Hz, 1H), 7.53 (m, 2H), 7.34 (dd, J=7.7, 8.2 Hz, 1H), 7.58 (d, J=8.7 Hz, 2H), 7.62 (d, J=16 Hz, 1H), 7.64 (d, J=16 Hz, 1H).

Melting Point 74-80° C., MS (ESI+) m/z 323 (M+1).

Example 217

Synthesis of (1E,6E)-1-(4-hydroxyphenyl)-7-(1-methyl-1H-pyrrazol-4-yl)hepta-1,6-diene-3,5-dione (CU198)

The title compound was synthesized using the same procedure employed for Example 22, but with 1-methyl-1H-pyrrazole-4-carboxaldehyde (12 mg, 0.11 mmol) instead of 3-hydroxy-4-methoxybenzaldehyde (16 mg, 0.11 mmol). The product was obtained as a solid (9.3 mg, 37%) having the following characteristics.

$^1$H NMR (δ, acetone-$d_6$): 3.90 (s, 3H), 5.89 (s, 1H), 6.54 (d, J=16 Hz, 1H), 6.64 (d, J=16 Hz, 1H), 6.89 (d, J=8.7 Hz, 2H), 7.56 (d, J=8.7 Hz, 2H), 7.56 (d, J=16 Hz, 1H), 7.58 (d, J=16 Hz, 1H), 7.79 (s, 1H), 7.96 (s, 1H).

Melting Point 234-238° C., MS (ESI+) m/z 297 (M+1).

Example 218

Synthesis of (1E,6E)-1-[2-hydroxy-6-(methoxymethoxy)phenyl]-7-(3-hydroxy-4-methoxyphenyl)hepta-1,6-diene-3,5-dione (CU313)

The title compound was synthesized using the same procedure employed for Example 29, but with 2,6-bis(methoxymethoxy)benzaldehyde (26 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. The product was obtained as a solid (3.6 mg, 10%) having the following characteristics.
$^1$H NMR (δ, acetone-$d_6$): 3.49 (s, 3H), 3.90 (s, 3H), 5.32 (s, 2H), 5.98 (s, 1H), 6.64 (d, J=8.2 Hz, 1H), 6.70 (d, J=16 Hz, 1H), 6.71 (d, J=7.7 Hz, 1H), 7.00 (d, J=8.2 Hz, 1H), 7.1~7.2 (m, 2H), 7.21 (d, J=1.9 Hz, 1H), 7.28 (d, J=16 Hz, 1H), 7.57 (d, J=16 Hz, 1H), 8.18 (d, J=16 Hz, 1H).
Melting Point 89-93° C., MS (ESI+) m/z 421.3 (M+Na).

Example 219

Synthesis of (1E,6E)-1-(2,6-dihydroxyphenyl)-7-(4-hydroxy-3-methoxyphenyl)hepta-1,6-diene-3,5-dione (CU314) and (1E,6E)-1-[2-hydroxy-6-(methoxymethoxy)phenyl]-7-(4-hydroxy-3-methoxyphenyl)hepta-1,6-diene-3,5-dione (CU315)

The title compound was synthesized using the same procedure employed for Example 1, but with 2,6-bis(methoxymethoxy)benzaldehyde (26 mg, 0.11 mmol) instead of 3-hydroxy-2-methoxybenzaldehyde (16 mg, 0.11 mmol), and the stirring time after addition of a 1:1 solution of 1N HCl and brine was extended to 5 h. (1E,6E)-1-(2,6-dihydroxyphenyl)-7-(4-hydroxy-3-methoxyphenyl)hepta-1,6-diene-3,5-dione (4.2 mg, 13%) and (1E,6E)-1-[2-hydroxy-6-(methoxymethoxy)phenyl]-7-(4-hydroxy-3-methoxyphenyl)hepta-1,6-diene-3,5-dione (4.8 mg, 14%) were obtained, respectively, as solids having the following characteristics.
(1E,6E)-1-(2,6-dihydroxyphenyl)-7-(4-hydroxy-3-methoxyphenyl)hepta-1,6-diene-3,5-dione (CU314)
$^1$H NMR (δ, acetone-$d_6$): 3.92 (s, 3H), 5.94 (s, 1H), 6.47 (d, J=8.2 Hz, 2H), 6.73 (d, J=16 Hz, 1H), 6.88 (d, J=8.2 Hz, 1H), 7.02 (t, J=8.2 Hz, 1H), 7.18 (dd, J=1.9, 8.2 Hz, 1H), 7.28 (d, J=16 Hz, 1H), 7.34 (d, J=1.9 Hz, 1H), 7.60 (d, J=16 Hz, 1H), 8.21 (d, J=16 Hz, 1H).
Melting Point 117-121° C., MS (ESI+) m/z 355.3 (M+1).
(1E,6E)-1-[2-hydroxy-6-(methoxymethoxy)phenyl]-7-(4-hydroxy-3-methoxyphenyl)hepta-1,6-diene-3,5-dione (CU315)
$^1$H NMR (δ, acetone-$d_6$): 3.49 (s, 3H), 3.92 (s, 3H), 5.32 (s, 2H), 5.95 (s, 1H), 6.64 (d, J=8.2 Hz, 1H), 6.70 (d, J=8.2 Hz, 1H), 6.73 (d, J=16 Hz, 1H), 6.88 (d, J=8.2 Hz, 1H), 7.1~7.2 (m, 2H), 7.27 (d, J=16 Hz, 1H), 7.34 (d, J=~2 Hz, 1H), 7.60 (d, J=16 Hz, 1H), 8.17 (d, J=16 Hz, 1H).
Melting Point 91-95° C., MS (ESI+) m/z 421.3 (M+Na).

Example 220

Synthesis of (1E,6E)-1-(4-hydroxy-3-methoxyphenyl)-7-[4-(methoxycarbonyl)phenyl]hepta-1,6-diene-3,5-dione (CU316)

The title compound was synthesized using the same procedure employed for Example 1, but with methyl 4-formylbenzoate (18 mg, 0.11 mmol) instead of 3-hydroxy-2-methoxybenzaldehyde (16 mg, 0.11 mmol). The product was obtained as a solid (15.2 mg, 45%), having the following characteristics.
$^1$H NMR (δ, acetone-$d_6$): 3.90 (s, 3H), 3.92 (s, 3H), 6.10 (s, 1H), 6.76 (d, J=16 Hz, 1H), 6.89 (d, J=8.2 Hz, 1H), 6.98 (d, J=16 Hz, 1H), 7.20 (dd, J=1.9, 8.2 Hz, 1H), 7.36 (d, J=1.9 Hz, 1H), 7.66 (d, J=16 Hz, 1H), 7.68 (d, J=16 Hz, 1H), 7.81 (d, J=8.7 Hz, 2H), 8.04 (d, J=8.7 Hz, 2H).
Melting Point 149-152° C., MS (ESI+) m/z 381.2 (M+1).

Example 221

Synthesis of (1E,6E)-1-(2,4-dihydroxyphenyl)-7-(4-hydroxyphenyl)hepta-1,6-diene-3,5-dione (CU317) and (1E,6E)-1-[4-dihydroxy-2-(methoxymethoxy)phenyl]-7-(4-hydroxyphenyl)hepta-1,6-diene-3,5-dione (CU319)

The title compound was synthesized using the same procedure employed for Example 22, but with 2,4-bis(methoxymethoxy)benzaldehyde (26 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. (1E,6E)-1-(2,4-dihydroxyphenyl)-7-(4-hydroxyphenyl)hepta-1,6-diene-3,5-dione (1.6 mg, 6%) and (1E,6E)-1-[4-dihydroxy-2-(methoxymethoxy)phenyl]-7-(4-hydroxyphenyl)hepta-1,6-diene-3,5-dione (3.8 mg, 12%) were obtained, respectively, as solids having the following characteristics.
(1E,6E)-1-(2,4-dihydroxyphenyl)-7-(4-hydroxyphenyl)hepta-1,6-diene-3,5-dione (CU317)
$^1$H NMR (δ, acetone-$d_6$): 5.94 (s, 1H), 6.44 (dd, J=2.4, 8.7 Hz, 1H), 6.49 (d, J=2.4 Hz, 1H), 6.67 (d, J=16 Hz, 1H), 6.74 (d, J=16 Hz, 1H), 6.89 (d, J=8.7 Hz, 2H), 7.49 (d, J=8.7 Hz, 1H), 7.56 (d, J=8.7 Hz, 2H), 7.58 (d, J=16 Hz, 1H), 7.95 (d, J=16 Hz, 1H), 8.6~9.3 (br s, OH).
MS (ESI+) m/z 325.3 (M+1).
(1E,6E)-1-[4-dihydroxy-2-(methoxymethoxy)phenyl]-7-(4-hydroxyphenyl)hepta-1,6-diene-3,5-dione (CU319)
$^1$H NMR (δ, acetone-$d_6$): 3.49 (s, 3H), 5.30 (s, 2H), 5.95 (s, 1H), 6.56 (dd, J=2.4, 8.7 Hz, 1H), 6.67 (d, J=16 Hz, 1H), 6.71 (d, J=2.4 Hz, 1H), 6.72 (d, J=16 Hz, 1H), 6.90 (d, J=8.7 Hz, 2H), 7.57 (d, J=8.7 Hz, 2H), 7.59 (d, J=8.7 Hz, 1H), 7.60 (d, J=16 Hz, 1H), 7.96 (d, J=16 Hz, 1H).
Melting Point 84-89° C., MS (ESI+) m/z 391.5 (M+Na).

Example 222

Synthesis of (1E,6E)-1-(2,6-dihydroxyphenyl)-7-(4-hydroxyphenyl)hepta-1,6-diene-3,5-dione (CU318) and (1E,6E)-1-[2-hydroxy-6-(methoxymethoxy)phenyl]-7-(4-hydroxyphenyl)hepta-1,6-diene-3,5-dione (CU320)

The title compound was synthesized using the same procedure employed for Example 22, but with 2,6-bis(methoxymethoxy)benzaldehyde (26 mg, 0.11 mmol) instead of 3-hydroxy-4-methoxybenzaldehyde (16 mg, 0.11 mmol), and the stirring time after addition of a 1:1 solution of 1N HCl and brine was extended to 5 h. (1E,6E)-1-(2,6-dihydroxyphenyl)-7-(4-hydroxyphenyl)hepta-1,6-diene-3,5-dione (1.7 mg, 6%) and (1E,6E)-1-[2-hydroxy-6-(methoxymethoxy)phenyl]-7-(4-hydroxyphenyl)hepta-1,6-diene-3,5-dione (3.2 mg, 10%) were obtained, respectively, as solids having the following characteristics.

(1E,6E)-1-(2,6-dihydroxyphenyl)-7-(4-hydroxyphenyl)hepta-1,6-diene-3,5-dione (CU318)

$^1$H NMR (δ, acetone-$d_6$): 5.94 (s, 1H), 6.48 (d, J=8.2 Hz, 2H), 6.68 (d, J=16 Hz, 1H), 6.90 (d, J=8.7 Hz, 2H), 7.01 (t, J=8.2 Hz, 1H), 7.28 (d, J=16 Hz, 1H), 7.57 (d, J=8.7 Hz, 2H), 7.61 (d, J=16 Hz, 1H), 8.21 (d, J=16 Hz, 1H), 8.8~9.0 (br s, OH), 9.1 (br s, OH).

MS (ESI+) m/z 325.3 (M+1).

(1E,6E)-1-[2-hydroxy-6-(methoxymethoxy)phenyl]-7-(4-hydroxyphenyl)hepta-1,6-diene-3,5-dione (CU320)

$^1$H NMR (δ, acetone-$d_6$): 3.49 (s, 3H), 5.31 (s, 2H), 5.96 (s, 1H), 6.65 (d, J=7.7 Hz, 1H), 6.69 (d, J=16 Hz, 1H), 6.70 (d, J=8.7 Hz, 1H), 6.90 (d, J=8.7 Hz, 2H), 7.14 (t, J=8.2 Hz, 1H), 7.27 (d, J=16 Hz, 1H), 7.57 (d, J=8.7 Hz, 2H), 7.62 (d, J=16 Hz, 1H), 8.17 (d, J=16 Hz, 1H).

Melting Point 148-152° C., MS (ESI+) m/z 369.4 (M+1), 391.4 (M+Na).

Example 223

Synthesis of (1E,6E)-1-(benzofuran-2-yl)-7-(4-hydroxyphenyl)hepta-1,6-diene-3,5-dione (CU321)

The title compound was synthesized using the same procedure employed for Example 22, but with benzofuran-2-carboxaldehyde (17 μL, 0.11 mmol) instead of 3-hydroxy-4-methoxybenzaldehyde (16 mg, 0.11 mmol). The product was obtained as a solid (13.9 mg, 48%) having the following characteristics.

$^1$H NMR (δ, acetone-$d_6$): 6.15 (s, 1H), 6.72 (d, J=16 Hz, 1H), 6.84 (d, J=16 Hz, 1H), 6.92 (d, J=8.7 Hz, 2H), 7.23 (s, 1H), 7.28 (ddd, J=~2, 7.2, 7.7 Hz, 1H), 7.41 (ddd, J=1.5, 7.2, 8.2 Hz, 1H), 7.55 (d, J=8.2 Hz, 1H), 7.57 (d, J=16 Hz, 1H), 7.59 (d, J=8.7 Hz, 2H), 7.69 (d, J=7.7 Hz, 1H), 7.69 (d, J=16 Hz, 1H).

Melting Point 173-178° C., MS (ESI+) m/z 333.3 (M+1).

Example 224

Synthesis of (1E,6E)-1-(4-hydroxyphenyl)-7-(quinolin-8-yl)hepta-1,6-diene-3,5-dione (CU323)

The title compound was synthesized using the same procedure employed for Example 22, but with quinoline-8-carboxaldehyde (18 mg, 0.11 mmol) instead of 3-hydroxy-4-methoxybenzaldehyde (16 mg, 0.11 mmol). The product was obtained as a solid (3.0 mg, 10%) having the following characteristics.

$^1$H NMR (δ, acetone-$d_6$): 6.14 (s, 1H), 6.76 (d, J=16 Hz, 1H), 6.92 (d, J=8.7 Hz, 2H), 7.21 (d, J=16 Hz, 1H), 7.60 (d, J=8.2 Hz, 1H), 7.61 (d, J=8.7 Hz, 2H), 7.67 (d, J=16 Hz, 1H), 7.68 (d, J=16 Hz, 1H), 8.04 (d, J=7.7 Hz, 1H), 8.26 (d, J=7.2 Hz, 1H), 8.39 (dd, J=1.9, 8.2 Hz, 1H), 8.9~9.0 (br s, 1H, OH), 8.97~9.05 (m, 2H).

Melting Point 112-117° C., MS (ESI+) m/z 344.3 (M+1).

Example 225

Synthesis of (1E,6E)-1-(4-hydroxyphenyl)-7-(quinolin-5-yl)hepta-1,6-diene-3,5-dione (CU324)

The title compound was synthesized using the same procedure employed for Example 22, but with quinoline-5-carboxaldehyde (18 mg, 0.11 mmol) instead of 3-hydroxy-4-methoxybenzaldehyde (16 mg, 0.11 mmol). The product was obtained as a solid (9.7 mg, 32%) having the following characteristics.

$^1$H NMR (δ, acetone-$d_6$): 6.27 (s, 1H), 6.74 (d, J=16 Hz, 1H), 6.81 (d, J=8.7 Hz, 2H), 7.04 (d, J=16 Hz, 1H), 7.58 (d, J=8.7 Hz, 2H), 7.61 (d, J=16 Hz, 1H), 7.62 (dd, J=4.3, 8.2 Hz, 1H), 7.82 (dd, J=7.7, 8.2 Hz, 1H), 8.08 (br d, J=3.4 Hz, 1H), 8.10 (br s, 1H), 8.35 (d, J=16 Hz, 1H), 8.74 (d, J=8.7 Hz, 1H), 8.95 (br d, J=2.9 Hz, 1H).

Melting Point 272-275° C., MS (ESI+) m/z 344.4 (M+1).

Example 226

Synthesis of (1E,6E)-1-(4-hydroxyphenyl)-7-[4-(pyridin-2-yl)phenyl]hepta-1,6-diene-3,5-dione (CU328)

The title compound was synthesized using the same procedure employed for Example 22, but with 4-(pyridin-2-yl)benzaldehyde (21 mg, 0.11 mmol) instead of 3-hydroxy-4-methoxybenzaldehyde (16 mg, 0.11 mmol). The product was obtained as a solid (18.0 mg, 55%) having the following characteristics.

$^1$H NMR (δ, acetone-$d_6$): 6.25 (s, 1H), 6.72 (d, J=16 Hz, 1H), 6.81 (d, J=8.7 Hz, 2H), 6.98 (d, J=16 Hz, 1H), 7.34~7.4 (m, 1H), 7.57 (d, J=8.7 Hz, 2H), 7.58 (d, J=16 Hz, 1H), 7.64 (d, J=16 Hz, 1H), 7.82 (d, J=8.2 Hz, 2H), 7.84~7.92 (m, 1H), 8.02 (d, J=7.7 Hz, 1H), 8.15 (d, J=8.2 Hz, 2H), 8.67 (br d, J=3.9 Hz, 1H).

Melting Point 229-232° C., MS (ESI+) m/z 370.3 (M+1).

Example 227

Synthesis of (1E,6E)-1-(4-hydroxyphenyl)-7-[4-(1H-imidazol-1-yl)phenyl]hepta-1,6-diene-3,5-dione (CU329)

The title compound was synthesized using the same procedure employed for Example 22, but with 4-(1H-imidazol-1-yl)benzaldehyde (20 mg, 0.11 mmol) instead of 3-hydroxy-4-methoxybenzaldehyde (16 mg, 0.11 mmol). The product was obtained as a solid (26.4 mg, 84%) having the following characteristics.

$^1$H NMR (δ, acetone-$d_6$): 6.12 (s, 1H), 6.72 (d, J=16 Hz, 1H), 6.81 (d, J=8.7 Hz, 2H), 6.96 (d, J=16 Hz, 1H), 7.11 (s, 1H), 7.57 (d, J=8.7 Hz, 2H), 7.58 (d, J=16 Hz, 1H), 7.62 (d, J=16 Hz, 1H), 7.73 (d, J=8.7 Hz, 2H), 7.82 (s, 1H), 7.85 (d, J=8.7 Hz, 2H), 8.35 (s, 1H).

Melting Point 255-260° C., MS (ESI+) m/z 359.3 (M+1).

Example 228

Synthesis of (1E,6E)-1-(4-hydroxyphenyl)-7-(1H-indol-4-yl)hepta-1,6-diene-3,5-dione (CU330)

The title compound was synthesized using the same procedure employed for Example 22, but with 1H-indole-4-carboxaldehyde (17 mg, 0.11 mmol) instead of 3-hydroxy-4-methoxybenzaldehyde (16 mg, 0.11 mmol). The product was obtained as a solid (15.6 mg, 53%) having the following characteristics.

$^1$H NMR (δ, acetone-$d_6$): 6.22 (s, 1H), 6.68 (d, J=16 Hz, 1H), 6.7~6.85 (m, 1H), 6.81 (d, J=8.7 Hz, 2H), 6.96 (d, J=16 Hz, 1H), 7.15 (dd, J=7.3, 8.2 Hz, 1H), 7.41 (d, J=7.3 Hz, 1H), 7.45~7.6 (m, 2H), 7.56 (d, J=8.7 Hz, 2H), 7.62 (d, J=16 Hz, 1H).

MS (ESI+) m/z 322.1 (M+1).

Example 229

Synthesis of (1E,6E)-1-(1-benzyl-1H-indol-3-yl)-7-(4-hydroxyphenyl)hepta-1,6-diene-3,5-dione (CU331)

(1) Synthesis of 1-benzyl-1H-indole-3-carboxaldehyde

To a solution of 1H-indole-3-carboxaldehyde (300 mg, 2.07 mmol) in 4.1 mL of dry dimethylsulfoxide was added sodium hydride (108 mg, 55%, 2.5 mmol) under nitrogen at 0° C. After the reaction mixture was stirred at room temperature for 30 min, benzyl bromide (0.40 mL, 2.5 mmol) was added with additional stirring for 2 h. The reaction mixture was diluted with 10 mL of ethyl acetate and 10 mL of saturated NH$_4$Cl aqueous solution at 0° C., successively, and extracted with 100 mL of ethyl acetate. The extract was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=80/20 to 70/30) to obtain the title compound as a pale brown solid (10.8 mg, 31%).

(2) (1E,6E)-1-(1-benzyl-1H-indol-3-yl)-7-(4-hydroxyphenyl)hepta-1,6-diene-3,5-dione (CU331)

The title compound was synthesized using the same procedure employed for Example 22, but with 1-benzyl-1H-indole-3-carboxaldehyde (27 mg, 0.11 mmol) instead of 3-hydroxy-4-methoxybenzaldehyde (16 mg, 0.11 mmol). The product was obtained as a solid (16.2 mg, 44%) having the following characteristics.

$^1$H NMR (δ, acetone-d$_6$): 5.46 (s, 2H), 6.09 (s, 1H), 6.63 (d, J=16 Hz, 1H), 6.74 (d, J=16 Hz, 1H), 6.80 (d, J=8.7 Hz, 2H), 7.15~7.35 (m, 7H), 7.49 (d, J=16 Hz, 1H), 7.5~7.58 (m, 1H), 7.53 (d, J=8.7 Hz, 2H), 7.85 (d, J=16 Hz, 1H), 7.99 (m, 1H), 8.14 (s, 1H).

Melting Point 243-249° C., MS (ESI+) m/z 422.4 (M+1).

Example 230

Synthesis of (1E,6E)-1-[6-(4-benzylpiperazin-1-yl)pyridin-3-yl]-7-(4-hydroxyphenyl)hepta-1,6-diene-3,5-dione (CU332)

The title compound was synthesized using the same procedure employed for Example 22, but with 6-(4-benzylpiperazino)nicotinaldehyde (32 mg, 0.11 mmol) instead of 3-hydroxy-4-methoxybenzaldehyde (16 mg, 0.11 mmol). The product was obtained as a solid (9.2 mg, 22%) having the following characteristics.

$^1$H NMR (δ, acetone-d$_6$): 2.4-2.6 (m, 2H), 3.55 (s, 2H), 3.69 (t, J=5 Hz, 2H), 5.95 (s, 1H), 6.65 (d, J=16 Hz, 1H), 6.66 (d, J=16 Hz, 1H), 6.86 (m, 1H), 6.90 (d, J=8.7 Hz, 2H), 7.2~7.4 (m, 5H), 7.56 (d, J=8.7 Hz, 2H), 7.58 (d, J=16 Hz, 1H), 7.59 (d, J=16 Hz, 1H), 7.88 (m, 1H), 8.35 (s, 1H).

Melting Point 132-138° C., MS (ESI+) m/z 468.4 (M+1).

Example 231

Synthesis of (1E,6E)-1-(4-hydroxyphenyl)-7-[6-(4-methylphenoxy)pyridin-3-yl]hepta-1,6-diene-3,5-dione (CU333)

The title compound was synthesized using the same procedure employed for Example 22, but with 6-(4-methylphenoxy)nicotinaldehyde (25 mg, 0.11 mmol) instead of 3-hydroxy-4-methoxybenzaldehyde (16 mg, 0.11 mmol). The product was obtained as a solid (7.2 mg, 20%) having the following characteristics.

$^1$H NMR (δ, acetone-d$_6$): 2.35 (s, 3H), 6.03 (s, 1H), 6.69 (d, J=16 Hz, 1H), 6.85 (d, J=16 Hz, 1H), 6.91 (d, J=8.7 Hz, 2H), 7.01 (d, J=8.7 Hz, 1H), 7.05 (d, J=8 Hz, 2H), 7.23 (d, J=8 Hz, 2H), 7.58 (d, J=8.7 Hz, 2H), 7.64 (d, J=16 Hz, 2H), 8.18 (dd, J=2, 8.7 Hz, 1H), 8.38 (s, 1H), 8.9 (br s, OH).

Melting Point 167-172° C., MS (ESI+) m/z 400.3 (M+1).

Example 232

Synthesis of (1E,6E)-1-(4-hydroxyphenyl)-7-(2-morpholinopyridin-3-yl)hepta-1,6-diene-3,5-dione (CU337)

The title compound was synthesized using the same procedure employed for Example 22, but with 2-morpholinonicotinaldehyde (22 mg, 0.11 mmol) instead of 3-hydroxy-4-methoxybenzaldehyde (16 mg, 0.11 mmol). The product was obtained as a solid (19.8 mg, 59%) having the following characteristics.

$^1$H NMR (δ, acetone-d$_6$): 3.21 (t, J=5 Hz, 2H), 3.82 (t, J=5 Hz, 2H), 6.04 (s, 1H), 6.71 (d, J=16 Hz, 1H), 6.84 (d, J=16 Hz, 1H), 6.91 (d, J=8.7 Hz, 2H), 7.03 (dd, J=4.8, 7.3 Hz, 1H), 7.58 (d, J=8.7 Hz, 2H), 7.65 (d, J=16 Hz, 1H), 7.74 (d, J=16 Hz, 1H), 7.96 (br d, J=7 Hz, 1H), 8.27 (br d, J=5 Hz, 1H), 8.9 (br s, OH).

Melting Point 159-165° C., MS (ESI+) m/z 379.3 (M+1).

Example 233

Synthesis of (1E,6E)-1-(4-hydroxyphenyl)-7-[1-(4-methylphenyl)-1H-pyrrol-2-yl]hepta-1,6-diene-3,5-dione (CU338)

The title compound was synthesized using the same procedure employed for Example 22, but with 1-(4-methylphenyl)-1H-pyrrole-2-carboxaldehyde (21 mg, 0.11 mmol) instead of 3-hydroxy-4-methoxybenzaldehyde (16 mg, 0.11 mmol). The product was obtained as a solid (20.2 mg, 62%) having the following characteristics.

$^1$H NMR (δ, acetone-d$_6$): 2.43 (s, 3H), 5.82 (s, 1H), 6.36 (br dd, J=3, 3 Hz, 1H), 6.48 (d, J=16 Hz, 1H), 6.61 (d, J=16 Hz, 1H), 6.89 (d, J=8.7 Hz, 2H), 6.95 (br d, J=3 Hz, 1H), 7.10 (m, 1H), 7.25 (d, J=8.2 Hz, 2H), 7.38 (d, J=8.2 Hz, 2H), 7.40 (d, J=16 Hz, 1H), 7.54 (d, J=8.7 Hz, 2H), 7.56 (d, J=16 Hz, 1H), 9.0 (br s, OH).

Melting Point 144-150° C., MS (ESI+) m/z 372.4 (M+1).

Example 234

Synthesis of (1E,6E)-1-(benzo[b]thiophen-2-yl)-7-(4-hydroxyphenyl)hepta-1,6-diene-3,5-dione (CU339)

The title compound was synthesized using the same procedure employed for Example 22, but with benzo[b]thiophene-2-carboxaldehyde (19 mg, 0.11 mmol) instead of 3-hydroxy-4-methoxybenzaldehyde (16 mg, 0.11 mmol). The product was obtained as a solid (12.0 mg, 39%) having the following characteristics.

$^1$H NMR (δ, acetone-d$_6$): 6.10 (s, 1H), 6.61 (d, J=16 Hz, 1H), 6.70 (d, J=16 Hz, 1H), 6.92 (d, J=8.7 Hz, 2H), 7.36~7.46

(m, 2H), 7.59 (d, J=8.7 Hz, 2H), 7.67 (d, J=16 Hz, 1H), 7.73 (s, 1H), 7.84~7.96 (m, 2H), 7.90 (d, J=16 Hz, 1H), 9.0 (br s, OH).

MS (ESI+) m/z 349.3 (M+1).

Example 235

Synthesis of (1E,6E)-1-(4-hydroxyphenyl)-7-[2-(4-methylphenoxy)pyridin-3-yl]hepta-1,6-diene-3,5-dione (CU340)

The title compound was synthesized using the same procedure employed for Example 22, but with 2-(4-methylphenoxy)nicotinaldehyde (25 mg, 0.11 mmol) instead of 3-hydroxy-4-methoxybenzaldehyde (16 mg, 0.11 mmol). The product was obtained as a solid (23.8 mg, 68%) having the following characteristics.

$^1$H NMR (δ, acetone-$d_6$): 2.35 (s, 3H), 6.08 (s, 1H), 6.71 (d, J=16 Hz, 1H), 6.90 (d, J=8.7 Hz, 2H), 7.05 (d, J=16 Hz, 1H), 7.07 (d, J=8.2 Hz, 2H), 7.15 (dd, J=4.8, 7.7 Hz, 1H), 7.23 (d, J=8.2 Hz, 2H), 7.58 (d, J=8.7 Hz, 2H), 7.66 (d, J=16 Hz, 1H), 7.93 (d, J=16 Hz, 1H), 8.06 (dd, J=1.5, 4~5 Hz, 1H), 8.17 (br d, J=7~8 Hz, 1H), 8.9 (br s, OH).

Melting Point 180-185° C., MS (ESI+) m/z 400.3 (M+1).

Example 236

Synthesis of (1E,6E)-1-(4-hydroxyphenyl)-7-(2-phenylthiazol-4-yl)hepta-1,6-diene-3,5-dione (CU342)

The title compound was synthesized using the same procedure employed for Example 22, but with 2-phenylthiazole-4-carboxaldehyde (22 mg, 0.11 mmol) instead of 3-hydroxy-4-methoxybenzaldehyde (16 mg, 0.11 mmol). The product was obtained as a solid (1.8 mg, 5%) having the following characteristics.

$^1$H NMR (δ, acetone-$d_6$): 6.14 (s, 1H), 6.72 (d, J=16 Hz, 1H), 6.92 (d, J=8.7 Hz, 2H), 7.12 (d, J=16 Hz, 1H), 7.5~7.6 (m, 3H), 7.60 (d, J=8.7 Hz, 2H), 7.65 (d, J=16 Hz, 1H), 7.69 (d, J=16 Hz, 1H), 7.92 (s, 1H), 8.03~8.1 (m, 2H), 8.9 (br s, OH).

MS (ESI+) m/z 376.3 (M+1).

Example 237

Synthesis of (1E,6E)-1-[2-(4-benzylpiperazin-1-yl)pyridin-3-yl]-7-(4-hydroxyphenyl)hepta-1,6-diene-3,5-dione (CU343)

The title compound was synthesized using the same procedure employed for Example 22, but with 2-(4-benzylpiperazino)nicotinaldehyde (32 mg, 0.11 mmol) instead of 3-hydroxy-4-methoxybenzaldehyde (16 mg, 0.11 mmol). The product was obtained as a solid (5.8 mg, 14%) having the following characteristics.

$^1$H NMR (δ, acetone-$d_6$): 2.63 (t, J=5 Hz, 2H), 3.26 (t, J=5 Hz, 2H), 3.60 (s, 2H), 6.03 (s, 1H), 6.70 (d, J=16 Hz, 1H), 6.83 (d, J=16 Hz, 1H), 6.91 (d, J=8.7 Hz, 2H), 7.00 (dd, J=4.8, 7.3 Hz, 1H), 7.24 (t, J=7 Hz, 1H), 7.32 (dd, J=7, 7 Hz, 2H), 7.38 (d, J=7.2 Hz, 2H), 7.59 (d, J=8.7 Hz, 2H), 7.65 (d, J=16 Hz, 1H), 7.74 (d, J=16 Hz, 1H), 7.95 (br d, J=7 Hz, 1H), 8.25 (dd, J=1.5, 4.8 Hz, 1H), 9.0 (br s, OH).

MS (ESI+) m/z 468.4 (M+1).

Example 238

Synthesis of (1E,6E)-1-(4-hydroxyphenyl)-7-(6-morpholinopyridin-3-yl)hepta-1,6-diene-3,5-dione (CU344)

The title compound was synthesized using the same procedure employed for Example 22, but with 6-morpholinonicotinaldehyde (22 mg, 0.11 mmol) instead of 3-hydroxy-4-methoxybenzaldehyde (16 mg, 0.11 mmol). The product was obtained as a solid (3.9 mg, 12%) having the following characteristics.

$^1$H NMR (δ, acetone-$d_6$): 3.62 (t, J=5 Hz, 2H), 3.74 (t, J=5 Hz, 2H), 5.96 (s, 1H), 6.66 (d, J=16 Hz, 1H), 6.68 (d, J=16 Hz, 1H), 6.87 (d, J=9.2 Hz, 1H), 6.90 (d, J=8.7 Hz, 2H), 7.56 (d, J=8.7 Hz, 2H), 7.58 (d, J=16 Hz, 1H), 7.59 (d, J=16 Hz, 1H), 7.92 (br dd, J=2, 9 Hz, 1H), 8.38 (br d, J=2 Hz, 1H), 8.9 (br s, OH).

MS (ESI+) m/z 379.4 (M+1).

Example 239

Synthesis of (1E,6E)-1-(4-hydroxyphenyl)-7-[5-(pyridin-2-yl)thiophen-2-yl]hepta-1,6-diene-3,5-dione (CU345)

The title compound was synthesized using the same procedure employed for Example 22, but with 5-(pyridin-2-yl)thiophene-2-carboxaldehyde (22 mg, 0.11 mmol) instead of 3-hydroxy-4-methoxybenzaldehyde (16 mg, 0.11 mmol). The product was obtained as a solid (2.4 mg, 7%) having the following characteristics.

$^1$H NMR (δ, acetone-$d_6$): 6.06 (s, 1H), 6.65 (d, J=16 Hz, 1H), 6.70 (d, J=16 Hz, 1H), 6.91 (d, J=8.7 Hz, 2H), 7.30 (dd, J=4.8, 7.2 Hz, 1H), 7.48 (d, J=3.9 Hz, 1H), 7.59 (d, J=8.7 Hz, 2H), 7.65 (d, J=16 Hz, 1H), 7.76 (d, J=3.9 Hz, 1H), 7.78 (d, J=16 Hz, 1H), 7.84 (m, 1H), 7.92 (d, J=8.2 Hz, 1H), 8.57 (br d, J=5 Hz, 1H), 8.9 (br s, OH).

MS (ESI+) m/z 376.3 (M+1).

Example 240

Synthesis of (1E,6E)-1-(1H-benzotriazol-5-yl)-7-(4-hydroxyphenyl)hepta-1,6-diene-3,5-dione (CU346)

(1) Synthesis of 1H-benzotriazole-5-carboxaldehyde

To a solution of 1H-benzotriazole-5-carboxylic acid (1.00 g, 6.13 mmol) in 30 mL of dry tetrahydrofuran was added lithium aluminum hydride (0.47 g, 12 mmol) under nitrogen at 0° C. After the reaction mixture was stirred at 70° C. for 90 h, saturated $Na_2SO_4$ aqueous solution was added carefully at 0° C. After the solution was stirred at room temperature for 30 min, a sufficient amount of $Na_2SO_4$ was added with additional stirring for drying. After filtration, the filtrate was concentrated in vacuo, and the residue was purified by silica gel column chromatography (chloroform/methanol=97/3 to 80/20) to obtain (1H-benzoimidazol-5-yl)methanol as a pale yellow solid (143 mg, 16%).

The above product (140 mg, 0.94 mmol) was dissolved in 2.7 mL of dry dichloromethane, and Dess-Martin periodinane (483 mg, 1.03 mmol) was added to the solution at room temperature. After the reaction mixture was stirred for 1 h, saturated $NaHCO_3$ aqueous solution was added. The mixture was extracted with chloroform three times, and the extracts were washed with brine, and dried over $Na_2SO_4$. After filtration, the filtrate was concentrated in vacuo, and the residue was purified by silica gel column chromatography (chloroform/methanol=99/1 to 93/7) to obtain the title compound as a white powder (106 mg, 77%).

(2) Synthesis of (1E,6E)-1-(1H-benzotriazol-5-yl)-7-(4-hydroxyphenyl)hepta-1,6-diene-3,5-dione (CU346)

The title compound was synthesized using the same procedure employed for Example 22, but with 1H-benzotriazole-5-carboxaldehyde (17 mg, 0.11 mmol) instead of 3-hydroxy-4-methoxybenzaldehyde (16 mg, 0.11 mmol). The product was obtained as a solid (2.1 mg, 7%) having the following characteristics.

$^1$H NMR (δ, acetone-$d_6$): 6.09 (s, 1H), 6.72 (d, J=16 Hz, 1H), 6.92 (d, J=8.7 Hz, 2H), 6.99 (d, J=16 Hz, 1H), 7.60 (d, J=8.7 Hz, 2H), 7.66 (d, J=16 Hz, 1H), 7.84 (d, J=16 Hz, 1H), 7.87 (m, 1H), 7.95 (br d, J=8 Hz, 1H), 8.21 (br s, 1H).

Melting Point 211-216° C., MS (ESI+) m/z 334.3 (M+1).

Example 241

Synthesis of (1E,6E)-1-(1H-benzimidazol-5-yl)-7-(4-hydroxyphenyl)hepta-1,6-diene-3,5-dione (CU347)

The title compound was synthesized using the same procedure employed for Example 22, but with 1H-benzimidazole-5-carboxaldehyde (17 mg, 0.11 mmol, prepared according to the procedure described in J. Med. Chem., (2005), 48, 5823-5836) instead of 3-hydroxy-4-methoxybenzaldehyde (16 mg, 0.11 mmol). The product was obtained as a solid (11.2 mg, 38%) having the following characteristics.

$^1$H NMR (δ, acetone-$d_6$): 6.05 (s, 1H), 6.70 (d, J=16 Hz, 1H), 6.86 (d, J=16 Hz, 1H), 6.91 (d, J=8.7 Hz, 2H), 7.5~7.7 (m, 3H), 7.58 (d, J=8.7 Hz, 2H), 7.81 (d, J=16 Hz, 1H), 7.94 (br s, 1H), 8.25 (br s, 1H).

MS (ESI+) m/z 333.3 (M+1).

Example 242

Synthesis of (1E,6E)-1-(4-hydroxyphenyl)-7-(quinoxalin-6-yl)hepta-1,6-diene-3,5-dione (CU348)

(1) Synthesis of quinoxaline-6-carboxaldehyde

6-Methylquinoxaline (500 mg, 3.47 mmol) and selenium dioxide (423 mg, 3.81 mmol) in a sealed vessel were stirred at 160° C. for 7 h. After cooled to room temperature, the reaction mixture was dissolved in ethyl acetate. The solution was washed with brine twice, and dried over MgSO$_4$. After filtration, the filtrate was concentrated in vacuo, and the residue was purified by silica gel column chromatography (hexane/ethyl acetate=80/20 to 60/40) to obtain the title compound as a pale brown solid (355 mg, 64%).

(2) Synthesis of (1E,6E)-1-(4-hydroxyphenyl)-7-(quinoxalin-6-yl)hepta-1,6-diene-3,5-dione (CU348)

The title compound was synthesized using the same procedure employed for Example 22, but with quinoxaline-6-carboxaldehyde (18 mg, 0.11 mmol) instead of 3-hydroxy-4-methoxybenzaldehyde (16 mg, 0.11 mmol). The product was obtained as a solid (1.8 mg, 6%) having the following characteristics.

$^1$H NMR (δ, acetone-$d_6$): 6.16 (s, 1H), 6.75 (d, J=16 Hz, 1H), 6.92 (d, J=8.7 Hz, 2H), 7.14 (d, J=16 Hz, 1H), 7.61 (d, J=8.7 Hz, 2H), 7.69 (d, J=16 Hz, 1H), 7.89 (d, J=16 Hz, 1H), 8.12 (d, J=9 Hz, 1H), 8.21 (dd, J=~2, 9 Hz, 1H), 8.33 (s, 1H), 8.8~9.0 (m, 2H).

Melting Point 251-255° C., MS (ESI+) m/z 345.2 (M+1).

Example 243

Synthesis of (1E,6E)-1-(4-hydroxyphenyl)-7-(1H-indazol-5-yl)hepta-1,6-diene-3,5-dione (CU349)

(1) Synthesis of 1H-indazole-5-carboxaldehyde

To a solution of methyl 1H-indazole-5-carboxylate (300 mg, 1.69 mmol, prepared according to the procedure described in JP-11-228513) in 8.5 mL of dry toluene was added diisobutylaluminum hydride (1 mol/L in n-hexane, 3.4 mL) under nitrogen at −78° C. After the reaction mixture was stirred at the same temperature for 3 h, saturated Na$_2$SO$_4$ aqueous solution was added carefully at 0° C. After the solution was stirred at room temperature, a sufficient amount of Na$_2$SO$_4$ was added with additional stirring for drying. After filtration, the filtrate was concentrated in vacuo, and the residue was purified by silica gel column chromatography (chloroform/methanol=98/2 to 85/15) to obtain (1H-indazol-5-yl)methanol (125 mg, 50%).

The above product (125 mg, 0.844 mmol) was dissolved in 6.8 mL of dry dichloromethane, and Dess-Martin periodinane (376 mg, 0.887 mmol) was added to the solution at room temperature. After the reaction mixture was stirred for 30 min, saturated NaHCO$_3$ aqueous solution was added. The mixture was extracted with chloroform, and the extract was washed with brine, and dried over MgSO$_4$. After filtration, the filtrate was concentrated in vacuo, and the residue was purified by silica gel column chromatography (chloroform/methanol=98/2 to 90/10) to obtain the title compound as a pale yellow solid (111 mg, 74%).

(2) Synthesis of (1E,6E)-1-(4-hydroxyphenyl)-7-(1H-indazol-5-yl)hepta-1,6-diene-3,5-dione (CU349)

The title compound was synthesized using the same procedure employed for Example 22, but with 1H-indazole-5-carboxaldehyde (17 mg, 0.11 mmol) instead of 3-hydroxy-4-methoxybenzaldehyde (16 mg, 0.11 mmol). The product was obtained as a solid (15.6 mg, 53%) having the following characteristics.

$^1$H NMR (δ, acetone-$d_6$): 6.04 (s, 1H), 6.69 (d, J=16 Hz, 1H), 6.85 (d, J=16 Hz, 1H), 6.91 (d, J=8.7 Hz, 2H), 7.58 (d, J=8.7 Hz, 2H), 7.63 (d, J=16 Hz, 1H), 7.64 (d, J=8.7 Hz, 1H), 7.77 (dd, J=1.5, 8.7 Hz, 1H), 7.81 (d, J=16 Hz, 1H), 8.08 (s, 1H), 8.13 (s, 1H), 8.9 (br s, OH), 12.3 (br s, 1H, NH).

Melting Point 148-152° C., MS (ESI+) m/z 333.0 (M+1).

Example 244

Synthesis of (1E,6E)-1,7-bis(1,4-benzodioxan-6-yl)hepta-1,6-diene-3,5-dione (CU356)

Acetylacetone (10.3 μL, 100 μmol) and boron trioxide (25 mg, 0.40 mmol) was placed in a 20 mL reaction vessel, and dissolved in 0.45 mL of ethyl acetate. To the stirring solution at 80° C. were added 1,4-benzodioxane-6-carboxaldehyde (41 mg, 0.25 mmol) and tri-n-butyl borate (57 μL, 0.21 mmol), successively. After the reaction mixture was stirred for 2 h at the same temperature, n-butylamine (22 μL, 0.22 mmol) was added with additional stirring for 1 h. The reaction mixture was treated with a 1:1 solution (3 mL) of 1N HCl and brine at room temperature, and was stirred at 50° C. for 5 min to 1 h (if necessary, the reaction mixture was neutralized with saturated NaHCO$_3$ aqueous solution). The organic layer was purified directly by silica gel column chromatography (eluting with hexane/ethyl acetate or chloroform/methanol) to obtain the title compound as a solid (20.0 mg, 51%) having the following characteristics.

$^1$H NMR (δ, acetone-d$_6$): 4.25~4.35 (s, 8H), 6.00 (s, 1H), 6.70 (d, J=16 Hz, 2H), 6.88 (d, J=8.2 Hz, 2H), 7.18 (d, J=8 Hz, 2H), 7.19 (s, 2H), 7.55 (d, J=16 Hz, 2H).

Melting Point 184-187° C., MS (ESI+) m/z 393.3 (M+1), 415.2 (M+Na).

Example 245

Synthesis of (1E,6E)-1,7-bis(3-hydroxy-5-methoxyphenyl)hepta-1,6-diene-3,5-dione (CU358)

The title compound was synthesized using the same procedure employed for Example 244, but with 3-hydroxy-5-methoxybenzaldehyde (38 mg, 0.25 mmol) instead of 1,4-benzodioxane-6-carboxaldehyde (41 mg, 0.25 mmol). The product was obtained as a solid (13.4 mg, 36%) having the following characteristics.

$^1$H NMR (δ, acetone-d$_6$): 3.81 (s, 6H), 6.09 (s, 1H), 6.48 (dd, J=2, 2 Hz, 2H), 6.75 (m, 2H), 6.77 (m, 2H), 6.79 (d, J=16 Hz, 2H), 7.56 (d, J=16 Hz, 2H).

Melting Point 147-151° C., MS (ESI+) m/z 369.2 (M+1).

Example 246

Synthesis of (1E,6E)-1,7-bis(2,5-dimethoxyphenyl)hepta-1,6-diene-3,5-dione (CU361)

The title compound was synthesized using the same procedure employed for Example 244, but with 2,5-dimethoxybenzaldehyde (42 mg, 0.25 mmol) instead of 1,4-benzodioxane-6-carboxaldehyde (41 mg, 0.25 mmol). The product was obtained as a solid (24.4 mg, 62%) having the following characteristics.

$^1$H NMR (δ, acetone-d$_6$): 3.80 (s, 6H), 3.88 (s, 6H), 6.04 (s, 1H), 6.91 (d, J=16 Hz, 2H), 6.98 (m, 2H), 7.01 (m, 2H), 7.26 (m, 2H), 7.98 (d, J=16 Hz, 2H).

Melting Point 119-122° C., MS (ESI+) m/z 397.3 (M+1).

Example 247

Synthesis of (1E,6E)-1,7-bis(2-chloro-4-hydroxyphenyl)hepta-1,6-diene-3,5-dione (CU362)

The title compound was synthesized using the same procedure employed for Example 244, but with 2-chloro-4-hydroxybenzaldehyde (39 mg, 0.25 mmol) instead of 1,4-benzodioxane-6-carboxaldehyde (41 mg, 0.25 mmol). The product was obtained as a solid (13.8 mg, 37%) having the following characteristics.

$^1$H NMR (δ, acetone-d$_6$): 6.04 (s, 1H), 6.77 (d, J=16 Hz, 2H), 6.89 (dd, J=2, 8.7 Hz, 2H), 6.98 (d, J=2 Hz, 2H), 7.79 (d, J=8.7 Hz, 2H), 7.99 (d, J=16 Hz, 2H).

Melting Point 248-254° C., MS (ESI+) m/z 377.0 (M+1).

Example 248

Synthesis of (1E,6E)-1,7-bis(3-hydroxy-2-methoxyphenyl)hepta-1,6-diene-3,5-dione (CU363)

The title compound was synthesized using the same procedure employed for Example 244, but with 3-hydroxy-2-methoxybenzaldehyde (38 mg, 0.25 mmol) instead of 1,4-benzodioxane-6-carboxaldehyde (41 mg, 0.25 mmol). The product was obtained as a solid (19.4 mg, 53%) having the following characteristics.

$^1$H NMR (δ, acetone-d$_6$): 3.85 (s, 6H), 6.12 (s, 1H), 6.89 (d, J=16 Hz, 2H), 6.97 (dd, J=2, 7.7 Hz, 2H), 7.02 (dd, J=7.7, 7.7 Hz, 2H), 7.24 (dd, J=2, 7.7 Hz, 2H), 7.95 (d, J=16 Hz, 2H), 8.3 (br s, OH).

Melting Point 62-65° C., MS (ESI+) m/z 369.3 (M+1).

Example 249

Synthesis of (1E,6E)-1,7-bis(2,4-dimethoxyphenyl)hepta-1,6-diene-3,5-dione (CU365)

The title compound was synthesized using the same procedure employed for Example 244, but with 2,4-dimethoxybenzaldehyde (42 mg, 0.25 mmol) instead of 1,4-benzodioxane-6-carboxaldehyde (41 mg, 0.25 mmol). The product was obtained as a solid (15.2 mg, 38%) having the following characteristics.

$^1$H NMR (δ, acetone-d$_6$): 3.86 (s, 6H), 3.93 (s, 6H), 5.92 (s, 1H), 6.59 (dd, J=2.4, 7.7 Hz, 2H), 6.62 (d, J=2.4 Hz, 2H), 6.75 (d, J=16 Hz, 2H), 7.63 (d, J=7.7 Hz, 2H), 7.91 (d, J=16 Hz, 2H).

Melting Point 139-142° C., MS (ESI+) m/z 397.2 (M+1), 419.3 (M+Na).

Example 250

Synthesis of (1E,6E)-1,7-bis(2-morpholinopyridin-3-yl)hepta-1,6-diene-3,5-dione (CU366)

The title compound was synthesized using the same procedure employed for Example 244, but with 2-morpholinonicotinaldehyde (48 mg, 0.25 mmol) instead of 1,4-benzodioxane-6-carboxaldehyde (41 mg, 0.25 mmol). The product was obtained as a solid (9.8 mg, 22%) having the following characteristics.

$^1$H NMR (δ, acetone-d$_6$): 3.23 (dd, J=4.4, 4.8 Hz, 8H), 3.83 (dd, J=4.4, 4.8 Hz, 8H), 6.11 (s, 1H), 6.89 (d, J=16 Hz, 2H), 7.04 (dd, J=4.8, 7.7 Hz, 2H), 7.79 (d, J=16 Hz, 2H), 7.98 (dd, J=2, 7.7 Hz, 2H), 8.29 (dd, J=2, 4.8 Hz, 2H).

Melting Point 192-195° C., MS (ESI+) m/z 449.4 (M+1).

Example 251

Synthesis of (1E,6E)-1,7-bis(4-dimethylamino-3-methoxyphenyl)hepta-1,6-diene-3,5-dione (CU367)

The title compound was synthesized using the same procedure employed for Example 244, but with 4-dimethylamino-3-methoxybenzaldehyde (45 mg, 0.25 mmol) instead of 1,4-benzodioxane-6-carboxaldehyde (41 mg, 0.25 mmol). The product was obtained as a gum (6.4 mg, 15%) having the following characteristics.

$^1$H NMR (δ, CDCl$_3$): 2.86 (s, 12H), 3.93 (s, 6H), 5.82 (s, 1H), 6.50 (d, J=16 Hz, 2H), 6.88 (d, J=8.2 Hz, 2H), 7.03 (d, J=2 Hz, 2H), 7.13 (dd, J=2, 8.2 Hz, 2H), 7.61 (d, J=16 Hz, 2H).

MS (ESI+) m/z 423.4 (M+1).

Example 252

Synthesis of (1E,6E)-1,7-bis(benzofuran-2-yl)hepta-1,6-diene-3,5-dione (CU369)

The title compound was synthesized using the same procedure employed for Example 244, but with benzofuran-2- carboxaldehyde (37 mg, 0.25 mmol) instead of 1,4-benzodioxane-6-carboxaldehyde (41 mg, 0.25 mmol). The product was obtained as a solid (6.0 mg, 17%) having the following characteristics.

$^1$H NMR (δ, acetone-$d_6$): 6.29 (s, 1H), 6.89 (d, J=16 Hz, 2H), 7.26~7.32 (m, 2H), 7.28 (s, 2H), 7.4-7.45 (m, 2H), 7.57 (d, J=8.2 Hz, 2H), 7.64 (d, J=16 Hz, 2H), 7.70 (d, J=7.7 Hz, 2H).

Melting Point 173-177° C.

Example 253

Synthesis of (1E,6E)-1,7-bis(4-phenoxyphenyl)hepta-1,6-diene-3,5-dione (CU370)

The title compound was synthesized using the same procedure employed for Example 244, but with 4-phenoxybenzaldehyde (50 mg, 0.25 mmol) instead of 1,4-benzodioxane-6-carboxaldehyde (41 mg, 0.25 mmol). The product was obtained as a solid (2.7 mg, 6%) having the following characteristics.

$^1$H NMR (δ, acetone-$d_6$): 6.08 (s, 1H), 6.80 (d, J=16 Hz, 2H), 7.03 (d, J=8.7 Hz, 4H), 7.09 (dd, J=1, 8.7 Hz, 4H), 7.18~7.24 (m, 2H), 7.4~7.47 (m, 4H), 7.67 (d, J=16 Hz, 2H), 7.72 (d, J=8.7 Hz, 4H).

Melting Point 193-196° C., MS (ESI+) m/z 461.5 (M+1).

Example 254

Synthesis of (1E,6E)-1,7-bis[6-(4-methylphenoxy)pyridin-3-yl]hepta-1,6-diene-3,5-dione (CU378)

The title compound was synthesized using the same procedure employed for Example 244, but with 6-(4-methylphenoxy)nicotinaldehyde (53 mg, 0.25 mmol) instead of 1,4-benzodioxane-6-carboxaldehyde (41 mg, 0.25 mmol). The product was obtained as a solid (18.0 mg, 37%) having the following characteristics.

$^1$H NMR (δ, acetone-$d_6$): 2.35 (s, 6H), 6.08 (s, 1H), 6.87 (d, J=16 Hz, 2H), 7.02 (d, J=8.7 Hz, 2H), 7.05 (d, J=8.2 Hz, 4H), 7.24 (d, J=8.2 Hz, 4H), 7.68 (d, J=16 Hz, 2H), 8.19 (dd, J=2, 8.7 Hz, 2H), 8.39 (d, J=2 Hz, 2H).

Melting Point 185-190° C., MS (ESI+) m/z 491.3 (M+1).

Example 255

Synthesis of (1E,6E)-1,7-bis(5-hydroxy-2-methoxyphenyl)hepta-1,6-diene-3,5-dione (CU380)

The title compound was synthesized using the same procedure employed for Example 244, but with 5-hydroxy-2-methoxybenzaldehyde (38 mg, 0.25 mmol) instead of 1,4-benzodioxane-6-carboxaldehyde (41 mg, 0.25 mmol). The product was obtained as a solid (3.9 mg, 11%) having the following characteristics.

$^1$H NMR (δ, acetone-$d_6$): 3.86 (s, 6H), 6.04 (s, 1H), 6.81 (d, J=16 Hz, 2H), 6.89 (dd, J=2.9, 8.7 Hz, 2H), 6.94 (d, J=8.7 Hz, 2H), 7.15 (d, J=2.9 Hz, 2H), 7.95 (d, J=16 Hz, 2H), 8.03 (br s, OH).

Melting Point 188-196° C., MS (ESI+) m/z 369.2 (M+1).

Example 256

Synthesis of (1E,6E)-1,7-bis(5-hydroxy-2-nitrophenyl)hepta-1,6-diene-3,5-dione (CU381)

The title compound was synthesized using the same procedure employed for Example 244, but with 5-hydroxy-2-nitrobenzaldehyde (42 mg, 0.25 mmol) instead of 1,4-benzodioxane-6-carboxaldehyde (41 mg, 0.25 mmol). The product was obtained as a solid (7.8 mg, 20%) having the following characteristics.

$^1$H NMR (δ, acetone-$d_6$): 6.24 (s, 1H), 6.78 (d, J=16 Hz, 2H), 7.07 (dd, J=2.4, 9.2 Hz, 2H), 7.23 (d, J=2 Hz, 2H), 8.09 (d, J=9.2 Hz, 2H), 8.17 (d, J=16 Hz, 2H).

Melting Point 253-262° C., MS (ESI+) m/z 399.1 (M+1), 421.1 (M+Na).

Example 257

Synthesis of (1E,6E)-1,7-bis(1H-indol-5-yl)hepta-1,6-diene-3,5-dione (CU382)

The title compound was synthesized using the same procedure employed for Example 244, but with 1H-indole-5-carboxaldehyde (36 mg, 0.25 mmol) instead of 1,4-benzodioxane-6-carboxaldehyde (41 mg, 0.25 mmol). The product was obtained as a solid (4.2 mg, 12%) having the following characteristics.

$^1$H NMR (δ, acetone-$d_6$): 6.05 (s, 1H), 6.56 (dd, J=2, 3 Hz, 2H), 6.79 (d, J=16 Hz, 2H), 7.39 (dd, J=3, 3 Hz, 2H), 7.49 (d, J=8.7 Hz, 2H), 7.51 (dd, J=2.4, 8.7 Hz, 2H), 7.81 (d, J=16 Hz, 2H), 7.91 (s, 2H), 10.5 (br s, 1H, NH).

Melting Point 263-266° C., MS (ESI+) m/z 355.3 (M+1), 377.3 (M+Na).

Example 258

Synthesis of (1E,6E)-1,7-bis(quinolin-5-yl)hepta-1,6-diene-3,5-dione (CU384)

The title compound was synthesized using the same procedure employed for Example 244, but with quinoline-5-carboxaldehyde (39 mg, 0.25 mmol) instead of 1,4-benzodioxane-6-carboxaldehyde (41 mg, 0.25 mmol). The product was obtained as a solid (4.0 mg, 11%) having the following characteristics.

$^1$H NMR (δ, $CDCl_3$): 5.96 (s, 1H), 6.78 (d, J=16 Hz, 2H), 7.52 (dd, J=4, 8 Hz, 2H), 7.76 (dd, J=7.7, 8.2 Hz, 2H), 7.89 (d, J=8.2 Hz, 2H), 8.18 (d, J=8.7 Hz, 2H), 8.46 (d, J=16 Hz, 2H), 8.61 (d, J=8.7 Hz, 2H), 8.99 (br d, J=4 Hz, 2H).

Melting Point 170-174° C., MS (ESI+) m/z 379.3 (M+1).

Example 259

Synthesis of (1E,6E)-1,7-bis[2-(4-benzylpiperazin-1-yl)pyridin-3-yl]hepta-1,6-diene-3,5-dione (CU385)

The title compound was synthesized using the same procedure employed for Example 244, but with 2-(4-benzylpiperazin-1-yl)nicotinaldehyde (70 mg, 0.25 mmol) instead of 1,4-benzodioxane-6-carboxaldehyde (41 mg, 0.25 mmol). The product was obtained as a solid (40.8 mg, 65%) having the following characteristics.

$^1$H NMR (δ, $CDCl_3$): 2.5~2.7 (m, 4H), 3.2~3.4 (m, 4H), 3.61 (s, 4H), 5.79 (s, 1H), 6.57 (d, J=16 Hz, 2H), 6.90 (dd, J=4.8, 7.7 Hz, 2H), 7.2~7.4 (m, 10H), 7.72 (dd, J=~2, 7.7 Hz, 2H), 7.75 (d, J=16 Hz, 2H), 8.27 (d d, J=~2, 4.8 Hz, 2H).

Melting Point 150-155° C., MS (ESI+) m/z 627.5 (M+1).

Example 260

Synthesis of (1E,6E)-1,7-bis[4-(4-methylpiperazin-1-yl)phenyl]hepta-1,6-diene-3,5-dione (CU386)

The title compound was synthesized using the same procedure employed for Example 244, but with 4-(4-methylpiperazin-1-yl)benzaldehyde (51 mg, 0.25 mmol) instead of 1,4-benzodioxane-6-carboxaldehyde (41 mg, 0.25 mmol). The product was obtained as a solid (10.0 mg, 21%) having the following characteristics.

$^1$H NMR (δ, CDCl$_3$): 2.35 (s, 6H), 2.56 (t, J=5 Hz, 4H), 3.31 (t, J=5 Hz, 4H), 5.75 (s, 1H), 6.45 (d, J=16 Hz, 2H), 6.88 (d, J=8.7 Hz, 4H), 7.46 (d, J=8.7 Hz, 4H), 7.58 (d, J=16 Hz, 2H).

Melting Point 212-217° C., MS (ESI+) m/z 473.3 (M+1).

Example 261

Synthesis of (1E,6E)-1,7-bis(3-chloro-4-hydroxyphenyl)hepta-1,6-diene-3,5-dione (CU387)

The title compound was synthesized using the same procedure employed for Example 244, but with 3-chloro-4-hydroxybenzaldehyde (39 mg, 0.25 mmol) instead of 1,4-benzodioxane-6-carboxaldehyde (41 mg, 0.25 mmol). The product was obtained as a solid (8.4 mg, 22%) having the following characteristics.

$^1$H NMR (δ, acetone-d$_6$): 6.02 (s, 1H), 6.76 (d, J=16 Hz, 2H), 7.07 (d, J=8.7 Hz, 2H), 7.52 (dd, J=1.9, 8.7 Hz, 2H), 7.57 (d, J=16 Hz, 2H), 7.74 (d, J=1.9 Hz, 2H).

Melting Point 203-208° C., MS (ESI+) m/z 377.2 (M+1).

Example 262

Synthesis of (1E,6E)-1,7-bis(3-phenoxyphenyl)hepta-1,6-diene-3,5-dione (CU388)

The title compound was synthesized using the same procedure employed for Example 244, but with 3-phenoxybenzaldehyde (50 mg, 0.25 mmol) instead of 1,4-benzodioxane-6-carboxaldehyde (41 mg, 0.25 mmol). The product was obtained as a solid (10.4 mg, 23%) having the following characteristics.

$^1$H NMR (δ, acetone-d$_6$): 6.11 (s, 1H), 6.86 (d, J=16 Hz, 2H), 6.95~7.1 (m, 6H), 7.1~7.2 (m, 2H), 7.3-7.5 (m, 10H), 7.65 (d, J=16 Hz, 2H).

MS (ESI+) m/z 461.2 (M+1).

Example 263

Synthesis of (1E,6E)-1,7-bis[1-(4-methylphenyl)-1H-pyrrol-2-yl]hepta-1,6-diene-3,5-dione (CU389)

The title compound was synthesized using the same procedure employed for Example 244, but with 1-(4-methylphenyl)-1H-pyrrole-2-carboxaldehyde (46 mg, 0.25 mmol) instead of 1,4-benzodioxane-6-carboxaldehyde (41 mg, 0.25 mmol). The product was obtained as a solid (6.8 mg, 16%) having the following characteristics.

$^1$H NMR (δ, acetone-d$_6$): 2.43 (s, 6H), 5.67 (s, 1H), 6.35 (dd, J=3.4, 3.4 Hz, 2H), 6.44 (d, J=16 Hz, 2H), 6.93 (br d, J=3 Hz, 2H), 7.09 (br s, 2H), 7.25 (d, J=8.2 Hz, 4H), 7.34 (d, J=16 Hz, 2H), 7.38 (d, J=8.2 Hz, 4H).

Melting Point 151-155° C., MS (ESI+) m/z 457.3 (M+Na).

Example 264

Synthesis of (1E,6E)-1,7-bis(2,6-dimethoxyphenyl)hepta-1,6-diene-3,5-dione (CU390)

The title compound was synthesized using the same procedure employed for Example 244, but with 2,6-dimethoxybenzaldehyde (42 mg, 0.25 mmol) instead of 1,4-benzodioxane-6-carboxaldehyde (41 mg, 0.25 mmol). The product was obtained as a solid (4.7 mg, 12%) having the following characteristics.

$^1$H NMR (δ, acetone-d$_6$): 3.94 (s, 12H), 5.91 (s, 1H), 6.72 (d, J=8.2 Hz, 4H), 7.21 (d, J=16 Hz, 2H), 7.34 (t, J=8.2 Hz, 2H), 8.13 (d, J=16 Hz, 2H).

Melting Point 180-184° C., MS (ESI+) m/z 397.2 (M+1), 419.2 (M+Na).

Example 265

Synthesis of (1E,6E)-1,7-bis(1H-indol-6-yl)hepta-1,6-diene-3,5-dione (CU391)

The title compound was synthesized using the same procedure employed for Example 244, but with 1H-indole-6-carboxaldehyde (36 mg, 0.25 mmol) instead of 1,4-benzodioxane-6-carboxaldehyde (41 mg, 0.25 mmol). The product was obtained as a solid (4.6 mg, 13%) having the following characteristics.

$^1$H NMR (δ, acetone-d$_6$): 6.06 (s, 1H), 6.52 (br d, J=3 Hz, 2H), 6.81 (d, J=16 Hz, 2H), 7.42~7.48 (m, 4H), 7.62 (d, J=8.2 Hz, 2H), 7.74 (br s, 2H), 7.79 (d, J=16 Hz, 2H), 10.5 (br s, 1H, NH).

Melting Point 247-255° C., MS (ESI+) m/z 354.7 (M+1), 376.8 (M+Na).

Example 266

Synthesis of (1E,6E)-1,7-bis(1H-indol-7-yl)hepta-1,6-diene-3,5-dione (CU392)

The title compound was synthesized using the same procedure employed for Example 244, but with 1H-indole-7-carboxaldehyde (36 mg, 0.25 mmol) instead of 1,4-benzodioxane-6-carboxaldehyde (41 mg, 0.25 mmol). The product was obtained as a solid (2.6 mg, 7%) having the following characteristics.

$^1$H NMR (δ, acetone-d$_6$): 6.16 (s, 1H), 6.58 (d, J=3.4 Hz, 2H), 6.98 (d, J=16 Hz, 2H), 7.12 (dd, J=7.2, 7.7 Hz, 2H), 7.44 (br d, J=3 Hz, 2H), 7.57 (d, J=7.2 Hz, 2H), 7.69 (d, J=7.7 Hz, 2H), 8.16 (d, J=16 Hz, 2H).

Melting Point 211-215° C., MS (ESI+) m/z 355.3 (M+1).

Example 267

Synthesis of (1E,6E)-1,7-bis(1H-indol-2-yl)hepta-1,6-diene-3,5-dione (CU393)

The title compound was synthesized using the same procedure employed for Example 244, but with 1H-indole-2-carboxaldehyde (36 mg, 0.25 mmol) instead of 1,4-benzodioxane-6-carboxaldehyde (41 mg, 0.25 mmol). The product was obtained as a solid (6.4 mg, 18%) having the following characteristics.

$^1$H NMR (δ, acetone-d$_6$): 5.95 (s, 1H), 6.78 (d, J=16 Hz, 2H), 6.94 (s, 2H), 7.05 (dd, J=7.2, 7.7 Hz, 2H), 7.20 (dd, J=7.7, 8.2 Hz, 2H), 7.40 (d, J=7.7 Hz, 2H), 7.60 (d, J=8.2 Hz, 2H), 7.71 (d, J=16 Hz, 2H), 10.7 (br s, 1H, NH).

Melting Point 264-268° C., MS (ESI+) m/z 355.3 (M+1).

Example 268

Synthesis of (1E,6E)-1-(4-hydroxyphenyl)-7-{4-[2-(tert-butoxycarbonylamino)acetylamino]phenyl}hepta-1,6-diene-3,5-dione (CU395)

(1) Synthesis of 4-[2-(tert-butoxycarbonylamino)acetylamino]benzaldehyde

To a solution of 4-aminobenzylalcohol (300 mg, 2.43 mmol), N-Boc-glycine (426 mg, 2.43 mmol), and 1-hydroxybenzotriazole (344 mg, 2.55 mmol) in 4.8 mL of dry N,N-dimethylformamide was added N,N-diisopropylethylamine (0.42 mL, 2.9 mmol). After addition of 1-ethyl-3-(3-dimethylaminopropyl)-3-ethylcarbodiimide monohydrochlorde (489 mg, 2.55 mmol) at 0° C., the solution was stirred at room temperature overnight. The reaction mixture was diluted with ethyl acetate, and the solution was washed with 1N HCl, saturated $NaHCO_3$ aqueous solution, brine, and dried over $MgSO_4$. After filtration, the filtrate was concentrated in vacuo to obtain crude 4-[2-(tert-butoxycarbonylamino)acetylamino]benzylalcohol.

The above product was dissolved in 9 mL of dry dichloromethane, and Dess-Martin periodinane (1.03 g, 2.43 mmol) was added to the solution at room temperature. After the reaction mixture was stirred for 30 min, saturated $NaHCO_3$ aqueous solution was added. The mixture was extracted with chloroform, and the extract was washed with brine, and dried over $MgSO_4$. After filtration, the solution was concentrated in vacuo, and the residue was purified by silica gel chromatography (hexane/ethyl acetate=60/40 to 30/70) to obtain the title compound as a white powder (200 mg, 30% in 2 steps).

(2) Synthesis of (1E,6E)-1-(4-hydroxyphenyl)-7-{4-[2-(tert-butoxydarbonylamino)acetylamino]phenyl}hepta-1,6-diene-3,5-dione (CU395)

The title compound was synthesized using the same procedure employed for Example 22, but with 4-[2-(tert-butoxycarbonylamino)acetylamino]benzaldehyde (31 mg, 0.11 mmol) instead of 3-hydroxy-4-methoxybenzaldehyde (16 mg, 0.11 mmol). The product was obtained as a solid (2.6 mg, 6%) having the following characteristics.

$^1$H NMR (δ, acetone-$d_6$): 1.43 (s, 9H), 3.90 (s, 2H), 6.02 (s, 1H), 6.2~6.3 (br s, 1H), 6.68 (d, J=16 Hz, 1H), 6.77 (d, J=16 Hz, 1H), 6.91 (d, J=8.7 Hz, 2H), 7.58 (d, J=8.7 Hz, 2H), 7.61 (d, J=16 Hz, 1H), 7.62 (d, J=16 Hz, 1H), 7.65 (d, J=8.2 Hz, 2H), 7.74 (br d, J=8.2 Hz, 2H).

MS (ESI+) m/z 465.4 (M+1), 487.3 (M+Na).

Example 269

Synthesis of (1E,6E)-1-(4-hydroxyphenyl)-7-[4-((S)-2-tert-butoxycarbonylamino-3-phenylpropionylamino)phenyl]hepta-1,6-diene-3,5-dione (CU396)

(1) Synthesis of 4-((S)-2-tert-butoxycarbonylamino-3-phenylpropionylamino)benzaldehyde The title compound was synthesized using the same procedure employed for Example 268 (1), but with N-Boc-phenylalanine (300 mg, 2.43 mmol) instead of N-Boc-glycine (426 mg, 2.43 mmol). The crude product was obtained as a solid (492 mg, ca. 60% purity).

(2) Synthesis of (1E,6E)-1-(4-hydroxyphenyl)-7-[4-((S)-2-tert-butoxycarbonylamino-3-phenylpropionylamino)phenyl]hepta-1,6-diene-3,5-dione (CU396)

The title compound was synthesized using the same procedure employed for Example 22, but with 4-((S)-2-tert-butoxycarbonylamino-3-phenylpropionylamino)benzaldehyde (40 mg, 0.11 mmol) instead of 3-hydroxy-4-methoxybenzaldehyde (16 mg, 0.11 mmol). The product was obtained as a solid (2.6 mg, 5%) having the following characteristics.

$^1$H NMR (δ, acetone-$d_6$): 1.36 (s, 9H), 3.01 (dd, J=8.7, 14 Hz, 1H), 3.22 (dd, J=5.8, 14 Hz, 1H), 4.5 (m, 1H), 6.02 (s, 1H), 6.21 (br d, J=8.2 Hz, 1H, NH), 6.68 (d, J=16 Hz, 1H), 6.77 (d, J=16 Hz, 1H), 6.91 (d, J=8.7 Hz, 2H), 7.18~7.32 (m, 5H), 7.57 (d, J=16 Hz, 1H), 7.58 (d, J=8.7 Hz, 2H), 7.62 (d, J=16 Hz, 1H), 7.64 (d, J=8.2 Hz, 2H), 7.71 (br d, J=8.2 Hz, 2H), 9.4 (br s, 1H).

Melting Point 116-121° C., MS (ESI+) m/z 555.4 (M+1), 577.3 (M+Na).

Example 270

Synthesis of (1E,6E)-1,7-bis(1-benzyl-1H-indol-3-yl)hepta-1,6-diene-3,5-dione (CU397)

The title compound was synthesized using the same procedure employed for Example 244, but with 1-benzyl-1H-indole-3-carboxaldehyde (59 mg, 0.25 mmol) instead of 1,4-benzodioxane-6-carboxaldehyde (41 mg, 0.25 mmol). The product was obtained as a solid (25.2 mg, 47%) having the following characteristics.

$^1$H NMR (δ, acetone-$d_6$): 5.53 (s, 4H), 6.05 (s, 1H), 6.79 (d, J=16 Hz, 2H), 7.2~7.4 (m, 14H), 7.51 (m, 2H), 7.92 (d, J=16 Hz, 2H), 7.95 (s, 2H), 8.04 (m, 2H).

Melting Point 206-213° C., MS (ESI+) m/z 535.4 (M+1), 557.4 (M+Na).

Example 271

Synthesis of (1E,6E)-1-(1-acetyl-1H-indol-3-yl)-7-(4-hydroxyphenyl)hepta-1,6-diene-3,5-dione (CU398)

(1) Synthesis of 1-acetyl-1H-indole-3-carboxaldehyde

To a solution of 1H-indole-3-carboxaldehyde (300 mg, 2.07 mmol) in 6.2 mL of dry dichloromethane were added pyridine (0.34 mL, 4.2 mmol), acetic anhydride (0.59 mL, 6.2 mmol), and N,N-dimethylaminopyridine (20 mg, 0.16 mmol) at room temperature, successively. After being stirred at room temperature for 2 h, the reaction mixture was diluted with ethyl acetate. The solution was washed with 1N HCl, saturated $NaHCO_3$ aqueous solution, brine, dried over $MgSO_4$, filtered, and concentrated in vacuo. The resulting solid was rinsed with diethyl ether/hexane to obtain the title compound as a white powder (235 mg, 77%).

(2) Synthesis of (1E,6E)-1-(1-acetyl-1H-indol-3-yl)-7-(4-hydroxyphenyl)hepta-1,6-diene-3,5-dione (CU398)

The title compound was synthesized using the same procedure employed for Example 22, but with 1-acetyl-1H-indole-3-carboxaldehyde (21 mg, 0.11 mmol) instead of 3-hydroxy-4-methoxybenzaldehyde (16 mg, 0.11 mmol). The product was obtained as a solid (4.4 mg, 13%) having the following characteristics.

$^1$H NMR (δ, acetone-$d_6$): 2.76 (s, 3H), 6.10 (s, 1H), 6.68 (d, J=16 Hz, 1H), 6.91 (d, J=8.7 Hz, 2H), 7.00 (d, J=16 Hz, 1H), 7.35~7.5 (m, 2H), 7.58 (d, J=8.7 Hz, 2H), 7.63 (d, J=16 Hz, 1H), 7.86 (d, J=16 Hz, 1H), 8.06 (dd, J=~2, 7 Hz, 1H), 8.31 (s, 1H), 8.48 (dd, J=~2, 7.2 Hz, 1H).

MS (ESI+) m/z 374.4 (M+1).

Example 272

Synthesis of (1E,6E)-1-(1-acetyl-1H-indol-6-yl)-7-(4-hydroxyphenyl)hepta-1,6-diene-3,5-dione (CU399)

(1) Synthesis of 1-acetyl-1H-indole-6-carboxaldehyde

To a solution of 1H-indole-6-carboxaldehyde (300 mg, 2.07 mmol) in 6.2 mL of dry dichloromethane were added pyridine (0.34 mL, 4.2 mmol), acetic anhydride (1.77 mL, 18.7 mmol), and N,N-dimethylaminopyridine (60 mg, 0.49 mmol) at room temperature, successively. After being stirred at room temperature overnight, the reaction mixture was diluted with ethyl acetate. The solution was washed with 1N HCl, saturated NaHCO$_3$ aqueous solution, brine, dried over MgSO$_4$, filtered, and concentrated in vacuo. The resulting solid was rinsed with diethyl ether/hexane to obtain the title compound as a pale orange powder (267 mg, 69%).

(2) Synthesis of (1E,6E)-1-(1-acetyl-1H-indol-6-yl)-7-(4-hydroxyphenyl)hepta-1,6-diene-3,5-dione (CU399)

The title compound was synthesized using the same procedure employed for Example 22, but with 1-acetyl-1H-indole-6-carboxaldehyde (21 mg, 0.11 mmol) instead of 3-hydroxy-4-methoxybenzaldehyde (16 mg, 0.11 mmol). The product was obtained as a solid (6.2 mg, 19%) having the following characteristics.

$^1$H NMR (δ, acetone-$d_6$): 2.72 (s, 3H), 6.12 (s, 1H), 6.70 (d, J=16 Hz, 1H), 6.74 (d, J=3.9 Hz, 1H), 6.87 (d, J=16 Hz, 1H), 6.91 (d, J=8.7 Hz, 2H), 7.59 (d, J=8.7 Hz, 2H), 7.6~7.68 (m, 2H), 7.64 (d, J=16 Hz, 1H), 7.79 (d, J=16 Hz, 1H), 7.87 (d, J=3.9 Hz, 1H), 8.70 (br s, 1H).

MS (ESI+) m/z 373.9 (M+1), 396.2 (M+Na).

Example 273

Synthesis of (1E,6E)-1-(1-benzyl-1H-indol-6-yl)-7-(4-hydroxyphenyl)hepta-1,6-diene-3,5-dione (CU400)

(1) Synthesis of 1-benzyl-1H-indole-6-carboxaldehyde

The title compound was synthesized using the same procedure employed for Example 229 (1), but with 1H-indole-6-carboxaldehyde (300 mg, 2.07 mmol) instead of 1H-indole-3-carboxaldehyde (300 mg, 2.07 mmol). The product was obtained as a purple solid (457 mg, 94%).

(2) Synthesis of (1E,6E)-1-(1-benzyl-1H-indol-6-yl)-7-(4-hydroxyphenyl)hepta-1,6-diene-3,5-dione (CU400)

The title compound was synthesized using the same procedure employed for Example 22, but with 1-benzyl-1H-indole-6-carboxaldehyde (27 mg, 0.11 mmol) instead of 3-hydroxy-4-methoxybenzaldehyde (16 mg, 0.11 mmol). The product was obtained as a solid (6.8 mg, 18%) having the following characteristics.

$^1$H NMR (δ, acetone-$d_6$): 5.52 (s, 2H), 5.99 (s, 1H), 6.56 (d, J=2.9 Hz, 1H), 6.67 (d, J=16 Hz, 1H), 6.81 (d, J=16 Hz, 1H), 6.91 (d, J=8.7 Hz, 2H), 7.23~7.35 (m, 5H), 7.43 (dd, J=~2, 8.2 Hz, 1H), 7.52 (d, J=2.9 Hz, 1H), 7.57 (d, J=8.7 Hz, 2H), 7.61 (d, J=16 Hz, 1H), 7.62 (d, J=8.2 Hz, 1H), 7.76 (d, J=16 Hz, 1H), 7.80 (s, 1H).

Melting Point 164-170° C., MS (ESI+) m/z 422.1 (M+1), 444.3 (M+Na).

Example 274

Synthesis of (1E,6E)-1-(4-hydroxyphenyl)-7-[1-(methylsulfonyl)-1H-indol-3-yl]hepta-1,6-diene-3,5-dione (CU401)

(1) Synthesis of 1-(methylsulfonyl)-1H-indole-3-carboxaldehyde

To a solution of 1H-indole-3-carboxaldehyde (300 mg, 2.07 mmol) in 4.1 mL of dry dimethylsulfoxide was added sodium hydride (108 mg, 55%, 2.5 mmol) under nitrogen at 0° C. After the reaction mixture was stirred for 30 min, methylsulfonyl chloride (0.19 mL, 2.5 mmol) was added with additional stirring for 1 h. The reaction mixture was diluted with 10 mL of ethyl acetate and 10 mL of saturated NH$_4$Cl aqueous solution at 0° C., successively, and the solution was extracted with 100 mL of ethyl acetate. The extract was washed with saturated NaHCO$_3$ aqueous solution, brine, and dried over MgSO$_4$. After filtration, the solution was concentrated in vacuo. The residue was purified by recrystallization (chloroform/hexane) to obtain the title compound as a pale red solid (300 mg, 65%).

(2) Synthesis of (1E,6E)-1-(4-hydroxyphenyl)-7-[1-(methylsulfonyl)-1H-indol-3-yl]hepta-1,6-diene-3,5-dione (CU401)

The title compound was synthesized using the same procedure employed for Example 22, but with 1-(methylsulfonyl)-1H-indole-3-carboxaldehyde (26 mg, 0.11 mmol) instead of 3-hydroxy-4-methoxybenzaldehyde (16 mg, 0.11 mmol). The product was obtained as a solid (6.6 mg, 18%) having the following characteristics.

$^1$H NMR (δ, acetone-$d_6$): 3.47 (s, 3H), 6.11 (s, 1H), 6.68 (d, J=16 Hz, 1H), 6.91 (d, J=8.7 Hz, 2H), 7.02 (d, J=16 Hz, 1H), 7.42~7.5 (m, 2H), 7.58 (d, J=8.7 Hz, 2H), 7.64 (d, J=16 Hz, 1H), 7.87 (d, J=16 Hz, 1H), 7.97 (dd, J=~2, 8 Hz, 1H), 8.04 (s, 1H), 8.12 (dd, J=~2, 8 Hz, 1H).

Melting Point 196-200° C., MS (ESI+) m/z 410.5 (M+1).

Example 275

Synthesis of (1E,6E)-1-(4-hydroxyphenyl)-7-[1-(methylsulfonyl)-1H-indol-6-yl]hepta-1,6-diene-3,5-dione (CU402)

(1) Synthesis of 1-(methylsulfonyl)-1H-indole-6-carboxaldehyde

The title compound was synthesized using the same procedure employed for Example 274 (1), but with 1H-indole-6-carboxaldehyde (300 mg, 2.07 mmol) instead of 1H-indole-3-carboxaldehyde (300 mg, 2.07 mmol), and was purified by silica gel column chromatography (hexane/ethyl acetate=75/25 to 60/40) instead of recrystallization. The product was obtained as a pale red solid (80 mg, 40%).

(2) Synthesis of (1E,6E)-1-(4-hydroxyphenyl)-7-[1-(methylsulfonyl)-1H-indol-6-yl]hepta-1,6-diene-3,5-dione (CU402)

The title compound was synthesized using the same procedure employed for Example 22, but with 1-(methylsulfonyl)-1H-indole-6-carboxaldehyde (26 mg, 0.11 mmol) instead of 3-hydroxy-4-methoxybenzaldehyde (16 mg, 0.11 mmol). The product was obtained as a solid (13.2 mg, 37%) having the following characteristics.

$^1$H NMR ($\delta$, acetone-$d_6$): 3.43 (s, 3H), 6.11 (s, 1H), 6.70 (d, J=16 Hz, 1H), 6.85 (d, J=2.9 Hz, 1H), 6.91 (d, J=8.7 Hz, 2H), 6.91 (d, J=16 Hz, 1H), 7.59 (d, J=8.7 Hz, 2H), 7.6~7.76 (m, 4H), 7.80 (d, J=16 Hz, 1H), 8.18 (s, 1H).

MS (ESI+) m/z 410.2 (M+1).

Example 276

Synthesis of (1E,6E)-1-(4-hydroxyphenyl)-7-(1-tosyl-1H-indol-3-yl)hepta-1,6-diene-3,5-dione (CU403)

(1) Synthesis of 1-tosyl-1H-indole-3-carboxaldehyde

To a solution of 1H-indole-3-carboxaldehyde (300 mg, 2.07 mmol) in 6.2 mL of dry dimethylsulfoxide was added sodium hydride (108 mg, 55%, 2.5 mmol) under nitrogen at 0° C. After the reaction mixture was stirred for 30 min at room temperature, p-toluenesulfonyl chloride (434 mg, 2.28 mmol) was added with additional stirring for 1 h. The reaction mixture was diluted with 10 mL of ethyl acetate and 10 mL of saturated NH$_4$Cl aqueous solution, successively, and the solution was extracted with 100 mL of ethyl acetate. The extract was washed with saturated NaHCO$_3$ aqueous solution, brine, and dried over MgSO$_4$ After filtration, the solution was concentrated in vacuo. The residue was purified by silica gel column chromatography (hexane/ethyl acetate=80/20 to 60/40) to obtain the title compound as a pale yellow solid (310 mg, 50%).

(2) Synthesis of (1E,6E)-1-(4-hydroxyphenyl)-7-(1-tosyl-1H-indol-3-yl)hepta-1,6-diene-3,5-dione (CU403)

The title compound was synthesized using the same procedure employed for Example 22, but with 1-tosyl-1H-indole-3-carboxaldehyde (34 mg, 0.11 mmol) instead of 3-hydroxy-4-methoxybenzaldehyde (16 mg, 0.11 mmol). The product was obtained as a solid (13.4 mg, 31%) having the following characteristics.

$^1$H NMR ($\delta$, acetone-$d_6$): 2.35 (s, 3H), 6.09 (s, 1H), 6.67 (d, J=16 Hz, 1H), 6.91 (d, J=8.7 Hz, 2H), 6.98 (d, J=16 Hz, 1H), 7.35~7.47 (m, 4H), 7.58 (d, J=8.7 Hz, 2H), 7.64 (d, J=16 Hz, 1H), 7.83 (d, J=16 Hz, 1H), 7.95 (d, J=8 Hz, 2H), 8.02 (d, J=7.7 Hz, 1H), 8.07 (d, J=8.2 Hz, 1H), 8.25 (s, 1H).

Melting Point 218-222° C., MS (ESI+) m/z 486.2 (M+1), 508.1 (M+Na).

Example 277

Synthesis of (1E,6E)-1-(4-hydroxyphenyl)-7-(1-tosyl-1H-indol-6-yl)hepta-1,6-diene-3,5-dione (CU404)

(1) Synthesis of 1-tosyl-1H-indole-6-carboxaldehyde

The title compound was synthesized using the same procedure employed for Example 276 (1), but with 1H-indole-6-carboxaldehyde (300 mg, 2.07 mmol) instead of 1H-indole-3-carboxaldehyde (300 mg, 2.07 mmol), and was purified by recrystallization (chloroform/hexane) instead of silica gel column chromatography. The product was obtained as a pale red powder (360 mg, 87%).

(2) Synthesis of (1E,6E)-1-(4-hydroxyphenyl)-7-(1-tosyl-1H-indol-6-yl)hepta-1,6-diene-3,5-dione (CU404)

The title compound was synthesized using the same procedure employed for Example 22, but with 1-tosyl-1H-indole-6-carboxaldehyde (34 mg, 0.11 mmol) instead of 3-hydroxy-4-methoxybenzaldehyde (16 mg, 0.11 mmol). The product was obtained as a solid (8.2 mg, 19%) having the following characteristics.

$^1$H NMR ($\delta$, acetone-$d_6$): 2.35 (s, 3H), 6.11 (s, 1H), 6.71 (d, J=16 Hz, 1H), 6.83 (d, J=3 Hz, 1H), 6.92 (d, J=8.7 Hz, 2H), 6.92 (d, J=16 Hz, 1H), 7.39 (d, J=8.2 Hz, 2H), 7.59 (d, J=8.7 Hz, 2H), 7.61~7.65 (m, 2H), 7.66 (d, J=16 Hz, 1H), 7.80 (d, J=3 Hz, 1H), 7.81 (d, J=16 Hz, 1H), 7.96 (d, J=8.2 Hz, 2H), 8.28 (s, 1H).

Melting Point 107-112° C., MS (ESI+) m/z 486.4 (M+1).

Example 278

Synthesis of (1E,6E)-1-[4-(tert-butoxycarbonylamino)phenyl]-7-(4-hydroxyphenyl)hepta-1,6-diene-3,5-dione (CU405)

(1) Synthesis of 4-(tert-butoxycarbonylamino)benzaldehyde

To a solution of 4-aminobenzyl alcohol (2.00 g, 16.2 mmol) in 10 mL of dioxane was added a solution of sodium hydroxide (0.65 g, 16 mmol) in 40 mL of water at room temperature. After addition of di-tert-butyl carbonate (4.95 g, 22.7 mmol), the reaction mixture was stirred at room temperature overnight. The mixture was diluted with diethyl ether, and the solution was washed with 1N HCl, saturated NaHCO$_3$ aqueous solution, brine, and dried over MgSO$_4$. After filtration, the filtrate was concentrated in vacuo to obtain crude 4-(tert-butoxycarbonylamino)benzyl alcohol.

The above crude product was dissolved in 48 mL of dry dichloromethane, and manganese dioxide (5.6 g, 64 mmol) was added to the solution at room temperature. After being stirred for 2 days, the reaction mixture was filtered through celite, and the filtrate was concentrated in vacuo. The residue was purified by silica gel column chromatography (chloroform/methanol=99/1 to 90/10) to obtain the title compound as a white powder (2.59 g, 72% in 2 steps).

(2) Synthesis of (1E,6E)-1-[4-(tert-butoxycarbonylamino)phenyl]-7-(4-hydroxyphenyl)hepta-1,6-diene-3,5-dione (CU405)

The title compound was synthesized using the same procedure employed for Example 22, but with 4-(tert-butoxycarbonylamino)benzaldehyde (25 mg, 0.11 mmol) instead of 3-hydroxy-4-methoxybenzaldehyde (16 mg, 0.11 mmol). The product was obtained as a solid (6.4 mg, 18%) having the following characteristics.

$^1$H NMR ($\delta$, acetone-$d_6$): 1.49 (s, 9H), 6.01 (s, 1H), 6.68 (d, J=16 Hz, 1H), 6.75 (d, J=16 Hz, 1H), 6.91 (d, J=8.7 Hz, 2H), 7.58 (d, J=8.7 Hz, 2H), 7.61 (d, J=16 Hz, 1H), 7.61 (d, J=16 Hz, 1H), 7.6~7.66 (m 4H), 8.65 (br s, 1H).

Melting Point 181-184° C., MS (ESI+) m/z 408.2 (M+1).

Example 279

Synthesis of (1E,6E)-1-[4-((R)-2-tert-butoxycarbonylamino-3-phenylpropionylamino)phenyl]-7-(4-hydroxyphenyl)hepta-1,6-diene-3,5-dione (CU406)

(1) Synthesis of 4-((R)-2-tert-butoxycarbonylamino-3-phenylpropionylamino)benzaldehyde The title compound was synthesized using the same procedure employed for Example 268 (1), but with N-Boc-D-phenylalanine (300 mg, 2.43 mmol) instead of N-Boc-glycine (426 mg, 2.43 mmol). The crude product was obtained as a solid (560 mg, ca. 60% purity).

(2) Synthesis of (1E,6E)-1-[4-((R)-2-tert-butoxycarbonylamino-3-phenylpropionylamino)phenyl]-7-(4-hydroxyphenyl)hepta-1,6-diene-3,5-dione (CU406)

The title compound was synthesized using the same procedure employed for Example 22, but with 4-((R)-2-tert-butoxycarbonylamino-3-phenylpropionylamino)benzaldehyde (40 mg, 0.11 mmol) instead of 3-hydroxy-4-methoxybenzaldehyde (16 mg, 0.11 mmol). The product was obtained as a solid (5.8 mg, 12%) having the following characteristics.

$^1$H NMR ($\delta$, acetone-$d_6$): 1.36 (s, 9H), 3.01 (dd, J=8.7, 14 Hz, 1H), 3.22 (dd, J=5.8, 14 Hz, 1H), 4.5 (m, 1H), 6.02 (s, 1H), 6.21 (br d, J=8.2 Hz, 1H, NH), 6.68 (d, J=16 Hz, 1H), 6.77 (d, J=16 Hz, 1H), 6.91 (d, J=8.7 Hz, 2H), 7.18~7.32 (m, 5H), 7.57 (d, J=16 Hz, 1H), 7.58 (d, J=8.7 Hz, 2H), 7.62 (d, J=16 Hz, 1H), 7.64 (d, J=8.2 Hz, 2H), 7.71 (br d, J=8.2 Hz, 2H), 9.4 (br s, 1H).

Melting Point 113-120° C., MS (ESI+) m/z 555.4 (M+1).

Example 280

Synthesis of (1E,6E)-1-(chromon-3-yl)-7-(4-hydroxyphenyl)hepta-1,6-diene-3,5-dione (CU407)

The title compound was synthesized using the same procedure employed for Example 22, but with chromone-3-carboxaldehyde (20 mg, 0.11 mmol) instead of 3-hydroxy-4-methoxybenzaldehyde (16 mg, 0.11 mmol). The product was obtained as a solid (5.4 mg, 17%) having the following characteristics.

$^1$H NMR ($\delta$, acetone-$d_6$): 6.04 (s, 1H), 6.72 (d, J=16 Hz, 1H), 6.92 (d, J=8.7 Hz, 2H), 7.45 (d, J=16 Hz, 1H), 7.55 (m, 1H), 7.59 (d, J=8.7 Hz, 2H), 7.62 (d, J=16 Hz, 1H), 7.65 (d, J=8 Hz, 1H), 7.67 (d, J=16 Hz, 1H), 7.84 (m, 1H), 8.23 (dd, J=~2, 8 Hz, 1H), 8.67 (s, 1H).

Melting Point 227-231° C., MS (ESI+) m/z 361.1 (M+1), 383.3 (M+Na).

Example 281

Synthesis of (1E,6E)-1-(4-aminophenyl)-7-(4-hydroxyphenyl)hepta-1,6-diene-3,5-dione (CU408)

To a solution of (1E,6E)-1-[4-(tert-butoxycarbonylamino)phenyl]-7-(4-hydroxyphenyl)hepta-1,6-diene-3,5-dione (22 mg, 54 μmol, synthesized in Example 278) in 1 mL of tetrahydrofuran was added 2 mL of 4N HCl/dioxane at room temperature. After being stirred at the same temperature for 1 h, the reaction mixture was neutralized with saturated NaHCO$_3$ aqueous solution. The mixture was extracted with chloroform, and the organic layer was dried over Na$_2$SO$_4$. After filtration, the filtrate was concentrated in vacuo and the residue was purified by silica gel column chromatography (hexane/ethyl acetate=70/30 to 50/50) to obtain the title compound as a solid (5.8 mg, 35%) having the following characteristics.

$^1$H NMR ($\delta$, acetone-$d_6$): 5.3 (2H, NH), 5.92 (s, 1H), 6.54 (d, J=16 Hz, 1H), 6.64 (d, J=16 Hz, 1H), 6.71 (d, J=8.7 Hz, 2H), 6.90 (d, J=8.7 Hz, 2H), 7.42 (d, J=8.7 Hz, 2H), 7.55 (d, J=8.7 Hz, 2H), 7.56 (d, J=16 Hz, 1H), 7.56 (d, J=16 Hz, 1H).

Melting Point 212-217° C., MS (ESI+) m/z 308.4 (M+1).

Example 282

Synthesis of (1E,6E)-1,7-bis(1-methyl-1H-indol-2-yl)hepta-1,6-diene-3,5-dione (CU409)

The title compound was synthesized using the same procedure employed for Example 244, but with 1-methyl-1H-indole-2-carboxaldehyde (40 mg, 0.25 mmol) instead of 1,4-benzodioxane-6-carboxaldehyde (41 mg, 0.25 mmol). The product was obtained as a solid (7.2 mg, 19%) having the following characteristics.

$^1$H NMR ($\delta$, acetone-$d_6$): 3.94 (s, 6H), 6.12 (s, 1H), 6.93 (d, J=16 Hz, 2H), 7.07 (m, 2H), 7.13 (s, 2H), 7.24 (m, 2H), 7.47 (d, J=8.2 Hz, 2H), 7.59 (d, J=8.2 Hz, 2H), 7.84 (d, J=16 Hz, 2H).

Melting Point 189-196° C., MS (ESI+) m/z 383.3 (M+1).

Example 283

Synthesis of (1E,6E)-1,7-bis(4-dimethylamino-2-methoxyphenyl)hepta-1,6-diene-3,5-dione (CU410)

The title compound was synthesized using the same procedure employed for Example 244, but with 4-dimethylamino-2-methoxybenzaldehyde (45 mg, 0.25 mmol) instead of 1,4-benzodioxane-6-carboxaldehyde (41 mg, 0.25 mmol). The product was obtained as a solid (2.6 mg, 6%) having the following characteristics.

$^1$H NMR ($\delta$, acetone-$d_6$): 3.05 (s, 12H), 3.92 (s, 6H), 5.79 (s, 1H), 6.31 (d, J=2.4 Hz, 2H), 6.37 (dd, J=2.4, 8.7 Hz, 2H), 6.60 (d, J=16 Hz, 2H), 7.50 (d, J=8.7 Hz, 2H), 7.90 (d, J=16 Hz, 2H).

Melting Point 76-86° C., MS (ESI+) m/z 423.4 (M+1).

Example 284

Synthesis of (1E,6E)-1,7-bis(4-dimethylamino-2-nitrophenyl)hepta-1,6-diene-3,5-dione (CU411)

The title compound was synthesized using the same procedure employed for Example 244, but with 4-dimethylamino-2-nitrobenzaldehyde (49 mg, 0.25 mmol) instead of 1,4-benzodioxane-6-carboxaldehyde (41 mg, 0.25 mmol). The product was obtained as a solid (13.6 mg, 30%) having the following characteristics.

$^1$H NMR ($\delta$, acetone-$d_6$): 3.13 (s, 12H), 6.02 (s, 1H), 6.74 (d, J=16 Hz, 2H), 7.05 (dd, J=3, 9 Hz, 2H), 7.17 (d, J=3 Hz, 2H), 7.82 (d, J=16 Hz, 2H), 7.84 (d, J=9 Hz, 2H).

Melting Point 245-250° C., MS (ESI+) m/z 453.4 (M+1), 475.3 (M+Na).

Example 285

Synthesis of (1E,6E)-1,7-bis(2-chloro-4-dimethylaminophenyl)hepta-1,6-diene-3,5-dione (CU412)

The title compound was synthesized using the same procedure employed for Example 244, but with 2-chloro-4-dimethylaminobenzaldehyde (46 mg, 0.25 mmol) instead of 1,4-benzodioxane-6-carboxaldehyde (41 mg, 0.25 mmol). The product was obtained as a solid (18.8 mg, 44%) having the following characteristics.

$^1$H NMR (δ, acetone-$d_6$): 3.06 (s, 12H), 5.94 (s, 1H), 6.66 (d, J=16 Hz, 2H), 6.7~6.8 (m, 4H), 7.75 (d, J=9.7 Hz, 2H), 7.99 (d, J=16 Hz, 2H).

Melting Point 238-241° C., MS (ESI+) m/z 431.3 (M+1).

Example 286

Synthesis of (1E,6E)-1,7-bis[4-diethylamino-2-(methoxymethoxy)phenyl)hepta-1,6-diene-3,5-dione (CU413)

The title compound was synthesized using the same procedure employed for Example 244, but with 4-diethylamino-2-(methoxymethoxy)benzaldehyde (59 mg, 0.25 mmol) instead of 1,4-benzodioxane-6-carboxaldehyde (41 mg, 0.25 mmol). The product was obtained as a solid (17.0 mg, 32%) having the following characteristics.

$^1$H NMR (δ, acetone-$d_6$): 1.18 (t, J=7 Hz, 12H), 3.45 (q, J=7 Hz, 8H), 3.50 (s, 6H), 5.31 (s, 4H), 5.79 (s, 1H), 6.43 (dd, J=2.4, 8.7 Hz, 2H), 6.49 (d, J=2.4 Hz, 2H), 6.58 (d, J=16 Hz, 2H), 7.52 (d, J=8.7 Hz, 2H), 7.93 (d, J=16 Hz, 2H).

MS (ESI+) m/z 539.5 (M+1), 561.5 (M+Na).

Example 287

Synthesis of (1E,6E)-1,7-bis(quinolin-8-yl)hepta-1,6-diene-3,5-dione (CU414)

The title compound was synthesized using the same procedure employed for Example 244, but with quinoline-8-carboxaldehyde (39 mg, 0.25 mmol) instead of 1,4-benzodioxane-6-carboxaldehyde (41 mg, 0.25 mmol). The product was obtained as a solid (2.4 mg, 6%) having the following characteristics.

$^1$H NMR (δ, acetone-$d_6$): 6.29 (s, 1H), 7.29 (d, J=16 Hz, 2H), 7.62 (dd, J=3.9, 8.7 Hz, 2H), 7.70 (dd, J=7.2, 8.2 Hz, 2H), 8.06 (dd, J=~2, 8~9 Hz, 2H), 8.30 (dd, J=~2, 7.2 Hz, 2H), 8.41 (dd, J=1.9, 8.2 Hz, 2H), 9.04 (dd, J=1.9, 3.9 Hz, 2H), 9.07 (d, J=16 Hz, 2H).

Melting Point 202-208° C., MS (ESI+) m/z 379.3 (M+1), 401.3 (M+Na).

Example 288

Synthesis of (1E,6E)-1-(4-hydroxyphenyl)-7-(4-methoxycoumarin-6-yl)hepta-1,6-diene-3,5-dione (CU415)

(1) Synthesis of 4-methoxycoumarin-6-carboxaldehyde

To a solution of 4-hydroxy-6-methylcoumarin (300 mg, 1.70 mmol) in 3.4 mL of dry N,N-dimethylformamide was added sodium hydride (89 mg, 55%, 2.0 mmol) under nitrogen at 0° C. After the reaction mixture was stirred at room temperature for 30 min, methyl iodide (0.16 mL, 2.6 mmol) was added with additional stirring for 30 min. The reaction mixture was diluted with 10 mL of ethyl acetate and 10 mL of saturated NH$_4$Cl aqueous solution at 0° C., successively, and the solution was extracted with 100 mL of ethyl acetate. The extract was washed with saturated NaHCO$_3$ aqueous solution, brine, and dried over MgSO$_4$. After filtration, the solution was concentrated in vacuo to obtain crude 4-methoxy-6-methylcoumarin (140 mg, 43%).

The above crude compound was dissolved in 0.7 mL of diethyl ether, 0.7 mL of acetic acid, and 0.7 mL of water. To the solution was added ceric ammonium nitrate (1.61 g, 2.94 mmol) at room temperature, and the reaction mixture was stirred at 100° C. for 30 min. The resulting mixture was diluted with water, and the solution was extracted with ethyl acetate. The extract was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=70/30 to 50/50) to obtain the title compound (17 mg, 11%).

(2) Synthesis of (1E,6E)-1-(4-hydroxyphenyl)-7-(4-methoxycoumarin-6-yl)hepta-1,6-diene-3,5-dione (CU415)

The title compound was synthesized using the same procedure employed for Example 22, but with 4-methoxycoumarin-6-carboxaldehyde (28 mg, 0.11 mmol) instead of 3-hydroxy-4-methoxybenzaldehyde (16 mg, 0.11 mmol). The product was obtained as a solid (7.3 mg, 21%) having the following characteristics.

$^1$H NMR (δ, acetone-$d_6$): 4.13 (s, 3H), 5.83 (s, 1H), 6.10 (s, 1H), 6.70 (d, J=16 Hz, 1H), 6.91 (d, J=8.7 Hz, 2H), 6.92 (d, J=16 Hz, 1H), 7.38 (d, J=8.7 Hz, 1H), 7.59 (d, J=8.7 Hz, 2H), 7.66 (d, J=16 Hz, 1H), 7.71 (d, J=16 Hz, 1H), 7.99 (dd, J=1.9, 8.7 Hz, 1H), 8.10 (d, J=1.9 Hz, 1H).

Melting Point 250-254° C., MS (ESI+) m/z 391.2 (M+1).

Example 289

Synthesis of (1E,6E)-1-(1-benzyl-1H-indol-3-yl)-7-(4-hydroxy-3-methoxyphenyl)hepta-1,6-diene-3,5-dione (CU416)

The title compound was synthesized using the same procedure employed for Example 1, but with 1-benzyl-1H-indole-3-carboxaldehyde (27 mg, 0.11 mmol) instead of 3-hydroxy-2-methoxybenzaldehyde (16 mg, 0.11 mmol). The product was obtained as a solid (16.2 mg, 41%) having the following characteristics.

$^1$H NMR (δ, acetone-$d_6$): 3.92 (s, 3H), 5.52 (s, 2H), 6.01 (s, 1H), 6.68 (d, J=16 Hz, 1H), 6.80 (d, J=16 Hz, 1H), 6.88 (d, J=8.2 Hz, 1H), 7.17 (dd, J=1.9, 8.2 Hz, 1H), 7.2~7.36 (m, 8H), 7.51 (m, 1H), 7.57 (d, J=16 Hz, 1H), 7.95 (d, J=16 Hz, 1H), 7.97 (s, 1H), 8.03 (m, 1H).

Melting Point 158-161° C., MS (ESI+) m/z 452.2 (M+1).

Example 290

Synthesis of (1E,6E)-1-(1-benzyl-1H-indol-3-yl)-7-(3-hydroxy-4-methoxyphenyl)hepta-1,6-diene-3,5-dione (CU417)

The title compound was synthesized using the same procedure employed for Example 29, but with 1-benzyl-1H-indole-3-carboxaldehyde (27 mg, 0.11 mmol) instead of 3-hydroxy-2-methoxybenzaldehyde (16 mg, 0.11 mmol). The product was obtained as a solid (16.4 mg, 41%) having the following characteristics.

$^1$H NMR (δ, acetone-$d_6$): 3.90 (s, 3H), 5.53 (s, 2H), 6.04 (s, 1H), 6.64 (d, J=16 Hz, 1H), 6.81 (d, J=16 Hz, 1H), 7.00 (d, J=8.2 Hz, 1H), 7.13 (dd, J=2, 8.2 Hz, 1H), 7.19 (d, J=2 Hz, 1H), 7.2~7.36 (m, 7H), 7.52 (m, 1H), 7.53 (d, J=16 Hz, 1H), 7.96 (d, J=16 Hz, 1H), 7.98 (s, 1H), 8.04 (m, 1H).

Melting Point 194-199° C., MS (ESI+) m/z 452.3 (M+1).

Example 291

Synthesis of (1E,6E)-1-{2-[(tert-butyldimethylsilyloxy)methyl]phenyl}-7-(4-hydroxyphenyl)hepta-1,6-diene-3,5-dione (CU418)

(1) Synthesis of 2-[(tert-butyldimethylsilyloxy)methyl]benzaldehyde

To a solution of 1,2-benzenedimethanol (500 mg, 3.62 mmol), N,N-diisopropylethylamine (0.76 mL, 4.4 mmol) in 3.6 mL of dichloromethane was added tert-butyldimethylsilyl chloride (573 mg, 3.80 mmol) at 0° C. The reaction mixture was allowed to warm to room temperature and was stirred for 1 day. The reaction mixture was diluted with diethyl ether, and the solution was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate=95/5 to 85/15) to obtain 2-[(tert-butyldimethylsilyloxy)methyl]benzylalcohol as a colorless oil (520 mg, 57%).

The above product was dissolved in 10 mL of dry dichloromethane, and Dess-Martin periodinane (0.92 g, 2.2 mmol) was added to the solution at room temperature. After the reaction mixture was stirred for 30 min, saturated NaHCO$_3$ aqueous solution was added. The mixture was extracted with diethyl ether, and the extract was washed with brine, and dried over MgSO$_4$. After filtration, the filtrate was concentrated in vacuo, and the residue was purified by silica gel column chromatography (hexane/ethyl acetate=95/5 to 85/15) to obtain the title compound as a colorless oil (485 mg, 95%).

(2) Synthesis of (1E,6E)-1-{2-[(tert-butyldimethylsilyloxy)methyl]phenyl}-7-(4-hydroxyphenyl)hepta-1,6-diene-3,5-dione (CU418)

The title compound was synthesized using the same procedure employed for Example 22, but with 2-[(tert-butyldimethylsilyloxy)methyl]benzaldehyde (28 mg, 0.11 mmol) instead of 3-hydroxy-4-methoxybenzaldehyde (16 mg, 0.11 mmol). The product was obtained as a gum (9.2 mg, 24%) having the following characteristics.

$^1$H NMR (δ, acetone-d$_6$): 0.14 (s, 6H), 0.93 (s, 9H), 4.93 (s, 2H), 6.05 (s, 1H), 6.70 (d, J=16 Hz, 1H), 6.78 (d, J=16 Hz, 1H), 6.91 (d, J=8.7 Hz, 2H), 7.32~7.42 (m, 2H), 7.49 (d, J=7.2 Hz, 1H), 7.59 (d, J=8.7 Hz, 2H), 7.64 (d, J=16 Hz, 1H), 7.76 (dd, J=~2, 8 Hz, 1H), 8.01 (d, J=16 Hz, 1H).

MS (ESI+) m/z 459.3 (M+Na).

Example 292

Synthesis of (1E,6E)-1-[1-(tert-butoxycarbonyl)-indolin-6-yl]-7-(4-hydroxyphenyl)hepta-1,6-diene-3,5-dione (CU419)

(1) Synthesis of 1-(tert-butoxycarbonyl)-indoline-6-carboxaldehyde

To a solution of 1H-indole-6-carboxaldehyde (200 mg, 1.38 mmol) and di-tert-butyl dicarbonate (316 mg, 1.45 mmol) in 1.4 mL of dry dichloromethane was added N,N-dimethylaminopyridine (17 mg, 0.14 mmol) at room temperature. After being stirred at the same temperature for 1 h, the reaction mixture was diluted with ethyl acetate. The solution was washed with 1N HCl, saturated NaHCO$_3$ aqueous solution, brine, and dried over MgSO$_4$. After filtration, the filtrate was concentrated in vacuo to obtain 1-(tert-butoxycarbonyl)-1H-indole-6-carboxaldehyde as a yellow gum (358 mg, 106%).

The above product (320 mg, 1.30 mmol) was dissolved in 9.0 mL of methanol, and palladium 10% on carbon (90 mg) was added to the solution under nitrogen. After the vessel was purged with hydrogen, the reaction mixture was stirred under 1 atm of hydrogen overnight. After the vessel was purged with nitrogen, palladium 10% on carbon was removed by filtration. After addition of 0.1 mL of triethylamine, the filtrate was concentrated in vacuo. The residue was purified by silica gel column chromatography (hexane/ethyl acetate=70/30 to 50/50) to obtain 1-(tert-butoxycarbonyl)-indoline-6-methanol as a colorless gum (163 mg, 50%).

The above product (163 mg, 0.654 mmol) was dissolved in 3.2 mL of dry dichloromethane, and Dess-Martin periodinane (290 mg, 0.68 mmol) was added to the solution at room temperature. After the reaction mixture was stirred for 30 min at the same temperature, saturated NaHCO$_3$ aqueous solution was added. The mixture was extracted with ethyl acetate, and the extract was washed with brine, and dried over MgSO$_4$. After filtration, the filtrate was concentrated in vacuo and the residue was purified by silica gel column chromatography (hexane/ethyl acetate=95/5 to 75/25) to obtain the title compound as a white powder (140 mg, 86%).

(2) Synthesis of (1E,6E)-1-[1-(tert-butoxycarbonyl)-indolin-6-yl]-7-(4-hydroxyphenyl)hepta-1,6-diene-3,5-dione (CU419)

The title compound was synthesized using the same procedure employed for Example 22, but with 1-(tert-butoxycarbonyl)-indoline-6-carboxaldehyde (27 mg, 0.11 mmol) instead of 3-hydroxy-4-methoxybenzaldehyde (16 mg, 0.11 mmol). The product was obtained as a solid (8.4 mg, 22%) having the following characteristics.

$^1$H NMR (δ, acetone-d$_6$): 1.58 (s, 9H), 3.13 (t, J=9 Hz, 2H), 4.00 (t, J=9 Hz, 2H), 6.12 (br s, 1H), 6.69 (d, J=16 Hz, 1H), 6.74 (br d, J=16 Hz, 1H), 6.91 (d, J=8.7 Hz, 2H), 7.22 (d, J=8~9 Hz, 1H), 7.24 (d, J=8~9 Hz, 1H), 7.58 (d, J=8.7 Hz, 2H), 7.63 (d, J=16 Hz, 1H), 7.65 (d, J=16 Hz, 1H), 8.1 (br s, 1H).

Melting Point 111-118° C., MS (ESI+) m/z 434.4 (M+1), 456.3 (M+Na).

Example 293

Synthesis of (1E,6E)-1-(2-benzyloxy-4-diethylaminophenyl)-7-(4-hydroxyphenyl)hepta-1,6-diene-3,5-dione (CU420)

(1) Synthesis of 2-benzyloxy-4-diethylaminobenzaldehyde

To a suspension of 4-diethylamino-2-hydroxybenzaldehyde (300 mg, 1.55 mmol) and potassium carbonate (0.43 g, 3.1 mmol) in 1.6 mL of acetone was added benzyl bromide (300 mg, 1.55 mmol) at 0° C. After being stirred at room temperature overnight, the reaction mixture was filtered to remove inorganic salts. The filtrate was diluted with diethyl ether, and the solution was washed with saturated NaHCO$_3$ aqueous solution, brine, and dried over MgSO$_4$. After filtration, the filtrate was concentrated in vacuo. The residue was purified by silica gel column chromatography (hexane/ethyl acetate=90/10) to obtain the title compound as a yellow oil (292 mg, 67%).

(2) Synthesis of (1E,6E)-1-(2-benzyloxy-4-diethylaminophenyl)-7-(4-hydroxyphenyl)hepta-1,6-diene-3,5-dione (CU420)

The title compound was synthesized using the same procedure employed for Example 22, but with 2-benzyloxy-4-diethylaminobenzaldehyde (32 mg, 0.11 mmol) instead of 3-hydroxy-4-methoxybenzaldehyde (16 mg, 0.11 mmol). The product was obtained as a gum (21.4 mg, 52%) having the following characteristics.

$^1$H NMR (δ, acetone-$d_6$): 1.13 (t, J=7.2 Hz, 6H), 3.43 (q, J=7.2 Hz, 4H), 5.28 (s, 2H), 5.80 (s, 1H), 6.34 (d, J=2.4 Hz, 1H), 6.36 (dd, J=2.4, 8.7 Hz, 1H), 6.62 (d, J=16 Hz, 1H), 6.64 (d, J=16 Hz, 1H), 6.89 (d, J=8.7 Hz, 2H), 7.35 (t, J=7.7 Hz, 1H), 7.43 (t, J=7.7 Hz, 2H), 7.49~7.56 (m, 4H), 7.54 (d, J=8.7 Hz, 2H), 8.00 (d, J=16 Hz, 1H).

MS (ESI+) m/z 470.3 (M+1), 492.2 (M+Na).

Example 294

Synthesis of (1E,6E)-1-(4-hydroxyphenyl)-7-[4-(methylamino)phenyl]hepta-1,6-diene-3,5-dione (CU421)

(1) Synthesis of 4-[N-(tert-butoxycarbony)-N-methylamino]benzaldehyde

To a solution of 4-(tert-butoxycarbonylamino)benzaldehyde (250 mg, 1.13 mmol, synthesized at Example 278 (1)) in 2.3 mL of dry N,N-dimethylformamide was added sodium hydride (59 mg, 55%, 1.4 mmol) under nitrogen at 0° C. After the reaction mixture was stirred at room temperature for 30 min, methyl iodide (105 μL, 1.69 mmol) was added with additional stirring overnight. After quench with saturated NH$_4$Cl aqueous solution, the mixture was extracted with diethyl ether. The extract was washed with saturated NaHCO$_3$ aqueous solution, brine, and dried over MgSO$_4$. After filtration, the filtrate was concentrated in vacuo. The residue was purified by silica gel column chromatography (hexane/ethyl acetate=80/20 to 60/40) to obtain the title compound (210 mg, 79%).

(2) Synthesis of (1E,6E)-1-(4-hydroxyphenyl)-7-[4-(methylamino)phenyl]hepta-1,6-diene-3,5-dione (CU421)

(1E,6E)-1-{[N-(tert-butoxycarbonyl)-N-methylamino]phenyl}-7-(4-hydroxyphenyl)hepta-1,6-diene-3,5-dione was synthesized using the same procedure employed for Example 22, but with 4-[N-(tert-butoxycarbony)-N-methylamino]benzaldehyde (26 mg, 0.11 mmol) instead of 3-hydroxy-4-methoxybenzaldehyde (16 mg, 0.11 mmol). The product was obtained as a solid (2.8 mg, 8%).

The title compound was synthesized from the above product (2.8 mg, 6.6 μmol) using the same procedure employed for Example 281, and was purified by silica gel chromatography (chloroform/methanol=100/0 to 95/5) to obtain the title compound as a solid (1.2 mg, 57%) having the following characteristic.

MS (ESI+) m/z 322.1 (M+1).

Example 295

Synthesis of (1E,6E)-1-[4-((S)-2-amino-3-phenylpropionylamino)phenyl]-7-(4-hydroxyphenyl)hepta-1,6-diene-3,5-dione (CU422)

The title compound was synthesized using the same procedure employed for Example 281, but with (1E,6E)-1-(4-hydroxyphenyl-7-[4-((S)-2-tert-butoxycarbonylamino-3-phenylpropionylamino)phenyl]hepta-1,6-diene-3,5-dione (30 mg, 54 μmol, synthesized in Example 269) as the starting material instead of (1E,6E)-1-[4-(tert-butoxycarbonylamino)phenyl]-7-(4-hydroxyphenyl)hepta-1,6-diene-3,5-dione, and was purified by silica gel chromatography (chloroform/methanol=97/3 to 85/15). The product was obtained as a solid (7.4 mg, 30%) having the following characteristics.

$^1$H NMR (δ, acetone-$d_6$): 2.95 (dd, J=8.2, 14 Hz, 1H), 3.19 (dd, J=3.9, 14 Hz, 1H), 3.92 (dd, J=3.9, 8.2 Hz, 1H), 6.07 (s, 1H), 6.71 (d, J=16 Hz, 1H), 6.88 (d, J=16 Hz, 1H), 6.91 (d, J=8.7 Hz, 2H), 7.22~7.38 (m, 7H), 7.59 (d, J=8.7 Hz, 2H), 7.65 (d, J=16 Hz, 1H), 7.66 (d, J=16 Hz, 1H), 7.75 (d, J=8.2 Hz, 2H).

MS (ESI+) m/z 455.3 (M+1).

Example 296

Synthesis of (1E,6E)-1-[4-((R)-2-amino-3-phenylpropionylamino)phenyl]-7-(4-hydroxyphenyl)hepta-1,6-diene-3,5-dione (CU423)

The title compound was synthesized using the same procedure employed for Example 281, but with (1E,6E)-1-(4-hydroxyphenyl)-7-[4-((R)-2-tert-butoxycarbonylamino-3-phenylpropionylamino)phenyl]hepta-1,6-diene-3,5-dione (30 mg, 54 μmol, synthesized in Example 279) as the starting material instead of (1E,6E)-1-[4-(tert-butoxycarbonylamino)phenyl]-7-(4-hydroxyphenyl)hepta-1,6-diene-3,5-dione, and was purified by silica gel chromatography (chloroform/methanol=97/3 to 85/15). The product was obtained as a solid (9.2 mg, 37%) having the following characteristics.

$^1$H NMR (δ, acetone-$d_6$): 2.95 (dd, J=8.2, 14 Hz, 1H), 3.19 (dd, J=3.9, 14 Hz, 1H), 3.92 (dd, J=3.9, 8.2 Hz, 1H), 6.07 (s, 1H), 6.71 (d, J=16 Hz, 1H), 6.88 (d, J=16 Hz, 1H), 6.91 (d, J=8.7 Hz, 2H), 7.22-7.38 (m, 7H), 7.59 (d, J=8.7 Hz, 2H), 7.65 (d, J=16 Hz, 1H), 7.66 (d, J=16 Hz, 1H), 7.75 (d, J=8.2 Hz, 2H).

Melting Point 161-167° C., MS (ESI+) m/z 455.3 (M+1).

Example 297

Synthesis of (1E,6E)-1-(2-hydroxymethylphenyl)-7-(4-hydroxyphenyl)hepta-1,6-diene-3,5-dione (CU424)

To a solution of (1E,6E)-1-{2-[(tert-butyldimethylslyloxy)methyl]phenyl}-7-(4-hydroxyphenyl)hepta-1,6-diene-3,5-dione (10 mg, 23 μmol, synthesized in Example 291) in 1 mL of dry tetrahydrofuran was added hydrogen fluoride pyridine complex (100 μL) at 0° C. After being stirred at room temperature for 30 min, the reaction mixture was neutralized with saturated NaHCO$_3$ aqueous solution. The mixture was extracted with ethyl acetate, and the extract was washed with 1N HCl, saturated NaHCO$_3$ aqueous solution, brine, and dried over MgSO$_4$. After filtration, the filtrate was concentrated in vacuo, and the residue was purified by silica gel column chromatography (hexane/ethyl acetate=70/30 to 50/50) to obtain the title compound as a solid (4.6 mg, 62%) having the following characteristics.

¹H NMR (δ, acetone-d₆): 4.81 (s, 2H), 6.06 (s, 1H), 6.71 (d, J=16 Hz, 1H), 6.78 (d, J=16 Hz, 1H), 6.91 (d, J=8.7 Hz, 2H), 7.34 (ddd, J=2, 7.2, 7.2 Hz, 1H), 7.38 (ddd, J=2, 7.2, 7.2 Hz, 1H), 7.50 (br d, J=7.2 Hz, 1H), 7.59 (d, J=8.7 Hz, 2H), 7.64 (d, J=16 Hz, 1H), 7.76 (br d, J=7.2 Hz, 1H), 8.04 (d, J=16 Hz, 1H).

Melting Point 173-180° C., MS (ESI+) m/z 345.2 (M+Na).

Example 298

Synthesis of (1E,6E)-1-(2-benzoyloxy-4-diethylaminophenyl)-7-(4-hydroxyphenyl)hepta-1,6-diene-3,5-dione (CU425)

(1) Synthesis of 2-benzoyloxy-4-diethylaminobenzaldehyde

To a solution of 4-diethylamino-2-hydroxybenzaldehyde (300 mg, 1.55 mmol), pyridine (0.19 mL, 2.3 mmol) in 1.6 mL of dry dichloromethane was added benzoyl chloride (216 µL, 1.84 mmol) at 0° C. After being stirred at room temperature overnight, the reaction mixture was diluted with ethyl acetate. The mixture was washed with 1N HCl, saturated NaHCO₃ aqueous solution, brine, and dried over MgSO₄. After filtration, the filtrate was concentrated in vacuo, and the residue was purified by silica gel column chromatography (hexane/ethyl acetate=90/10 to 80/20) to obtain the title compound as a white solid (432 mg, 94%).

(2) Synthesis of (1E,6E)-1-(2-benzoyloxy-4-diethylaminophenyl)-7-(4-hydroxyphenyl)hepta-1,6-diene-3,5-dione (CU425)

The title compound was synthesized using the same procedure employed for Example 22, but with 2-benzyloxy-4-diethylaminobenzaldehyde (34 mg, 0.11 mmol) instead of 3-hydroxy-4-methoxybenzaldehyde (16 mg, 0.11 mmol). The product was obtained as a solid (13.8 mg, 32%) having the following characteristics.

¹H NMR (δ, acetone-d₆): 1.20 (t, J=7 Hz, 6H), 3.49 (q, J=7 Hz, 4H), 5.81 (s, 1H), 6.58 (d, J=16 Hz, 1H), 6.61 (d, J=16 Hz, 1H), 6.65 (d, J=2.4 Hz, 1H), 6.73 (dd, J=2.4, 9.2 Hz, 1H), 6.89 (d, J=8.7 Hz, 2H), 7.52 (d, J=16 Hz, 1H), 7.53 (d, J=8.7 Hz, 2H), 7.66 (dd, J=7, 8 Hz, 2H), 7.68 (d, J=16 Hz, 1H), 7.72 (d, J=9.2 Hz, 1H), 7.78 (m, 1H), 8.25 (dd, J=1.5, 8.2 Hz, 2H).

Melting Point 212-215° C., MS (ESI+) m/z 484.4 (M+1), 506.3 (M+Na).

Example 299

Synthesis of (1E,6E)-1-(4-diethylamino-2-prenyloxyphenyl)-7-(4-hydroxyphenyl)hepta-1,6-diene-3,5-dione (CU426)

(1) Synthesis of 4-diethylamino-2-prenyloxybenzaldehyde

To a suspension of 4-diethylamino-2-hydroxybenzaldehyde (300 mg, 1.55 mmol), potassium carbonate (428 mg, 3.10 mmol), and tetrabutylammonium iodide (57 mg, 0.15 mmol) in 1.6 mL of dry N,N-dimethylformamide was added prenyl bromide (0.27 mL, 2.3 mmol) at 0° C. After being stirred at room temperature for 7 h, the reaction mixture was filtered to remove inorganic salts. The filtrate was diluted with diethyl ether, and the solution was washed with water, saturated NaHCO₃ aqueous solution, brine, and dried over MgSO₄. After filtration, the filtrate was concentrated in vacuo, and the residue was purified by silica gel column chromatography (hexane/ethyl acetate=90/10 to 75/25) to obtain the title compound as a pale yellow gum (377 mg, 93%).

(2) Synthesis of (1E,6E)-1-(4-diethylamino-2-prenyloxyphenyl)-7-(4-hydroxyphenyl)hepta-1,6-diene-3, 5-dione (CU426)

The title compound was synthesized using the same procedure employed for Example 22, but with 4-diethylamino-2-prenyloxybenzaldehyde (30 mg, 0.11 mmol) instead of 3-hydroxy-4-methoxybenzaldehyde (16 mg, 0.11 mmol). The product was obtained as a solid (13.6 mg, 35%) having the following characteristics.

¹H NMR (δ, acetone-d₆): 1.19 (t, J=7 Hz, 6H), 1.79 (s, 3H), 1.80 (s, 3H), 3.47 (q, J=7 Hz, 4H), 4.69 (d, J=6.3 Hz, 2H), 5.53 (m, 1H), 5.84 (s, 1H), 6.28 (d, J=2.4 Hz, 1H), 6.36 (dd, J=2.4, 9.2 Hz, 1H), 6.61 (d, J=16 Hz, 1H), 6.63 (d, J=16 Hz, 1H), 6.89 (d, J=8.7 Hz, 2H), 7.49 (d, J=9.2 Hz, 1H), 7.54 (d, J=16 Hz, 1H), 7.55 (d, J=8.7 Hz, 2H), 7.95 (d, J=16 Hz, 1H).

Melting Point 69-76° C., MS (ESI+) m/z 448.4 (M+1), 470.4 (M+Na).

Example 300

Synthesis of (1E,6E)-1,7-bis(2-benzoyloxy-4-diethylaminophenyl)hepta-1,6-diene-3,5-dione (CU427)

The title compound was synthesized using the same procedure employed for Example 244, but with 2-benzoyloxy-4-diethylaminobenzaldehyde (74 mg, 0.25 mmol) instead of 1,4-benzodioxane-6-carboxaldehyde (41 mg, 0.25 mmol). The product was obtained as a solid (12.2 mg, 19%) having the following characteristics.

¹H NMR (δ, acetone-d₆): 1.19 (t, J=7 Hz, 12H), 3.48 (q, J=7 Hz, 8H), 5.66 (s, 1H), 6.53 (d, J=16 Hz, 2H), 6.63 (d, J=2.4 Hz, 2H), 6.71 (dd, J=2.4, 9.2 Hz, 2H), 7.61 (d, J=16 Hz, 2H), 7.63 (dd, J=7, 8 Hz, 4H), 7.68 (d, J=9.2 Hz, 2H), 7.76 (t, J=7 Hz, 2H), 8.22 (dd, J=1.5, 8 Hz, 4H).

Melting Point 192-196° C., MS (ESI+) m/z 659.5 (M+1).

Example 301

Synthesis of (1E,6E)-1,7-bis(2-benzyloxy-4-diethylaminophenyl)hepta-1,6-diene-3,5-dione (CU428)

The title compound was synthesized using the same procedure employed for Example 244, but with 2-benzyloxy-4-diethylaminobenzaldehyde (71 mg, 0.25 mmol) instead of 1,4-benzodioxane-6-carboxaldehyde (41 mg, 0.25 mmol). The product was obtained as a solid (12.4 mg, 20%) having the following characteristics.

¹H NMR (δ, acetone-d₆): 1.13 (t, J=7 Hz, 12H), 3.43 (q, J=7 Hz, 8H), 5.27 (s, 4H), 5.66 (s, 1H), 6.34 (d, J=2.4 Hz, 2H), 6.36 (dd, J=2.4, 8.7 Hz, 2H), 6.60 (d, J=16 Hz, 2H), 7.34 (t, J=8 Hz, 2H), 7.42 (t, J=8 Hz, 4H), 7.49 (d, J=8.7 Hz, 2H), 7.53 (d, J=8 Hz, 4H), 7.95 (d, J=16 Hz, 2H).

MS (ESI+) m/z 631.5 (M+1).

Example 302

Synthesis of (1E,6E)-1-(4-diethylamino-2-isopropyloxyphenyl)-7-(4-hydroxyphenyl)hepta-1,6-diene-3,5-dione (CU429)

(1) Synthesis of 4-diethylamino-2-isopropyloxybenzaldehyde

To a suspension of 4-diethylamino-2-hydroxybenzaldehyde (300 mg, 1.55 mmol), potassium carbonate (428 mg, 3.10 mmol), and cesium carbonate (50 mg, 0.15 mmol) in 1.6 mL of dry N,N-dimethylformamide was added 2-iodopropane (0.47 mL, 4.7 mmol) at room temperature. After being stirred at the same temperature for 7 h, the reaction mixture was filtered to remove inorganic salts. The filtrate was diluted with diethyl ether, and the solution was washed with water, saturated $NaHCO_3$ aqueous solution, brine, and dried over $MgSO_4$. After filtration, the filtrate was concentrated in vacuo, and the residue was purified by silica gel column chromatography (hexane/ethyl acetate=90/10 to 75/25) to obtain the title compound as a colorless oil (333 mg, 91%).

(2) Synthesis of (1E,6E)-1-(4-diethylamino-2-isopropyloxyphenyl)-7-(4-hydroxyphenyl)hepta-1,6-diene-3,5-dione (CU429)

The title compound was synthesized using the same procedure employed for Example 22, but with 4-diethylamino-2-isopropyloxybenzaldehyde (27 mg, 0.11 mmol) instead of 3-hydroxy-4-methoxybenzaldehyde (16 mg, 0.11 mmol). The product was obtained as a gum (19.4 mg, 52%) having the following characteristics.

$^1$H NMR (δ, acetone-$d_6$): 1.17 (t, J=7 Hz, 6H), 1.39 (d, J=6.3 Hz, 6H), 3.47 (q, J=7 Hz, 4H), 4.74 (m, 1H), 5.85 (s, 1H), 6.29 (d, J=2.4 Hz, 1H), 6.37 (dd, J=2.4, 8.7 Hz, 1H), 6.61 (d, J=16 Hz, 1H), 6.64 (d, J=16 Hz, 1H), 6.89 (d, J=8.7 Hz, 2H), 7.49 (d, J=8.7 Hz, 1H), 7.50 (d, J=16 Hz, 1H), 7.55 (d, J=8.7 Hz, 2H), 7.95 (d, J=16 Hz, 1H).

MS (ESI+) m/z 422.4 (M+1).

Example 303

Synthesis of (1E,6E)-1-[4-diethylamino-2-(2-hydroxyethoxy)phenyl]-7-(4-hydroxyphenyl)hepta-1,6-diene-3,5-dione (CU430)

(1) Synthesis of 4-diethylamino-2-(2-hydroxyethoxy)benzaldehyde

To a solution of 4-diethylamino-2-hydroxybenzaldehyde (1.00 g, 5.17 mmol) in 10 mL of dry N,N-dimethylformamide was added sodium hydride (250 mg, 55%, 5.7 mmol) under nitrogen at 0° C. After the reaction mixture was stirred at room temperature for 30 min, 2-bromoethanol (1.1 mL, 15 mmol) was added with additional stirring at 50° C. overnight. After quench with $NH_4Cl$ aqueous solution at 0° C., the solution was extracted with ethyl acetate three times. The extracts were washed with saturated $NaHCO_3$ aqueous solution, brine, and dried over $MgSO_4$. After filtration, the filtrate was concentrated in vacuo, and the residue was purified by silica gel column chromatography (hexane/ethyl acetate=75/25 to 25/75) to obtain the title compound as a brown gum (566 mg, 46%).

(2) Synthesis of (1E,6E)-1-[4-diethylamino-2-(2-hydroxyethoxy)phenyl]-7-(4-hydroxyphenyl)hepta-1,6-diene-3,5-dione (CU430)

The title compound was synthesized using the same procedure employed for Example 22, but with 4-diethylamino-2-(2-hydroxyethoxy)benzaldehyde (27 mg, 0.11 mmol) instead of 3-hydroxy-4-methoxybenzaldehyde (16 mg, 0.11 mmol). The product was obtained as a solid (13.8 mg, 37%) having the following characteristics.

$^1$H NMR (δ, acetone-$d_6$): 1.19 (t, J=7 Hz, 6H), 3.48 (q, J=7 Hz, 4H), 3.97 (t, J=4.8 Hz, 2H), 4.18 (t, J=4.8 Hz, 2H), 5.86 (s, 1H), 6.32 (d, J=2.4 Hz, 1H), 6.37 (dd, J=2.4, 9 Hz, 1H), 6.63 (d, J=16 Hz, 1H), 6.65 (d, J=16 Hz, 1H), 6.89 (d, J=8.7 Hz, 2H), 7.48 (d, J=9 Hz, 1H), 7.54 (d, J=16 Hz, 1H), 7.55 (d, J=8.7 Hz, 2H), 7.95 (d, J=16 Hz, 1H).

Melting Point 182-186° C., MS (ESI+) m/z 424.4 (M+1).

Example 304

Synthesis of (1E,6E)-1,7-bis(4-diethylamino-2-prenyloxyphenyl)hepta-1,6-diene-3,5-dione (CU431)

The title compound was synthesized using the same procedure employed for Example 244, but with 4-diethylamino-2-prenyloxybenzaldehyde (65 mg, 0.25 mmol) instead of 1,4-benzodioxane-6-carboxaldehyde (41 mg, 0.25 mmol). The product was obtained as a solid (3.0 mg, 5%) having the following characteristics.

$^1$H NMR (δ, acetone-$d_6$): 1.19 (t, J=7 Hz, 12H), 1.79 (s, 6H), 1.80 (s, 6H), 3.46 (q, J=7 Hz, 8H), 4.69 (d, J=6.8 Hz, 4H), 5.53 (m, 2H), 5.71 (s, 1H), 6.28 (d, J=2.4 Hz, 2H), 6.35 (dd, J=2.4, 8.7 Hz, 2H), 6.57 (d, J=16 Hz, 2H), 7.47 (d, J=8.7 Hz, 2H), 7.90 (d, J=16 Hz, 2H).

Melting Point 107-113° C., MS (ESI+) m/z 587.5 (M+1).

Example 305

Synthesis of (1E,6E)-1,7-bis(4-diethylamino-2-isopropyloxyphenyl)hepta-1,6-diene-3,5-dione (CU433)

The title compound was synthesized using the same procedure employed for Example 244, but with 4-diethylamino-2-isopropyloxybenzaldehyde (59 mg, 0.25 mmol) instead of 1,4-benzodioxane-6-carboxaldehyde (41 mg, 0.25 mmol). The product was obtained as a solid (18.2 mg, 34%) having the following characteristics.

$^1$H NMR (δ, acetone-$d_6$): 1.18 (t, J=7 Hz, 12H), 1.38 (d, J=6.3 Hz, 12H), 3.46 (q, J=7 Hz, 8H), 4.72 (m, 2H), 5.75 (s, 1H), 6.28 (d, J=2.4 Hz, 2H), 6.36 (dd, J=2.4, 9.2 Hz, 2H), 6.58 (d, J=16 Hz, 2H), 7.48 (d, J=9.2 Hz, 2H), 7.90 (d, J=16 Hz, 2H).

Melting Point 63-66° C., MS (ESI+) m/z 535.4 (M+1).

Example 306

Synthesis of (1E,6E)-1-{4-[2-(amino)acetylamino]phenyl}-7-(4-hydroxyphenyl)hepta-1,6-diene-3,5-dione (CU434)

The title compound was synthesized using the same procedure employed for Example 281, but with (1E,6E)-1-{4-[2-(tert-butoxycarbonylamino)acetylamino]phenyl}-7-(4-hydroxyphenyl)hepta-1,6-diene-3,5-dione (18 mg, 39 μmol, synthesized in Example 268) as the starting material instead of (1E,6E)-1-[4-(tert-butoxycarbonylamino)phenyl]-7-(4-hydroxyphenyl)hepta-1,6-diene-3,5-dione, and was purified by silica gel chromatography (chloroform/methanol=95/5 to 80/20). The product was obtained as a solid (1.5 mg, 11%) having the following characteristic.

MS (ESI+) m/z 365.3 (M+1).

Example 307

Synthesis of (1E,6E)-1,7-bis[4-diethylamino-2-(2-hydroxyethoxy)phenyl]hepta-1,6-diene-3,5-dione (CU435)

The title compound was synthesized using the same procedure employed for Example 244, but with 4-diethylamino-2-(2-hydroxyethoxy)benzaldehyde (59 mg, 0.25 mmol) instead of 1,4-benzodioxane-6-carboxaldehyde (41 mg, 0.25 mmol). The product was obtained as a solid (19.2 mg, 36%) having the following characteristic.

MS (ESI+) m/z 539.4 (M+1), 561.3 (M+Na).

Example 308

Synthesis of (1E,6E)-1-(4-hydroxyphenyl)-7-(indolin-6-yl)hepta-1,6-diene-3,5-dione (CU436)

The title compound was synthesized using the same procedure employed for Example 281, but with (1E,6E)-1-[1-(tert-butoxycarbony)-indolin-6-yl]-7-(4-hydroxyphenyl)hepta-1,6-diene-3,5-dione (14 mg, 32 µmol, synthesized in Example 292) as the starting material instead of (1E,6E)-1-[4-(tert-butoxycarbonylamino)phenyl]-7-(4-hydroxyphenyl)hepta-1,6-diene-3,5-dione, and was purified by silica gel chromatography (chloroform/methanol=100/0 to 95/5). The product was obtained as a solid (1.4 mg, 13%) having the following characteristic.

MS (ESI+) m/z 334.3 (M+1).

Example 309

Synthesis of (1E,6E)-1-(2-benzyloxy-4-diethylaminophenyl)-7-(4-hydroxy-3-methoxyphenyl)hepta-1,6-diene-3,5-dione (CU437)

The title compound was synthesized using the same procedure employed for Example 1, but with 2-benzyloxy-4-diethylaminobenzaldehyde (33 mg, 0.11 mmol) instead of 3-hydroxy-2-methoxybenzaldehyde (16 mg, 0.11 mmol). The product was obtained as a solid (21.8 mg, 50%) having the following characteristics.

$^1$H NMR (δ, acetone-$d_6$): 1.13 (t, J=7 Hz, 6H), 3.43 (q, J=7 Hz, 4H), 3.92 (s, 3H), 5.28 (s, 2H), 5.80 (s, 1H), 6.34 (d, J=2.4 Hz, 1H), 6.36 (dd, J=2.4, 8.7 Hz, 1H), 6.63 (d, J=16 Hz, 1H), 6.66 (d, J=16 Hz, 1H), 6.87 (d, J=8.2 Hz, 1H), 7.16 (dd, J=1.9, 8.2 Hz, 1H), 7.32 (d, J=1.9 Hz, 1H), 7.35 (t, J=8 Hz, 1H), 7.43 (t, J=8 Hz, 2H), 7.50 (d, J=8.7 Hz, 1H), 7.53 (d, J=16 Hz, 1H), 7.54 (d, J=8 Hz, 2H), 8.01 (d, J=16 Hz, 1H).

Melting Point 60-65° C., MS (ESI+) m/z 500.4 (M+1), 522.5 (M+Na).

Example 310

Synthesis of (1E,6E)-1-(2-benzyloxy-4-diethylaminophenyl)-7-(3-hydroxy-4-methoxyphenyl)hepta-1,6-diene-3,5-dione (CU438)

The title compound was synthesized using the same procedure employed for Example 29, but with 2-benzyloxy-4-diethylaminobenzaldehyde (33 mg, 0.11 mmol) instead of 3-hydroxy-2-methoxybenzaldehyde (16 mg, 0.11 mmol). The product was obtained as a solid (23.6 mg, 54%) having the following characteristics.

$^1$H NMR (δ, acetone-$d_6$): 1.13 (t, J=7 Hz, 6H), 3.43 (q, J=7 Hz, 4H), 3.89 (s, 3H), 5.28 (s, 2H), 5.83 (s, 1H), 6.34 (d, J=2 Hz, 1H), 6.37 (dd, J=2, 8.7 Hz, 1H), 6.62 (d, J=16 Hz, 1H), 6.65 (d, J=16 Hz, 1H), 6.98 (d, J=8.2 Hz, 1H), 7.11 (dd, J=2.4, 8.2 Hz, 1H), 7.19 (d, J=2.4 Hz, 1H), 7.35 (t, J=7.2 Hz, 1H), 7.43 (t, J=7.2 Hz, 2H), 7.49 (d, J=16 Hz, 1H), 7.50 (d, J=8.7 Hz, 1H), 7.54 (d, J=7.2 Hz, 2H), 8.02 (d, J=16 Hz, 1H).

Melting Point 72-77° C., MS (ESI+) m/z 500.5 (M+1).

Example 311

Synthesis of (1E,6E)-1-(4-diethylamino-2-isopropyloxyphenyl)-7-(4-hydroxy-3-methoxyphenyl)hepta-1,6-diene-3,5-dione (CU439)

The title compound was synthesized using the same procedure employed for Example 1, but with 4-diethylamino-2-isopropyloxybenzaldehyde (27 mg, 0.11 mmol) instead of 3-hydroxy-2-methoxybenzaldehyde (16 mg, 0.11 mmol). The product was obtained as a solid (20.8 mg, 52%) having the following characteristics.

$^1$H NMR (δ, acetone-$d_6$): 1.19 (t, J=7 Hz, 6H), 1.38 (d, J=6.3 Hz, 6H), 3.47 (q, J=7 Hz, 4H), 3.92 (s, 3H), 4.74 (m, 1H), 5.84 (s, 1H), 6.29 (d, J=2.4 Hz, 1H), 6.37 (dd, J=2.4, 8.7 Hz, 1H), 6.61 (d, J=16 Hz, 1H), 6.68 (d, J=16 Hz, 1H), 6.87 (d, J=8.2 Hz, 1H), 7.15 (dd, J=1.9, 8.2 Hz, 1H), 7.32 (d, J=1.9 Hz, 1H), 7.48 (d, J=8.7 Hz, 1H), 7.53 (d, J=16 Hz, 1H), 7.94 (d, J=16 Hz, 1H).

Melting Point 156-160° C., MS (ESI+) m/z 452.5 (M+1).

Example 312

Synthesis of (1E,6E)-1-(4-diethylamino-2-isopropyloxyphenyl)-7-(3-hydroxy-4-methoxyphenyl)hepta-1,6-diene-3,5-dione (CU440)

The title compound was synthesized using the same procedure employed for Example 29, but with 4-diethylamino-2-isopropyloxybenzaldehyde (27 mg, 0.11 mmol) instead of 3-hydroxy-2-methoxybenzaldehyde (16 mg, 0.11 mmol). The product was obtained as a solid (23.8 mg, 60%) having the following characteristics.

$^1$H NMR (δ, acetone-$d_6$): 1.19 (t, J=7 Hz, 6H), 1.38 (d, J=6.3 Hz, 6H), 3.47 (q, J=7 Hz, 4H), 3.89 (s, 3H), 4.74 (m, 1H), 5.88 (s, 1H), 6.29 (d, J=2 Hz, 1H), 6.37 (dd, J=2, 8.7 Hz, 1H), 6.62 (d, J=16 Hz, 1H), 6.64 (d, J=16 Hz, 1H), 6.99 (d, J=8.2 Hz, 1H), 7.11 (dd, J=1.9, 8.2 Hz, 1H), 7.19 (d, J=1.9 Hz, 1H), 7.49 (d, J=8.7 Hz, 1H), 7.50 (d, J=16 Hz, 1H), 7.98 (d, J=16 Hz, 1H).

Melting Point 117-120° C., MS (ESI+) m/z 452.5 (M+1).

Example 313

Synthesis of (1E,6E)-1-(4-diethylamino-2-prenyloxyphenyl)-7-(4-hydroxy-3-methoxyphenyl)hepta-1,6-diene-3,5-dione (CU441)

The title compound was synthesized using the same procedure employed for Example 1, but with 4-diethylamino-2-prenyloxybenzaldehyde (30 mg, 0.11 mmol) instead of 3-hydroxy-2-methoxybenzaldehyde (16 mg, 0.11 mmol). The product was obtained as a solid (24.8 mg, 59%) having the following characteristics.

¹H NMR (δ, acetone-d₆): 1.19 (t, J=7 Hz, 6H), 1.78 (s, 3H), 1.80 (s, 3H), 3.46 (q, J=7 Hz, 4H), 3.92 (s, 3H), 4.69 (d, J=6.7 Hz, 2H), 5.52 (m, 1H), 5.83 (s, 1H), 6.28 (d, J=2.4 Hz, 1H), 6.35 (dd, J=2.4, 8.7 Hz, 1H), 6.60 (d, J=16 Hz, 1H), 6.67 (d, J=16 Hz, 1H), 6.87 (d, J=8 Hz, 1H), 7.15 (dd, J=2, 8 Hz, 1H), 7.32 (d, J=2 Hz, 1H), 7.48 (d, J=8.7 Hz, 1H), 7.53 (d, J=16 Hz, 1H), 7.96 (d, J=16 Hz, 1H).
MS (ESI+) m/z 478.5 (M+1), 500.5 (M+Na).

Example 314

Synthesis of (1E,6E)-1-(4-diethylamino-2-prenyloxyphenyl)-7-(3-hydroxy-4-methoxyphenyl)hepta-1,6-diene-3,5-dione (CU442)

The title compound was synthesized using the same procedure employed for Example 29, but with 4-diethylamino-2-prenyloxybenzaldehyde (30 mg, 0.11 mmol) instead of 3-hydroxy-2-methoxybenzaldehyde (16 mg, 0.11 mmol). The product was obtained as a solid (19.2 mg, 46%) having the following characteristics.
¹H NMR (δ, acetone-d₆): 1.19 (t, J=7 Hz, 6H), 1.78 (s, 3H), 1.80 (s, 3H), 3.47 (q, J=7 Hz, 4H), 3.89 (s, 3H), 4.70 (d, J=6.8 Hz, 2H), 5.53 (m, 1H), 5.86 (s, 1H), 6.28 (d, J=2 Hz, 1H), 6.36 (dd, J=2, 8.7 Hz, 1H), 6.61 (d, J=16 Hz, 1H), 6.63 (d, J=16 Hz, 1H), 6.99 (d, J=8.2 Hz, 1H), 7.11 (dd, J=2.4, 8.2 Hz, 1H), 7.19 (d, J=2.4 Hz, 1H), 7.50 (d, J=16 Hz, 1H), 7.51 (d, J=8.7 Hz, 1H), 7.96 (d, J=16 Hz, 1H).
Melting Point 139-143° C., MS (ESI+) m/z 478.5 (M+1).

Example 315

Synthesis of (1E,6E)-1-(1-benzyl-1H-indol-6-yl)-7-(4-hydroxy-3-methoxyphenyl)hepta-1,6-diene-3,5-dione (CU443)

The title compound was synthesized using the same procedure employed for Example 1, but with 1-benzyl-1H-indole-6-carboxaldehyde (27 mg, 0.11 mmol) instead of 3-hydroxy-2-methoxybenzaldehyde (16 mg, 0.11 mmol). The product was obtained as a solid (14.0 mg, 35%) having the following characteristics.
¹H NMR (δ, acetone-d₆): 3.92 (s, 3H), 5.52 (s, 2H), 5.99 (s, 1H), 6.56 (d, J=3 Hz, 1H), 6.72 (d, J=16 Hz, 1H), 6.80 (d, J=16 Hz, 1H), 6.88 (d, J=8.2 Hz, 1H), 7.18 (dd, J=2, 8.2 Hz, 1H), 7.25 (d, J=2 Hz, 1H), 7.24~7.35 (m, 5H), 7.43 (d, J=8.2 Hz, 1H), 7.52 (d, J=3 Hz, 1H), 7.60 (d, J=16 Hz, 1H), 7.62 (d, J=8.2 Hz, 1H), 7.76 (d, J=16 Hz, 1H), 7.79 (s, 1H).
Melting Point 180-184° C., MS (ESI+) m/z 452.4 (M+1), 474.4 (M+Na).

Example 316

Synthesis of (1E,6E)-1-(1-benzyl-1H-indol-6-yl)-7-(3-hydroxy-4-methoxyphenyl)hepta-1,6-diene-3,5-dione (CU444)

The title compound was synthesized using the same procedure employed for Example 29, but with 1-benzyl-1H-indole-6-carboxaldehyde (27 mg, 0.11 mmol) instead of 3-hydroxy-2-methoxybenzaldehyde (16 mg, 0.11 mmol). The product was obtained as a solid (12.4 mg, 31%) having the following characteristics.
¹H NMR (δ, acetone-d₆): 3.90 (s, 3H), 5.53 (s, 2H), 6.01 (s, 1H), 6.56 (d, J=3.4 Hz, 1H), 6.68 (d, J=16 Hz, 1H), 6.82 (d, J=16 Hz, 1H), 7.00 (d, J=8.7 Hz, 1H), 7.14 (dd, J=1.9, 8.7 Hz, 1H), 7.21 (d, J=1.9 Hz, 1H), 7.24~7.35 (m, 5H), 7.44 (dd, J=~2, 8.2 Hz, 1H), 7.52 (d, J=3.4 Hz, 1H), 7.56 (d, J=16 Hz, 1H), 7.63 (d, J=8.2 Hz, 1H), 7.77 (d, J=16 Hz, 1H), 7.81 (s, 1H).
Melting Point 190-194° C., MS (ESI+) m/z 452.4 (M+1).

Example 317

Synthesis of (1E,6E)-1-(4-hydroxyphenyl)-7-(coumarin-6-yl)hepta-1,6-diene-3,5-dione (CU445)

(1) Synthesis of coumarin-6-carboxaldehyde

6-Methylcoumarin (400 mg, 2.50 mmol) was dissolved in 1.0 mL of diethyl ether, 1.0 mL of acetic acid, and 1.0 mL of water. After addition of ceric ammonium nitrate (5.5 g, 1.0 mmol) at room temperature, the reaction mixture was stirred at 100° C. for 1 h. The resulting mixture was diluted with water, and the solution was extracted with ethyl acetate. The extract was washed with water, saturated NaHCO₃ aqueous solution, brine, and dried over MgSO₄. After filtration, the filtrate was concentrated in vacuo, and the residue was purified by silica gel column chromatography (hexane/ethyl acetate=75/25 to 50/50) to obtain the title compound as a pale yellow powder (80 mg, 18%).

(2) Synthesis of (1E,6E)-1-(4-hydroxyphenyl)-7-(coumarin-6-yl)hepta-1,6-diene-3,5-dione (CU445)

The title compound was synthesized using the same procedure employed for Example 22, but with coumarin-6-carboxaldehyde (20 mg, 0.11 mmol) instead of 3-hydroxy-4-methoxybenzaldehyde (16 mg, 0.11 mmol). The product was obtained as a solid (13.6 mg, 43%) having the following characteristics.
¹H NMR (δ, acetone-d₆): 6.06 (s, 1H), 6.48 (d, J=9.7 Hz, 1H), 6.71 (d, J=16 Hz, 1H), 6.9 (m, 1H), 6.91 (d, J=16 Hz, 1H), 6.91 (d, J=8.7 Hz, 2H), 7.40 (d, J=8.7 Hz, 1H), 7.59 (d, J=8.7 Hz, 2H), 7.65 (d, J=16 Hz, 1H), 7.69 (d, J=16 Hz, 1H), 7.97 (d, J=~2, 8.7 Hz, 1H), 8.02 (d, J=9.7 Hz, 1H).
Melting Point 240-246° C., MS (ESI+) m/z 361.1 (M+1).

Example 318

Synthesis of (1E,6E)-1,7-bis[3-methoxy-2-(methoxymethoxy)phenyl]hepta-1,6-diene-3,5-dione (CU446)

The title compound was synthesized using the same procedure employed for Example 244, but with 3-methoxy-2-(methoxymethoxy)benzaldehyde (49 mg, 0.25 mmol) instead of 1,4-benzodioxane-6-carboxaldehyde (41 mg, 0.25 mmol). The product was obtained as a gum (26.4 mg, 58%) having the following characteristics.
¹H NMR (δ, acetone-d₆): 3.57 (s, 6H), 3.88 (s, 6H), 5.16 (s, 4H), 6.10 (s, 1H), 6.87 (d, J=16 Hz, 2H), 7.11 (dd, J=1.9, 8.2 Hz, 2H), 7.13 (dd, J=7, 8 Hz, 2H), 7.36 (dd, J=1.9, 7.2 Hz, 2H), 8.14 (d, J=16 Hz, 2H).
MS (ESI+) m/z 457.3 (M+1), 479.4 (M+Na).

Example 319

Synthesis of (1E,6E)-1,7-bis[5-methoxy-2-(methoxymethoxy)phenyl]hepta-1,6-diene-3,5-dione (CU447)

The title compound was synthesized using the same procedure employed for Example 244, but with 5-methoxy-2-

(methoxymethoxy)benzaldehyde (49 mg, 0.25 mmol) instead of 1,4-benzodioxane-6-carboxaldehyde (41 mg, 0.25 mmol). The product was obtained as a solid (32.0 mg, 70%) having the following characteristics.

$^1$H NMR (δ, acetone-$d_6$): 3.48 (s, 6H), 3.82 (s, 6H), 5.26 (s, 4H), 6.06 (s, 1H), 6.93 (d, J=16 Hz, 2H), 6.97 (dd, J=3, 9.2 Hz, 2H), 7.16 (d, J=9.2 Hz, 2H), 7.29 (d, J=3 Hz, 2H), 8.02 (d, J=16 Hz, 2H).

Melting Point 140-143° C., MS (ESI+) m/z 457.4 (M+1), 479.4 (M+Na).

Example 320

Synthesis of (1E,6E)-1-[4-diethylamino-2-(4-methoxybenzyloxy)phenyl]-7-(4-hydroxyphenyl)hepta-1,6-diene-3,5-dione (CU448)

(1) Synthesis of 4-diethylamino-2-(4-methoxybenzyloxy)benzaldehyde

To a suspension of 4-diethylamino-2-hydroxybenzaldehyde (300 mg, 1.55 mmol), potassium carbonate (428 mg, 3.10 mmol), and tetrabutylammonium iodide (57 mg, 0.15 mmol) in 1.6 mL of dry N,N-dimethylformamide was added 4-methoxybenzyl chloride (0.31 mL, 2.3 mmol) at 0° C. After being stirred at room temperature for 2 h, the reaction mixture was filtered to remove inorganic salts. The filtrate was diluted with diethyl ether, and the solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 80/20) to obtain the title compound as a colorless oil (493 mg, quant.).

(2) Synthesis of (1E,6E)-1-[4-diethylamino-2-(4-methoxybenzyloxy)phenyl]-7-(4-hydroxyphenyl)hepta-1,6-diene-3,5-dione (CU448)

The title compound was synthesized using the same procedure employed for Example 22, but with 4-diethylamino-2-(4-methoxybenzyloxy)benzaldehyde (36 mg, 0.11 mmol) instead of 3-hydroxy-4-methoxybenzaldehyde (16 mg, 0.11 mmol). The product was obtained as a solid (30.0 mg, 68%) having the following characteristics.

$^1$H NMR (δ, acetone-$d_6$): 1.15 (t, J=7 Hz, 6H), 3.44 (q, J=7 Hz, 4H), 3.81 (s, 3H), 5.18 (s, 2H), 5.79 (s, 1H), 6.34~6.38 (m, 2H), 6.61 (d, J=16 Hz, 1H), 6.62 (d, J=16 Hz, 1H), 6.90 (d, J=8.7 Hz, 2H), 6.99 (d, J=8.7 Hz, 2H), 7.46 (d, J=8.7 Hz, 2H), 7.46~7.55 (m, 2H), 7.54 (d, J=8.7 Hz, 2H), 7.97 (d, J=16 Hz, 1H).

Melting Point 71-78° C., MS (ESI+) m/z 500.4 (M+1).

Example 321

Synthesis of (1E,6E)-1-[4-diethylamino-2-(pyridin-3-ylmethoxy)phenyl]-7-(4-hydroxyphenyl)hepta-1,6-diene-3,5-dione (CU449)

(1) Synthesis of 4-diethylamino-2-(pyridin-3-ylmethoxy)benzaldehyde

The title compound was synthesized using the same procedure employed for Example 320 (1), but with 3-chloromethylpyridine hydrochloride instead of 4-methoxybenzyl chloride, and was purified by silica gel chromatography eluting with chloroform/methanol=99/1 to 93/7. The product was obtained as a yellow-white powder (219 mg, 50%).

(2) Synthesis of (1E,6E)-1-[4-diethylamino-2-(pyridin-3-ylmethoxy)phenyl]-7-(4-hydroxyphenyl)hepta-1,6-diene-3,5-dione (CU449)

The title compound was synthesized using the same procedure employed for Example 22, but with 4-diethylamino-2-(pyridin-3-ylmethoxy)benzaldehyde (33 mg, 0.11 mmol) instead of 3-hydroxy-4-methoxybenzaldehyde (16 mg, 0.11 mmol). The product was obtained as a solid (18.6 mg, 45%) having the following characteristics.

$^1$H NMR (δ, acetone-$d_6$): 1.15 (t, J=7 Hz, 6H), 3.46 (q, J=7 Hz, 4H), 5.33 (s, 2H), 5.80 (s, 1H), 6.38-6.42 (m, 2H), 6.61 (d, J=16 Hz, 1H), 6.61 (d, J=16 Hz, 1H), 6.89 (d, J=8.7 Hz, 2H), 7.45 (dd, J=5, 7.7 Hz, 1H), 7.5~7.58 (m, 4H), 7.94 (m, 1H), 7.97 (d, J=16 Hz, 1H), 8.58 (d, J=1.5, 5 Hz, 1H), 8.77 (d, J=~2 Hz, 1H).

Melting Point 180-186° C., MS (ESI+) m/z 471.5 (M+1).

Example 322

Synthesis of (1E,6E)-1-[2-(2-chloro-6-fluorobenzyloxy)-4-diethylaminophenyl]-7-(4-hydroxyphenyl)hepta-1,6-diene-3,5-dione (CU450)

(1) Synthesis of 2-(2-chloro-6-fluorobenzyloxy)-4-diethylaminobenzaldehyde

The title compound was synthesized using the same procedure employed for Example 320 (1), but with 2-chloro-6-fluorobenzyl chloride instead of 4-methoxybenzyl chloride, and was purified by silica gel chromatography eluting with hexane/ethyl acetate=85/15 to 70/30. The product was obtained as a colorless oil (439 mg, 84%).

(2) Synthesis of (1E,6E)-1-[2-(2-chloro-6-fluorobenzyloxy)-4-diethylaminophenyl]-7-(4-hydroxyphenyl)hepta-1,6-diene-3,5-dione (CU450)

The title compound was synthesized using the same procedure employed for Example 22, but with 2-(2-chloro-6-fluorobenzyloxy)-4-diethylaminobenzaldehyde (38 mg, 0.11 mmol) instead of 3-hydroxy-4-methoxybenzaldehyde (16 mg, 0.11 mmol). The product was obtained as a solid (31.8 mg, 69%) having the following characteristics.

$^1$H NMR (δ, acetone-$d_6$): 1.20 (t, J=7 Hz, 6H), 3.50 (q, J=7 Hz, 4H), 5.38 (d, J=1.5 Hz, 2H), 5.74 (s, 1H), 6.41 (dd, J=2.4, 8.7 Hz, 1H), 6.51 (d, J=2.4 Hz, 1H), 6.55 (d, J=16 Hz, 1H), 6.58 (d, J=16 Hz, 1H), 6.89 (d, J=8.7 Hz, 2H), 7.26 (br t, J=9 Hz, 1H), 7.39 (br d, J=9 Hz, 1H), 7.48~7.56 (m, 5H), 7.89 (d, J=16 Hz, 1H).

Melting Point 172-175° C., MS (ESI+) m/z 522.4 (M+1).

Example 323

Synthesis of (1E,6E)-1-[2-(2,4-dichlorobenzyloxy)-4-diethylaminophenyl]-7-(4-hydroxyphenyl)hepta-1,6-diene-3,5-dione (CU451)

(1) Synthesis of 2-(2,4-dichlorobenzyloxy)-4-diethylaminobenzaldehyde

The title compound was synthesized using the same procedure employed for Example 320 (1), but with 2,4-dichlorobenzyl chloride instead of 4-methoxybenzyl chloride, and was purified by silica gel chromatography eluting with hexane/ethyl acetate=85/15 to 70/30. The product was obtained as a white solid (244 mg, 45%).

(2) Synthesis of (1E,6E)-1-[2-(2,4-dichlorobenzyloxy)-4-diethylaminophenyl]-7-(4-hydroxyphenyl)hepta-1,6-diene-3,5-dione (CU451)

The title compound was synthesized using the same procedure employed for Example 22, but with 2-(2,4-dichlorobenzyloxy)-4-diethylaminobenzaldehyde (40 mg, 0.11 mmol) instead of 3-hydroxy-4-methoxybenzaldehyde (16 mg, 0.11 mmol). The product was obtained as a solid (25.4 mg, 54%) having the following characteristics.
$^1$H NMR (δ, acetone-$d_6$): 1.14 (t, J=7 Hz, 6H), 3.44 (q, J=7 Hz, 4H), 5.34 (s, 2H), 5.82 (s, 1H), 6.28 (d, J=2 Hz, 1H), 6.39 (dd, J=2, 8.7 Hz, 1H), 6.60 (d, J=16 Hz, 1H), 6.61 (d, J=16 Hz, 1H), 6.89 (d, J=8.7 Hz, 2H), 7.46 (dd, J=1.9, 8.2 Hz, 1H), 7.5~7.58 (m, 4H), 7.59 (d, J=1.9 Hz, 1H), 7.65 (d, J=8.2 Hz, 1H), 7.89 (d, J=16 Hz, 1H).
Melting Point 73-80° C., MS (ESI+) m/z 538.3 (M+1), 560.3 (M+Na).

Example 324

Synthesis of (1E,6E)-1-[2-(4-tert-butylbenzyloxy)-4-diethylaminophenyl]-7-(4-hydroxyphenyl)hepta-1,6-diene-3,5-dione (CU452)

(1) Synthesis of 2-(4-tert-butylbenzyloxy)-4-diethylaminobenzaldehyde

The title compound was synthesized using the same procedure employed for Example 320 (1), but with 4-tert-butylbenzyl chloride instead of 4-methoxybenzyl chloride, and was purified by silica gel chromatography eluting with hexane/ethyl acetate=85/15 to 70/30. The product was obtained as a colorless oil (410 mg, 78%).

(2) Synthesis of (1E,6E)-1-[2-(4-tert-butylbenzyloxy)-4-diethylaminophenyl]-7-(4-hydroxyphenyl)hepta-1,6-diene-3,5-dione (CU452)

The title compound was synthesized using the same procedure employed for Example 22, but with 2-(4-tert-butylbenzyloxy)-4-diethylaminobenzaldehyde (39 mg, 0.11 mmol) instead of 3-hydroxy-4-methoxybenzaldehyde (16 mg, 0.11 mmol). The product was obtained as a solid (26.6 mg, 58%) having the following characteristics.
$^1$H NMR (δ, acetone-$d_6$): 1.12 (t, J=7 Hz, 6H), 1.33 (s, 9H), 3.43 (q, J=7 Hz, 4H), 5.24 (s, 2H), 5.79 (s, 1H), 6.33 (br s, 1H), 6.36 (br d, J=8.7 Hz, 1H), 6.60 (d, J=16 Hz, 1H), 6.63 (d, J=16 Hz, 1H), 6.90 (d, J=8.7 Hz, 2H), 7.43~7.52 (m, 5H), 7.53 (d, J=16 Hz, 1H), 7.54 (d, J=8.7 Hz, 2H), 8.01 (d, J=16 Hz, 1H).
Melting Point 187-190° C., MS (ESI+) m/z 526.5 (M+1), 548.4 (M+Na).

Example 325

Synthesis of (1E,6E)-1-(4-hydroxy-3-methoxyphenyl)-7-(quinolin-8-yl)hepta-1,6-diene-3,5-dione (CU453)

The title compound was synthesized using the same procedure employed for Example 1, but with quinoline-8-carboxaldehyde (18 mg, 0.11 mmol) instead of 3-hydroxy-2-methoxybenzaldehyde (16 mg, 0.11 mmol). The product was obtained as a solid (2.5 mg, 8%) having the following characteristics.
$^1$H NMR (δ, acetone-$d_6$): 3.93 (s, 3H), 6.13 (s, 1H), 6.80 (d, J=16 Hz, 1H), 6.90 (d, J=8.2 Hz, 1H), 7.20 (d, J=16 Hz, 1H), 7.21 (dd, J=1.9, 8.2 Hz, 1H), 7.38 (d, J=2 Hz, 1H), 7.60 (dd, J=3.9, 8.2 Hz, 1H), 7.66 (d, J=16 Hz, 1H), 7.68 (dd, J=7.3, 8.2 Hz, 1H), 8.04 (dd, J=~2, 8.2 Hz, 1H), 8.25 (br d, J=7.3 Hz, 1H), 8.39 (dd, J=1.5, 8.2 Hz, 1H), 9.00 (d, J=16 Hz, 1H), 9.02 (m, 1H).
Melting Point 83-87° C., MS (ESI+) m/z 374.4 (M+1).

Example 326

Synthesis of (1E,6E)-1-(3-hydroxy-4-methoxyphenyl)-7-(quinolin-8-yl)hepta-1,6-diene-3,5-dione (CU454)

The title compound was synthesized using the same procedure employed for Example 29, but with quinoline-8-carboxaldehyde (18 mg, 0.11 mmol) instead of 3-hydroxy-2-methoxybenzaldehyde (16 mg, 0.11 mmol). The product was obtained as a solid (2.7 mg, 8%) having the following characteristics.
$^1$H NMR (δ, acetone-$d_6$): 3.91 (s, 3H), 6.15 (s, 1H), 6.76 (d, J=16 Hz, 1H), 7.02 (d, J=8.2 Hz, 1H), 7.17 (dd, J=1.9, 8.2 Hz, 1H), 7.21 (d, J=16 Hz, 1H), 7.24 (d, J=2 Hz, 1H), 7.60 (dd, J=3.9, 8 Hz, 1H), 7.63 (d, J=16 Hz, 1H), 7.68 (dd, J=7.3, 8.2 Hz, 1H), 8.04 (dd, J=~2, 8.2 Hz, 1H), 8.26 (br d, J=7.3 Hz, 1H), 8.39 (dd, J=1.9, 8.2 Hz, 1H), 9.01 (d, J=16 Hz, 1H), 9.02 (m, 1H).
Melting Point 80-85° C., MS (ESI+) m/z 374.4 (M+1).

Example 327

Synthesis of (1E,6E)-1-(2-hydroxy-5-methoxyphenyl)-7-[5-methoxy-2-(methoxymethoxy)phenyl]hepta-1,6-diene-3,5-di one (CU456)

To a solution of (1E,6E)-1,7-bis[5-methoxy-2-(methoxymethoxy)phenyl]hepta-1,6-diene-3,5-dione (14 mg, 31 μmol, synthesized in Example 319) in 1.6 mL of dry dichloromethane was added 0.4 mL of trifluoroacetic acid under nitrogen at 0° C. After being stirred at room temperature for 2 h, the reaction mixture was neutralized with saturated NaHCO$_3$ aqueous solution. The mixture was extracted with ethyl acetate, and the extract was washed with brine, and dried over MgSO$_4$. After filtration, the filtrate was concentrated in vacuo, and the residue was purified by silica gel column chromatography (hexane/ethyl acetate=75/25 to 60/40) to obtain (1E,6E)-1,7-bis(2-hydroxy-5-methoxyphenyl)hepta-1,6-diene-3,5-dione (5.0 mg, 44%) and (1E,6E)-1-(2-hydroxy-5-methoxyphenyl)-7-[5-methoxy-2-(methoxymethoxy)phenyl]hepta-1,6-diene-3,5-dione (5.8 mg, 46%) as solids, respectively. (1E,6E)-1-(2-hydroxy-5-methoxyphenyl)-7-[5-methoxy-2-(methoxymethoxy)phenyl]hepta-1,6-diene-3,5-dione (CU456)
$^1$H NMR (δ, acetone-$d_6$): 3.48 (s, 3H), 3.78 (s, 3H), 3.81 (s, 3H), 5.25 (s, 2H), 6.05 (s, 1H), 6.87 (dd, J=2.9, 9 Hz, 1H), 6.90 (d, J=9.2 Hz, 1H), 6.93 (d, J=16 Hz, 1H), 6.94 (d, J=16 Hz, 1H), 6.96 (dd, J=2.9, 8.7 Hz, 1H), 7.16 (d, J=9.2 Hz, 1H), 7.21 (d, J=2.9 Hz, 1H), 7.29 (d, J=2.9 Hz, 1H), 8.01 (d, J=16 Hz, 1H), 8.02 (d, J=16 Hz, 1H).
Melting Point 131-138° C., MS (ESI+) m/z 413.4 (M+1), 435.4 (M+Na).

Example 328

Synthesis of (1E,6E)-1-(4-hydroxyphenyl)-7-(4-nitro-1H-indol-3-yl)hepta-1,6-diene-3,5-dione (CU461)

The title compound was synthesized using the same procedure employed for Example 22, but with 4-nitro-1H-indole-3-carboxaldehyde (22 mg, 0.11 mmol, prepared according to the procedure described in J. Heterocyclic. Chem., (1979), 16, 993) instead of 3-hydroxy-4-methoxybenzaldehyde (16 mg, 0.11 mmol).
The product was obtained as a solid (11.2 mg, 34%) having the following characteristics.
$^1$H NMR ($\delta$, acetone-$d_6$): 5.92 (s, 1H), 6.57 (d, J=16 Hz, 1H), 6.68 (d, J=16 Hz, 1H), 6.90 (d, J=8.7 Hz, 2H), 7.38 (t, J=8 Hz, 1H), 7.57 (d, J=8.7 Hz, 2H), 7.59 (d, J=16 Hz, 1H), 7.93 (d, J=8 Hz, 2H), 8.20 (d, J=16 Hz, 1H), 8.31 (s, 1H).
Melting Point 228-232° C., MS (ESI+) m/z 377.5 (M+1), 399.3 (M+Na).

Example 329

Synthesis of (1E,6E)-1-(4-hydroxy-3-methoxyphenyl)-7-(4-nitro-1H-indol-3-yl)hepta-1,6-diene-3,5-dione (CU462)

The title compound was synthesized using the same procedure employed for Example 1, but with 4-nitro-1H-indole-3-carboxaldehyde (22 mg, 0.11 mmol) instead of 3-hydroxy-2-methoxybenzaldehyde (16 mg, 0.11 mmol). The product was obtained as a solid (8.0 mg, 22%) having the following characteristics.
$^1$H NMR ($\delta$, acetone-$d_6$): 3.92 (s, 3H), 5.92 (s, 1H), 6.56 (d, J=16 Hz, 1H), 6.73 (d, J=16 Hz, 1H), 6.88 (d, J=8.2 Hz, 1H), 7.18 (dd, J=2, 8.2 Hz, 1H), 7.35 (d, J=~2 Hz, 1H), 7.39 (t, J=8 Hz, 1H), 7.58 (d, J=16 Hz, 1H), 7.93 (d, J=8 Hz, 2H), 8.19 (d, J=16 Hz, 1H), 8.30 (s, 1H).
Melting Point 232-237° C., MS (ESI+) m/z 407.4 (M+1), 429.4 (M+Na).

Example 330

Synthesis of (1E,6E)-1-(3-hydroxy-4-methoxyphenyl)-7-(4-nitro-1H-indol-3-yl)hepta-1,6-diene-3,5-dione (CU463)

The title compound was synthesized using the same procedure employed for Example 29, but with 4-nitro-1H-indole-3-carboxaldehyde (22 mg, 0.11 mmol) instead of 3-hydroxy-2-methoxybenzaldehyde (16 mg, 0.11 mmol). The product was obtained as a solid (14.0 mg, 39%) having the following characteristics.
$^1$H NMR ($\delta$, acetone-$d_6$): 3.90 (s, 3H), 5.94 (s, 1H), 6.58 (d, J=16 Hz, 1H), 6.68 (d, J=16 Hz, 1H), 7.00 (d, J=8.2 Hz, 1H), 7.14 (dd, J=1.9, 8.2 Hz, 1H), 7.21 (d, J=1.9 Hz, 1H), 7.39 (t, J=8 Hz, 1H), 7.54 (d, J=16 Hz, 1H), 7.93 (d, J=8 Hz, 2H), 8.21 (d, J=16 Hz, 1H), 8.32 (s, 1H).
Melting Point 226-233° C., MS (ESI+) m/z 407.4 (M+1), 429.4 (M+Na).

Example 331

Synthesis of (1E,6E)-1-(3-bromophenyl)-7-(4-hydroxyphenyl)hepta-1,6-diene-3,5-dione (CU464)

The title compound was synthesized using the same procedure employed for Example 22, but with 3-bromobenzaldehyde (21 µL, 0.11 mmol) instead of 3-hydroxy-4-methoxybenzaldehyde (16 mg, 0.11 mmol). The product was obtained as a solid (21.4 mg, 66%) having the following characteristics.
$^1$H NMR ($\delta$, acetone-$d_6$): 6.07 (s, 1H), 6.70 (d, J=16 Hz, 1H), 6.91 (d, J=8.7 Hz, 2H), 6.93 (d, J=16 Hz, 1H), 7.39 (t, J=8 Hz, 1H), 7.57 (m, 1H), 7.59 (d, J=16 Hz, 1H), 7.59 (d, J=8.7 Hz, 2H), 7.66 (d, J=16 Hz, 1H), 7.68 (br d, J=7-8 Hz, 1H), 7.90 (m, 1H).
Melting Point 156-160° C., MS (ESI+) m/z 371.2 (M+1).

Example 332

Synthesis of (1E,6E)-1-(5-chloro-2-nitrophenyl)-7-(4-hydroxyphenyl)hepta-1,6-diene-3,5-dione (CU465)

The title compound was synthesized using the same procedure employed for Example 22, but with 5-chloro-2-nitrobenzaldehyde (21 mg, 0.11 mmol) instead of 3-hydroxy-4-methoxybenzaldehyde (16 mg, 0.11 mmol). The product was obtained as a solid (16.4 mg, 50%) having the following characteristics.
$^1$H NMR ($\delta$, acetone-$d_6$): 6.14 (s, 1H), 6.74 (d, J=16 Hz, 1H), 6.91 (d, J=8.7 Hz, 2H), 6.98 (d, J=16 Hz, 1H), 7.61 (d, J=8.7 Hz, 2H), 7.69 (dd, J=2.4, 8.7 Hz, 1H), 7.69 (d, J=16 Hz, 1H), 7.94 (d, J=16 Hz, 1H), 7.99 (d, J=2.4 Hz, 1H), 8.12 (d, J=8.7 Hz, 1H).
Melting Point 241-250° C., MS (ESI+) m/z 372.4 (M+1).

Example 333

Synthesis of (1E,6E)-1-(5-bromo-2-fluorophenyl)-7-(4-hydroxyphenyl)hepta-1,6-diene-3,5-dione (CU466)

The title compound was synthesized using the same procedure employed for Example 22, but with 5-bromo-2-fluorobenzaldehyde (24 µL, 0.11 mmol) instead of 3-hydroxy-4-methoxybenzaldehyde (16 mg, 0.11 mmol). The product was obtained as a solid (11.4 mg, 33%) having the following characteristics.
$^1$H NMR ($\delta$, acetone-$d_6$): 6.11 (s, 1H), 6.73 (d, J=16 Hz, 1H), 6.91 (d, J=8.7 Hz, 2H), 7.02 (d, J=16 Hz, 1H), 7.22 (dd, J=8.7, 10.6 Hz, 1H), 7.58~7.63 (m, 1H), 7.60 (d, J=8.7 Hz, 2H), 7.66 (d, J=16 Hz, 1H), 7.68 (d, J=16 Hz, 1H), 7.99 (dd, J=2.4, 6.8 Hz, 1H).
Melting Point 177-203° C., MS (ESI+) m/z 389.3 (M+1).

Example 334

Synthesis of (1E,6E)-1-(4-hydroxyphenyl)-7-(2-trifluoromethylphenyl)hepta-1,6-diene-3,5-dione (CU467)

The title compound was synthesized using the same procedure employed for Example 22, but with 2-trifluoromethylbenzaldehyde (20 µL, 0.11 mmol) instead of 3-hydroxy-4-methoxybenzaldehyde (16 mg, 0.11 mmol). The product was obtained as a solid (14.8 mg, 47%) having the following characteristics.
$^1$H NMR ($\delta$, acetone-$d_6$): 6.10 (s, 1H), 6.74 (d, J=16 Hz, 1H), 6.91 (d, J=8.7 Hz, 2H), 6.93 (d, J=16 Hz, 1H), 7.60 (d, J=8.7 Hz, 2H), 7.62 (d, J=16 Hz, 1H), 7.68 (d, J=16 Hz, 1H), 7.73 (t, J=8 Hz, 1H), 7.81 (d, J=7.7 Hz, 1H), 7.96 (m, 1H), 8.02 (d, J=8.2 Hz, 1H).
Melting Point 181-185° C., MS (ESI+) m/z 361.4 (M+1).

Example 335

Synthesis of (1E,6E)-1-(3,5-difluorophenyl)-7-(4-hydroxyphenyl)hepta-1,6-diene-3,5-dione (CU468)

The title compound was synthesized using the same procedure employed for Example 22, but with 3,5-difluorobenzaldehyde (17 μL, 0.11 mmol) instead of 3-hydroxy-4-methoxybenzaldehyde (16 mg, 0.11 mmol). The product was obtained as a solid (9.8 mg, 34%) having the following characteristics.
$^1$H NMR (δ, acetone-$d_6$): 6.08 (s, 1H), 6.72 (d, J=16 Hz, 1H), 6.91 (d, J=8.7 Hz, 2H), 6.98 (d, J=16 Hz, 1H), 7.02~7.1 (m, 1H), 7.34~7.42 (m, 2H), 7.59 (d, J=16 Hz, 1H), 7.60 (d, J=8.7 Hz, 2H), 7.67 (d, J=16 Hz, 1H).
Melting Point 153-156° C., MS (ESI+) m/z 329.4 (M+1).

Example 336

Synthesis of (1E,6E)-1-[3-(hydroxycarbonyl)phenyl]-7-(4-hydroxyphenyl)hepta-1,6-diene-3,5-dione (CU469)

The title compound was synthesized using the same procedure employed for Example 22, but with 3-formylbenzoic acid (17 mg, 0.11 mmol) instead of 3-hydroxy-4-methoxybenzaldehyde (16 mg, 0.11 mmol). The product was obtained as a solid (13.4 mg, 45%) having the following characteristics.
$^1$H NMR (δ, acetone-$d_6$): 6.71 (d, J=16 Hz, 1H), 6.91 (d, J=8.7 Hz, 2H), 6.97 (d, J=16 Hz, 1H), 7.56-7.62 (m, 1H), 7.59 (d, J=8.7 Hz, 2H), 7.66 (d, J=16 Hz, 1H), 7.70 (d, J=16 Hz, 1H), 7.94 (d, J=7.7 Hz, 1H), 8.06 (d, J=7.7 Hz, 1H), 8.31 (s, 1H).
MS (ESI+) m/z 337.3 (M+1).

Example 337

Synthesis of (1E,6E)-1-(2-chloro-5-nitrophenyl)-7-(4-hydroxyphenyl)hepta-1,6-diene-3,5-dione (CU470)

The title compound was synthesized using the same procedure employed for Example 22, but with 2-chloro-5-nitrobenzaldehyde (21 mg, 0.11 mmol) instead of 3-hydroxy-4-methoxybenzaldehyde (16 mg, 0.11 mmol). The product was obtained as a solid (14.6 mg, 45%) having the following characteristics.
$^1$H NMR (δ, acetone-$d_6$): 6.20 (s, 1H), 6.75 (d, J=16 Hz, 1H), 6.92 (d, J=8.7 Hz, 2H), 7.19 (d, J=16 Hz, 1H), 7.61 (d, J=8.7 Hz, 2H), 7.71 (d, J=16 Hz, 1H), 7.82 (d, J=8.7 Hz, 1H), 7.95 (d, J=16 Hz, 1H), 8.24 (dd, J=2.9, 8.7 Hz, 1H), 8.68 (d, J=2.9 Hz, 1H).
MS (ESI+) m/z 371.9 (M+1).

Example 338

Synthesis of (1E,6E)-1-(4-bromo-2-fluorophenyl)-7-(4-hydroxyphenyl)hepta-1,6-diene-3,5-dione (CU471)

The title compound was synthesized using the same procedure employed for Example 22, but with 4-bromo-2-fluorobenzaldehyde (23 mg, 0.11 mmol) instead of 3-hydroxy-4-methoxybenzaldehyde (16 mg, 0.11 mmol). The product was obtained as a solid (9.0 mg, 26%) having the following characteristics.
$^1$H NMR (δ, acetone-$d_6$): 6.10 (s, 1H), 6.72 (d, J=16 Hz, 1H), 6.91 (d, J=8.7 Hz, 2H), 7.96 (d, J=16 Hz, 1H), 7.46~7.54 (m, 2H), 7.59 (d, J=8.7 Hz, 2H), 7.67 (d, J=16 Hz, 1H), 7.67 (d, J=16 Hz, 1H), 7.77 (dd, J=8, 9 Hz, 1H).
Melting Point 223-232° C., MS (ESI+) m/z 389.2 (M+1).

Example 339

Synthesis of (1E,6E)-1-(biphenyl-2-yl)-7-(4-hydroxyphenyl)hepta-1,6-diene-3,5-dione (CU472)

The title compound was synthesized using the same procedure employed for Example 22, but with 2-phenylbenzaldehyde (20 μL, 0.11 mmol) instead of 3-hydroxy-4-methoxybenzaldehyde (16 mg, 0.11 mmol). The product was obtained as a solid (6.6 mg, 20%) having the following characteristics.
$^1$H NMR (δ, acetone-$d_6$): 5.99 (s, 1H), 6.68 (d, J=16 Hz, 1H), 6.82 (d, J=16 Hz, 1H), 6.90 (d, J=8.7 Hz, 2H), 7.34~7.53 (m, 8H), 7.58 (d, J=8.7 Hz, 2H), 7.62 (d, J=16 Hz, 1H), 7.66 (d, J=16 Hz, 1H), 7.77 (dd, J=1.5, 7~8 Hz, 1H).
Melting Point 180-188° C., MS (ESI+) m/z 369.3 (M+1), 391.3 (M+Na).

Example 340

Synthesis of (1E,6E)-1-(2-fluoro-5-trifluoromethylphenyl)-7-(4-hydroxyphenyl)hepta-1,6-diene-3,5-dione (CU473)

The title compound was synthesized using the same procedure employed for Example 22, but with 2-fluoro-5-trifluoromethylbenzaldehyde (22 μL, 0.11 mmol) instead of 3-hydroxy-4-methoxybenzaldehyde (16 mg, 0.11 mmol). The product was obtained as a solid (2.6 mg, 8%) having the following characteristics.
$^1$H NMR (δ, acetone-$d_6$): 6.14 (s, 1H), 6.73 (d, J=16 Hz, 1H), 6.92 (d, J=8.7 Hz, 2H), 7.12 (d, J=16 Hz, 1H), 7.48 (dd, J=9, 10 Hz, 1H), 7.60 (d, J=8.7 Hz, 2H), 7.69 (d, J=16 Hz, 1H), 7.74 (d, J=16 Hz, 1H), 7.81 (m, 1H), 8.19 (dd, J=~2, 7-8 Hz, 1H).
Melting Point 168-174° C., MS (ESI+) m/z 379.3 (M+1).

Example 341

Synthesis of (1E,6E)-1-[3-(di-n-propylaminocarbonyl)phenyl]-7-(4-hydroxyphenyl)hepta-1,6-diene-3,5-dione (CU474)

(1) Synthesis of 3-(di-n-propylaminocarbonyl)benzaldehyde

To a solution of 3-formylbenzoic acid (300 mg, 2.00 mmol), N,N-diisopropylethylamine (0.70 mL, 4.0 mmol), and di-n-propylamine (0.41 mL, 3.0 mmol) in 4 mL of dry dichloromethane was added 1-ethyl-3-(3-dimethylaminopropyl)-3-ethylcarbodiimide monohydrochloride (575 mg, 3.00 mmol) at 0° C. After being stirred at room temperature overnight, the reaction mixture was diluted with diethyl ether. The solution was washed with 1N HCl, saturated NaHCO$_3$ aqueous solution, brine, and dried over MgSO$_4$. After filtration, the filtrate was concentrated in vacuo to obtain the title compound as a colorless oil (95 mg, 20%).

(2) Synthesis of (1E,6E)-1-[3-(di-n-propylaminocarbonyl)phenyl]-7-(4-hydroxyphenyl)hepta-1,6-diene-3,5-dione (CU474)

The title compound was synthesized using the same procedure employed for Example 22, but with 3-(di-n-propylaminocarbonyl)benzaldehyde (27 mg, 0.11 mmol) instead of 3-hydroxy-4-methoxybenzaldehyde (16 mg, 0.11 mmol). The product was obtained as a solid (7.0 mg, 19%) having the following characteristics.

$^1$H NMR (δ, acetone-d$_6$): 0.73 (br s, 3H), 0.95 (br s, 3H), 1.58 (br s, 2H), 1.67 (br s, 2H), 3.23 (br s, 2H), 3.45 (br s, 2H), 6.08 (s, 1H), 6.70 (d, J=16 Hz, 1H), 6.91 (d, J=8.7 Hz, 2H), 6.92 (d, J=16 Hz, 1H), 7.38 (d, J=7.7 Hz, 1H), 7.50 (dd, J=7.7, 7.7 Hz, 1H), 7.59 (d, J=8.7 Hz, 2H), 7.65 (d, J=16 Hz, 1H), 7.67 (d, J=16 Hz, 1H), 7.67 (s, 1H), 7.73 (d, J=7.7 Hz, 1H).

Melting Point 159-165° C., MS (ESI+) m/z 420.5 (M+1).

Example 342

Synthesis of (1E,6E)-1-(5-benzyloxy-2-nitrophenyl)-7-(4-hydroxyphenyl)hepta-1,6-diene-3,5-dione (CU475)

(1) Synthesis of 5-benzyloxy-2-nitrobenzaldehyde

To a suspension of 5-hydroxy-2-nitrobenzaldehyde (300 mg, 1.80 mmol), potassium carbonate (498 mg, 3.60 mmol), and tetrabutylammonium iodide (66 mg, 0.18 mmol) in 1.8 mL of dry N,N-dimethylformamide was added benzyl bromide (0.32 mL, 2.7 mmol) at 0° C. After being stirred at room temperature for 5 h, the reaction mixture was filtrated to remove inorganic salts. The filtrate was diluted with diethyl ether, and the solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 75/25) to obtain the title compound as a pale yellow solid (405 mg, 87%).

(2) Synthesis of (1E,6E)-1-(5-benzyloxy-2-nitrophenyl)-7-(4-hydroxyphenyl)hepta-1,6-diene-3,5-dione (CU475)

The title compound was synthesized using the same procedure employed for Example 22, but with 5-benzyloxy-2-nitrobenzaldehyde (29 mg, 0.11 mmol) instead of 3-hydroxy-4-methoxybenzaldehyde (16 mg, 0.11 mmol). The product was obtained as a solid (17.8 mg, 46%) having the following characteristics.

$^1$H NMR (δ, acetone-d$_6$): 5.35 (s, 2H), 6.10 (s, 1H), 6.73 (d, J=16 Hz, 1H), 6.84 (d, J=16 Hz, 1H), 6.91 (d, J=8.7 Hz, 2H), 7.25 (dd, J=2.9, 9.2 Hz, 1H), 7.35~7.48 (m, 4H), 7.55 (d, J=8.2 Hz, 2H), 7.60 (d, J=8.7 Hz, 2H), 7.68 (d, J=16 Hz, 1H), 8.10 (d, J=16 Hz, 1H), 8.14 (d, J=9.2 Hz, 1H).

Melting Point 168-172° C., MS (ESI+) m/z 466.1 (M+Na).

Example 343

Synthesis of (1E,6E)-1-[2-(hydroxycarbonyl)phenyl]-7-(4-hydroxyphenyl)hepta-1,6-diene-3,5-dione (CU476)

The title compound was synthesized using the same procedure employed for Example 22, but with 2-formylbenzoic acid (17 mg, 0.11 mmol) instead of 3-hydroxy-4-methoxybenzaldehyde (16 mg, 0.11 mmol). The product was obtained as a solid (9.0 mg, 30%) having the following characteristic.

MS (ESI+) m/z 359.4 (M+Na).

Example 344

Synthesis of (1E,6E)-1-(4-hydroxyphenyl)-7-(2-nitrophenyl)hepta-1,6-diene-3,5-dione (CU477)

The title compound was synthesized using the same procedure employed for Example 22, but with 2-nitrobenzaldehyde (17 mg, 0.11 mmol) instead of 3-hydroxy-4-methoxybenzaldehyde (16 mg, 0.11 mmol). The product was obtained as a solid (5.4 mg, 18%) having the following characteristic.

MS (ESI+) m/z 338.3 (M+1).

Example 345

Synthesis of (1E,6E)-1-(4-hydroxyphenyl)-7-[2-(methoxycarbonyl)phenyl]hepta-1,6-diene-3,5-dione (CU478)

The title compound was synthesized using the same procedure employed for Example 22, but with methyl 2-formylbenzoate (19 mg, 0.11 mmol) instead of 3-hydroxy-4-methoxybenzaldehyde (16 mg, 0.11 mmol). The product was obtained as a solid (12.4 mg, 40%) having the following characteristics.

$^1$H NMR (δ, acetone-d$_6$): 3.92 (s, 3H), 6.08 (s, 1H), 6.72 (d, J=16 Hz, 1H), 6.75 (d, J=16 Hz, 1H), 6.91 (d, J=8.7 Hz, 2H), 7.52 (dd, J=7, 7.7 Hz, 1H), 7.60 (d, J=8.7 Hz, 2H), 7.64 (dd, J=7, 7.7 Hz, 1H), 7.66 (d, J=16 Hz, 1H), 7.86 (d, J=7.7 Hz, 1H), 7.95 (d, J=7.7 Hz, 1H), 8.42 (d, J=16 Hz, 1H).

Melting Point 145-150° C., MS (ESI+) m/z 351.5 (M+1), 373.4 (M+Na).

Example 346

Synthesis of (1E,6E)-1-[2-(dimethylaminocarbonyl)phenyl]-7-(4-hydroxyphenyl)hepta-1,6-diene-3,5-dione (CU479)

(1) Synthesis of 2-formyl-N,N-dimethylbenzamide

To a solution of 2-formylbenzoic acid (500 mg, 3.33 mmol), N,N-diisopropylethylamine (0.58 mL, 3.3 mmol), and dimethylamine/ethanol solution (1.2 mL, 5.6 M, 6.7 mmol) in 3.3 mL of dichloromethane was added 1-ethyl-3-(3-dimethylaminopropyl)-3-ethylcarbodiimide monohydrochloride (1.28 g, 6.67 mmol) at 0° C. After being stirred at room temperature overnight, the reaction mixture was diluted with diethyl ether. The solution was washed with 1N HCl, saturated NaHCO$_3$ aqueous solution, brine, and dried over MgSO$_4$. After filtration, the filtrate was concentrated in vacuo to obtain the title compound as a pale yellow oil (113 mg, 19%).

(2) Synthesis of (1E,6E)-1-[2-(dimethylaminocarbonyl)phenyl]-7-(4-hydroxyphenyl)hepta-1,6-diene-3,5-dione (CU479)

The title compound was synthesized using the same procedure employed for Example 22, but with 2-formyl-N,N-dimethylbenzamide (20 mg, 0.11 mmol) instead of 3-hydroxy-4-methoxybenzaldehyde (16 mg, 0.11 mmol). The product was obtained as a solid (15.0 mg, 47%) having the following characteristics.

$^1$H NMR (δ, acetone-d$_6$): 2.81 (s, 3H), 3.11 (s, 3H), 6.03 (s, 1H), 6.71 (d, J=16 Hz, 1H), 6.85 (d, J=16 Hz, 1H), 6.91 (d, J=8.7 Hz, 2H), 7.31 (m, 1H), 7.47 (m, 2H), 7.59 (d, J=8.7 Hz, 2H), 7.61 (d, J=16 Hz, 1H), 7.65 (d, J=16 Hz, 1H), 7.87 (m, 1H).

Melting Point 210-218° C., MS (ESI+) m/z 364.4 (M+1).

Example 347

Synthesis of (1E,6E)-1-[2-(dimethylaminosulfonyl) phenyl]-7-(4-hydroxyphenyl)hepta-1,6-diene-3,5-dione (CU480)

(1) Synthesis of 2-formyl-N,N-dimethylbenzenesulfonamide

To a solution of 2-sulfobenzaldehyde sodium salt (2.0 g, 9.6 mmol) in 0.8 mL of dry N,N-dimethylformamide was added thionyl chloride (7.0 mL, 96 mmol) under nitrogen at 0° C. After being stirred at 100° C. for 3 min, the reaction mixture was diluted with diethyl ether and water at 0° C., successively. The separated organic layer was washed with water, brine, and dried over MgSO$_4$. After filtration, the filtrate was concentrated in vacuo to obtain crude 2-formylbenzenesulfonyl chloride (0.75 g). To a solution of the above product, pyridine (0.57 mL, 7.0 mmol), and N,N-dimethylaminopyridine (21 mg, 0.17 mmol) in 3.5 mL of dry dichloromethane was added dimethylamine/ethanol solution (0.62 mL, 5.6 M, 3.5 mmol) at 0° C. After being stirred at room temperature overnight, the reaction mixture was diluted with ethyl acetate. The solution was washed with 1N HCl, saturated NaHCO$_3$ aqueous solution, brine, and dried over MgSO$_4$. After filtration, the filtrate was concentrated in vacuo, and the residue was purified with silica gel column chromatography (hexane/ethyl acetate=80/20 to 50/50) to obtain the title compound as a colorless oil (280 mg, 2 steps 14%).

(2) Synthesis of (1E,6E)-1-[2-(dimethylaminosulfonyl)phenyl]-7-(4-hydroxyphenyl)hepta-1,6-diene-3,5-dione (CU480)

The title compound was synthesized using the same procedure employed for Example 22, but with 2-formyl-N,N-dimethylbenzenesulfonamide (24 mg, 0.11 mmol) instead of 3-hydroxy-4-methoxybenzaldehyde (16 mg, 0.11 mmol). The product was obtained as a solid (12.4 mg, 35%) having the following characteristics.

$^1$H NMR (δ, acetone-d$_6$): 2.77 (s, 6H), 6.09 (s, 1H), 6.73 (d, J=16 Hz, 1H), 6.81 (d, J=16 Hz, 1H), 6.91 (d, J=8.7 Hz, 2H), 7.60 (d, J=8.7 Hz, 2H), 7.62 (m, 1H), 7.67 (d, J=16 Hz, 1H), 7.73 (m, 1H), 7.98 (d, J=8 Hz, 1H), 7.98 (d, J=8 Hz, 1H), 8.57 (d, J=16 Hz, 1H).

Melting Point 86-90° C., MS (ESI+) m/z 400.4 (M+1), 422.4 (M+Na).

Example 348

Synthesis of (1E,6E)-1-(4-hydroxyphenyl)-7-(5-methoxy-2-nitrophenyl)hepta-1,6-diene-3,5-dione (CU481)

(1) Synthesis of 5-methoxy-2-nitrobenzaldehyde

To a solution of 5-hydroxy-2-nitrobenzaldehyde (300 mg, 1.80 mmol) in 3.6 mL of dry N,N-dimethylformamide was added sodium hydride (94 mg, 55%, 2.1 mmol) under nitrogen at 0° C. After the solution was stirred at room temperature for 30 min, methyl iodide (0.17 mL, 2.7 mmol) was added with additional stirring for 30 min. The reaction mixture was quenched with saturated NH$_4$Cl aqueous solution at 0° C., and the mixture was extracted with diethyl ether. The extract was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=80/20 to 70/30) to obtain the title compound as a pale yellow powder (298 mg, 91%).

(2) Synthesis of (1E,6E)-1-(4-hydroxyphenyl)-7-(5-methoxy-2-nitrophenyl)hepta-1,6-diene-3,5-dione (CU481)

The title compound was synthesized using the same procedure employed for Example 22, but with 5-methoxy-2-nitrobenzaldehyde (21 mg, 0.11 mmol) instead of 3-hydroxy-4-methoxybenzaldehyde (16 mg, 0.11 mmol). The product was obtained as a solid (10.4 mg, 32%) having the following characteristics.

$^1$H NMR (δ, acetone-d$_6$): 4.01 (s, 3H), 6.10 (s, 1H), 6.73 (d, J=16 Hz, 1H), 6.84 (d, J=16 Hz, 1H), 6.91 (d, J=8.7 Hz, 2H), 7.17 (dd, J=2.9, 9.2 Hz, 1H), 7.36 (d, J=3 Hz, 1H), 7.60 (d, J=8.7 Hz, 2H), 7.68 (d, J=16 Hz, 1H), 8.10 (d, J=16 Hz, 1H), 8.14 (d, J=9.2 Hz, 1H).

Melting Point 151-155° C., MS (ESI+) m/z 368.5 (M+1), 390.5 (M+Na).

Example 349

Synthesis of (1E,6E)-1-(2-aminophenyl)-7-(4-hydroxyphenyl)hepta-1,6-diene-3,5-dione (CU482)

To a solution of (1E,6E)-1-(4-hydroxyphenyl)-7-(2-nitrophenyl)hepta-1,6-diene-3,5-dione (26 mg, 77 μmol, synthesized in Example 344) in 3.0 mL of ethyl acetate was added anhydrous tin(II) chloride (57 mg, 0.30 mmol) at room temperature. After being stirred at 60° C. for 1.5 h, the reaction mixture was cooled to room temperature, and was diluted with 10% methanol/chloroform and saturated NaHCO$_3$ aqueous solution, successively. The mixture was shaken before filtration to remove inorganic salts. The organic layer after separation was washed with brine, and dried over MgSO$_4$. After filtration, the filtrate was concentrated in vacuo, and the residue was purified by silica gel column chromatography (hexane/ethyl acetate=70/30 to 60/40) to obtain the title compound as a solid (11.0 mg, 46%) having the following characteristics.

$^1$H NMR (δ, acetone-d$_6$): 5.2 (br s, 2H, NH), 6.02 (s, 1H), 6.65 (dd, J=7, 8 Hz, 1H), 6.67 (d, J=16 Hz, 1H), 6.67 (d, J=16 Hz, 1H), 6.80 (d, J=7.7 Hz, 1H), 6.90 (d, J=8.7 Hz, 2H), 7.12 (m, 1H), 7.49 (dd, J=~2, 8.2 Hz, 1H), 7.57 (d, J=8.7 Hz, 2H), 7.61 (d, J=16 Hz, 1H), 7.88 (d, J=16 Hz, 1H).

Melting Point 186-193° C., MS (ESI+) m/z 308.3 (M+1), 330.4 (M+Na).

Example 350

Synthesis of (1E,6E)-1-(4-hydroxyphenyl)-7-[2-(methylsulfonyloxy)phenyl]hepta-1,6-diene-3,5-dione (CU483)

(1) Synthesis of 2-formylphenyl methanesulfonate

To a solution of 2-hydroxybenzaldehyde (0.30 mL, 2.8 mmol) and pyridine (0.91 mL, 11.2 mmol) in 5.6 mL of dichloromethane was added methanesulfonyl chloride (0.65 mL, 8.4 mmol) at 0° C. After being stirred at room temperature overnight, the reaction mixture was diluted with ethyl acetate. The solution was washed with 1N HCl, saturated NaHCO₃ aqueous solution, brine, and dried over MgSO₄. After filtration, the filtrate was concentrated in vacuo, and the residue was purified by silica gel column chromatography (hexane/ethyl acetate=75/25 to 50/50) to obtain the title compound as a white solid (553 mg, 98%).

(2) Synthesis of (1E,6E)-1-(4-hydroxyphenyl)-7-[2-(methylsulfonyloxy)phenyl]hepta-1,6-diene-3,5-dione (CU483)

The title compound was synthesized using the same procedure employed for Example 22, but with 2-formylphenyl methanesulfonate (23 mg, 0.11 mmol) instead of 3-hydroxy-4-methoxybenzaldehyde (16 mg, 0.11 mmol). The product was obtained as a solid (7.2 mg, 21%) having the following characteristics.

¹H NMR (δ, acetone-$d_6$): 3.41 (s, 3H), 6.09 (s, 1H), 6.72 (d, J=16 Hz, 1H), 6.91 (d, J=8.7 Hz, 2H), 6.94 (d, J=16 Hz, 1H), 7.42~7.56 (m, 3H), 7.59 (d, J=8.7 Hz, 2H), 7.67 (d, J=16 Hz, 1H), 7.90 (d, J=16 Hz, 1H), 7.94 (dd, J=~2, 9 Hz, 1H).

Melting Point 163-167° C., MS (ESI+) m/z 387.4 (M+1), 409.3 (M+Na).

Example 351

Synthesis of (1E,6E)-1-(4-hydroxyphenyl)-7-[2-(methylthio)phenyl]hepta-1,6-diene-3,5-dione (CU484)

The title compound was synthesized using the same procedure employed for Example 22, but with 2-(methylthio)benzaldehyde (18 μL, 0.11 mmol) instead of 3-hydroxy-4-methoxybenzaldehyde (16 mg, 0.11 mmol). The product was obtained as a solid (7.4 mg, 25%) having the following characteristics.

¹H NMR (δ, acetone-$d_6$): 2.53 (s, 3H), 6.06 (s, 1H), 6.72 (d, J=16 Hz, 1H), 6.80 (d, J=16 Hz, 1H), 6.91 (d, J=8.7 Hz, 2H), 7.24 (m, 1H), 7.40 (dd, J=8, 8.2 Hz, 1H), 7.42 (d, J=7.7 Hz, 1H), 7.59 (d, J=8.7 Hz, 2H), 7.66 (d, J=16 Hz, 1H), 7.73 (d, J=7.7 Hz, 1H), 8.10 (d, J=16 Hz, 1H).

Melting Point 157-160° C., MS (ESI+) m/z 339.3 (M+1), 361.4 (M+Na).

Example 352

Synthesis of (1E,6E)-1-(4-hydroxyphenyl)-7-[2-(methylsulfinyl)phenyl]hepta-1,6-diene-3,5-dione (CU485)

(1) Synthesis of 2-(methylsulfinyl)benzaldehyde

To a solution of 2-(methylthio)benzaldehyde (500 mg, 3.28 mmol) in 6.6 mL of dichloromethane was added m-chlorobenzoic peracid (0.85 g, 4.9 mmol) at 0° C. After being stirred at room temperature for 1 h, the reaction mixture was diluted with ethyl acetate. The solution was washed with saturated NaHCO₃ aqueous solution, brine, and dried over MgSO₄. After filtration, the filtrate was concentrated in vacuo, and the residue was purified by silica gel column chromatography (hexane/ethyl acetate=50/50 to 15/85) to obtain the title compound as a white crystal (493 mg, 89%).

(2) Synthesis of (1E,6E)-1-(4-hydroxyphenyl)-7-[2-(methylsulfinyl)phenyl]hepta-1,6-diene-3,5-dione (CU485)

The title compound was synthesized using the same procedure employed for Example 22, but with 2-(methylsulfinyl) benzaldehyde (19 mg, 0.11 mmol) instead of 3-hydroxy-4-methoxybenzaldehyde (16 mg, 0.11 mmol). The product was obtained as a solid (5.6 mg, 18%) having the following characteristics.

¹H NMR (δ, acetone-$d_6$): 2.69 (s, 3H), 6.10 (s, 1H), 6.72 (d, J=16 Hz, 1H), 6.91 (d, J=16 Hz, 1H), 6.91 (d, J=8.7 Hz, 2H), 7.60 (d, J=8.7 Hz, 2H), 7.61 (m, 1H), 7.68 (d, J=16 Hz, 1H), 7.69 (ddd, J=1.0, 7.7, 8 Hz, 1H), 7.83 (d, J=16 Hz, 1H), 7.89 (d, J=7.7 Hz, 1H), 8.01 (dd, J=1.0, 7.7 Hz, 1H).

MS (ESI+) m/z 355.4 (M+1), 377.3 (M+Na).

Example 353

Synthesis of (1E,6E)-1-(2-bromophenyl)-7-(4-hydroxyphenyl)hepta-1,6-diene-3,5-dione (CU486)

The title compound was synthesized using the same procedure employed for Example 22, but with 2-bromobenzaldehyde (21 mg, 0.11 mmol) instead of 3-hydroxy-4-methoxybenzaldehyde (16 mg, 0.11 mmol). The product was obtained as a solid (22.2 mg, 68%) having the following characteristics.

¹H NMR (δ, acetone-$d_6$): 6.09 (s, 1H), 6.72 (d, J=16 Hz, 1H), 6.87 (d, J=16 Hz, 1H), 6.91 (d, J=8.7 Hz, 2H), 7.33 (ddd, J=~2, 7.3, 7~8 Hz, 1H), 7.45 (dd, J=7.3, 7.7 Hz, 1H), 7.60 (d, J=8.7 Hz, 2H), 7.67 (d, J=16 Hz, 1H), 7.70 (dd, J=~2, 7.3 Hz, 1H), 7.88 (dd, J=~2, 7.7 Hz, 1H), 7.98 (d, J=16 Hz, 1H).

Melting Point 155-159° C., MS (ESI+) m/z 371.4 (M+1).

Example 354

Synthesis of (1E,6E)-1-(1-bromonaphthalen-2-yl)-7-(4-hydroxyphenyl)hepta-1,6-diene-3,5-dione (CU487)

The title compound was synthesized using the same procedure employed for Example 22, but with 1-bromonaphthalene-2-carboxaldehyde (27 mg, 0.11 mmol) instead of 3-hydroxy-4-methoxybenzaldehyde (16 mg, 0.11 mmol). The product was obtained as a solid (22.8 mg, 62%) having the following characteristics.

¹H NMR (δ, acetone-$d_6$): 6.14 (s, 1H), 6.75 (d, J=16 Hz, 1H), 6.92 (d, J=8.7 Hz, 2H), 7.01 (d, J=16 Hz, 1H), 7.5~7.74 (m, 3H), 7.61 (d, J=8.7 Hz, 2H), 7.69 (d, J=16 Hz, 1H), 7.95~8.0 (m, 2H), 8.32 (d, J=16 Hz, 1H), 8.38 (d, J=8.7 Hz, 1H).

MS (ESI+) m/z 421.4 (M+1).

Example 355

Synthesis of (1E,6E)-1-(2-amino-5-hydroxyphenyl)-7-(4-hydroxyphenyl)hepta-1,6-diene-3,5-dione (CU488)

The title compound was synthesized using the same procedure employed for Example 349, but with (1E,6E)-1-(5-hydroxy-2-nitrophenyl)-7-(4-hydroxyphenyl)hepta-1,6-diene-3,5-dione (26 mg, 73 μmol, synthesized in Example 106) as the starting material instead of (1E,6E)-1-(4-hydroxyphenyl)-7-(2-nitrophenyl)hepta-1,6-diene-3,5-dione, and was purified by silica gel column chromatography eluting with hexane/ethyl acetate=60/40 to 30/70. The product was obtained as a solid (6.8 mg, 37%) having the following characteristics.

¹H NMR (δ, acetone-$d_6$): 4.7 (br s, 2H, NH), 6.01 (s, 1H), 6.58 (d, J=16 Hz, 1H), 6.67 (d, J=16 Hz, 1H), 6.70 (d, J=8.7 Hz, 1H), 6.72 (dd, J=2.4, 8.7 Hz, 1H), 6.90 (d, J=8.7 Hz, 2H), 6.97 (d, J=2.4 Hz, 1H), 7.57 (d, J=8.7 Hz, 2H), 7.61 (d, J=16 Hz, 1H), 7.85 (d, J=16 Hz, 1H).

Melting Point 186-192° C., MS (ESI+) m/z 346.3 (M+Na).

Example 356

Synthesis of (1E,6E)-1-(2-amino-5-benzyloxyphenyl)-7-(4-hydroxyphenyl)hepta-1,6-diene-3,5-dione (CU489)

The title compound was synthesized using the same procedure employed for Example 349, but with (1E,6E)-1-(5-benzyloxy-2-nitrophenyl)-7-(4-hydroxyphenyl)hepta-1,6-diene-3,5-dione (10 mg, 22 µmol, synthesized in Example 342) as the starting material instead of (1E,6E)-1-(4-hydroxyphenyl)-7-(2-nitrophenyl)hepta-1,6-diene-3,5-dione, and was purified by silica gel column chromatography eluting with hexane/ethyl acetate=75/25 to 60/40. The product was obtained as a solid (3.3 mg, 35%) having the following characteristics.

$^1$H NMR (δ, acetone-$d_6$): 4.8 (br s, 2H, NH), 5.07 (s, 2H), 6.01 (s, 1H), 6.67 (d, J=16 Hz, 1H), 6.69 (d, J=16 Hz, 1H), 6.78 (d, J=8.7 Hz, 1H), 6.89 (dd, J=2.9, 8.7 Hz, 1H), 6.90 (d, J=8.7 Hz, 2H), 7.19 (d, J=2.9 Hz, 1H), 7.32 (t, J=7.2 Hz, 1H), 7.39 (t, J=7.2 Hz, 2H), 7.48 (d, J=7.2 Hz, 2H), 7.56 (d, J=8.7 Hz, 2H), 7.61 (d, J=16 Hz, 1H), 7.86 (d, J=16 Hz, 1H).

Melting Point 175-179° C., MS (ESI+) m/z 436.7 (M+Na).

Example 357

Synthesis of (1E,6E)-1-(4-hydroxyphenyl)-7-[5-(4-methoxybenzyloxy)-2-nitrophenyl]hepta-1,6-diene-3,5-dione (CU490)

(1) Synthesis of 5-(4-methoxybenzyloxy)-2-nitrobenzaldehyde

The title compound was synthesized using the same procedure employed for Example 342 (1), but with 4-methoxybenzyl chloride instead of benzyl bromide, and was purified by silica gel column chromatography eluting with hexane/ethyl acetate=90/10 to 70/30. The product was obtained as a pale yellow powder (462 mg, 89%).

(2) Synthesis of (1E,6E)-1-(4-hydroxyphenyl)-7-[5-(4-methoxybenzyloxy)-2-nitrophenyl]hepta-1,6-diene-3,5-dione (CU490)

The title compound was synthesized using the same procedure employed for Example 22, but with 5-(4-methoxybenzyloxy)-2-nitrobenzaldehyde (33 mg, 0.11 mmol) instead of 3-hydroxy-4-methoxybenzaldehyde (16 mg, 0.11 mmol). The product was obtained as a solid (13.6 mg, 33%) having the following characteristics.

$^1$H NMR (δ, acetone-$d_6$): 3.82 (s, 3H), 5.26 (s, 2H), 6.10 (s, 1H), 6.73 (d, J=16 Hz, 1H), 6.84 (d, J=16 Hz, 1H), 6.91 (d, J=8.7 Hz, 2H), 6.99 (d, J=8.7 Hz, 2H), 7.23 (dd, J=2.9, 8.7 Hz, 1H), 7.44 (d, J=2.9 Hz, 1H), 7.46 (d, J=8.7 Hz, 2H), 7.60 (d, J=8.7 Hz, 2H), 7.68 (d, J=16 Hz, 1H), 8.10 (d, J=16 Hz, 1H), 8.13 (d, J=8.7 Hz, 1H).

MS (ESI+) m/z 496.5 (M+Na).

Example 358

Synthesis of (1E,6E)-1-(4-hydroxyphenyl)-7-[2-nitro-5-(pyridin-3-ylmethoxy)phenyl]hepta-1,6-diene-3,5-dione (CU491)

(1) Synthesis of 2-nitro-5-(pyridin-3-ylmethoxy)benzaldehyde

The title compound was synthesized using the same procedure employed for Example 342 (1), but with 3-chloromethylpyridine hydrochloride instead of benzyl bromide, and was purified by silica gel column chromatography eluting with hexane/ethyl acetate=60/40 to 30/70. The product was obtained as a pale yellow powder (49 mg, 11%).

(2) Synthesis of (1E,6E)-1-(4-hydroxyphenyl)-7-[2-nitro-5-(pyridin-3-ylmethoxy)phenyl]hepta-1,6-diene-3,5-dione (CU491)

The title compound was synthesized using the same procedure employed for Example 22, but with 2-nitro-5-(pyridin-3-ylmethoxy)benzaldehyde (30 mg, 0.11 mmol) instead of 3-hydroxy-4-methoxybenzaldehyde (16 mg, 0.11 mmol). The product was obtained as a solid (4.8 mg, 12%) having the following characteristics.

$^1$H NMR (δ, acetone-$d_6$): 5.42 (s, 2H), 6.10 (s, 1H), 6.73 (d, J=16 Hz, 1H), 6.86 (d, J=16 Hz, 1H), 6.91 (d, J=8.7 Hz, 2H), 7.29 (dd, J=2.9, 9.2 Hz, 1H), 7.45 (dd, J=5.4, 7.7 Hz, 1H), 7.51 (d, J=3 Hz, 1H), 7.60 (d, J=8.7 Hz, 2H), 7.68 (d, J=16 Hz, 1H), 7.95 (br d, J=8.2 Hz, 1H), 8.10 (d, J=16 Hz, 1H), 8.16 (d, J=9.2 Hz, 1H), 8.60 (dd, J=~2, 5 Hz, 1H), 8.76 (d, J=~2 Hz, 1H).

MS (ESI+) m/z 445.6 (M+1).

Example 359

Synthesis of (1E,6E)-1-[5-(2-chloro-6-fluorobenzyloxy)-2-nitrophenyl]-7-(4-hydroxyphenyl)hepta-1,6-diene-3,5-dione (CU492)

(1) Synthesis of 5-(2-chloro-6-fluorobenzyloxy)-2-nitrobenzaldehyde

The title compound was synthesized using the same procedure employed for Example 342 (1), but with 2-chloro-6-fluorobenzyl chloride instead of benzyl bromide, and was purified by silica gel column chromatography eluting with hexane/ethyl acetate=90/10 to 70/30. The product was obtained as a pale yellow powder (487 mg, 87%).

(2) Synthesis of (1E,6E)-1-[5-(2-chloro-6-fluorobenzyloxy)-2-nitrophenyl]-7-(4-hydroxyphenyl)hepta-1,6-diene-3,5-dione (CU492)

The title compound was synthesized using the same procedure employed for Example 22, but with 5-(2-chloro-6-fluorobenzyloxy)-2-nitrobenzaldehyde (35 mg, 0.11 mmol) instead of 3-hydroxy-4-methoxybenzaldehyde (16 mg, 0.11 mmol). The product was obtained as a solid (11.2 mg, 26%) having the following characteristics.

$^1$H NMR (δ, acetone-$d_6$): 5.47 (d, J=1.5 Hz, 1H), 6.11 (s, 1H), 6.73 (d, J=16 Hz, 1H), 6.91 (d, J=16 Hz, 1H), 6.91 (d, J=8.7 Hz, 2H), 7.29 (dd, J=9, 10 Hz, 1H), 7.30 (dd, J=2.9, 9.2 Hz, 1H), 7.43 (d, J=8.2 Hz, 1H), 7.52~7.57 (m, 1H), 7.53 (d, J=2.9 Hz, 1H), 7.60 (d, J=8.7 Hz, 2H), 7.68 (d, J=16 Hz, 1H), 8.11 (d, J=16 Hz, 1H), 8.17 (d, J=9.2 Hz, 1H).

Melting Point 180-183° C., MS (ESI+) m/z 496.5 (M+1), 518.5 (M+Na).

Example 360

Synthesis of (1E,6E)-1-[5-(2,4-dichlorobenzyloxy)-2-nitrophenyl]-7-(4-hydroxyphenyl)hepta-1,6-diene-3,5-dione (CU493)

(1) Synthesis of 5-(2,4-dichlorobenzyloxy)-2-nitrobenzaldehyde

The title compound was synthesized using the same procedure employed for Example 342 (1), but with 2,4-dichlorobenzyl chloride instead of benzyl bromide, and was purified by recrystallization (hexane/diethyl ether) instead of silica gel column chromatography. The product was obtained as a pale yellow powder (289 mg, 49%).

(2) Synthesis of (1E,6E)-1-[5-(2,4-dichlorobenzyloxy)-2-nitrophenyl]-7-(4-hydroxyphenyl)hepta-1,6-diene-3,5-dione (CU493)

The title compound was synthesized using the same procedure employed for Example 22, but with 5-(2,4-dichlorobenzyloxy)-2-nitrobenzaldehyde (37 mg, 0.11 mmol) instead of 3-hydroxy-4-methoxybenzaldehyde (16 mg, 0.11 mmol). The product was obtained as a solid (18.4 mg, 41%) having the following characteristics.

$^1$H NMR (δ, acetone-$d_6$): 5.42 (s, 1H), 6.10 (s, 1H), 6.72 (d, J=16 Hz, 1H), 6.87 (d, J=16 Hz, 1H), 6.91 (d, J=8.7 Hz, 2H), 7.29 (dd, J=2.4, 9.2 Hz, 1H), 7.48 (dd, J=1.9, 8.2 Hz, 1H), 7.52 (d, J=2.4 Hz, 1H), 7.59 (d, J=8.7 Hz, 2H), 7.61 (d, J=1.9 Hz, 1H), 7.68 (d, J=16 Hz, 1H), 7.72 (d, J=8.2 Hz, 1H), 8.10 (d, J=16 Hz, 1H), 8.16 (d, J=9.2 Hz, 1H).

Melting Point 157-161° C., MS (ESI+) m/z 512.3 (M+1), 534.4 (M+Na).

Example 361

Synthesis of (1E,6E)-1-[5-(4-tert-butylbenzyloxy)-2-nitrophenyl]-7-(4-hydroxyphenyl)hepta-1,6-diene-3,5-dione (CU494)

(1) Synthesis of 5-(4-tert-butylbenzyloxy)-2-nitrobenzaldehyde

The title compound was synthesized using the same procedure employed for Example 342 (1), but with 4-tert-butylbenzyl chloride instead of benzyl bromide, and was purified by silica gel column chromatography eluting with hexane/ethyl acetate=90/10. The product was obtained as a pale yellow oil (476 mg, 84%).

(2) Synthesis of (1E,6E)-1-[5-(4-tert-butylbenzyloxy)-2-nitrophenyl]-7-(4-hydroxyphenyl)hepta-1,6-diene-3,5-dione (CU494)

The title compound was synthesized using the same procedure employed for Example 22, but with 5-(4-tert-butylbenzyloxy)-2-nitrobenzaldehyde (36 mg, 0.11 mmol) instead of 3-hydroxy-4-methoxybenzaldehyde (16 mg, 0.11 mmol). The product was obtained as a solid (26.0 mg, 59%) having the following characteristics.

$^1$H NMR (δ, acetone-$d_6$): 1.33 (s, 9H), 5.31 (s, 1H), 6.10 (s, 1H), 6.73 (d, J=16 Hz, 1H), 6.84 (d, J=16 Hz, 1H), 6.91 (d, J=8.7 Hz, 2H), 7.24 (dd, J=2.4, 9.2 Hz, 1H), 7.44~7.5 (m, 5H), 7.60 (d, J=8.7 Hz, 2H), 7.68 (d, J=16 Hz, 1H), 8.11 (d, J=16 Hz, 1H), 8.14 (d, J=9.2 Hz, 1H).

MS (ESI+) m/z 500.6 (M+1), 522.6 (M+Na).

Example 362

Synthesis of (1E,6E)-1-(2-dimethylaminophenyl)-7-(4-hydroxyphenyl)hepta-1,6-diene-3,5-dione (CU495)

(1) Synthesis of 2-dimethylaminobenzaldehyde

To a suspension of 2-fluorobenzaldehyde (250 μL, 2.37 mmol) and potassium carbonate (328 mg, 2.37 mmol) in 5 mL of dry N,N-dimethylformamide was added dimethylamine/ethanol solution (0.65 mL, 5.6 M, 3.6 mmol) at room temperature. After being stirred at 110° C. for 12 h, the reaction mixture was diluted with ethyl acetate. The solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 80/20) to obtain the title compound as a yellow oil (299 mg, 85%).

(2) Synthesis of (1E,6E)-1-(2-dimethylaminophenyl)-7-(4-hydroxyphenyl)hepta-1,6-diene-3,5-dione (CU495)

The title compound was synthesized using the same procedure employed for Example 22, but with 2-dimethylaminobenzaldehyde (17 mg, 0.11 mmol) instead of 3-hydroxy-4-methoxybenzaldehyde (16 mg, 0.11 mmol). The product was obtained as a solid (16.4 mg, 56%) having the following characteristics.

$^1$H NMR (δ, acetone-$d_6$): 2.76 (s, 6H), 6.04 (s, 1H), 6.71 (d, J=16 Hz, 1H), 6.77 (d, J=16 Hz, 1H), 6.91 (d, J=8.7 Hz, 2H), 7.04 (dd, J=7.2, 7.7 Hz, 1H), 7.14 (d, J=7.7 Hz, 1H), 7.34 (br dd, J=7, 7 Hz, 1H), 7.58 (d, J=8.7 Hz, 2H), 7.64 (d, J=16 Hz, 1H), 7.66 (br d, J=7 Hz, 1H), 8.02 (d, J=16 Hz, 1H).

Melting Point 68-72° C., MS (ESI+) m/z 336.5 (M+1), 358.4 (M+Na).

Example 363

Synthesis of (1E,6E)-1-(4-hydroxyphenyl)-7-[2-(pyrrolidin-1-yl)phenyl]hepta-1,6-diene-3,5-dione (CU496)

(1) Synthesis of 2-(pyrrolidin-1-yl)benzaldehyde

The title compound was synthesized using the same procedure employed for Example 362 (1), but with pyrrolidine instead of dimethylamine/ethanol solution, and was purified by silica gel column chromatography eluting with hexane/ethyl acetate=90/10 to 80/20. The product was obtained as a yellow oil (371 mg, 89%).

(2) Synthesis of (1E,6E)-1-(4-hydroxyphenyl)-7-[2-(pyrrolidin-1-yl)phenyl]hepta-1,6-diene-3,5-dione (CU496)

The title compound was synthesized using the same procedure employed for Example 22, but with 2-(pyrrolidin-1- yl)benzaldehyde (20 mg, 0.11 mmol) instead of 3-hydroxy-4-methoxybenzaldehyde (16 mg, 0.11 mmol). The product was obtained as a solid (5.2 mg, 16%) having the following characteristics.

$^1$H NMR (δ, acetone-$d_6$): 1.96 (m, 4H), 3.28 (t, J=7 Hz, 4H), 6.01 (s, 1H), 6.62 (d, J=16 Hz, 1H), 6.69 (d, J=16 Hz, 1H), 6.87 (dd, J=7, 8 Hz, 1H), 6.91 (d, J=8.7 Hz, 2H), 6.96 (d, J=8.2 Hz, 1H), 7.25 (ddd, J=1.5, 7, 8 Hz, 1H), 7.56 (br d, J=7 Hz, 1H), 7.58 (d, J=8.7 Hz, 2H), 7.62 (d, J=16 Hz, 1H), 7.99 (d, J=16 Hz, 1H).

Melting Point 73-80° C., MS (ESI+) m/z 362.5 (M+1).

Example 364

Synthesis of (1E,6E)-1-(4-hydroxyphenyl)-7-[2-(piperidin-1-yl)phenyl]hepta-1,6-diene-3,5-dione (CU497)

(1) Synthesis of 2-(piperidin-1-yl)benzaldehyde

The title compound was synthesized using the same procedure employed for Example 362 (1), but with piperidine instead of dimethylamine/ethanol solution, and was purified by silica gel column chromatography eluting with hexane/ethyl acetate=90/10 to 85/15. The product was obtained as a yellow oil (378 mg, 84%).

(2) Synthesis of (1E,6E)-1-(4-hydroxyphenyl)-7-[2-(piperidin-1-yl)phenyl]hepta-1,6-diene-3,5-dione (CU497)

The title compound was synthesized using the same procedure employed for Example 22, but with 2-(piperidin-1-yl)benzaldehyde (22 mg, 0.11 mmol) instead of 3-hydroxy-4-methoxybenzaldehyde (16 mg, 0.11 mmol). The product was obtained as a solid (11.0 mg, 33%) having the following characteristics.

$^1$H NMR (δ, acetone-$d_6$): 1.61 (m, 2H), 1.77 (m, 4H), 2.92 (t, J=5.3 Hz, 4H), 6.04 (s, 1H), 6.71 (d, J=16 Hz, 1H), 6.79 (d, J=16 Hz, 1H), 6.91 (d, J=8.7 Hz, 2H), 7.06 (d, J=7.2 Hz, 1H), 7.12 (d, J=8.2 Hz, 1H), 7.35 (ddd, J=1.5, 7, 8 Hz, 1H), 7.59 (d, J=8.7 Hz, 2H), 7.64 (d, J=16 Hz, 1H), 7.68 (dd, J=~2, 7.7 Hz, 1H), 8.04 (d, J=16 Hz, 1H).

Melting Point 77-84° C., MS (ESI+) m/z 376.5 (M+1).

Example 365

Synthesis of (1E,6E)-1-(4-hydroxyphenyl)-7-(2-morpholinophenyl)hepta-1,6-diene-3,5-dione (CU498)

(1) Synthesis of 2-morpholinobenzaldehyde

The title compound was synthesized using the same procedure employed for Example 362 (1), but with morpholine instead of dimethylamine/ethanol solution, and was purified by silica gel column chromatography eluting with hexane/ethyl acetate=90/10 to 75/25. The product was obtained as a yellow oil (196 mg, 43%).

(2) Synthesis of (1E,6E)-1-(4-hydroxyphenyl)-7-(2-morpholinophenyl)hepta-1,6-diene-3,5-dione (CU498)

The title compound was synthesized using the same procedure employed for Example 22, but with 2-morpholinobenzaldehyde (22 mg, 0.11 mmol) instead of 3-hydroxy-4-methoxybenzaldehyde (16 mg, 0.11 mmol). The product was obtained as a solid (26.2 mg, 79%) having the following characteristics.

$^1$H NMR (δ, acetone-$d_6$): 2.95 (t, J=5 Hz, 4H), 3.84 (t, J=5 Hz, 4H), 6.04 (s, 1H), 6.71 (d, J=16 Hz, 1H), 6.81 (d, J=16 Hz, 1H), 6.91 (d, J=8.7 Hz, 2H), 7.12 (dd, J=7.2, 7.7 Hz, 1H), 7.15 (d, J=8.2 Hz, 1H), 7.39 (ddd, J=1.5, 7, 8 Hz, 1H), 7.59 (d, J=8.7 Hz, 2H), 7.64 (d, J=16 Hz, 1H), 7.69 (dd, J=2, 7.7 Hz, 1H), 8.05 (d, J=16 Hz, 1H).

Melting Point 188-192° C., MS (ESI+) m/z 378.5 (M+1), 400.6 (M+Na).

Example 366

Synthesis of (1E,6E)-1-{2-[4-(tert-butoxycarbonyl)piperazin-1-yl]phenyl}-7-(4-hydroxyphenyl)hepta-1,6-diene-3,5-dione (CU499)

(1) Synthesis of 2-[4-(tert-butoxycarbonyl)piperazin-1-yl]benzaldehyde

The title compound was synthesized using the same procedure employed for Example 362 (1), but with 4-(tert-butoxycarbonyl)piperazine instead of dimethylamine/ethanol solution, and was purified by silica gel column chromatography eluting with hexane/ethyl acetate=90/10 to 80/20. The product was obtained as a yellow oil (220 mg, 32%).

(2) Synthesis of (1E,6E)-1-{2-[4-(tert-butoxycarbonyl)piperazin-1-yl]phenyl}-7-(4-hydroxyphenyl)hepta-1,6-diene-3,5-dione (CU499)

The title compound was synthesized using the same procedure employed for Example 22, but with 2-[4-(tert-butoxycarbonyl)piperazin-1-yl]benzaldehyde (33 mg, 0.11 mmol) instead of 3-hydroxy-4-methoxybenzaldehyde (16 mg, 0.11 mmol). The product was obtained as a solid (22.0 mg, 52%) having the following characteristics.

$^1$H NMR (δ, acetone-$d_6$): 1.47 (s, 9H), 2.93 (t, J=4.8 Hz, 4H), 3.62 (br s, 4H), 6.06 (s, 1H), 6.71 (d, J=16 Hz, 1H), 6.81 (d, J=16 Hz, 1H), 6.91 (d, J=8.7 Hz, 2H), 7.13 (t, J=7.2 Hz, 1H), 7.16 (d, J=8.2 Hz, 1H), 7.39 (ddd, J=1.5, 7, 8 Hz, 1H), 7.59 (d, J=8.7 Hz, 2H), 7.64 (d, J=16 Hz, 1H), 7.71 (dd, J=~2, 7.7 Hz, 1H), 8.06 (d, J=16 Hz, 1H).

Melting Point 115-121° C., MS (ESI+) m/z 499.6 (M+Na).

Example 367

Synthesis of (1E,6E)-1-(4-hydroxyphenyl)-7-{2-[4-(methylsulfonyl)piperazin-1-yl]phenyl}hepta-1,6-diene-3,5-dione (CU500)

(1) Synthesis of 2-[4-(methylsulfonyl)piperazin-1-yl]benzaldehyde

The title compound was synthesized using the same procedure employed for Example 362 (1), but with 4-(methylsulfonyl)piperazine instead of dimethylamine/ethanol solution, and was purified by silica gel column chromatography eluting with hexane/ethyl acetate=80/20 to 60/40. The product was obtained as a pale yellow powder (112 mg, 18%).

(2) Synthesis of (1E,6E)-1-(4-hydroxyphenyl)-7-{2-[4-(methylsulfonyl)piperazin-1-yl]phenyl}hepta-1,6-diene-3,5-dione (CU500)

The title compound was synthesized using the same procedure employed for Example 22, but with 2-[4-(methylsulfonyl)piperazin-1-yl]benzaldehyde (31 mg, 0.11 mmol) instead of 3-hydroxy-4-methoxybenzaldehyde (16 mg, 0.11 mmol). The product was obtained as a solid (26.0 mg, 65%) having the following characteristics.

$^1$H NMR (δ, acetone-$d_6$): 2.95 (s, 3H), 3.08 (t, J=4.8 Hz, 4H), 3.45 (t, J=4.8 Hz, 4H), 6.05 (s, 1H), 6.71 (d, J=16 Hz, 1H), 6.82 (d, J=16 Hz, 1H), 6.91 (d, J=8.7 Hz, 2H), 7.15 (dd, J=7.2, 7.7 Hz, 1H), 7.21 (d, J=8.2 Hz, 1H), 7.41 (ddd, J=1.5, 7, 8 Hz, 1H), 7.59 (d, J=8.7 Hz, 2H), 7.65 (d, J=16 Hz, 1H), 7.72 (dd, J=~2, 7.7 Hz, 1H), 8.04 (d, J=16 Hz, 1H).

Melting Point 126-131° C., MS (ESI+) m/z 455.6 (M+1), 477.5 (M+Na).

Example 368

Synthesis of (1E,6E)-1-{2-[4-(2-hydroxyethyl)piperazin-1-yl]phenyl}-7-(4-hydroxyphenyl)hepta-1,6-diene-3,5-dione (CU501)

(1) Synthesis of 2-[4-(2-hydroxyethyl)piperazin-1-yl]benzaldehyde

The title compound was synthesized using the same procedure employed for Example 362 (1), but with 4-(2-hydroxyethyl)piperazine instead of dimethylamine/ethanol solution, and was purified by silica gel column chromatography eluting with chloroform/methanol=98/2 to 90/10. The product was obtained as a pale yellow powder (289 mg, 52%).

(2) Synthesis of (1E,6E)-1-{2-[4-(2-hydroxyethyl)piperazin-1-yl]phenyl}-7-(4-hydroxyphenyl)hepta-1,6-diene-3,5-dione (CU501)

The title compound was synthesized using the same procedure employed for Example 22, but with 2-[4-(2-hydroxyethyl)piperazin-1-yl]benzaldehyde (27 mg, 0.11 mmol) instead of 3-hydroxy-4-methoxybenzaldehyde (16 mg, 0.11 mmol). The product was obtained as a solid (22.4 mg, 61%) having the following characteristics.

$^1$H NMR (δ, acetone-$d_6$): 2.60 (t, J=5.8 Hz, 2H), 2.72 (br s, 4H), 2.99 (t, J=4.8 Hz, 4H), 3.64 (t, J=5.8 Hz, 2H), 6.04 (s, 1H), 6.70 (d, J=16 Hz, 1H), 6.80 (d, J=16 Hz, 1H), 6.91 (d, J=8.7 Hz, 2H), 7.09 (dd, J=7.2, 7.7 Hz, 1H), 7.14 (d, J=7.7 Hz, 1H), 7.37 (ddd, J=2, 7, 8 Hz, 1H), 7.59 (d, J=8.7 Hz, 2H), 7.64 (d, J=16 Hz, 1H), 7.69 (br d, J=7.7 Hz, 1H), 8.04 (d, J=16 Hz, 1H).

Melting Point 102-110° C., MS (ESI+) m/z 421.5 (M+1).

Example 369

Synthesis of (1E,6E)-1-{4-bromo-2-[4-(2-hydroxyethyl)piperazin-1-yl]phenyl}-7-(4-hydroxyphenyl)hepta-1,6-diene-3,5-dione (CU502)

(1) Synthesis of 4-bromo-2-[4-(2-hydroxyethyl)piperazin-1-yl]benzaldehyde

To a suspension of 4-bromo-2-fluorobenzaldehyde (281 μL, 2.37 mmol) and potassium carbonate (328 mg, 2.37 mmol) in 5 mL of dry N,N-dimethylformamide was added 4-(2-hydroxyethyl)piperazine (463 mg, 3.56 mmol) at room temperature. After being stirred at 110° C. for 12 h, the reaction mixture was diluted with ethyl acetate. The solution was washed with water, saturated NaHCO$_3$ aqueous solution, brine, and dried over MgSO$_4$. After filtration, the filtrate was concentrated in vacuo, and the residue was purified by silica gel column chromatography (chloroform/methanol=98/2 to 90/10) to obtain the title compound as a pale yellow powder (364 mg, 49%).

(2) Synthesis of (1E,6E)-1-{4-bromo-2-[4-(2-hydroxyethyl)piperazin-1-yl]phenyl}-7-(4-hydroxyphenyl)hepta-1,6-diene-3,5-dione (CU502)

The title compound was synthesized using the same procedure employed for Example 22, but with 4-bromo-2-[4-(2-hydroxyethyl)piperazin-1-yl]benzaldehyde (36 mg, 0.11 mmol) instead of 3-hydroxy-4-methoxybenzaldehyde (16 mg, 0.11 mmol). The product was obtained as a solid (11.2 mg, 25%) having the following characteristics.

$^1$H NMR (δ, acetone-$d_6$): 2.59 (t, J=5.8 Hz, 2H), 2.72 (br s, 4H), 2.98 (t, J=4.8 Hz, 4H), 3.64 (t, J=5.8 Hz, 2H), 6.06 (s, 1H), 6.71 (d, J=16 Hz, 1H), 6.87 (d, J=16 Hz, 1H), 6.91 (d, J=8.7 Hz, 2H), 7.09 (d, J=8.7 Hz, 1H), 7.49 (dd, J=2.4, 8.7 Hz, 1H), 7.59 (d, J=8.7 Hz, 2H), 7.66 (d, J=16 Hz, 1H), 7.82 (d, J=2.4 Hz, 1H), 7.91 (d, J=16 Hz, 1H).

Melting Point 127-133° C., MS (ESI+) m/z 499.5 (M+1).

Example 370

Synthesis of (1E,6E)-1-(4-hydroxyphenyl)-7-(1-phenylnaphthalen-2-yl)hepta-1,6-diene-3,5-dione (CU503)

(1) Synthesis of 1-phenyl-2-naphthaldehyde

To a suspension of 1-bromo-2-naphthaldehyde (502 mg, 2.14 mmol), sodium carbonate (270 mg, 2.55 mmol), and phenylboronic acid (339 mg, 2.78 mmol) in 4.2 mL of N,N-dimethylformamide/water (2:1) was added palladium acetate (24 mg, 0.11 mmol) under nitrogen. After being stirred at room temperature overnight, the reaction mixture was filtered. The filtrate was diluted with diethyl ether, and the solution was washed with brine, and dried over MgSO$_4$. After filtration, the filtrate was concentrated in vacuo, and the residue was purified by silica gel column chromatography (hexane/ethyl acetate=95/5 to 85/15) to obtain the title compound as a white powder (416 mg, 84%).

(2) Synthesis of (1E,6E)-1-(4-hydroxyphenyl)-7-(1-phenylnaphthalen-2-yl)hepta-1,6-diene-3,5-dione (CU503)

The title compound was synthesized using the same procedure employed for Example 22, but with 1-phenylnaphthaldehyde (27 mg, 0.11 mmol) instead of 3-hydroxy-4-methoxybenzaldehyde (16 mg, 0.11 mmol). The product was obtained as a solid (25.6 mg, 70%) having the following characteristics.

$^1$H NMR (δ, acetone-$d_6$): 5.97 (s, 1H), 6.66 (d, J=16 Hz, 1H), 6.90 (d, J=16 Hz, 1H), 6.90 (d, J=8.7 Hz, 2H), 7.33 (dd, J=2, 8 Hz, 2H), 7.44 (d, J=3.9 Hz, 2H), 7.52~7.64 (m, 8H), 7.97 (d, J=7.7 Hz, 1H), 7.99 (d, J=8.7 Hz, 1H), 8.03 (d, J=8.7 Hz, 1H).

Melting Point 218-222° C., MS (ESI+) m/z 419.6 (M+1), 441.4 (M+Na).

Example 371

Synthesis of (1E,6E)-1-(biphenyl-3-yl)-7-(4-hydroxyphenyl)hepta-1,6-diene-3,5-dione (CU504)

(1) Synthesis of biphenyl-3-carboxaldehyde

The title compound was synthesized using the same procedure employed for Example 370 (1), but with 3-bromobenzaldehyde as the starting material instead of 1-bromo-2-naphthaldehyde. The product was obtained as a colorless oil (320 mg, 82%).

(2) Synthesis of (1E,6E)-1-(biphenyl-3-yl)-7-(4-hydroxyphenyl)hepta-1,6-diene-3,5-dione (CU504)

The title compound was synthesized using the same procedure employed for Example 22, but with biphenyl-3-carboxaldehyde (21 mg, 0.11 mmol) instead of 3-hydroxy-4-methoxybenzaldehyde (16 mg, 0.11 mmol). The product was obtained as a solid (26.4 mg, 81%) having the following characteristics.
$^1$H NMR (δ, acetone-$d_6$): 6.08 (s, 1H), 6.70 (d, J=16 Hz, 1H), 6.91 (d, J=8.7 Hz, 2H), 6.99 (d, J=16 Hz, 1H), 7.40 (t, J=7 Hz, 1H), 7.49 (t, J=7 Hz, 2H), 7.54 (dd, J=2, 8 Hz, 1H), 7.59 (d, J=8.7 Hz, 2H), 7.66~7.76 (m, 3H), 7.66 (d, J=16 Hz, 1H), 7.73 (d, J=7~8 Hz, 2H), 7.98 (s, 1H).
Melting Point 176-182° C., MS (ESI+) m/z 369.5 (M+1).

Example 372

Synthesis of 1-(4-dimethylaminophenyl)-7-(4-hydroxy-3-methoxyphenyl)heptane-3,5-dione (CU505)

To a solution of (1E,6E)-1-(4-dimethylaminophenyl)-7-(4-hydroxy-3-methoxyphenyl)hepta-1,6-diene-3,5-dione (15 mg, 41 μmol, synthesized in Example 9) in 3.0 mL of ethyl acetate was added palladium 5% on carbon (30 mg) under nitrogen. After the vessel was purged with hydrogen, the reaction mixture was stirred under 1 atm of hydrogen at room temperature for 1.5 h. After the vessel was purged with nitrogen, the reaction mixture was filtered to remove palladium 5% on carbon. The filtrate was concentrated in vacuo, and the residue was purified by silica gel column chromatography (hexane/ethyl acetate=75/25 to 65/35) to obtain the title compound as a gum (8.0 mg, 53%) having the following characteristics.
$^1$H NMR (δ, acetone-$d_6$): 2.5~2.6 (m, 4H×0.7), 2.7~2.85 (m, 4H+4H×0.3), 2.87 (s, 6H×0.3), 2.88 (s, 6H×0.7), 3.64 (2H×0.3), 3.81 (s, 3H), 5.64 (s, 1H×0.7), 6.6~6.7 (m, 3H), 6.71 (d, J=8.2 Hz, 1H×0.3), 6.72 (d, J=8.2 Hz, 1H×0.7), 6.81 (d, J=2 Hz, 1H×0.3), 6.84 (d, J=2 Hz, 1H×0.7), 7.01 (d, J=8.7 Hz, 2H×0.3), 7.04 (d, J=8.7 Hz, 2H×0.7), 7.31 (br s, 1H×0.3), 7.33 (br s, 1H×0.7).
MS (ESI+) m/z 370.6 (M+1).

Example 373

Synthesis of 1-(3-hydroxyphenyl)-7-(4-hydroxyphenyl)heptane-3,5-dione (CU506)

The title compound was synthesized using the same procedure employed for Example 372, but with (1E,6E)-1-(3-hydroxyphenyl)-7-(4-hydroxyphenyl)hepta-1,6-diene-3,5-dione (20 mg, 65 μmol, synthesized in Example 59) as the starting material instead of (1E,6E)-1-(4-dimethylaminophenyl)-7-(4-hydroxy-3-methoxyphenyl)hepta-1,6-diene-3,5-dione, and was purified by silica gel column chromatography eluting with hexane/ethyl acetate=70/30 to 60/40. The product was obtained as a gum (15.5 mg, 77%) having the following characteristics.
$^1$H NMR (δ, acetone-$d_6$): 2.5~2.6 (m, 4H×0.7), 2.7~2.9 (m, 4H+4H×0.3), 3.65 (2H×0.3), 5.65 (s, 1H×0.7), 6.62~6.76 (m, 5H), 7.0~7.11 (m, 3H), 8.15 (br s, 2H, OH).
MS (ESI+) m/z 335.4 (M+Na).

Example 374

Synthesis of 1-(4-hydroxy-2-methoxyphenyl)-7-(4-hydroxyphenyl)heptane-3,5-dione (CU507)

The title compound was synthesized using the same procedure employed for Example 372, but with (1E,6E)-1-(4-hydroxy-2-methoxyphenyl)-7-(4-hydroxyphenyl)hepta-1,6-diene-3,5-dione (20 mg, 59 μmol, synthesized in Example 63) as the starting material instead of (1E,6E)-1-(4-dimethylaminophenyl)-7-(4-hydroxy-3-methoxyphenyl)hepta-1,6-diene-3,5-dione, and was purified by silica gel column chromatography eluting with hexane/ethyl acetate=65/35 to 55/45. The product was obtained as a gum (14.4 mg, 72%) having the following characteristics.
$^1$H NMR (δ, acetone-$d_6$): 2.49 (t, J=8 Hz, 2H×0.7), 2.55 (t, J=8 Hz, 2H×0.7), 2.7~2.9 (m, 4H+4H×0.3), 3.63 (2H×0.3), 3.75 (s, 3H×0.3), 3.77 (s, 3H×0.7), 5.61 (s, 1H×0.7), 6.32 (dd, J=2, 8.2 Hz, 1H×0.3), 6.33 (dd, J=2, 8.2 Hz, 1H×0.7), 6.42 (d, J=2 Hz, 1H×0.3), 6.44 (d, J=2 Hz, 1H×0.7), 6.73 (d, J=8.7 Hz, 2H×0.3), 6.74 (d, J=8.7 Hz, 2H×0.7), 6.91 (d, J=8.2 Hz, 1H×0.3), 6.92 (d, J=8.2 Hz, 1H×0.7), 7.02 (d, J=8.7 Hz, 2H×0.3), 7.05 (d, J=8.7 Hz, 2H×0.7), 8.12 (br s, 2H, OH).
MS (ESI+) m/z 365.6 (M+Na).

Example 375

Synthesis of 1-(9-ethyl-9H-carbazol-3-yl)-7-(3-hydroxy-4-methoxyphenyl)heptane-3,5-dione (CU508)

The title compound was synthesized using the same procedure employed for Example 372, but with (1E,6E)-1-(9-ethyl-9H-carbazol-3-yl)-7-(3-hydroxy-4-methoxyphenyl) hepta-1,6-diene-3,5-dione (20 mg, 59 μmol, synthesized in Example 84) as the starting material instead of (1E,6E)-1-(4-dimethylaminophenyl)-7-(4-hydroxy-3-methoxyphenyl) hepta-1,6-diene-3,5-dione, and was purified by silica gel column chromatography eluting with hexane/ethyl acetate=75/25 to 65/35. The product was obtained as a solid (13.1 mg, 65%) having the following characteristics.
$^1$H NMR (δ, acetone-$d_6$): 1.37 (m, 3H), 2.55 (t, J=8 Hz, 2H×0.7), 2.7~2.9 (m, 4H), 2.94 (t, J=7 Hz, 2H×0.3), 3.02 (t, J=7 Hz, 2H×0.3), 3.08 (t, J=8 Hz, 2H×0.7), 3.69 (2H×0.3), 3.77 (s, 3H×0.3), 3.78 (s, 3H×0.7), 4.45 (m, 2H), 5.69 (s, 1H×0.7), 6.57 (dd, J=2, 8.2 Hz, 1H×0.3), 6.60 (dd, J=2, 8.2 Hz, 1H×0.7), 6.68 (d, J=2 Hz, 1H×0.3), 6.71 (d, J=2 Hz, 1H×0.7), 6.77 (d, J=8.2 Hz, 1H×0.3), 6.79 (d, J=8.2 Hz, 1H×0.7), 7.17 (t, J=7 Hz, 1H), 7.32 (d, J=1.5, 8.7 Hz, 1H×0.3), 7.34 (d, J=1.5, 8.7 Hz, 1H×0.7), 7.38~7.49 (m, 2H), 7.52 (d, J=8.2 Hz, 1H), 7.97 (br s, 1H×0.3), 8.01 (br s, 1H×0.7), 8.11 (d, J=7.7 Hz, 1H).
Melting Point 97-100° C., MS (ESI+) m/z 466.6 (M+Na).

Example 376

Synthesis of 1-(4-dimethylaminonaphthalen-1-yl)-7-(4-hydroxyphenyl)heptane-3,5-dione (CU509)

The title compound was synthesized using the same procedure employed for Example 372, but with (1E,6E)-1-(4-dimethylaminonaphthalen-1-yl)-7-(4-hydroxyphenyl)hepta-1,6-diene-3,5-dione (20 mg, 52 μmol, synthesized in Example 94) as the starting material instead of (1E,6E)-1-(4-dimethylaminophenyl)-7-(4-hydroxy-3-methoxyphenyl) hepta-1,6-diene-3,5-dione, and was purified by silica gel column chromatography eluting with hexane/ethyl acetate=90/

10 to 80/20. The product was obtained as a gum (16.5 mg, 82%) having the following characteristics.

$^1$H NMR (δ, acetone-$d_6$): 2.56 (t, J=8 Hz, 2H×0.7), 2.7~2.9 (m, 4H), 2.82 (s, 6H×0.3), 2.83 (s, 6H×0.7), 2.93 (t, J=8 Hz, 2H×0.3), 3.25 (t, J=8 Hz, 2H×0.3), 3.31 (t, J=8 Hz, 2H×0.7), 3.70 (2H×0.3), 5.68 (s, 1H×0.7), 6.75 (d, J=8.7 Hz, 2H), 7.0~7.08 (m, 1H), 7.05 (d, J=8.7 Hz, 2H), 7.28 (t, J=7 Hz, 1H), 7.46~7.56 (m, 2H), 8.01 (dd, J=2, 8 Hz, 1H×0.3), 8.05 (dd, J=2, 8 Hz, 1H×0.7), 8.1 (br s, 1H, OH), 8.28 (dd, J=1.9, 7.2 Hz, 1H×0.3), 8.29 (dd, J=1.9, 7.2 Hz, 1H×0.7).

MS (ESI+) m/z 390.5 (M+1).

Example 377

Synthesis of 1-(4-hydroxyphenyl)-7-(1H-indol-6-yl)heptane-3,5-dione (CU510)

The title compound was synthesized using the same procedure employed for Example 372, but with (1E,6E)-1-(4-hydroxyphenyl)-7-(1H-indol-6-yl)hepta-1,6-diene-3,5-dione (28 mg, 85 µmol, synthesized in Example 149) as the starting material instead of (1E,6E)-1-(4-dimethylaminophenyl)-7-(4-hydroxy-3-methoxyphenyl)hepta-1,6-diene-3,5-dione, and was purified by silica gel column chromatography eluting with hexane/ethyl acetate=75/25 to 65/35. The product was obtained as a gum (18.4 mg, 66%) having the following characteristics.

$^1$H NMR (δ, acetone-$d_6$): 2.4-3.0 (m, 8H), 3.65 (2H×0.3), 5.65 (s, 1H×0.7), 6.40 (d, J=2.4 Hz, 1H), 6.73 (d, J=8.7 Hz, 2H×0.3), 6.74 (d, J=8.7 Hz, 2H×0.7), 6.88 (dd, J=2, 8.2 Hz, 1H×0.3), 6.91 (dd, J=2, 8.2 Hz, 1H×0.7), 7.02 (d, J=8.7 Hz, 2H×0.3), 7.03 (d, J=8.7 Hz, 2H×0.7), 7.25 (d, J=2.4 Hz, 1H), 7.26 (s, 1H×0.3), 7.27 (s, 1H×0.7), 7.46 (d, J=8.2 Hz, 1H×0.3), 7.47 (d, J=8.2 Hz, 1H×0.7), 8.03 (br s, 1H×0.3), 8.11 (br s, 1H×0.7), 10.1 (br s, 1H, NH).

MS (ESI+) m/z 358.5 (M+Na).

Example 378

Synthesis of 1,7-bis(2-chloro-4-hydroxyphenyl)heptane-3,5-dione (CU511)

The title compound was synthesized using the same procedure employed for Example 372, but with (1E,6E)-1,7-bis(2-chloro-4-hydroxyphenyl)hepta-1,6-diene-3,5-dione (27 mg, 71 µmol, synthesized in Example 247) as the starting material instead of (1E,6E)-1-(4-dimethylaminophenyl)-7-(4-hydroxy-3-methoxyphenyl)hepta-1,6-diene-3,5-dione, and was purified by silica gel column chromatography eluting with hexane/ethyl acetate=65/35 to 55/45. The product was obtained as a gum (15.1 mg, 56%) having the following characteristics.

$^1$H NMR (δ, acetone-$d_6$): 2.57 (t, J=8 Hz, 4H×0.7), 2.7~2.9 (m, 4H+4H×0.3), 3.72 (2H×0.3), 5.66 (s, 1H×0.7), 6.73 (dd, J=2.4, 8.2 Hz, 2H×0.3), 6.74 (dd, J=2.4, 8.2 Hz, 2H×0.7), 6.86 (d, J=2.4 Hz, 2H×0.3), 6.87 (d, J=2.4 Hz, 2H×0.7), 7.14 (d, J=8.2 Hz, 2H×0.3), 7.15 (d, J=8.2 Hz, 2H×0.7), 8.6 (br s, 2H, OH).

MS (ESI+) m/z 403.4 (M+Na).

Example 379

Synthesis of 1,7-bis(5-hydroxy-2-methoxyphenyl)heptane-3,5-dione (CU512)

The title compound was synthesized using the same procedure employed for Example 372, but with (1E,6E)-1,7-bis(5-hydroxy-2-methoxyphenyl)hepta-1,6-diene-3,5-dione (19 mg, 52 µmol, synthesized in Example 255) as the starting material instead of (1E,6E)-1-(4-dimethylaminophenyl)-7-(4-hydroxy-3-methoxyphenyl)hepta-1,6-diene-3,5-dione, and was purified by silica gel column chromatography eluting with hexane/ethyl acetate=60/40 to 50/50. The product was obtained as a solid (14.0 mg, 73%) having the following characteristics.

$^1$H NMR (δ, acetone-$d_6$): 2.54 (t, J=8 Hz, 4H×0.7), 2.7~2.9 (m, 4H+4H×0.3), 3.66 (2H×0.3), 3.73 (s, 6H×0.3), 3.75 (s, 6H×0.7), 5.66 (s, 1H×0.7), 6.6~6.68 (m, 4H), 6.75 (d, J=8.2 Hz, 2H×0.3), 6.77 (d, J=8.2 Hz, 2H×0.7), 7.8 (br s, 2H, OH).

Melting Point 163-169° C., MS (ESI+) m/z 373.5 (M+1), 395.5 (M+Na).

Example 380

Synthesis of (1E,6E)-1-(4-hydroxyphenyl)-7-[2-(pyridin-3-yl)phenyl]hepta-1,6-diene-3,5-dione (CU513)

(1) Synthesis of 2-(pyridin-3-yl)benzaldehyde

To a suspension of 1-bromobenzaldehyde (250 µL, 2.14 mmol), sodium carbonate (270 mg, 2.55 mmol), and 3-pyridineboronic acid (289 mg, 2.35 mmol) in 4.2 mL of N,N-dimethylformamide/water (2:1) were added palladium acetate (24 mg, 0.11 mmol) and triphenylphosphine (115 mg, 0.44 mmol) under nitrogen. After being stirred at 110° C. overnight, the reaction mixture was filtered. The filtrate was diluted with chloroform, and the solution was washed with brine, and dried over $MgSO_4$. After filtration, the filtrate was concentrated in vacuo, and the residue was purified by silica gel column chromatography (chloroform/methanol=99/1 to 95/5) to obtain the title compound as a white powder (250 mg, 64%).

(2) Synthesis of (1E,6E)-1-(4-hydroxyphenyl)-7-[2-(pyridin-3-yl)phenyl]hepta-1,6-diene-3,5-dione (CU513)

The title compound was synthesized using the same procedure employed for Example 22, but with 2-(pyridin-3-yl)benzaldehyde (21 mg, 0.11 mmol) instead of 3-hydroxy-4-methoxybenzaldehyde (16 mg, 0.11 mmol). The product was obtained as a solid (6.4 mg, 20%) having the following characteristics.

$^1$H NMR (δ, acetone-$d_6$): 6.01 (s, 1H), 6.68 (d, J=16 Hz, 1H), 6.85 (d, J=16 Hz, 1H), 6.90 (d, J=8.7 Hz, 2H), 7.44 (dd, J=2, 8.7 Hz, 1H), 7.48~7.56 (m, 3H), 7.58 (d, J=8.7 Hz, 2H), 7.59 (d, J=16 Hz, 1H), 7.63 (d, J=16 Hz, 1H), 7.78 (m, 1H), 7.94 (dd, J=2, 6.8 Hz, 1H), 8.59 (d, J=2 Hz, 1H), 8.65 (dd, J=1.5, 4.8 Hz, 1H).

Melting Point 180-189° C., MS (ESI+) m/z 370.4 (M+1).

Example 381

Synthesis of (1E,6E)-1-(4-hydroxyphenyl)-7-[2-(pyridin-4-yl)phenyl]hepta-1,6-diene-3,5-dione (CU514)

(1) Synthesis of 2-(pyridin-4-yl)benzaldehyde

The title compound was synthesized using the same procedure employed for Example 380 (1), but with 4-pyridineboronic acid instead of 3-pyridineboronic acid. The product was obtained as a white powder (328 mg, 84%).

(2) Synthesis of (1E,6E)-1-(4-hydroxyphenyl)-7-[2-(pyridin-4-yl)phenyl]hepta-1,6-diene-3,5-dione (CU514)

The title compound was synthesized using the same procedure employed for Example 22, but with 2-(pyridin-4-yl)benzaldehyde (21 mg, 0.11 mmol) instead of 3-hydroxy-4-methoxybenzaldehyde (16 mg, 0.11 mmol). The product was obtained as a solid (5.4 mg, 17%) having the following characteristics.

$^1$H NMR (δ, acetone-$d_6$): 6.01 (s, 1H), 6.69 (d, J=16 Hz, 1H), 6.85 (d, J=16 Hz, 1H), 6.90 (d, J=8.7 Hz, 2H), 7.38 (dd, J=1.5, 4.8 Hz, 2H), 7.45 (m, 1H), 7.5~7.56 (m, 3H), 7.58 (d, J=8.7 Hz, 2H), 7.59 (d, J=16 Hz, 1H), 7.94 (m, 1H), 8.70 (dd, J=1.5, 4.8 Hz, 2H).

Melting Point 249-256° C., MS (ESI+) m/z 370.4 (M+1).

Example 382

Synthesis of (1E,6E)-1-(4-hydroxyphenyl)-7-[2-(piperazin-1-yl)phenyl]hepta-1,6-diene-3,5-dione ditrifluoroacetic acid salt (CU515)

To a solution of (1E,6E)-1-{2-[4-(tert-butoxycarbonyl)piperazin-1-yl]phenyl}-7-(4-hydroxyphenyl)hepta-1,6-diene-3,5-dione (11 mg, 23 μmol, synthesized in Example 366) in 1.6 mL of dry dichloromethane was added 0.4 mL of trifluoroacetic acid under nitrogen at 0° C. After being stirred at room temperature for 30 min, the reaction mixture was concentrated in vacuo. The residue was azeotroped with tetrahydrofuran and diethyl ether, successively, to obtain the title compound as a solid (14 mg, quant.) having the following characteristics.

$^1$H NMR (δ, acetone-$d_6$): 3.32 (d, J=5 Hz, 4H), 3.58 (d, J=5 Hz, 4H), 6.70 (d, J=16 Hz, 1H), 6.85 (d, J=16 Hz, 1H), 6.92 (d, J=8.7 Hz, 2H), 7.18 (dd, J=7.2, 7.7 Hz, 1H), 7.23 (d, J=8.2 Hz, 1H), 7.42 (dd, J=7.2, 8.2 Hz, 1H), 7.58 (d, J=8.7 Hz, 2H), 7.64 (d, J=16 Hz, 1H), 7.73 (d, J=7.7 Hz, 1H), 8.01 (d, J=16 Hz, 1H).

Melting Point 139-150° C., MS (ESI+) m/z 377.5 (M+1).

Example 383

Synthesis of (E)-1-(4-hydroxy-2-methoxyphenyl)-7-(4-hydroxyphenyl)hept-1-ene-3,5-dione (CU517)

(1) Synthesis of 6-(4-hydroxyphenyl)hexane-2,4-dione

To a solution of 6-(4-hydroxyphenyl)hex-5-ene-2,4-dione (1.00 g, 4.90 mmol) in 50 mL of ethyl acetate was added palladium 5% on carbon (200 mg) under nitrogen. After the vessel was purged with hydrogen, the reaction mixture was stirred under 1 atm of hydrogen at room temperature for 12 h. After the vessel was purged with nitrogen, the reaction mixture was filtered to remove palladium 5% on carbon. The filtrate was concentrated in vacuo, and the residue was purified by silica gel column chromatography (hexane/ethyl acetate=70/30 to 60/40) to obtain the title compound as a colorless oil (802 mg, 80%) having the following characteristics.

$^1$H NMR (δ, acetone-$d_6$): 2.00 (s, 3H×0.7), 2.14 (s, 3H×0.3), 2.56 (t, J=7.7 Hz, 2H×0.7), 2.74~2.84 (m, 2H+2H×0.3), 3.65 (2H×0.3), 5.64 (s, 1H×0.7), 6.73 (d, J=8.7 Hz, 2H×0.3), 6.74 (d, J=8.7 Hz, 2H×0.7), 7.03 (d, J=8.7 Hz, 2H×0.3), 7.05 (d, J=8.7 Hz, 2H×0.7), 8.1 (br s, 1H, OH).

MS (ESI+) m/z 207.3 (M+1).

(2) Synthesis of (E)-1-(4-hydroxy-2-methoxyphenyl)-7-(4-hydroxyphenyl)hept-1-ene-3,5-dione (CU517)

6-(4-Hydroxyphenyl)hexane-2,4-dione (18 mg, 87 μmol) and boron trioxide (22 mg, 0.32 mmol) was placed in a 20 mL reaction vessel, and dissolved in 0.4 mL of ethyl acetate. To the stirring solution at 80° C. were added 4-hydroxy-2-methoxybenzaldehyde (12 mg, 78 μmol) and tri-n-butyl borate (50 μL, 0.19 mmol). After the reaction mixture was stirred for 2 h at the same temperature, n-butylamine (19 μL, 0.19 mmol) was added with additional stirring for 1 h. The reaction mixture was treated with a 1:1 solution (1 mL) of 1N HCl and brine, and was stirred at 50° C. for 5 min to 1 h (if necessary, the reaction mixture was neutralized by saturated NaHCO$_3$ aqueous solution). The organic layer was purified directly by silica gel column chromatography (eluting with hexane/ethyl acetate or chloroform/methanol) to obtain the title compound as a solid (11.6 mg, 44%) having the following characteristics.

$^1$H NMR (δ, acetone-$d_6$): 2.65 (t, J=8 Hz, 2H), 2.85 (t, J=8 Hz, 2H), 3.87 (s, 3H), 5.74 (s, 1H), 6.49 (dd, J=1.9, 8.7 Hz, 1H), 6.53 (d, J=1.9 Hz, 1H), 6.57 (d, J=16 Hz, 1H), 6.74 (d, J=8.7 Hz, 2H), 7.07 (d, J=8.7 Hz, 2H), 7.50 (d, J=8.7 Hz, 1H), 7.84 (d, J=16 Hz, 1H).

Melting Point 131-135° C., MS (ESI+) m/z 341.4 (M+1), 363.4 (M+Na).

Example 384

Synthesis of (E)-1-(4-dimethylaminonaphthalen-1-yl)-7-(4-hydroxyphenyl)hept-1-ene-3,5-dione (CU518)

The title compound was synthesized using the same procedure employed for Example 383 (2), but with 4-dimethylamino-1-naphthaldehyde (16 mg, 78 μmol) instead of 4-hydroxy-2-methoxybenzaldehyde (12 mg, 78 μmol). The product was obtained as a solid (9.6 mg, 32%) having the following characteristics.

$^1$H NMR (δ, acetone-$d_6$): 2.71 (t, J=8 Hz, 2H), 2.89 (t, J=8 Hz, 2H), 2.93 (s, 6H), 5.91 (s, 1H), 6.71 (d, J=16 Hz, 1H), 6.76 (d, J=8.7 Hz, 2H), 7.09 (d, J=8.7 Hz, 2H), 7.15 (d, J=8.2 Hz, 1H), 7.56 (dd, J=6.8, 8.2 Hz, 1H), 7.62 (dd, J=6.8, 8.2 Hz, 1H), 7.88 (d, J=8.2 Hz, 1H), 8.1 (br s, 1H, OH), 8.25 (d, J=8 Hz, 1H), 8.27 (d, J=8 Hz, 1H), 8.39 (d, J=16 Hz, 1H).

Melting Point 44-49° C., MS (ESI+) m/z 388.5 (M+1), 410.5 (M+Na).

Example 385

Synthesis of (E)-7-(4-hydroxyphenyl)-7-(1H-indol-6-yl)hept-1-ene-3,5-dione (CU519)

The title compound was synthesized using the same procedure employed for Example 383 (2), but with 1H-indole-6-carboxaldehyde (11 mg, 78 μmol) instead of 4-hydroxy-2-methoxybenzaldehyde (12 mg, 78 μmol). The product was obtained as a solid (8.8 mg, 34%) having the following characteristics.

$^1$H NMR (δ, acetone-$d_6$): 2.68 (t, J=8 Hz, 2H), 2.87 (t, J=8 Hz, 2H), 5.83 (s, 1H), 6.51 (m, 1H), 6.66 (d, J=16 Hz, 1H), 6.75 (d, J=8.7 Hz, 2H), 7.08 (d, J=8.7 Hz, 2H), 7.39 (dd, J=1.5, 8.2 Hz, 1H), 7.45 (dd, J=2.9, 2.9 Hz, 1H), 7.60 (d, J=8.2 Hz, 1H), 7.69 (s, 1H), 7.71 (d, J=16 Hz, 1H), 8.10 (br s, 1H, OH), 10.5 (br s, 1H, NH).
Melting Point 119-123° C., MS (ESI+) m/z 359.6 (M+Na).

Example 386

Synthesis of (E)-1-(1-benzyl-1H-indol-6-yl)-7-(4-hydroxyphenyl)hept-1-ene-3,5-dione (CU520)

The title compound was synthesized using the same procedure employed for Example 383 (2), but with 1-benzyl-1H-indole-6-carboxaldehyde (19 mg, 78 μmol) instead of 4-hydroxy-2-methoxybenzaldehyde (12 mg, 78 μmol). The product was obtained as a solid (19.6 mg, 59%) having the following characteristics.
$^1$H NMR (δ, acetone-$d_6$): 2.67 (t, J=8 Hz, 2H), 2.86 (t, J=8 Hz, 2H), 5.51 (s, 2H), 5.80 (s, 1H), 6.55 (d, J=2.9 Hz, 1H), 6.68 (d, J=16 Hz, 1H), 6.75 (d, J=8.7 Hz, 2H), 7.07 (d, J=8.7 Hz, 2H), 7.22~7.34 (m, 5H), 7.40 (br d, J=8 Hz, 1H), 7.50 (d, J=2.9 Hz, 1H), 7.61 (d, J=8.2 Hz, 1H), 7.70 (d, J=16 Hz, 1H), 7.76 (s, 1H), 8.1 (br s, 1H, OH).
Melting Point 45-50° C., MS (ESI+) m/z 424.6 (M+1), 446.6 (M+Na).

Example 387

Synthesis of (E)-1-(2-chloro-4-hydroxyphenyl)-7-(4-hydroxyphenyl)hept-1-ene-3,5-dione (CU522)

The title compound was synthesized using the same procedure employed for Example 383 (2), but with 2-chloro-4-hydroxybenzaldehyde (12 mg, 78 μmol) instead of 4-hydroxy-2-methoxybenzaldehyde (12 mg, 78 μmol). The product was obtained as a solid (9.2 mg, 34%) having the following characteristics.
$^1$H NMR (δ, acetone-$d_6$): 2.70 (t, J=8 Hz, 2H), 2.86 (t, J=8 Hz, 2H), 5.82 (s, 1H), 6.61 (d, J=16 Hz, 1H), 6.75 (d, J=8.7 Hz, 2H), 6.87 (d, J=2.4, 8.7 Hz, 1H), 6.96 (d, J=2.4 Hz, 1H), 7.07 (d, J=8.7 Hz, 2H), 7.74 (d, J=8.7 Hz, 1H), 7.89 (d, J=16 Hz, 1H).
MS (ESI+) m/z 345.4 (M+1), 367.4 (M+Na).

Example 388

Synthesis of (E)-1-(4-dimethylamino-2-nitrophenyl)-7-(4-hydroxyphenyl)hept-1-ene-3,5-dione (CU523)

The title compound was synthesized using the same procedure employed for Example 383 (2), but with 4-dimethylamino-2-nitrobenzaldehyde (15 mg, 78 μmol) instead of 4-hydroxy-2-methoxybenzaldehyde (12 mg, 78 μmol). The product was obtained as a solid (12.2 mg, 41%) having the following characteristics.
$^1$H NMR (δ, acetone-$d_6$): 2.68 (t, J=8 Hz, 2H), 2.86 (t, J=8 Hz, 2H), 3.12 (s, 6H), 5.81 (s, 1H), 6.58 (d, J=16 Hz, 1H), 6.74 (d, J=8.7 Hz, 2H), 7.04 (d, J=2.4, 9.2 Hz, 1H), 7.07 (d, J=8.7 Hz, 2H), 7.15 (d, J=2.4 Hz, 1H), 7.75 (d, J=16 Hz, 1H), 7.79 (d, J=9.2 Hz, 1H), 8.1 (br s, 1H, OH).
Melting Point 136-142° C., MS (ESI+) m/z 383.5 (M+1), 405.4 (M+Na).

Example 389

Synthesis of (E)-1-(2-chloro-4-dimethylaminophenyl)-7-(4-hydroxyphenyl)hept-1-ene-3,5-dione (CU524)

The title compound was synthesized using the same procedure employed for Example 383 (2), but with 2-chloro-4-dimethylaminobenzaldehyde (14 mg, 78 μmol) instead of 4-hydroxy-2-methoxybenzaldehyde (12 mg, 78 μmol). The product was obtained as a solid (15.6 mg, 54%) having the following characteristics.
$^1$H NMR (δ, acetone-$d_6$): 2.66 (t, J=8 Hz, 2H), 2.86 (t, J=8 Hz, 2H), 3.05 (s, 6H), 5.77 (s, 1H), 6.52 (d, J=16 Hz, 1H), 6.7~6.76 (m, 4H), 7.07 (d, J=8.7 Hz, 2H), 7.70 (d, J=9.7 Hz, 1H), 7.93 (d, J=16 Hz, 1H), 8.1 (br s, 1H, OH).
Melting Point 120-129° C., MS (ESI+) m/z 372.5 (M+1).

Example 390

Synthesis of (E)-1-(biphenyl-2-yl)-7-(4-hydroxyphenyl)hept-1-ene-3,5-dione (CU525)

The title compound was synthesized using the same procedure employed for Example 383 (2), but with 2-phenylbenzaldehyde (15 μL, 78 μmol) instead of 4-hydroxy-2-methoxybenzaldehyde (12 mg, 78 μmol). The product was obtained as a solid (13.8 mg, 48%) having the following characteristics.
$^1$H NMR (δ, acetone-$d_6$): 2.68 (t, J=8 Hz, 2H), 2.84 (t, J=8 Hz, 2H), 5.81 (s, 1H), 6.68 (d, J=16 Hz, 1H), 6.74 (d, J=8.7 Hz, 2H), 7.06 (d, J=8.7 Hz, 2H), 7.32~7.52 (m, 8H), 7.59 (d, J=16 Hz, 1H), 7.86 (dd, J=1.5, 7.3 Hz, 1H), 8.1 (br s, 1H, OH).
MS (ESI+) m/z 371.5 (M+1), 393.5 (M+Na).

Example 391

Synthesis of (1E,6E)-1-(4-hydroxybiphenyl-2-yl)-7-(4-hydroxyphenyl)hepta-1,6-diene-3,5-dione (CU526)

(1) Synthesis of 4-hydroxybiphenyl-2-carboxaldehyde

The title compound was synthesized using the same procedure employed for Example 370 (1), but with 2-bromo-4-hydroxybenzaldehyde (300 mg, 1.49 mmol) instead of 1-bromo-2-naphthaldehyde (502 mg, 2.14 mmol), and was purified by silica gel column chromatography eluting with hexane/ethyl acetate=80/20 to 70/30. The product was obtained as a pale yellow powder (242 mg, 82%).

(2) Synthesis of (1E,6E)-1-(4-hydroxybiphenyl-2-yl)-7-(4-hydroxyphenyl)hepta-1,6-diene-3,5-dione (CU526)

The title compound was synthesized using the same procedure employed for Example 22, but with 4-hydroxybiphenyl-2-carboxaldehyde (23 mg, 0.11 mmol) instead of 3-hydroxy-4-methoxybenzaldehyde (16 mg, 0.11 mmol). The product was obtained as a solid (15.8 mg, 47%) having the following characteristics.
$^1$H NMR (δ, acetone-$d_6$): 5.98 (s, 1H), 6.67 (d, J=16 Hz, 1H), 6.73 (d, J=16 Hz, 1H), 6.90 (d, J=8.7 Hz, 2H), 6.99 (dd, J=2.4, 8.2 Hz, 1H), 7.24 (d, J=8.2 Hz, 1H), 7.28~7.34 (m, 3H), 7.39 (dd, J=7, 8 Hz, 1H), 7.46 (dd, J=7, 8 Hz, 2H), 7.57 (d, J=8.7 Hz, 2H), 7.61 (d, J=16 Hz, 1H), 7.62 (d, J=16 Hz, 1H).
Melting Point 179-186° C., MS (ESI+) m/z 385.4 (M+1), 407.4 (M+Na).

Example 392

Synthesis of (1E,6E)-1-(4-benzyloxybiphenyl-2-yl)-7-(4-hydroxyphenyl)hepta-1,6-diene-3,5-dione (CU527)

(1) Synthesis of 4-benzyloxybiphenyl-2-carboxaldehyde

To a suspension of 4-hydroxybiphenyl-2-carboxaldehyde (80 mg, 0.40 mmol), potassium carbonate (111 mg, 0.80 mmol), and tetrabutylammonium iodide (15 mg, 0.04 mmol) in 0.8 mL of dry N,N-dimethylformamide was added benzyl bromide (72 µL, 0.60 mmol) at 0° C. After being stirred at room temperature overnight, the reaction mixture was diluted with diethyl ether. The solution was washed with water, saturated $NaHCO_3$ aqueous solution, brine, and dried over $MgSO_4$. After filtration, the filtrate was concentrated in vacuo, and the residue was purified by silica gel column chromatography (hexane/ethyl acetate=95/5 to 80/20) to obtain the title compound as a white crystal (112 mg, 77%).

(2) Synthesis of (1E,6E)-1-(4-benzyloxybiphenyl-2-yl)-7-(4-hydroxyphenyl)hepta-1,6-diene-3,5-dione (CU527)

The title compound was synthesized using the same procedure employed for Example 22, but with 4-benzyloxybiphenyl-2-carboxaldehyde (33 mg, 0.11 mmol) instead of 3-hydroxy-4-methoxybenzaldehyde (16 mg, 0.11 mmol). The product was obtained as a solid (22.6 mg, 54%) having the following characteristics.

$^1$H NMR (δ, acetone-$d_6$): 5.26 (s, 2H), 5.97 (s, 1H), 6.67 (d, J=16 Hz, 1H), 6.85 (d, J=16 Hz, 1H), 6.90 (d, J=8.7 Hz, 2H), 7.16 (dd, J=2.4, 8.7 Hz, 1H), 7.3~7.5 (m, 8H), 7.44 (d, J=8.7 Hz, 1H), 7.51~7.59 (m, 3H), 7.55 (d, J=8.7 Hz, 2H), 7.62 (d, J=16 Hz, 1H), 7.64 (d, J=16 Hz, 1H).

Melting Point 172-178° C., MS (ESI+) m/z 475.5 (M+1), 497.4 (M+Na).

Example 393

Synthesis of (1E,6E)-1-(4-hydroxyphenyl)-7-[2-(naphthalen-1-yl)phenyl]hepta-1,6-diene-3,5-dione (CU528)

(1) Synthesis of 2-(naphthalen-1-yl)benzaldehyde

To a suspension of 1-bromobenzaldehyde (200 µL, 1.71 mmol), sodium carbonate (218 mg, 2.06 mmol), and 1-naphthaleneboronic acid (353 mg, 2.05 mmol) in 3.4 mL of N,N-dimethylformamide/water (2:1) was added palladium acetate (20 mg, 89 µmol) under nitrogen. After being stirred at room temperature overnight, the reaction mixture was filtered. The filtrate was diluted with diethyl ether, and the solution was washed with brine, and dried over $MgSO_4$. After filtration, the filtrate was concentrated in vacuo, and the residue was purified by silica gel column chromatography (hexane/ethyl acetate=90/10 to 80/20) to obtain the title compound as a white solid (346 mg, 87%).

(2) Synthesis of (1E,6E)-1-(4-hydroxyphenyl)-7-[2-(naphthalen-1-yl)phenyl]hepta-1,6-diene-3,5-dione (CU528)

The title compound was synthesized using the same procedure employed for Example 22, but with 2-(naphthalen-1-yl)benzaldehyde (27 mg, 0.11 mmol) instead of 3-hydroxy-4-methoxybenzaldehyde (16 mg, 0.11 mmol). The product was obtained as a solid (17.0 mg, 46%) having the following characteristics.

$^1$H NMR (δ, acetone-$d_6$): 5.86 (s, 1H), 6.60 (d, J=16 Hz, 1H), 6.79 (d, J=16 Hz, 1H), 6.88 (d, J=8.7 Hz, 2H), 7.26 (d, J=16 Hz, 1H), 7.36~7.46 (m, 4H), 7.5~7.6 (m, 6H), 7.62 (dd, J=7, 9 Hz, 1H), 8.0~8.05 (m, 3H).

Melting Point 95-101° C., MS (ESI+) m/z 419.4 (M+1), 441.4 (M+Na).

Example 394

Synthesis of (1E,6E)-1-(4-hydroxyphenyl)-7-[2-(naphthalen-2-yl)phenyl]hepta-1,6-diene-3,5-dione (CU529)

(1) Synthesis of 2-(naphthalen-2-yl)benzaldehyde

The title compound was synthesized using the same procedure employed for Example 393 (1), but with 2-naphthaleneboronic acid instead of 1-naphthaleneboronic acid. The product was obtained as a colorless oil (192 mg, 48%).

(2) Synthesis of (1E,6E)-1-(4-hydroxyphenyl)-7-[2-(naphthalen-2-yl)phenyl]hepta-1,6-diene-3,5-dione (CU529)

The title compound was synthesized using the same procedure employed for Example 22, but with 2-(naphthalen-2-yl)benzaldehyde (27 mg, 0.11 mmol) instead of 3-hydroxy-4-methoxybenzaldehyde (16 mg, 0.11 mmol). The product was obtained as a solid (15.8 mg, 43%) having the following characteristics.

$^1$H NMR (δ, acetone-$d_6$): 5.99 (s, 1H), 6.65 (d, J=16 Hz, 1H), 6.85 (d, J=16 Hz, 1H), 6.89 (d, J=8.7 Hz, 2H), 7.46~7.62 (m, 9H), 7.71 (d, J=16 Hz, 1H), 7.89 (s, 1H), 7.95 (d, J=7.2 Hz, 1H), 7.96~8.02 (m, 2H), 8.03 (d, J=8.2 Hz, 1H).

Melting Point 105-114° C., MS (ESI+) m/z 441.4 (M+Na).

Example 395

Synthesis of (E)-1-(5-hydroxy-2-nitrophenyl)-7-(4-hydroxyphenyl)hept-1-ene-3,5-dione (CU530)

The title compound was synthesized using the same procedure employed for Example 383 (2), but with 5-hydroxy-2-nitrobenzaldehyde (13 mg, 78 µmol) instead of 4-hydroxy-2-methoxybenzaldehyde (12 mg, 78 µmol). The product was obtained as a solid (6.0 mg, 22%) having the following characteristics.

$^1$H NMR (δ, acetone-$d_6$): 2.74 (t, J=8 Hz, 2H), 2.87 (t, J=8 Hz, 2H), 5.91 (s, 1H), 6.60 (d, J=16 Hz, 1H), 6.75 (d, J=8.7 Hz, 2H), 7.03 (dd, J=2, 8.7 Hz, 1H), 7.08 (d, J=8.7 Hz, 2H), 7.17 (d, J=2 Hz, 1H), 8.04 (d, J=16 Hz, 1H), 8.06 (d, J=8.7 Hz, 1H).

Melting Point 62-70° C., MS (ESI+) m/z 356.4 (M+1), 378.4 (M+Na).

Example 396

Synthesis of (1E,6E)-1-(5-benzyloxy-2-bromophenyl)-7-(4-hydroxyphenyl)hepta-1,6-diene-3,5-dione (CU531)

(1) Synthesis of 5-benzyloxy-2-bromobenzaldehyde

To a suspension of 2-bromo-5-hydroxybenzaldehyde (100 mg, 0.50 mmol), potassium carbonate (138 mg, 1.00 mmol), and tetrabutylammonium iodide (18 mg, 0.05 mmol) in 1.0 mL of dry N,N-dimethylformamide was added benzyl bromide (89 μL, 0.74 mmol) at 0° C. After being stirred at room temperature overnight, the reaction mixture was diluted with diethyl ether, and the solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=95/5 to 80/20) to obtain the title compound as a colorless oil (140 mg, 97%).

(2) Synthesis of (1E,6E)-1-(5-benzyloxy-2-bromophenyl)-7-(4-hydroxyphenyl)hepta-1,6-diene-3,5-dione (CU531)

The title compound was synthesized using the same procedure employed for Example 22, but with 5-benzyloxy-2-bromobenzaldehyde (33 mg, 0.11 mmol) instead of 3-hydroxy-4-methoxybenzaldehyde (16 mg, 0.11 mmol). The product was obtained as a solid (4.2 mg, 10%) having the following characteristic.

MS (ESI+) m/z 377.4 (M+1).

Example 397

Synthesis of (1E,6E)-1-(2-bromo-5-hydroxyphenyl)-7-(4-hydroxyphenyl)hepta-1,6-diene-3,5-dione (CU532)

The title compound was synthesized using the same procedure employed for Example 22, but with 2-bromo-5-hydroxybenzaldehyde (23 mg, 0.11 mmol, prepared according to the procedure described in Synthetic Communications, (2007), 37, 579) instead of 3-hydroxy-4-methoxybenzaldehyde (16 mg, 0.11 mmol). The product was obtained as a solid (25.6 mg, 75%) having the following characteristics.

$^1$H NMR (δ, acetone-d$_6$): 6.08 (s, 1H), 6.72 (d, J=16 Hz, 1H), 6.77 (d, J=16 Hz, 1H), 6.86 (d, J=8.7 Hz, 1H), 6.91 (d, J=8.7 Hz, 2H), 7.31 (br s, 1H), 7.49 (d, J=8.7 Hz, 1H), 7.60 (d, J=8.7 Hz, 2H), 7.67 (d, J=16 Hz, 1H), 7.90 (d, J=16 Hz, 1H).

Melting Point 182-186° C., MS (ESI+) m/z 387.4 (M+1).

Example 398

Synthesis of (1E,6E)-1-(4-bromo-2-dimethylaminophenyl)-7-(4-hydroxyphenyl)hepta-1,6-diene-3,5-dione (CU533)

(1) Synthesis of 4-bromo-2-dimethylaminobenzaldehyde

To a suspension of 4-bromo-2-fluorobenzaldehyde (500 mg, 2.46 mmol) and potassium carbonate (340 mg, 2.46 mmol) in 5 mL of dry N,N-dimethylformamide was added dimethylamine/ethanol solution (0.67 mL, 5.6 M, 3.8 mmol) at room temperature. After being stirred at 110° C. overnight, the reaction mixture was diluted with ethyl acetate. The solution was washed with water, saturated NaHCO$_3$ aqueous solution, brine, and dried over MgSO$_4$. After filtration, the filtrate was concentrated in vacuo, and the residue was purified by silica gel column chromatography (hexane/ethyl acetate=95/5 to 80/20) to obtain the title compound as a yellow oil (458 mg, 81%).

(2) Synthesis of (1E,6E)-1-(4-bromo-2-dimethylaminophenyl)-7-(4-hydroxyphenyl)hepta-1,6-diene-3,5-dione (CU533)

The title compound was synthesized using the same procedure employed for Example 22, but with 4-bromo-2-dimethylaminobenzaldehyde (26 mg, 0.11 mmol) instead of 3-hydroxy-4-methoxybenzaldehyde (16 mg, 0.11 mmol). The product was obtained as a solid (13.0 mg, 36%) having the following characteristics.

$^1$H NMR (δ, acetone-d$_6$): 2.79 (s, 6H), 6.05 (s, 1H), 6.70 (d, J=16 Hz, 1H), 6.79 (d, J=16 Hz, 1H), 6.91 (d, J=8.7 Hz, 2H), 7.19 (dd, J=1.9, 8.2 Hz, 1H), 7.25 (d, J=1.9 Hz, 1H), 7.58 (d, J=8.2 Hz, 1H), 7.58 (d, J=8.7 Hz, 2H), 7.64 (d, J=16 Hz, 1H), 7.87 (d, J=16 Hz, 1H).

Melting Point 74-81° C., MS (ESI+) m/z 414.4 (M+1).

Example 399

Synthesis of (1E,6E)-1-(5-bromo-2-dimethylaminophenyl)-7-(4-hydroxyphenyl)hepta-1,6-diene-3,5-dione (CU534)

(1) Synthesis of 5-Bromo-2-Dimethylaminobenzaldehyde

The title compound was synthesized using the same procedure employed for Example 398 (1), but with 5-bromo-2-fluorobenzaldehyde (500 mg, 2.46 mmol) instead of 4-bromo-2-fluorobenzaldehyde. The product was obtained as a pale yellow solid (507 mg, 89%).

(2) Synthesis of (1E,6E)-1-(5-bromo-2-dimethylaminophenyl)-7-(4-hydroxyphenyl)hepta-1,6-diene-3,5-dione (CU534)

The title compound was synthesized using the same procedure employed for Example 22, but with 5-bromo-2-dimethylaminobenzaldehyde (26 mg, 0.11 mmol) instead of 3-hydroxy-4-methoxybenzaldehyde (16 mg, 0.11 mmol). The product was obtained as a solid (15.8 mg, 43%) having the following characteristics.

$^1$H NMR (δ, acetone-d$_6$): 2.76 (s, 6H), 6.07 (s, 1H), 6.71 (d, J=16 Hz, 1H), 6.85 (d, J=16 Hz, 1H), 6.91 (d, J=8.7 Hz, 2H), 7.08 (d, J=8.7 Hz, 1H), 7.46 (dd, J=2.4, 8.7 Hz, 1H), 7.59 (d, J=8.7 Hz, 2H), 7.65 (d, J=16 Hz, 1H), 7.78 (d, J=2.4 Hz, 1H), 7.88 (d, J=16 Hz, 1H).

Melting Point 68-72° C., MS (ESI+) m/z 414.3 (M+1).

Example 400

Synthesis of (1E,6E)-1-(2-dimethylamino-5-trifluoromethylphenyl)-7-(4-hydroxyphenyl)hepta-1,6-diene-3,5-dione (CU535)

(1) Synthesis of 2-dimethylamino-5-trifluoromethylbenzaldehyde

The title compound was synthesized using the same procedure employed for Example 398 (1), but with 2-fluoro-5-trifluoromethylbenzaldehyde (500 mg, 2.60 mmol) instead of 4-bromo-2-fluorobenzaldehyde. The product was obtained as a yellow oil (332 mg, 59%).

(2) Synthesis of (1E,6E)-1-(2-dimethylamino-5-trifluoromethylphenyl)-7-(4-hydroxyphenyl)hepta-1,6-diene-3,5-dione (CU535)

The title compound was synthesized using the same procedure employed for Example 22, but with 2-dimethylamino-5-trifluoromethylbenzaldehyde (25 mg, 0.11 mmol) instead of 3-hydroxy-4-methoxybenzaldehyde (16 mg, 0.11 mmol). The product was obtained as a solid (18.0 mg, 51%) having the following characteristics.

$^1$H NMR (δ, acetone-$d_6$): 2.87 (s, 6H), 6.10 (s, 1H), 6.71 (d, J=16 Hz, 1H), 6.91 (d, J=8.7 Hz, 2H), 6.92 (d, J=16 Hz, 1H), 7.25 (d, J=8.7 Hz, 1H), 7.59 (d, J=8.7 Hz, 2H), 7.62 (br d, J=8.7 Hz, 1H), 7.66 (d, J=16 Hz, 1H), 7.87 (d, J=16 Hz, 1H), 7.91 (br s, 1H).

Melting Point 68-74° C., MS (ESI+) m/z 404.4 (M+1).

Example 401

Synthesis of (1E,6E)-1-(3-dimethylaminobiphenyl-4-yl)-7-(4-hydroxyphenyl)hepta-1,6-diene-3,5-dione (CU536)

(1) Synthesis of 3-dimethylaminobiphenyl-4-carboxaldehyde

To a suspension of 4-bromo-2-dimethylaminobenzaldehyde (250 mg, 1.10 mmol), sodium carbonate (140 mg, 1.32 mmol), and phenylboronic acid (210 mg, 1.65 mmol) in 2.2 mL of N,N-dimethylformamide/water (2:1) was added palladium acetate (13 mg, 58 μmol) under nitrogen. After being stirred at 100° C. overnight, the reaction mixture was filtered. The filtrate was diluted with ethyl acetate, and the solution was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 80/20) to obtain the title compound as a yellow oil (226 mg, 91%).

(2) Synthesis of (1E,6E)-1-(3-dimethylaminobiphenyl-4-yl)-7-(4-hydroxyphenyl)hepta-1,6-diene-3,5-dione (CU536)

The title compound was synthesized using the same procedure employed for Example 22, but with 3-dimethylaminobiphenyl-4-carboxaldehyde (26 mg, 0.11 mmol) instead of 3-hydroxy-4-methoxybenzaldehyde (16 mg, 0.11 mmol). The product was obtained as a solid (28.0 mg, 77%) having the following characteristics.

$^1$H NMR (δ, acetone-$d_6$): 2.84 (s, 6H), 6.05 (s, 1H), 6.71 (d, J=16 Hz, 1H), 6.82 (d, J=16 Hz, 1H), 6.91 (d, J=8.7 Hz, 2H), 7.34 (d, J=1.5, 8.2 Hz, 1H), 7.38 (t, J=7.2 Hz, 1H), 7.40 (d, J=1.5 Hz, 1H), 7.47 (dd, J=7.2, 7.7 Hz, 2H), 7.59 (dd, J=8.7 Hz, 2H), 7.64 (d, J=16 Hz, 1H), 7.71 (dd, J=1.5, 7.7 Hz, 2H), 7.75 (d, J=8.2 Hz, 1H), 8.05 (d, J=16 Hz, 1H).

Melting Point 83-88° C., MS (ESI+) m/z 412.2 (M+1).

Example 402

Synthesis of (1E,6E)-1-(4-dimethylaminobiphenyl-3-yl)-7-(4-hydroxyphenyl)hepta-1,6-diene-3,5-dione (CU537)

(1) Synthesis of 4-dimethylaminobiphenyl-3-carboxaldehyde

The title compound was synthesized using the same procedure employed for Example 401 (1), but with 5-bromo-2-dimethylaminobenzaldehyde instead of 4-bromo-2-dimethylaminobenzaldehyde. The product was obtained as a yellow crystal (217 mg, 88%).

(2) Synthesis of (1E,6E)-1-(4-dimethylaminobiphenyl-3-yl)-7-(4-hydroxyphenyl)hepta-1,6-diene-3,5-dione (CU537)

The title compound was synthesized using the same procedure employed for Example 22, but with 4-dimethylaminobiphenyl-3-carboxaldehyde (26 mg, 0.11 mmol) instead of 3-hydroxy-4-methoxybenzaldehyde (16 mg, 0.11 mmol). The product was obtained as a solid (21.8 mg, 60%) having the following characteristics.

$^1$H NMR (δ, acetone-$d_6$): 2.81 (s, 6H), 6.08 (s, 1H), 6.70 (d, J=16 Hz, 1H), 6.91 (d, J=8.7 Hz, 2H), 6.96 (d, J=16 Hz, 1H), 7.22 (d, J=8.2 Hz, 1H), 7.34 (t, J=7.2 Hz, 1H), 7.45 (dd, J=7.2, 8.2 Hz, 2H), 7.58 (dd, J=8.7 Hz, 2H), 7.64 (d, J=16 Hz, 1H), 7.64 (d, J=1.9, 8.2 Hz, 1H), 7.68 (dd, J=1.5, 8.2 Hz, 2H), 7.95 (d, J=1.9 Hz, 1H), 8.05 (d, J=16 Hz, 1H).

Melting Point 82-88° C., MS (ESI+) m/z 412.4 (M+1).

Example 403

Synthesis of (1E,6E)-1-[5-hydroxy-2-(naphthalen-1-yl)phenyl]-7-(4-hydroxyphenyl)hepta-1,6-diene-3,5-dione (CU538)

(1) Synthesis of 5-hydroxy-2-(naphthalen-1-yl)benzaldehyde

To a suspension of 2-bromo-5-hydroxybenzaldehyde (300 mg, 1.49 mmol), sodium carbonate (190 mg, 1.79 mmol), and 1-naphthaleneboronic acid (384 mg, 2.23 mmol) in 3.0 mL of N,N-dimethylformamide/water (2:1) was added palladium acetate (18 mg, 80 μmol) under nitrogen. After being stirred at room temperature overnight, the reaction mixture was filtered. The filtrate was diluted with ethyl acetate, and the solution was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=85/15 to 75/25) to obtain the title compound as a white solid (274 mg, 74%).

(2) Synthesis of (1E,6E)-1-[5-hydroxy-2-(naphthalen-1-yl)phenyl]-7-(4-hydroxyphenyl)hepta-1,6-diene-3,5-dione (CU538)

The title compound was synthesized using the same procedure employed for Example 22, but with 5-hydroxy-2-(naphthalen-1-yl)benzaldehyde (28 mg, 0.11 mmol) instead of 3-hydroxy-4-methoxybenzaldehyde (16 mg, 0.11 mmol). The product was obtained as a solid (26.2 mg, 69%) having the following characteristics.

$^1$H NMR (δ, acetone-$d_6$): 5.85 (s, 1H), 6.59 (d, J=16 Hz, 1H), 6.69 (d, J=16 Hz, 1H), 6.88 (d, J=8.7 Hz, 2H), 7.06 (d, J=2.4, 8.2 Hz, 1H), 7.20 (d, J=8.2 Hz, 1H), 7.21 (d, J=16 Hz, 1H), 7.35 (d, J=6.8 Hz, 1H), 7.4~7.61 (m, 8H), 7.98 (d, J=8.2 Hz, 1H), 7.99 (d, J=8.2 Hz, 1H), 8.8 (br s, 1H, OH).

Melting Point 215-221° C., MS (ESI+) m/z 435.4 (M+1), 457.4 (M+Na).

Example 404

Synthesis of (1E,6E)-1-(2-bromo-4-hydroxy-5-methoxyphenyl)-7-(4-hydroxyphenyl)hepta-1,6-diene-3,5-dione (CU539)

The title compound was synthesized using the same procedure employed for Example 22, but with 2-bromo-4-hydroxy-5-methoxybenzaldehyde (26 mg, 0.11 mmol, prepared according to the procedure described in J. Org. Chem., (2002), 67, 6493.) instead of 3-hydroxy-4-methoxybenzaldehyde (16 mg, 0.11 mmol). The product was obtained as a solid (24.2 mg, 66%) having the following characteristics.

$^1$H NMR (δ, acetone-$d_6$): 3.94 (s, 3H), 5.99 (s, 1H), 6.68 (d, J=16 Hz, 1H), 6.79 (d, J=16 Hz, 1H), 6.91 (d, J=8.7 Hz, 2H), 7.13 (s, 1H), 7.48 (s, 1H), 7.57 (d, J=8.7 Hz, 2H), 7.63 (d, J=16 Hz, 1H), 7.93 (d, J=16 Hz, 1H).

Melting Point 237-242° C., MS (ESI+) m/z 417.3 (M+1), 439.3 (M+Na).

Example 405

Synthesis of (E)-1-(2,4-dimethoxyphenyl)-7-(4-hydroxyphenyl)hept-1-ene-3,5-dione (CU540)

The title compound was synthesized using the same procedure employed for Example 383 (2), but with 2,4-dimethoxybenzaldehyde (13 mg, 78 μmol) instead of 4-hydroxy-2-methoxybenzaldehyde (12 mg, 78 μmol). The product was obtained as a solid (14.4 mg, 52%) having the following characteristics.

$^1$H NMR (δ, acetone-$d_6$): 2.66 (t, J=8 Hz, 2H), 2.86 (t, J=8 Hz, 2H), 3.86 (s, 3H), 3.92 (s, 3H), 5.76 (s, 1H), 6.58 (dd, J=2.4, 8.7 Hz, 1H), 6.62 (d, J=16 Hz, 1H), 6.62 (d, J=2.4 Hz, 1H), 6.75 (d, J=8.7 Hz, 2H), 7.07 (d, J=8.7 Hz, 2H), 7.59 (d, J=8.7 Hz, 1H), 7.84 (d, J=16 Hz, 1H), 8.1 (br s, 1H, OH).

MS (ESI+) m/z 355.4 (M+1), 377.4 (M+Na).

Example 406

Synthesis of (E)-1-(4-hydroxybiphenyl-2-yl)-7-(4-hydroxyphenyl)hept-1-ene-3,5-dione (CU541)

The title compound was synthesized using the same procedure employed for Example 383 (2), but with 4-hydroxybiphenyl-2-carboxaldehyde (16 mg, 78 μmol) instead of 4-hydroxy-2-methoxybenzaldehyde (12 mg, 78 μmol). The product was obtained as a solid (15.0 mg, 50%) having the following characteristics.

$^1$H NMR (δ, acetone-$d_6$): 2.68 (t, J=8 Hz, 2H), 2.84 (t, J=8 Hz, 2H), 5.81 (s, 1H), 6.59 (d, J=16 Hz, 1H), 6.74 (d, J=8.2 Hz, 2H), 6.98 (dd, J=2.9, 8.2 Hz, 1H), 7.06 (d, J=8.2 Hz, 2H), 7.23 (d, J=8.2 Hz, 1H), 7.28 (d, J=2.9 Hz, 1H), 7.29 (d, J=7 Hz, 1H), 7.38 (t, J=7 Hz, 1H), 7.45 (dd, J=7, 7 Hz, 2H), 7.55 (d, J=16 Hz, 1H).

Melting Point 148-158° C., MS (ESI+) m/z 387.4 (M+1), 409.4 (M+Na).

Example 407

Synthesis of (E)-1-[5-hydroxy-2-(naphthalen-1-yl)phenyl]-7-(4-hydroxyphenyl)hept-1-ene-3,5-dione (CU542)

The title compound was synthesized using the same procedure employed for Example 383 (2), but with 5-hydroxy-2-(naphthalen-1-yl)benzaldehyde (20 mg, 78 μmol) instead of 4-hydroxy-2-methoxybenzaldehyde (12 mg, 78 μmol). The product was obtained as a solid (17.2 mg, 51%) having the following characteristics.

$^1$H NMR (δ, acetone-$d_6$): 2.60 (t, J=8 Hz, 2H), 2.77 (t, J=8 Hz, 2H), 5.68 (s, 1H), 6.56 (d, J=16 Hz, 1H), 6.72 (d, J=8.2 Hz, 2H), 7.01 (d, J=8.2 Hz, 2H), 7.04 (dd, J=2.4, 8.2 Hz, 1H), 7.14 (d, J=16 Hz, 1H), 7.19 (d, J=8.2 Hz, 1H), 7.34 (d, J=6.8 Hz, 1H), 7.40 (d, J=2.4 Hz, 1H), 7.4~7.54 (m, 3H), 7.58 (dd, J=7.2, 8.2 Hz, 1H), 7.97 (d, J=8.2 Hz, 1H), 7.98 (d, J=8.2 Hz, 1H).

Melting Point 138-142° C., MS (ESI+) m/z 437.4 (M+1), 459.5 (M+Na).

Example 408

Synthesis of (1E,6E)-1-(2-bromo-5-hydroxy-4-methoxyphenyl)-7-(4-hydroxyphenyl)hepta-1,6-diene-3,5-dione (CU543)

The title compound was synthesized using the same procedure employed for Example 22, but with 2-bromo-5-hydroxy-4-methoxybenzaldehyde (26 mg, 0.11 mmol, prepared according to the procedure described in Zhejiang Daxue Xuebao, Gongxueban, (2006), 40, 520) instead of 3-hydroxy-4-methoxybenzaldehyde (16 mg, 0.11 mmol). The product was obtained as a solid (13.2 mg, 36%) having the following characteristics.

$^1$H NMR (δ, acetone-$d_6$): 3.93 (s, 3H), 6.04 (s, 1H), 6.71 (d, J=16 Hz, 1H), 6.72 (d, J=16 Hz, 1H), 6.91 (d, J=8.7 Hz, 2H), 7.21 (s, 1H), 7.35 (s, 1H), 7.59 (d, J=8.7 Hz, 2H), 7.64 (d, J=16 Hz, 1H), 7.90 (d, J=16 Hz, 1H).

Melting Point 224-229° C., MS (ESI+) m/z 417.3 (M+1).

Example 409

Synthesis of (1E,6E)-1-(2,4-dibromo-5-hydroxyphenyl)-7-(4-hydroxyphenyl)hepta-1,6-diene-3,5-dione (CU544)

The title compound was synthesized using the same procedure employed for Example 22, but with 2,4-dibromo-5-hydroxybenzaldehyde (32 mg, 0.11 mmol, prepared according to the procedure described in Tetrahedron: Asymmetry, (2002), 13, 2261) instead of 3-hydroxy-4-methoxybenzaldehyde (16 mg, 0.11 mmol). The product was obtained as a solid (17.2 mg, 42%) having the following characteristics.

$^1$H NMR (δ, acetone-$d_6$): 6.07 (s, 1H), 6.72 (d, J=16 Hz, 1H), 6.75 (d, J=16 Hz, 1H), 6.91 (d, J=8.7 Hz, 2H), 7.44 (s, 1H), 7.59 (d, J=8.7 Hz, 2H), 7.67 (d, J=16 Hz, 1H), 7.82 (s, 1H), 7.82 (d, J=16 Hz, 1H).

Melting Point 255-259° C., MS (ESI+) m/z 465.2 (M+1).

Example 410

Synthesis of (E)-1-(4-diethylamino-2-isopropyloxyphenyl)-7-(4-hydroxyphenyl)hept-1-ene-3,5-dione (CU545)

The title compound was synthesized using the same procedure employed for Example 383 (2), but with 4-diethylamino-2-isopropyloxybenzaldehyde (18 mg, 78 μmol) instead of 4-hydroxy-2-methoxybenzaldehyde (12 mg, 78 μmol). The product was obtained as a solid (15.6 mg, 47%) having the following characteristics.

$^1$H NMR (δ, acetone-$d_6$): 1.18 (t, J=7 Hz, 6H), 1.36 (d, J=6.3 Hz, 6H), 2.61 (t, J=8 Hz, 2H), 2.85 (t, J=8 Hz, 2H), 3.46 (q, J=7 Hz, 4H), 4.72 (m, 1H), 5.67 (s, 1H), 6.28 (d, J=2.4 Hz, 1H), 6.35 (dd, J=2.4, 8.7 Hz, 1H), 6.47 (d, J=16 Hz, 1H), 6.74 (d, J=8.7 Hz, 2H), 7.07 (d, J=8.7 Hz, 2H), 7.45 (d, J=8.7 Hz, 1H), 7.87 (d, J=16 Hz, 1H), 8.1 (br s, 1H, OH).

MS (ESI+) m/z 424.6 (M+1).

Example 411

Synthesis of (E)-1-(3-chloro-4-hydroxyphenyl)-7-(4-hydroxyphenyl)hept-1-ene-3,5-dione (CU546)

The title compound was synthesized using the same procedure employed for Example 383 (2), but with 3-chloro-4-hydroxybenzaldehyde (13 mg, 78 µmol) instead of 4-hydroxy-2-methoxybenzaldehyde (12 mg, 78 µmol). The product was obtained as a solid (19.6 mg, 73%) having the following characteristics.

$^1$H NMR (δ, acetone-$d_6$): 2.68 (t, J=8 Hz, 2H), 2.86 (t, J=8 Hz, 2H), 5.81 (s, 1H), 6.62 (d, J=16 Hz, 1H), 6.75 (d, J=8.2 Hz, 2H), 7.05 (d, J=8.2 Hz, 1H), 7.07 (d, J=8.2 Hz, 2H), 7.48 (dd, J=2, 8.2 Hz, 1H), 7.49 (d, J=16 Hz, 1H), 7.69 (d, J=2 Hz, 1H).

Melting Point 45-51° C., MS (ESI+) m/z 345.4 (M+1).

Example 412

Synthesis of (E)-1-(5-benzyloxy-2-nitrophenyl)-7-(4-hydroxyphenyl)hept-1-ene-3,5-dione (CU548)

The title compound was synthesized using the same procedure employed for Example 383 (2), but with 5-benzyloxy-2-nitrobenzaldehyde (20 mg, 78 µmol) instead of 4-hydroxy-2-methoxybenzaldehyde (12 mg, 78 µmol). The product was obtained as a solid (6.8 mg, 20%) having the following characteristics.

$^1$H NMR (δ, acetone-$d_6$): 2.74 (t, J=8 Hz, 2H), 2.87 (t, J=8 Hz, 2H), 5.34 (s, 2H), 5.90 (s, 1H), 6.73 (d, J=16 Hz, 1H), 6.75 (d, J=8.7 Hz, 2H), 7.07 (d, J=8.7 Hz, 2H), 7.24 (dd, J=2.9, 9.2 Hz, 1H), 7.36~7.46 (m, 3H), 7.44 (d, J=2.9 Hz, 1H), 7.52 (d, J=7.2 Hz, 2H), 8.04 (d, J=16 Hz, 1H), 8.13 (d, J=9.2 Hz, 1H). MS (ESI+) m/z 446.5 (M+1), 468.5 (M+Na).

Example 413

Synthesis of (E)-1-(2-bromo-5-hydroxyphenyl)-7-(4-hydroxyphenyl)hept-1-ene-3,5-dione (CU549)

The title compound was synthesized using the same procedure employed for Example 383 (2), but with 2-bromo-5-hydroxybenzaldehyde (16 mg, 78 µmol) instead of 4-hydroxy-2-methoxybenzaldehyde (12 mg, 78 µmol). The product was obtained as a solid (8.0 mg, 26%) having the following characteristics.

$^1$H NMR (δ, acetone-$d_6$): 2.73 (t, J=8 Hz, 2H), 2.87 (t, J=8 Hz, 2H), 5.89 (s, 1H), 6.65 (d, J=16 Hz, 1H), 6.75 (d, J=8.7 Hz, 2H), 6.84 (dd, J=2.9, 8.7 Hz, 1H), 7.08 (d, J=8.7 Hz, 2H), 7.26 (d, J=2.9 Hz, 1H), 7.48 (d, J=8.7 Hz, 1H), 7.83 (d, J=16 Hz, 1H).

Melting Point 161-165° C., MS (ESI+) m/z 389.2 (M+1), 411.2 (M+Na).

Test Example 1

β-Secretase Enzyme Inhibition Assay

Compounds were dissolved in dimethylsulfoxide (DMSO), and further diluted in 0.1 M sodium acetate buffer (with 150 mM sodium chloride, pH 4.5). The solution with no compound was used as a negative control. Then, 100 µL of these solutions (compound concentration: 3 µM), 1 µL of recombinant human β-secretase (rhBACE-1, R&D), and 5 µL of the fluorescent substrate peptide were mixed in a black 96-well plate (Nunc). After mixtures were incubated in the dark at 37° C. for 2 hr, the fluorescence intensities of the mixtures were measured by fluorescence microplate reader (Wallac) at 540 nm for excitation and at 590 nm for emission. The inhibition ratio was calculated as a percentage of the negative control. The sequence of the peptide was Ser-Glu-Val-Asn-Leu-Asp-Ala-Glu-Lys-Arg, and labeled with fluorescent donor (Cy3) at Ser-1 and with quencher (Cy5Q) at Lys-9, respectively (Invitrogen). Inhibitory activities (%) of each compound are shown in FIG. 1. CU001, CU017, CU030, CU031, CU094, CU104, CU110, CU112, CU116, CU121, CU122, CU148, CU176, CU187, CU189, CU190, CU193, CU194 and CU198 strongly inhibited BACE-1 enzyme activity.

Test Example 2

Aβ3-42 aggregation Inhibition Assay

Aβ1-42 was dissolved in a 0.1% NH$_3$ solution at a concentration of 100 µM and centrifuged for 1.5 hr at 200,000 g, and the supernatant are used in the assay. 25 µM of Aβ solution diluted by 100 mM phosphate buffer (pH 7.4), and compound solution containing 2% DMSO were mixed in equal amount. The mixtures were incubated for 24 hr at 37° C. in a black 96-well plate. After incubation, 6 µM thioflavin T (Sigma) in 100 mM of glycine-NaOH buffer, pH 8.5, was added, and fluorescence was measured at 440 nm for excitation and at 486 nm for emission.

The results were shown in Table 1. The IC$_{50}$ of curcumin was 9.8 µM in this assay.

TABLE 1

| Test compound | IC$_{50}$ (µM) |
|---|---|
| Compound of Example 42 | 0.28 |
| Compound of Example 59 | 0.09 |
| Compound of Example 124 | 0.88 |
| Compound of Example 138 | 1.10 |

Test Example 3

Aβ1-42 Degradation Assay

Aβ1-42 (Peptide Institute) was dissolved in a 0.1% NH$_3$ solution at a concentration of 60 µM, and incubated for 24 hr at 37° C. to form the aggregation. 25 µM of the aggregated Aβ solution diluted by 100 mM phosphate buffer (pH 7.4) and the compound dilution containing 2% DMSO were mixed in equal amount. The mixtures were incubated for 1 hr at 37° C. in a black 96-well plate. After incubation, 6 µM thioflavin T (Sigma) in 100 mM of glycine-NaOH buffer, pH 8.5, was added, and fluorescence was measured for excitation at 440 nm and emission at 486 nm. The solution with DMSO only, instead of the compound solution, was used as a negative control. The activity was calculated as a percentage of the negative control.

The results were shown in Table 2. The EC$_{50}$ of curcumin was 18 µM in this assay.

TABLE 2

| Test compound | IC$_{50}$ (µM) |
|---|---|
| Compound of Example 4 | 3.3 |
| Compound of Example 16 | 0.4 |
| Compound of Example 18 | 1.1 |
| Compound of Example 19 | 5.3 |

Test Example 4

Cytoprotection from Aβ1-42-Induced Cell Cytotoxicity

Cerebral cortex was obtained from 19-20 day-old embryonic Wistar rat. The tissue was minced, dissociated using scalpel blades and Pasteur pipette, and centrifuged at 100 rpm. Precipitated cells were filtered using 100 μM cell strainer, and single cells were prepared. These cells were suspended in Eagle's Minimum Essential Medium (EMEM) containing 10% Fetal bovine serum, and plated into 48-well tissue culture plates (Becton Dickinson) at 200 μL/well and $1.7 \times 10^5$ cells/cm². Cultures were incubated at 37° C. in a humidified atmosphere of 5% $CO_2$.

After 3, 5, and 7 days in culture, the medium was replaced.

After 9 days, compounds were dissolved in DMSO and diluted in culture media so that the final concentration of DMSO in culture media was 0.1%, and each solution was added to each well at 200 mL/well for 24 hr. The control solution contained 0.1% DMSO.

After 24 hr, Aβ1-42 was dissolved in a 0.1% $NH_3$ solution at a concentration of 500 μM and diluted in culture media to a final concentration of 5 μM, and the Aβ solution was added to each well at 200 μM/well for 48 hr. After 48 hr, cultures were treated with 0.5% MTT solution (Nacalai Tesque) for 35 min. The MTT solution was replaced with 2-propanol (200 μL), and the culture plates were shook to dissolve formazan. Absorption of the solution was measured at 570 nm. Cell viability was expressed as percentage survival, with 100% survival taken as observed in control cultures.

The results were shown in Table 3. The minimal effective concentration (MEC) of curcumin was 10 μM in this assay.

TABLE 3

| Test compound | MEC (μM) |
| --- | --- |
| Compound of Example 59 | 0.1 |
| Compound of Example 71 | 3.0 |
| Compound of Example 213 | 1.0 |

Test Example 5

Calculation of 50% Inhibitory Concentration (IC50) of BACE-1

Compounds were dissolved in 0.1 M sodium acetate buffer (with 150 mM sodium chloride, pH 4.5) to each concentration with DMSO (concentration of compounds: 0.3, 0.9, 3.0, 9.0, and 30.0). The final concentration of DMSO was 10%. The solution with no compound was used as a negative control. 15 μL of these solutions, recombinant human BACE-1 (1.0 U/ml, Invitrogen), and the fluorescent substrate peptide (2.5 nM) were mixed in a black 384-well plate (Costar). Then, mixtures were incubated in the dark at 37° C. for 2.5 hr. The fluorescence intensities of the mixtures were measured at 540 nm for excitation and at 590 nm for emission. The inhibition ratio was calculated as a percentage of the negative control. The sequence of the peptide was Ser-Glu-Val-Asn-Leu-Asp-Ala-Glu-Lys-Arg, and labeled with Cy3 at Ser-1 and with Cy5Q at Lys-9. Final concentrations of compounds were as follows: 0.01, 0.03, 1.0, 3.0, 5.0, and 10.0 μM. 50% Inhibitory concentration (IC50) of each compound are shown in FIG. 2. The compounds with indole ring (CU189, CU461, CU520 and so on) and the compounds with the 2-nitro or halogenated benzene (CU131, CU132, CU133, CU381, CU475, CU530, CU531, and CU532) showed inhibitory effect on BACE-1 activity at relatively low concentration.

The invention claimed is:

1. A compound represented by the following general formula (I) or a salt thereof:

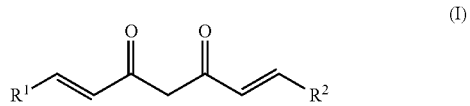

wherein $R^1$ represents a phenyl group which is substituted by one or more substituents independently selected from the group consisting of hydroxy and methoxy group, and $R^2$ represents a 1H-indol-2-yl, 1H-indol-3-yl, 1H-indol-4-yl, 1H-indol-5-yl, 1H-indol-6-yl, or 1H-indol-7-yl group which may be substituted by one or two or more substituent(s) selected from a substituent group A; and the substituent group A is a group selected from the group consisting of halogen atoms, alkyl groups having 1 to 6 carbon atom(s), alkoxy groups having 1 to 6 carbon atom(s), dialkylamino groups (wherein the alkyl group has 1 to 6 carbon atom(s)), alkylamino groups (wherein the alkyl group has 1 to 6 carbon atom(s)), amino groups, alkoxyalkoxy groups having 2 to 6 carbon atoms, hydroxy groups, acetylamino groups, phenoxy groups, methanesulfonyl groups, methylthio groups, nitro groups, 3-dimethylaminopropoxy groups, 2-dimethylaminoethoxy groups, dimethylaminomethoxy groups, acetoxy groups, methoxycarbonyl groups, pyridin-2-yl groups, 1H-imidazol-1-yl groups, 4-benzylpiperazin-1-yl groups, 4-methylphenoxy groups, morpholino groups, 4-methylphenyl groups, phenyl groups, benzimidazol-1-yl groups, 4-methylpiperazin-1-yl groups, 2-(t-butoxycarbonylamino)acetylamino groups, 2-t-butoxycarbonylamino-3-phenylpropionylamino groups, benzyl groups, acetyl groups, tosyl groups, methylsulfonyloxy groups, t-butoxycarbonylamino groups, N-(t-butoxycarbonyl)-N-methylamino groups, t-butyldimethylsilyloxy groups, t-butyldimethylsilyloxymethyl groups, 2-amino-3-phenylpropionylamino groups, hydroxymethyl groups, benzoyloxy groups, prenyloxy groups, benzyloxy groups, i-propyloxy groups, 2-hydroxyethoxy groups, 2-(amino)acetylamino groups, 4-methoxybenzyloxy groups, pyridin-3-ylmethoxy groups, 2-chloro-6-fluorobenzyloxy groups, 2,4-dichlorobenzyloxy groups, 4-t-butylbenzyloxy groups, trifluoromethyl groups, hydroxycarbonyl groups, dimethylaminocarbonyl groups, dimethylaminosulfonyl groups, methylsulfinyl groups, pyrrolidin-1-yl groups, piperidin-1-yl groups, t-butoxycarbonylpiperazin-1-yl groups, methylsulfonylpiperazin-1-yl groups, 2-hydroxyethylpiperazin-1-yl groups, pyridin-3-yl groups, pyridin-4-yl groups, piperazin-3-yl groups, naphthalen-1-yl groups, and naphthalen-2-yl groups.

2. The compound or a salt thereof according to claim 1, characterized in that in the general formula (I), $R^1$ is a 4-hydroxy-3-methoxyphenyl, 4-hydroxyphenyl, or 3-hydroxy-4-methoxyphenyl group.

3. The compound or a salt thereof according to claim 1, characterized in that in the general formula (I), $R^2$ is a 1H-indol-2-yl, 1H-indol-3-yl, 1H-indol-4-yl, 1H-indol-5-yl, 1H-indol-6-yl, H-indol-7-yl, 1-methyl-1H-indol-3-yl, 1-methyl-1H-indol-2-yl, 1-benzyl-1H-indol-3-yl, 1-benzyl-1H- indol-6-yl, 1-acetyl-1H-indol-3-yl, 1-acetyl-1H-indol-6-yl, 1-methylsulfonyl-1H-indol-3-yl, 1-methylsulfonyl-1H-indol-6-yl, 1-tosyl-1H-indol-3-yl, 1-tosyl-1H-indol-6-yl, or 4-nitro-1H-indol-3-yl group.

4. The compound or a salt thereof according to claim 2, characterized in that in the general formula (I), $R^2$ is a 1H-indol-2-yl, 1H-indol-3-yl, 1H-indol-4-yl, 1H-indol-5-yl, 1H-indol-6-yl, 1H-indol-7-yl, 1-methyl-1H-indol-3-yl, 1-methyl-1H-indol-2-yl, 1-benzyl-1H-indol-3-yl, 1-benzyl-1H-indol-6-yl, 1-acetyl-1H-indol-3-yl, 1-acetyl-1H-indol-6-yl, 1-methylsulfonyl-1H-indol-3-yl, 1-methylsulfonyl-1H-indol-6-yl, 1-tosyl-1H-indol-3-yl, 1-tosyl-1H-indol-6-yl, or 4-nitro-1H-indol-3-yl group.

\* \* \* \* \*